(12) United States Patent
Dasseux et al.

(10) Patent No.: US 9,388,232 B2
(45) Date of Patent: Jul. 12, 2016

(54) APOLIPOPROTEIN A-I MIMICS

(71) Applicant: Cerenis Therapeutics Holding SA, Labege (FR)

(72) Inventors: Jean-Louis Dasseux, Toulouse (FR); Anna Shenderova Schwendeman, Superior Township, MI (US); Lingyu Zhu, Shanghai (CN)

(73) Assignee: Cerenis Therapeutics Holding SA, Labege (FR)

( * ) Notice: Subject to any disclaimer, the term of this patent is extended or adjusted under 35 U.S.C. 154(b) by 0 days.

(21) Appl. No.: 14/614,771

(22) Filed: Feb. 5, 2015

(65) Prior Publication Data

US 2015/0141330 A1 May 21, 2015

Related U.S. Application Data

(60) Division of application No. 13/766,561, filed on Feb. 13, 2013, now Pat. No. 8,993,597, which is a continuation of application No. 12/705,094, filed on Feb. 12, 2010, now Pat. No. 8,378,068.

(60) Provisional application No. 61/152,960, filed on Feb. 16, 2009, provisional application No. 61/152,966, filed on Feb. 16, 2009, provisional application No. 61/152,962, filed on Feb. 16, 2009.

(51) Int. Cl.
| | | |
|---|---|---|
| A61K 38/16 | (2006.01) | |
| C07K 14/775 | (2006.01) | |
| A61K 38/17 | (2006.01) | |

(52) U.S. Cl.
CPC ............... *C07K 14/775* (2013.01); *A61K 38/16* (2013.01); *A61K 38/1709* (2013.01)

(58) Field of Classification Search
CPC ... A61K 38/16; A61K 38/1709; C07K 14/775
USPC .......................................................... 514/7.4
See application file for complete search history.

(56) References Cited

U.S. PATENT DOCUMENTS

| | | | |
|---|---|---|---|
| 4,229,360 A | 10/1980 | Schneider et al. | |
| 4,411,894 A | 10/1983 | Schrank et al. | |
| 4,643,988 A | 2/1987 | Segrest et al. | |
| 4,857,319 A | 8/1989 | Crowe et al. | |
| 4,880,635 A | 11/1989 | Janoff et al. | |
| 5,733,879 A | 3/1998 | Rosseneu et al. | |
| 5,955,055 A | 9/1999 | Lees et al. | |
| 5,972,890 A | 10/1999 | Lees et al. | |
| 6,004,925 A | 12/1999 | Dasseux et al. | |
| 6,037,323 A | 3/2000 | Dasseux et al. | |
| 6,046,166 A | 4/2000 | Dasseux et al. | |
| 6,265,377 B1 | 7/2001 | Dasseux et al. | |
| 6,287,590 B1 | 9/2001 | Dasseux | |
| 6,329,341 B1 | 12/2001 | Dasseux et al. | |
| 6,376,464 B1 | 4/2002 | Dasseux et al. | |
| 6,455,088 B1 | 9/2002 | Dasseux | |
| 6,506,799 B1 | 1/2003 | Dasseux | |
| 6,518,412 B1 | 2/2003 | Dasseux et al. | |
| 6,573,239 B1 | 6/2003 | Dasseux et al. | |
| 6,602,854 B1 | 8/2003 | Dasseux et al. | |
| 6,630,450 B1 | 10/2003 | Dasseux et al. | |
| 6,716,816 B1 | 4/2004 | Dasseux et al. | |
| 6,734,169 B2 | 5/2004 | Dasseux et al. | |
| 6,743,778 B2 | 6/2004 | Kohno | |
| 6,753,313 B1 | 6/2004 | Cornut et al. | |
| 6,844,327 B2 | 1/2005 | Dasseux et al. | |
| 6,900,177 B1 | 5/2005 | Dasseux et al. | |
| 7,144,862 B2 | 12/2006 | Fogelman et al. | |
| 7,157,425 B2 | 1/2007 | Dasseux et al. | |
| 7,189,411 B2 | 3/2007 | Dasseux | |
| 7,189,689 B2 | 3/2007 | Dasseux et al. | |
| 7,211,565 B2 | 5/2007 | Dasseux et | |
| 7,250,407 B2 | 7/2007 | Dasseux et al. | |
| 7,273,848 B2 | 9/2007 | Dasseux et al. | |
| 7,307,058 B2 | 12/2007 | Dasseux et al. | |
| 7,312,190 B2 | 12/2007 | Dasseux et al. | |
| 7,566,695 B2 | 7/2009 | Dasseux et al. | |
| 7,569,546 B2 | 8/2009 | Bachovchin | |
| 7,868,135 B2 | 1/2011 | Cameron et al. | |
| 8,119,590 B2 | 2/2012 | Bisgaier et al. | |
| 8,124,580 B2 | 2/2012 | Bachovchin | |
| 8,163,699 B2 | 4/2012 | Tardiff | |
| 8,206,750 B2 | 6/2012 | Dasseux | |
| 8,378,068 B2 | 2/2013 | Dasseux et al. | |
| 8,617,615 B2 | 12/2013 | Dasseux | |
| 2003/0045460 A1 | 3/2003 | Fogelman et al. | |
| 2003/0109442 A1 | 6/2003 | Bisgaier et al. | |

(Continued)

FOREIGN PATENT DOCUMENTS

| | | |
|---|---|---|
| EP | 0162414 | 11/1985 |
| JP | 61-152632 | 7/1986 |

(Continued)

OTHER PUBLICATIONS

Supplementary European Search Report for European Application No. 07719817, mailed Jan. 27, 2010, 8 pages.
European Search Report for European Application No. 12167547, mailed Nov. 22, 2012, 6 pages.
Office Action for U.S. Appl. No. 12/227,872, mailed Jan. 27, 2011, 17 pages.
International Preliminary Report on Patentability for International Application No. PCT/CA2007/000895, dated Dec. 3, 2008, 10 pages.
International Search Report and Written Opinion for International Application No. PCT/CA2007/000895, mailed Oct. 12, 2007, 14 pages.

(Continued)

*Primary Examiner* — Julie Ha
(74) *Attorney, Agent, or Firm* — Cooley LLP

(57) ABSTRACT

Provided are peptides, compositions thereof, and methods for treating or preventing dyslipidemia, a cardiovascular disease, endothelial dysfunction, a macrovascular disorder, or a microvascular disorder.

9 Claims, 23 Drawing Sheets

(56) References Cited

U.S. PATENT DOCUMENTS

| | | |
|---|---|---|
| 2003/0171277 A1 | 9/2003 | Fogelman et al. |
| 2004/0067873 A1 | 4/2004 | Dasseux et al. |
| 2004/0073297 A1 | 4/2004 | Rohde et al. |
| 2005/0080013 A1 | 4/2005 | Dasseux et al. |
| 2006/0069030 A1 | 3/2006 | Bachovchin |
| 2006/0217312 A1 | 9/2006 | Dasseux et al. |
| 2006/0252694 A1 | 11/2006 | Dasseux et al. |
| 2007/0167351 A1 | 7/2007 | Dasseux et al. |
| 2007/0197442 A1 | 8/2007 | Pressler et al. |
| 2008/0050351 A1 | 2/2008 | Dasseux et al. |
| 2008/0058270 A1 | 3/2008 | Dasseux et al. |
| 2008/0138284 A1 | 6/2008 | Brewer et al. |
| 2008/0214434 A1 | 9/2008 | Stroes |
| 2008/0269111 A1 | 10/2008 | Dasseux et al. |
| 2009/0081293 A1 | 3/2009 | Murase et al. |
| 2009/0186808 A1 | 7/2009 | Tardif |
| 2010/0267631 A1 | 10/2010 | Dasseux et al. |
| 2011/0092430 A1 | 4/2011 | Tardif |
| 2012/0021982 A1 | 1/2012 | Tardif et al. |
| 2013/0231459 A1 | 9/2013 | Dasseux et al. |

FOREIGN PATENT DOCUMENTS

| | | |
|---|---|---|
| WO | WO 93/25581 | 12/1993 |
| WO | WO 94/13819 | 6/1994 |
| WO | WO 96/04916 | 2/1996 |
| WO | WO 96/37608 | 11/1996 |
| WO | WO 99/16409 | 4/1999 |
| WO | WO 99/16458 | 4/1999 |
| WO | WO 99/16459 | 4/1999 |
| WO | WO 03/026492 | 4/2003 |
| WO | WO 2005/000878 | 1/2005 |
| WO | WO 2006/100567 | 9/2006 |
| WO | WO 2007/004060 | 1/2007 |
| WO | WO 2007/137400 | 12/2007 |
| WO | WO 2008/094905 | 8/2008 |
| WO | WO 2008/156873 | 12/2008 |
| WO | WO 2010/083611 | 7/2010 |
| WO | WO 2010/093918 | 8/2010 |

OTHER PUBLICATIONS

Office Action for U.S. Appl. No. 12/956,615, mailed Jun. 7, 2012, 17 pages.
Supplementary European Search Report for European Application No. 10741801, mailed Feb. 27, 2013, 9 pages.
Office Action for U.S. Appl. No. 12/705,094, mailed Jul. 10, 2012, 18 pages.
International Preliminary Report on Patentability for International Application No. PCT/US2010/024096, dated Aug. 16, 2011, 5 pages.
International Search Report and Written Opinion for International Application No. PCT/US2010/024096, mailed Jul. 16, 2010, 9 pages.
Office Action for U.S. Appl. No. 13/766,561, mailed Aug. 1, 2014, 16 pages.
Ameli, S. et al., "Recombinant apolipoprotein A-I Milano reduces intimal thickening after balloon injury in hypercholesterolemic rabbits," Circulation, 90(4):1935-1941 (1994).
Anantharamaiah et al, "Use of synthetic peptide analogues to localize lecithin:cholesterol acyltransferase activating domain in apolipoprotein A-I," Arteriosclerosis Thromb Vasc Biol., 10:95-105 (1990).
Anantharamaiah, "Synthetic peptide analogs of apolipoproteins," Methods Enzymol., 128:627-647 (1986).
Anantharamaiah et al., "Studies of synthetic peptide analogs of the amphipathic helix. Structure of complexes with dimyristoyl phosphatidylcholine," J Biol. Chem., 260(18):10248-10255 (1985).
Anantharamaiah et al., "Role of amphipathic helixes in HDL structure/function," Adv Exp Med Biol., 285:131-140 (1991).
Badimon et al., "Regression of atherosclerotic lesions by high density lipoprotein plasma fraction in the cholesterol-fed rabbit," J Clin Invest., 85(4):1234-1241 (1990).

Barrans et al., "Pre-beta HDL: structure and metabolism," Biochim Biophys Acta, 1300(2):73-85 (1996).
Beitz et al., "Does a HDL injection reduce the development of serum hyperlipidemia and progression of fatty streaks in cholesterol fed rabbits?", Prostaglandins Leukot Essent Fatty Acids, 147(2):149-152 (1992).
Bender, Heart Valve Disease, Chapter 13 in the Yale University School of Medicine Heart Book, pp. 167-175 (1992).
Berard et al., "High plasma HDL concentrations associated with enhanced atherosclerosis in transgenic mice overexpressing lecithin-cholesteryl acyltransferase," Nat Med., 3(7):744-749 (1997).
Berendsen, H.J.C., "A glimpse of the holy grail?" Science, 282:642-643 (1998).
Blondelle et al., "Influence of tryptophan residues on melittin's hemolytic activity," Biochim Biophys Acta, 1202(2):331-336 (1993).
Bodary, P. F. et al., "Gene transfer of an ApoA-I mimetic peptide reduces atherosclerosis in mice," J Am Coll Cardiol., 43(5s2): A465-A466 (2004).
Bradley, C. M. et al., "Limits of Cooperativity in a Structurally Modular Protein: Response of the Notch Ankyrin Domain to Analogous Alanine Substitutions in Each Repeat," J. Mol. Biol., 324:373-386 (2002).
Braschi et al., "Apolipoprotein A-I charge and conformation regulate the clearance of reconstituted high density lipoprotein in vivo," J Lipid Res., 40(3):522-532 (1999).
Brasseur et al., "Differentiation of lipid-associating helices by use of three-dimensional molecular hydrophobicity potential calculations," J Biol. Chem., 266(24):16120-16127 (1991).
Brasseur et al., "Mode of assembly of amphipathic helical segments in model high-density lipoproteins," Biochim Biophys Acta, 1043(3):245-252 (1990).
Brasseur, R. et al., "Synthetic model peptides for apolipoproteins. I. Design and properties of synthetic model peptides for the amphipathic helices of the plasma apolipoproteins," Biochimica Biophysica Acta, 1170(1):1-7 (1993).
Brewer et al., "HDL metabolism and the role of HDL in the treatment of high-risk patients with cardiovascular disease," Curr Cardiol Rep., 9:486-492 (2007).
Brouillette et al., "Structural models of human apolipoprotein A-I," Biochim Biophys Acta, 1256(2):103-129 (1995).
Brouillette, C. G. et al., "Structural models of human apolipoprotein A-I: a critical analysis and review," Biochim Biophys Acta, 1531(1-2):4-46 (2001).
Brown et al., "HDL as a treatment target," J Clin Lipidol., 4:5-16 (2010).
Burkey et al., "Overexpression of human apolipoprotein A-I in transgenic rats and the hyperlipoproteinemia associated with experimental nephrosis," J Lipid Res., 36(7):1463-1473 (1995).
Busseuil et al., "Late neointimal tissue growth behind the stent after intravascular gamma-radiation," Int J Radiat Oncol Biol. Phys., 58(1):259-266 (2004).
Busseuil, D. et al., "Regression of aortic valve stenosis by ApoA-I mimetic peptide infusions in rabbits," British Journal of Pharmacology, 154:765-773 (2008).
Carabello, "Clinical practice—Aortic stenosis," N Engl J Med., 346(9):677-682 (2002).
Chan, K. L. et al., "Effect of Lipid Lowering with Rosuvastatin on Pregression of Aortic Stenosis, Results of the Aortic Stenosis Progression Observation: Measuring Effects of Rosuvastatin (Astronomer) Trial," Circulation, 121(2):306-314 (2010).
Cheung et al., "Altered particle size distribution of apolipoprotein A-I-containing lipoproteins in subjects with coronary artery disease," J Lipid Res., 32(3):383-394 (1991).
Collet et al., "Evolution of mammalian apolipoprotein A-I and conservation of antigenicity: correlation with primary and secondary structure," J Lipid Res., 38(4):634-644 (1997).
Copeland, T. D. et al., "Substitution of proline with pipecolic acid at the scissile bond converts a peptide substrate of HIV proteinase into a selective inhibitor," Biochem Biophys Res Commun, 169(1):310-314 (1990).
Corijn et al., "Synthetic model peptides for apolipoproteins. II. Characterization of the discoidal complexes generated between

(56) References Cited

OTHER PUBLICATIONS phospholipids and synthetic model peptides for apolipoproteins," Biochim Biophys Acta 1170(1):8-16 (1993).
Cowell et al, "A Randomized Trial of Intensive Lipid-Lowering Therapy in Calcific Aortic Stenosis," N Engl J Med., 352(23):2389-2397 (2005).
Cox et al., "The interaction of calmodulin with amphiphilic peptides," J Biol. Chem., 260(4):2527-2534 (1985).
Davidson et al., "The influence of apolipoprotein structure on the efflux of cellular free cholesterol to high density lipoprotein," J Biol. Chem., 269(37):22975-22982 (1994).
Davidson et al., "The role of apolipoprotein AI domains in lipid binding," Proc. Natl Acad Sci USA, 93(24):13605-13610 (1996).
Degoma, et al., "Beyond high-density lipoprotein cholesterol levels evaluating high-density lipoprotein function as influenced by novel therapeutic approaches," J. Am Coll Cardiol., 51:2199-2211 (2008).
Demoor et al., "Branched synthetic constructs that mimic the physico-chemical properties of apolipoprotein AI in reconstituted high-density lipoproteins," Eur J Biochem., 239(1):74-84 (1996).
Dorland's Illustrated Medical Dictionary, 1561, 29th ed., pp. 140, 166, and 1561 (2000).
Drolet, M-C. et al., "Experimental Aortic Valve Stenosis in Rabbits," Journal of the American College of Cardiology, 41(7):1211-1217 (2003).
Dufourcq et al., "Morphological changes of phosphatidylcholine bilayers induced by melittin: vesicularization, fusion, discoidal particles," Biochim Biophys Acta, 859(1):33-48 (1986).
Duverger et al., "Inhibition of atherosclerosis development in cholesterol-fed human apolipoprotein A-I-transgenic rabbits," Circulation, 94(4):713-717 (1996).
Duverger et al., "Transgenic rabbits expressing human apolipoprotein A-I in the liver," Arterioscler Thromb Vasc Biol., 16(12):1424-1429 (1996).
Emmanuel et al., "Identification of specific amphipathic alpha-helical sequence of human apolipoprotein A-IV involved in lecithin:cholesterol acyltransferase activation," J Biol. Chem., 269(47):29883-29890 (1994).
Epand et al., "Mechanisms for the modulation of membrane bilayer properties by amphipathic helical peptides," Biopolymers, 37(5):319-338 (1995).
Epand et al., "Studies of synthetic peptide analogs of the amphipathic helix. Effect of charge distribution, hydrophobicity, and secondary structure on lipid association and lecithin:cholesterol acyltransferase activation," J Biol. Chem., 262(19):9389-9396 (1987).
Esposito et al., "Lysine as helix C-capping residue in a synthetic peptide," Biopolymers, 41(1):27-35 (1997).
Fabre, A. C. et al., "P2Y13 receptor is critical for reverse cholesterol transport," Hepatology, 52:1477-1483 (2010).
Fielding et al., "Molecular physiology of reverse cholesterol transport," J Lipid Res., 36(2):211-228 (1995).
Fournier et al., "Role of HDL phospholipid in efflux of cell cholesterol to whole serum: studies with human apoA-1 transgenic rats," J Lipid Res., 37(8):1704-1711 (1996).
Francone et al., "Expression of human lecithin-cholesterol acyltransferase in transgenic mice. Effect of human apolipoprotein AI and human apolipoprotein aII on plasma lipoprotein cholesterol metabolism," J Clin Invest., 96(3):1440-1448 (1995).
Freeman, R. V. et al., "Spectrum of Calcific Aortic Valve Disease, Pathogenesis, Disease Progression, and Treatment Strategies," Contemporary Reviews in Cardiovascular Medicine, Circulation, 111(24):3316-3326 (2005).
Fruchart et al., "Apolipoprotein A-containing lipoprotein particles: physiological role, quantification, and clinical significance," Clin Chem., 38(6):793-797 (1992).
Fukushima et al., "Chain length-function correlation of amphiphilic peptides. Synthesis and surface properties of a tetratetracontapeptide segment of apolipoprotein A-I," The Journal of Biological Chemistry, 255(22):10651-10657 (1980).

Garber et al., "Turnover of synthetic class A amphipathic peptide analogues of exchangeable apolipoproteins in rats. Correlation with physical properties," Arterioscler Thromb., 12(8):886-894 (1992).
Godin, et al., "Remodeling of carotid artery is associated with increased expression of matrix metalloproteinases in mouse blood flow cessation model," Circulation, 102:2861-2866 (2000).
Gordon et al., "High-density lipoprotein cholesterol and cardiovascular disease. Four prospective American studies," Circulation, 79(1):8-15 (1989).
Gordon et al., "High-density lipoprotein—the clinical implications of recent studies," N Engl J Med., 321(19):1311-1316 (1989).
Groebke et al., "Template-nucleated alanine-lysine helices are stabilized by position-dependent interactions between the lysine side chain and the helix barrel," Proc Natl Acad Sci USA, 93(9):4025-4029 (1996).
Guasch et al. "Charge selectivity of the glomerular filtration barrier in healthy and nephrotic humans," J Clin Invest., 92(5):2274-2282 (1993).
Hatano, M. et al., "Properties of a toxic phospholipid in the northern blenny roe," Toxicon, 12:231-236 (1974).
Holvoet et al., "Phospholipid binding and lecithin-cholesterol acyltransferase activation properties of apolipoprotein A-I mutants," Biochemistry, 34(41):13334-13342 (1995).
Huygheus-Despointes, B. M. P. et al., "Measuring the strength of side-chain hydrogen bonds in peptide helices: the Gin Asp (i, i + 4) interaction," Biochemistry, 34(41):13267-13271 (1995).
Ivan, et al., "Expansive arterial remodeling is associated with increased neointimal macrophage foam cell content: the murine model of macrophage-rich carotid artery lesions," Circulation, 105:2686-2691 (2002).
Jacquet, S. et al., "The nucleotide receptor $P2Y_{13}$ is a key regulator of hepatic high-density lipoprotein (HDL) endocytosis," Cell Mol. Life Sci., 62:2508-2515 (2005).
Ji et al., "Properties of an N-terminal proteolytic fragment of apolipoprotein Al in solution and in reconstituted high density lipoproteins," J Biol. Chem., 270(19):11290-11297 (1995).
Johnson et al., "Single bilayer liposomes," Biochim Biophys Acta, 233(3):820-826 (1971).
Jonas, "Reconstitution of high-density lipoproteins," Methods Enzymol., 128:553-582 (1986).
Kaiser et al., "Color test for detection of free terminal amino groups in the synthesis of peptides," Anal Biochem., 34(2):595-598 (1970).
Kaiser et al., "Secondary structures of proteins and peptides in amphiphilic environments. (A review)," Proc Natl Aced Sci USA, 80(4):1137-1143 (1983).
Kannelis et al., "Studies of synthetic peptide analogs of the amphipathic helix. Effect of charged amino acid residue topography on lipid affinity," J Biol. Chem., 255(23):11464-11472 (1980).
Kaul, S. et al., "Intramural delivery of recombinant apolipoprotein A-lmilano/phospholipid complex (ETC-216) inhibits in-stent stenosis in porcine coronary arteries," Circulation, 107(1):2551-2554 (2003).
Khan et al., "Single dose intravenous infusion of ETC-642, a 22-mer ApoA-I-analogue and phospholipids complex, elevates HDL-C in atherosclerosis patients," Circulation, 108(Suppl):IV:563-4 (2003).
Khera, et al., "Cholesterol efflux capacity, high-density lipoprotein function, and atherosclerosis," N Engl J Med., 364:127-135 (2011).
Kim, Y-C. et al., "Synthesis of pyridoxal phosphate derivatives with antagonist activity at the P2Y13 receptor," Biochem Pharmacol., 70(2):266-274 (2005).
Koizumi et al., "Behavior of human apolipoprotein A-I: phospholipid and apoHDL:phospholipid complexes in vitro and after injection into rabbits," J Lipid Res., 29(11):1405-1415 (1988).
Kneib-Cordonnier et al., Int. J. Peptide Protein Res., 35:527-538 (1990).
Knott et al., "Human apolipoprotein B: structure of carboxyl-terminal domains, sites of gene expression, and chromosomal localization," Science, 230(4721):37-43 (1985).
Labeur et al., "Design of a new class of amphipathic helical peptides for the plasma apolipoproteins that promote cellular cholesterol efflux but do not activate LCAT," Arterioscler Thromb Vasc Biol., 17(3):580-588 (1997).

(56) References Cited

OTHER PUBLICATIONS

Lacko et al., "International Symposium on the Role of HDL in Disease Prevention: report on a meeting," J Lipid Res., 38(6):1267-1273 (1997).
Lee, et al. Expert Rev Cardiovasc Ther., 8:1325-1334 (2010).
Lessner et al., "Compensatory vascular remodeling during atherosclerotic lesion growth depends on matrix metalloproteinase-9 activity," Arterioscler Thromb Vasc Biol., 24:2123-2129 (2004).
Li et al., "Alpha-helical, but not beta-sheet, propensity of proline is determined by peptide environment," Proc Natl Acad Sci USA, 93(13):6676-6681 (1996).
Lins et al., "Enzymatic hydrolysis of reconstituted dimyristoylphosphatidylcholineapo A-I complexes," Biochim Biophys Acta, 1151(2):137-142 (1993).
Liu et al., "Human apolipoprotein A-I prevents atherosclerosis associated with apolipoprotein[a] in transgenic mice," J Lipid Res., 35(12):2263-2267 (1994).
Lund-Katz et al., "Nuclear magnetic resonance investigation of the interactions with phospholipid of an amphipathic alpha-helix-forming peptide of the apolipoprotein class," J Biol. Chem., 265(21): 12217-12223 (1990).
Lund-Katz et al., "Microenvironments of basic amino acids in amphipathic alpha-helices bound to phospholipid: 13C NMR studies using selectively labeled peptides," Biochemistry, 34(28):9219-9226 (1995).
Mackey, R. H. et al., "High-Density Lipoprotein Cholesterol and Particle Concentrations, Carotid Atherosclerosis, and Coronary Events," Journal of the American College of Cardiology, vol. xx, No. x (2012), 9 pages.
Marqusee et al., "Helix stabilization by Glu−. . . Lys+ salt bridges in short peptides of de novo design," Proc Natl Acad Sci USA, 84(24):8898-8902 (1987).
Martinez, L. O. et al., "Ectopic β-chain of ATP synthase is an apolipoprotein A-I receptor in hepatic HDL endocytosis," Nature, 421:75-79 (2003).
McMullen, T. P. W. et al., "Cholesterol-phospholipid interactions, the liquid-ordered phase and lipid rafts in model and biological membranes," Current Opinion in Colloid and Interface Science, 8:459-468 (2004).
Mendez et al., "Synthetic amphipathic helical peptides that mimic apolipoprotein A-I in clearing cellular cholesterol," J Clin Invest., 94(4):1698-1705 (1994).
Meyers et al., "Pharmacologic augmentation of high-density lipoproteins: mechanisms of currently available and emerging therapies," Curr Opin Cardiol., 20(4):307-312 (2005).
Mezdour et al., "Exogenous supply of artificial lipoproteins does not decrease susceptibility to atherosclerosis in cholesterol-fed rabbits," Atherosclerosis, 113(2):237-246 (1995).
Miller et al., "Associations of high-density lipoprotein subclasses and apolipoproteins with ischemic heart disease and coronary atherosclerosis," Am Heart Journal, 113(2 Pt 2):589-597 (1987).
Minnich et al., "Site-directed mutagenesis and structure-function analysis of the human apolipoprotein A-I. Relation between lecithincholesterol acyltransferase activation and lipid binding," J Biol. Chem., 267(23):16553-16560 (1992).
Mishra et al., "Interactions of synthetic peptide analogs of the class A amphipathic helix with lipids. Evidence for the snorkel hypothesis," J Biol. Chem., 269(10):7185-7191 (1994).
Mishra et al., "Effect of the arrangement of tandem repeating units of class A amphipathic alpha-helixes on lipid interaction," J Biol. Chem., 270(4): 1602-1611 (1995).
Navab et al, "Apolipoprotein A-I Mimetic Peptides," Arterioscler Thromb Vasc Biol., 25(7):1325-1331 (2005).
Navab et al., "Human apolipoprotein A-I and A-I mimetic peptides: potential for atherosclerosis reversal," Curr Opin Lipidol., 15(6):645-649 (2004).
Nedelec et al., "Comparative study of myelin proteolipid apoprotein solvation by multilayer membranes of synthetic DPPC and biological lipid extract from bovine brain. An FT-IR investigation," Biochimie, 71(1):145-151 (1989).

Newby, D. E. et al., "Emerging medical treatments for aortic stenosis: statins, angiotensin converting enzyme inhibitors, or both?" Heart, 92(6):729-734 (2006).
Ngo, J. T. et al., "Computational Complexity, Protein Structure Prediction, and the Levinthal Paradox," The Protein Folding Problem and Tertiary Structure Prediction, K. Mere Jr. and S. LeGrand Edition, pp. 491-495 (1994).
Nissen et al, "Effect of Recombinant ApoA-I Milano on Coronary Atherosclerosis in Patients With Acute Coronary Syndromes: A Randomized Controlled Trial," JAMA, 290(17):2292-2300 (2003).
Nissen et al, "Effect of Very High-Intensity Statin Therapy on Regression of Coronary Atherosclerosis: the Asteroid trial," JAMA, 295(13):1556-1565 (2006).
Novaro, G. M. et al., "Effect of Hydroxymethylglutaryl Coenzyme A Reductase Inhibitors on the Progression of Calcific Aortic Stenosis," Circulation, 104:2205-2209 (2001).
Palgunachari et al., "Only the two end helixes of eight tandem amphipathic helical domains of human apo A-I have significant lipid affinity. Implications for HDL assembly," Arterioscler Thromb Vasc Biol., 16(2):328-338 (1996).
Paszty et al., "Apolipoprotein AI trans gene corrects apolipoprotein E deficiencyinduced atherosclerosis in mice," J Clin Invest., 94(2):899-903 (1994).
Pipkorn, R. et al., "High-throughput peptide synthesis and peptide purification strategy at the low micromol-scale using the 96-well format," J. Peptide Res., 59:105-114 (2002).
Plump et al., "Human apolipoprotein A-I gene expression increases high density lipoprotein and suppresses atherosclerosis in the apolipoprotein E-deficient mouse," Proc Natl Acad Sci USA, 91(20):9607-9611 (1994).
Ponsin et al., "In vitro binding of synthetic acylated lipid-associating peptides to high-density lipoproteins: effect of hydrophobicity," Biochemistry, 23(22):5337-5342 (1984).
Ponsin et al., "Lipid-peptide association and activation of lecithin: cholesterol acyltransferase. Effect of alpha-helicity," J Biol. Chem., 261(20):9202-9205 (1986).
Pownall et al., "Activation of lecithin:cholesterol acyltransferase by a synthetic model lipid-associating peptide," Proc Natl Aced Sci USA, 77(6):3154-3158 (1980).
Rajamannan, N. M., "Calcific Aortic Stenosis: Lessons Learned From Experimental and Clinical Studies," Arterioscler Thromb Vasc Biol., 29:162-168 (2009).
Rajamannan, N. M., "Atorvastatin inhibits hypercholesterolemia-induced calcification in the aortic valves via the Lrp5 receptor pathway," Circulation, 112(1):I-229-I-234 (2005).
Rogers et al., "Truncation of the amino terminus of human apolipoprotein A-I substantially alters only the lipid-free conformation," Biochemistry, 36(2):288-300 (1997).
Rossebo, A. B. et al., "Intensive Lipid Lowering with Simvastatin and Ezetimibe in Aortic Stenosis," The New England Journal of Medicine, 359(13):1343-1356 (2008).
Rossebo, A. B. et al., "Hyperlipidemia and aortic valve disease," Current Opinion in Lipidology, 15(4):447-451 (2004).
Rosseneu et al., "Physiological significance of apolipoprotein mutants," FASEB Journal, 9(9):768-776 (1995).
Rubin et al., "Inhibition of early atherogenesis in transgenic mice by human apolipoprotein AI," Nature, 353(6341):265-267 (1991).
Rudinger, J., "Characteristics of the amino acids as components of a peptide hormone sequence," in Peptide Hormones, JA Parsons, (Ed.), University Park Press, pp. 1-7 (1976).
Schinzel, R. et al., "The phosphate recognition site of Escherichia coli maltodextrin phosphorylase," FEBS, 286(1,2):125-128 (1991).
Schnolzer et al., "Constructing proteins by dovetailing unprotected synthetic peptides: backbone-engineered HIV protease," Science, 256(5054):221-225 (1992).
Schultz et al., "Protein composition determines the anti-atherogenic properties of HDL in transgenic mice," Nature, 365(6448):762-764 (1993).
Schwartz, et al., "Preferential utilization of free cholesterol from highdensity lipoproteins for biliary cholesterol secretion in man," Science, 200:62-64 (1978).
Segrest et al., "A molecular theory of lipid-protein interactions in the plasma lipoproteins," FEBS Lett., 38(3):247-258 (1974).

(56) References Cited

OTHER PUBLICATIONS

Segrest et al., "Molecular packing of high density lipoproteins: a postulated functional role," FEBS Lett., 69(1):111-115 (1976).

Segrest et al., "Studies of synthetic peptide analogs of the amphipathic helix. Competitive displacement of exchangeable apolipoproteins from native lipoproteins," J Biol. Chem., 258(4):2290-2295 (1983).

Segrest et al., "Amphipathic helix motif: classes and properties," Proteins, 8(2):103-117 (1990).

Segrest et al., "The amphipathic helix in the exchangeable apolipoproteins: a review of secondary structure and function," J Lipid Res., 33(2):141-166 (1992).

Segrest et al., "The amphipathic α helix: a multifunctional structural motif in plasma apolipoproteins," Adv Protein Chem., 45:303-369 (1994).

Shah, P. K. et al, "High-Dose Recombinant Apolipoprotein A-I$_{Milano}$ Mobilizes Tissue Cholesterol and Rapidly Reduces Plaque Lipid and Macrophage Content in Apolipoprotein e-Deficient Mice," Circulation, 103(25):3047-3050 (2001).

SIGMA Genosys, "Designing custom peptides," accessed Dec. 16, 2004, pp. 1-2.

Sorci-Thomas et al., "Apolipoprotein A-I domains involved in lecithin-cholesterol acyltransferase activation. Structure:function relationships," J Biol. Chem., 268(28):21403-21409 (1993).

Sorci-Thomas et al., "Alteration in apolipoprotein A-I 22-mer repeat order results in a decrease in lecithin:cholesterol acyltransferase reactivity," J Biol. Chem., 272(11):7278-7284 (1997).

Sparks, D. L. et al., "Effect of the surface lipid composition of reconstituted LPA-I on apolipoprotein A-I structure and lecithin:cholesterol acyltransferase activity," Biochim. Biophys. Acta, 1390(2):160-172 (1998).

Sparks et al., "Effect of the cholesterol content of reconstituted LpA-I on lecithin:cholesterol acyltransferase activity," J Biol. Chem., 270(10):5151-5157 (1995).

Sparrow, J. T. et al., "Phospholipid binding studies with synthetic apolipoprotein fragments," Ann N Y Acad Sci., 348:187-211 (1980).

Sparrow, J. T. et al., "Apolipoprotein/lipid interactions: studies with synthetic polypeptides," Critical Reviews in Biochemistry and Molecular Biology, 13(1):87-107 (1982).

Spuhler et al., "Binding of apolipoprotein A-I model peptides to lipid bilayers. Measurement of binding isotherms and peptide-lipid headgroup interactions," J Biol. Chem., 269(39):23904-23910 (1994).

Srinivas et al., "Inhibition of virus-induced cell fusion by apolipoprotein A-I and its amphipathic peptide analogs," J Cell Biochem., 45(2):224-237 (1991).

Tam, "Synthetic peptide vaccine design: synthesis and properties of a high-density multiple antigenic peptide system," Proc Natl Acad Sci USA, 85(15):5409-5413 (1988).

Tardif et al, "Effects of Reconstituted High-Density Lipoprotein Infusions on Coronary Atherosclerosis: A Randomized Controlled Trial," JAMA, 297(15):1675-1682 (2007).

Tardy, C. et al., "CER-001, a HDL-mimetic, stimulates the reverse lipid transport and atherosclerosis regression in high cholesterol diet-fed LDL-receptor deficient mice," Atherosclerosis, 232:110-118 (2014).

Tytler et al., "Reciprocal effects of apolipoprotein and lytic peptide analogs on membranes. Cross-sectional molecular shapes of amphipathic alpha helices control membrane stability," J Biol. Chem., 268(29):22112-22118 (1993).

Vanloo et al., "LCAT activation properties of apo A-I CNBr fragments and conversion of discoidal complexes into spherical particles," Biochim Biophys Acta, 1128(2-3):258-266 (1992).

Venkatachalapathi, Y. V. et al., "Effect of end group blockage on the properties of a class A amphipathic helical peptide," Proteins: Structure, Function and Genetics, 15(4):349-359 (1993).

Venkatachalapathi et al., "Molecular Conformation and Biological Interactions," Indian Academy of Sciences, Bangalore, pp. 585-596 (1991).

Voet, D. et al., Section 9-3. Abnormal Hemoglobins, in Biochemistry, Second Edition, John Wiley & Sons, Inc., 1995, pp. 235-241.

Wang et al., "Conformation of human serum apolipoprotein A-I(166-185) in the presence of sodium dodecyl sulfate or dodecylphosphocholine by IH-NMR and CD. Evidence for specific peptide-SDS interactions," Biochim Biophys Acta, 1301(3):174-184 (1996).

Wilmot et al., "Analysis and prediction of the different types of beta-turn in proteins," J Mol Biol., 203(1):221-232 (1988).

Yancey et al., "Efflux of cellular cholesterol and phospholipid to lipid-free apolipoproteins and class A amphipathic peptides," Biochemistry, 34(24):7955-7965 (1995).

Yilmaz et al., "Lipid Profile of Patients with Aortic Stenosis Might be Predictive of Rate of Progression," American Heart Journal, 147(5):915-918 (2004).

Yokoyama et al., "The mechanism of activation of lecithin:cholesterol 9I. acyltransferase by apolipoprotein A-I and an amphiphilic peptide," J Biol. Chem., 255(15):7333-7339 (1980).

Blom, D. et al., "Altered lipoprotein metabolism in P2Y$_{13}$ knockout mice," Biochimica et Biophysica Acta, 1801:1349-1360 (2010).

Goffinet, M. et al., "P2Y13 Receptor Regulates HDL Metabolism and Atherosclerosis in Vivo," Plos ONE, 9(4):e95807 (2014).

```
                        SEQUENCE LISTING

<160> NUMBER OF SEQ ID NOS: 531

<210> SEQ ID NO 1
<211> LENGTH: 22
<212> TYPE: PRT
<213> ORGANISM: Artificial Sequence
<220> FEATURE:
<223> OTHER INFORMATION: Segrest consensus sequence

<400> SEQUENCE: 1

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 2
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 2

Lys Leu Lys Gln Lys Leu Trp Glu Leu Leu Glu Asn Leu Leu Glu Arg
1               5                   10                  15

Phe Leu Asp Leu Val Xaa
            20

<210> SEQ ID NO 3
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 3

Lys Leu Lys Gln Lys Leu Ala Glu Leu Gly Glu Asn Leu Leu Glu Arg
1               5                   10                  15

Phe Leu Asp Leu Val Xaa
            20
```

```
<210> SEQ ID NO 4
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Inp

<400> SEQUENCE: 4

Lys Leu Lys Gln Lys Xaa Ala Glu Leu Gly Glu Asn Leu Leu Glu Arg
1               5                   10                  15

Phe Leu Asp Leu Val Xaa
            20

<210> SEQ ID NO 5
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 5

Lys Leu Lys Gln Lys Leu Trp Glu Leu Gly Glu Asn Leu Leu Glu Arg
1               5                   10                  15

Phe Leu Asp Leu Val Xaa
            20

<210> SEQ ID NO 6
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 6

Lys Leu Lys Gln Lys Leu Ala Glu Leu Gly Glu Asn Trp Leu Glu Arg
1               5                   10                  15

Phe Leu Asp Leu Val Xaa
            20

<210> SEQ ID NO 7
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
```

```
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Inp

<400> SEQUENCE: 7

Xaa Leu Xaa Gln Xaa Leu Ala Glu Leu Gly Glu Asn Leu Leu Glu Arg
1               5                   10                  15

Phe Leu Asp Leu Val Xaa
            20

<210> SEQ ID NO 8
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 8

Lys Leu Lys Gln Lys Leu Ala Glu Leu Gly Glu Asn Leu Leu Glu Arg
1               5                   10                  15

Phe Phe Asp Leu Val Xaa
            20

<210> SEQ ID NO 9
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 9

Lys Leu Lys Gln Lys Leu Ala Glu Leu Gly Glu Asn Leu Leu Glu Arg
1               5                   10                  15

Phe Leu Glu Leu Val Xaa
            20

<210> SEQ ID NO 10
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 10

Lys Leu Lys Gln Lys Leu Ala Glu Leu Leu Glu Asn Leu Gly Glu Arg
1               5                   10                  15

Phe Leu Asp Leu Val Xaa
            20
```

-continued

```
<210> SEQ ID NO 11
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 11

Lys Leu Lys Gln Lys Leu Ala Glu Leu Leu Glu Asn Gly Leu Glu Arg
1               5                   10                  15

Phe Leu Asp Leu Val Xaa
            20

<210> SEQ ID NO 12
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 12

Lys Leu Lys Gln Lys Leu Ala Glu Gly Leu Glu Asn Leu Leu Glu Arg
1               5                   10                  15

Phe Leu Asp Leu Val Xaa
            20

<210> SEQ ID NO 13
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 13

Lys Leu Lys Gln Lys Leu Gly Glu Leu Leu Glu Asn Leu Leu Glu Arg
1               5                   10                  15

Phe Leu Asp Leu Val Xaa
            20

<210> SEQ ID NO 14
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 14

Lys Leu Lys Gln Lys Gly Ala Glu Leu Leu Glu Asn Leu Leu Glu Arg
1               5                   10                  15

Phe Leu Asp Leu Val Xaa
            20
```

```
<210> SEQ ID NO 15
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (7)..(7)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Inp

<400> SEQUENCE: 15

Lys Leu Lys Gln Lys Leu Xaa Glu Leu Leu Glu Asn Leu Leu Glu Arg
1               5                   10                  15

Phe Leu Asp Leu Val Xaa
            20

<210> SEQ ID NO 16
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 16

Lys Leu Lys Gln Lys Leu Ala Glu Leu Leu Glu Asn Leu Leu Glu Arg
1               5                   10                  15

Phe Leu Asp Leu Val Xaa
            20

<210> SEQ ID NO 17
<211> LENGTH: 23
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (23)..(23)
<223> OTHER INFORMATION: Xaa=Inp

<400> SEQUENCE: 17

Lys Lys Leu Lys Gln Lys Leu Ala Glu Leu Leu Glu Asn Leu Leu Glu
1               5                   10                  15

Arg Phe Leu Asp Leu Val Xaa
            20

<210> SEQ ID NO 18
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=Inp
```

```
<400> SEQUENCE: 18

Lys Leu Lys Gln Lys Leu Ala Glu Leu Xaa Glu Asn Leu Leu Glu Arg
1               5                   10                  15

Phe Leu Asp Leu Val Xaa
            20

<210> SEQ ID NO 19
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 19

Lys Leu Lys Gln Lys Leu Ala Glu Leu Leu Glu Asn Leu Leu Glu Lys
1               5                   10                  15

Phe Leu Asp Leu Val Xaa
            20

<210> SEQ ID NO 20
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Inp

<400> SEQUENCE: 20

Lys Leu Lys Gln Lys Xaa Ala Glu Leu Leu Glu Asn Leu Leu Glu Arg
1               5                   10                  15

Phe Leu Asp Leu Val Xaa
            20

<210> SEQ ID NO 21
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 21

Lys Leu Lys Gln Lys Leu Ala Glu Leu Leu Glu Gln Leu Leu Glu Lys
1               5                   10                  15

Phe Leu Asp Leu Val Xaa
            20

<210> SEQ ID NO 22
<211> LENGTH: 22
<212> TYPE: PRT
<213> ORGANISM: Artificial Sequence
<220> FEATURE:
```

```
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Inp

<400> SEQUENCE: 22

Xaa Leu Xaa Gln Xaa Leu Ala Glu Leu Leu Glu Asn Leu Leu Glu Arg
1               5                   10                  15

Phe Leu Asp Leu Val Xaa
            20

<210> SEQ ID NO 23
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 23

Lys Leu Lys Gln Lys Leu Ala Glu Leu Leu Glu Asn Trp Leu Glu Arg
1               5                   10                  15

Phe Leu Asp Leu Val Xaa
            20

<210> SEQ ID NO 24
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 24

Lys Leu Lys Gln Lys Leu Ala Glu Leu Leu Glu Asn Leu Leu Glu Arg
1               5                   10                  15

Leu Leu Asp Leu Val Xaa
            20

<210> SEQ ID NO 25
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 25
```

Lys Leu Lys Gln Lys Leu Ala Glu Leu Leu Glu Gln Leu Leu Glu Lys
1               5                   10                  15

Phe Leu Glu Leu Val Xaa
            20

<210> SEQ ID NO 26
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 26

Lys Leu Lys Gln Lys Leu Ala Glu Leu Leu Glu Gln Leu Leu Glu Lys
1               5                   10                  15

Phe Leu Glu Leu Leu Xaa
            20

<210> SEQ ID NO 27
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 27

Lys Leu Lys Lys Gln Leu Ala Glu Leu Leu Glu Asn Leu Leu Glu Arg
1               5                   10                  15

Phe Leu Asp Leu Val Xaa
            20

<210> SEQ ID NO 28
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=Inp

<400> SEQUENCE: 28

Lys Leu Lys Gln Lys Leu Ala Glu Leu Xaa Glu Asn Leu Leu Glu Arg
1               5                   10                  15

Phe Phe Asp Leu Val Xaa
            20

<210> SEQ ID NO 29
<211> LENGTH: 22
<212> TYPE: PRT
<213> ORGANISM: Artificial Sequence
<220> FEATURE:
<223> OTHER INFORMATION: APO A-1 mimic
<220> FEATURE:

```
<221> NAME/KEY: MISC_FEATURE
<222> LOCATION: (22)..(22)
<223> OTHER INFORMATION: Xaa=Inp

<400> SEQUENCE: 29

Lys Leu Lys Gln Lys Leu Leu Glu Leu Leu Glu Asn Leu Leu Glu Arg
1               5                   10                  15

Phe Leu Asp Leu Val Xaa
            20

<210> SEQ ID NO 30
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (9)..(9)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Inp

<400> SEQUENCE: 30

Lys Leu Lys Gln Lys Leu Ala Glu Xaa Leu Glu Asn Leu Leu Glu Arg
1               5                   10                  15

Phe Leu Asp Leu Val Xaa
            20

<210> SEQ ID NO 31
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 31

Lys Leu Lys Gln Lys Leu Ala Glu Trp Leu Glu Asn Leu Leu Glu Arg
1               5                   10                  15

Phe Leu Asp Leu Val Xaa
            20

<210> SEQ ID NO 32
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (16)..(16)
<223> OTHER INFORMATION: Xaa=Orn
```

```
<220> FEATURE:
<221> NAME/KEY: MISC_FEATURE
<222> LOCATION: (22)..(22)
<223> OTHER INFORMATION: Xaa=Inp

<400> SEQUENCE: 32

Xaa Leu Xaa Gln Xaa Leu Ala Glu Leu Leu Glu Asn Leu Leu Glu Xaa
1               5                   10                  15

Phe Leu Asp Leu Val Xaa
            20

<210> SEQ ID NO 33
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa-Inp

<400> SEQUENCE: 33

Lys Leu Lys Gln Lys Leu Phe Glu Leu Leu Glu Asn Leu Leu Glu Arg
1               5                   10                  15

Phe Leu Asp Leu Val Xaa
            20

<210> SEQ ID NO 34
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 34

Lys Leu Lys Lys Gln Leu Ala Glu Leu Leu Glu Arg Leu Leu Asp Asn
1               5                   10                  15

Phe Leu Glu Leu Val Xaa
            20

<210> SEQ ID NO 35
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 35

Lys Leu Lys Gln Lys Leu Ala Glu Leu Leu Glu Arg Leu Leu Asp Asn
1               5                   10                  15

Phe Leu Glu Leu Val Xaa
            20

<210> SEQ ID NO 36
<211> LENGTH: 22
<212> TYPE: PRT
<213> ORGANISM: Artificial Sequence
<220> FEATURE:
```

```
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa-Inp

<400> SEQUENCE: 36

Lys Leu Lys Gln Arg Leu Ala Asp Leu Leu Glu Asn Leu Leu Glu Lys
1               5                   10                  15

Phe Leu Glu Leu Val Xaa
            20

<210> SEQ ID NO 37
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 37

Lys Leu Lys Lys Gln Leu Ala Glu Leu Leu Asn Glu Leu Leu Glu Arg
1               5                   10                  15

Phe Leu Asp Leu Val Xaa
            20

<210> SEQ ID NO 38
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 38

Lys Leu Lys Lys Asn Leu Ala Gln Leu Leu Asp Glu Leu Leu Arg Glu
1               5                   10                  15

Phe Leu Glu Leu Val Xaa
            20

<210> SEQ ID NO 39
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 39

Lys Leu Lys Gln Asn Leu Ala Lys Leu Leu Asp Glu Leu Leu Arg Glu
1               5                   10                  15

Phe Leu Glu Leu Val Xaa
            20

<210> SEQ ID NO 40
<211> LENGTH: 22
<212> TYPE: PRT
<213> ORGANISM: Artificial Sequence
```

```
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 40

Lys Leu Lys Gln Lys Leu Ala Glu Leu Leu Glu Gln Leu Leu Asp Lys
1               5                   10                  15

Phe Leu Glu Leu Ala Xaa
            20

<210> SEQ ID NO 41
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 41

Lys Leu Lys Gln Lys Leu Ala Glu Leu Leu Glu Gln Leu Leu Glu Lys
1               5                   10                  15

Leu Leu Glu Leu Leu Xaa
            20

<210> SEQ ID NO 42
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=Inp

<400> SEQUENCE: 42

Lys Leu Lys Gln Lys Trp Ala Glu Leu Xaa Glu Asn Leu Leu Glu Arg
1               5                   10                  15

Phe Leu Asp Leu Val Xaa
            20

<210> SEQ ID NO 43
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 43

Lys Leu Lys Lys Lys Leu Ala Lys Leu Leu Glu Glu Leu Leu Glu Arg
1               5                   10                  15

Phe Leu Asp Leu Val Xaa
            20
```

<210> SEQ ID NO 44
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 44

Lys Leu Lys Lys Gln Leu Ala Glu Leu Leu Glu Arg Leu Leu Glu Asn
1               5                   10                  15

Phe Leu Asp Leu Val Xaa
            20

<210> SEQ ID NO 45
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=D-Val
<220> FEATURE:
<221> NAME/KEY: MISC_FEATURE
<222> LOCATION: (22)..(22)
<223> OTHER INFORMATION: Xaa=Inp

<400> SEQUENCE: 45

Lys Leu Lys Gln Lys Leu Ala Glu Leu Leu Glu Asn Leu Leu Glu Arg
1               5                   10                  15

Phe Leu Asp Leu Xaa Xaa
            20

<210> SEQ ID NO 46
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=Inp

<400> SEQUENCE: 46

Lys Leu Lys Gln Lys Leu Ala Glu Leu Leu Glu Asn Leu Leu Glu Arg
1               5                   10                  15

Phe Leu Xaa

<210> SEQ ID NO 47
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 47

Lys Lys Lys Gln Lys Leu Ala Glu Leu Leu Glu Asn Leu Leu Glu Arg
1               5                   10                  15

```
Phe Leu Asp Leu Val Xaa
            20

<210> SEQ ID NO 48
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=Inp

<400> SEQUENCE: 48

Gln Lys Leu Ala Glu Leu Leu Glu Asn Leu Leu Glu Arg Phe Leu Asp
1               5                   10                  15

Leu Val Xaa

<210> SEQ ID NO 49
<211> LENGTH: 21
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=Inp

<400> SEQUENCE: 49

Lys Leu Lys Gln Lys Leu Ala Glu Leu Leu Glu Asn Leu Leu Glu Arg
1               5                   10                  15

Phe Leu Asp Leu Xaa
            20

<210> SEQ ID NO 50
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 50

Lys Leu Lys Lys Gln Leu Ala Asn Leu Leu Asp Leu Leu Arg Glu
1               5                   10                  15

Phe Leu Glu Leu Val Xaa
            20

<210> SEQ ID NO 51
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=Inp

<400> SEQUENCE: 51

Glu Leu Leu Glu Asn Leu Leu Glu Arg Phe Leu Asp Leu Val Xaa
1               5                   10                  15
```

```
<210> SEQ ID NO 52
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=Inp

<400> SEQUENCE: 52

Lys Leu Lys Gln Lys Leu Ala Glu Leu Leu Glu Asn Leu Leu Xaa
1               5                   10                  15

<210> SEQ ID NO 53
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Inp

<400> SEQUENCE: 53

Lys Leu Lys Gln Leu Leu Glu Asn Leu Leu Glu Arg Phe Leu Asp Leu
1               5                   10                  15

Val Xaa

<210> SEQ ID NO 54
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Inp

<400> SEQUENCE: 54

Lys Leu Lys Gln Lys Leu Glu Glu Leu Leu Glu Arg Phe Leu Asp Leu
1               5                   10                  15

Val Xaa

<210> SEQ ID NO 55
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Inp

<400> SEQUENCE: 55

Lys Leu Lys Gln Lys Leu Glu Glu Leu Leu Glu Lys Phe Leu Glu Leu
1               5                   10                  15

Val Xaa

<210> SEQ ID NO 56
<211> LENGTH: 18
<212> TYPE: PRT
```

<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Inp

<400> SEQUENCE: 56

Lys Leu Lys Gln Lys Leu Leu Glu Leu Leu Glu Arg Phe Leu Asp Leu
1               5                   10                  15

Val Xaa

<210> SEQ ID NO 57
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Inp

<400> SEQUENCE: 57

Lys Leu Lys Gln Trp Leu Glu Asn Leu Leu Glu Arg Phe Leu Asp Leu
1               5                   10                  15

Val Xaa

<210> SEQ ID NO 58
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Inp

<400> SEQUENCE: 58

Lys Leu Lys Lys Gln Leu Glu Glu Leu Leu Glu Arg Phe Leu Asp Leu
1               5                   10                  15

Val Xaa

<210> SEQ ID NO 59
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=Inp

<400> SEQUENCE: 59

Lys Lys Leu Gln Leu Leu Ala Glu Leu Leu Glu Arg Phe Ala Asp Leu
1               5                   10                  15

Val Xaa

<210> SEQ ID NO 60
<211> LENGTH: 18
<212> TYPE: PRT
<213> ORGANISM: Artificial Sequence
<220> FEATURE:
<223> OTHER INFORMATION: APO A-1 mimic

```
<220> FEATURE:
<221> NAME/KEY: MISC_FEATURE
<222> LOCATION: (18)..(18)
<223> OTHER INFORMATION: Xaa=Inp

<400> SEQUENCE: 60

Lys Lys Leu Gln Ala Leu Ala Glu Leu Leu Glu Arg Phe Ala Asp Leu
1               5                   10                  15

Val Xaa

<210> SEQ ID NO 61
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=Inp

<400> SEQUENCE: 61

Lys Leu Lys Gln Lys Leu Glu Glu Trp Gly Glu Arg Phe Leu Asp Leu
1               5                   10                  15

Val Xaa

<210> SEQ ID NO 62
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=Inp

<400> SEQUENCE: 62

Lys Leu Lys Lys Gln Leu Asp Glu Leu Leu Arg Glu Phe Leu Glu Leu
1               5                   10                  15

Val Xaa

<210> SEQ ID NO 63
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=Inp

<400> SEQUENCE: 63

Lys Leu Lys Gln Glu Leu Lys Glu Leu Leu Glu Arg Phe Leu Asp Leu
1               5                   10                  15

Val Xaa

<210> SEQ ID NO 64
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(22)
```

<223> OTHER INFORMATION: N-terminal acetylated and C-terminal amidated
<220> FEATURE:
<221> NAME/KEY: MISC_FEATURE
<222> LOCATION: (22)..(22)
<223> OTHER INFORMATION: Xaa=Inp

<400> SEQUENCE: 64

Lys Leu Lys Gln Lys Leu Ala Glu Leu Gly Glu Asn Leu Leu Glu Arg
1               5                   10                  15
Phe Leu Asp Leu Val Xaa
                20

<210> SEQ ID NO 65
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 65

Lys Leu Lys Gln Lys Leu Glu Glu Leu Leu Glu Arg Leu Leu Asp Leu
1               5                   10                  15
Val Xaa

<210> SEQ ID NO 66
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 66

Lys Leu Lys Gln Lys Leu Glu Glu Leu Leu Glu Lys Phe Leu Asp Leu
1               5                   10                  15
Val Xaa

<210> SEQ ID NO 67
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 67

Lys Leu Lys Gln Lys Leu Glu Glu Leu Leu Glu Arg Phe Leu Asp Leu

-continued

```
1               5                   10                  15

Val Xaa

<210> SEQ ID NO 68
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 68

Lys Leu Lys Gln Lys Leu Glu Glu Leu Leu Glu Arg Phe Leu Glu Leu
1               5                   10                  15

Val Xaa

<210> SEQ ID NO 69
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 69

Lys Leu Lys Gln Lys Leu Glu Glu Leu Leu Glu Lys Phe Leu Glu Leu
1               5                   10                  15

Val Xaa

<210> SEQ ID NO 70
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 70

Lys Leu Lys Asn Lys Leu Glu Glu Leu Leu Glu Arg Phe Leu Asp Leu
1               5                   10                  15

Val Xaa

<210> SEQ ID NO 71
<211> LENGTH: 18
<212> TYPE: PRT
<213> ORGANISM: Artificial Sequence
<220> FEATURE:
```

```
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 71

Lys Leu Lys Gln Lys Leu Glu Glu Leu Leu Glu Arg Phe Leu Asp Leu
1               5                   10                  15

Leu Xaa

<210> SEQ ID NO 72
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 72

Lys Leu Lys Gln Lys Leu Glu Glu Trp Leu Glu Arg Phe Leu Asp Leu
1               5                   10                  15

Val Xaa

<210> SEQ ID NO 73
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 73

Lys Leu Lys Gln Lys Leu Glu Glu Leu Leu Glu Lys Phe Leu Asp Leu
1               5                   10                  15

Leu Xaa

<210> SEQ ID NO 74
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp
```

```
<400> SEQUENCE: 74

Arg Leu Lys Gln Arg Leu Glu Glu Leu Leu Asp Lys Phe Leu Glu Leu
1               5                   10                  15

Ala Xaa

<210> SEQ ID NO 75
<211> LENGTH: 18
<212> TYPE: PRT
<213> ORGANISM: Artificial Sequence
<220> FEATURE:
<223> OTHER INFORMATION: ApoA-1 mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 75

Lys Leu Lys Gln Lys Leu Glu Glu Leu Leu Glu Arg Phe Phe Asp Leu
1               5                   10                  15

Val Xaa

<210> SEQ ID NO 76
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 76

Lys Leu Lys Gln Lys Leu Glu Glu Leu Trp Glu Arg Phe Leu Asp Leu
1               5                   10                  15

Val Xaa

<210> SEQ ID NO 77
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 77

Lys Leu Lys Gln Lys Leu Glu Glu Leu Leu Glu Lys Leu Leu Glu Leu
1               5                   10                  15

Leu Xaa

<210> SEQ ID NO 78
<211> LENGTH: 18
```

```
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 78

Lys Leu Lys Gln Lys Leu Glu Glu Leu Leu Glu Lys Leu Leu Glu Leu
1               5                   10                  15

Val Xaa

<210> SEQ ID NO 79
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 79

Lys Leu Arg Gln Arg Leu Glu Glu Leu Leu Asp Lys Phe Leu Glu Leu
1               5                   10                  15

Ala Xaa

<210> SEQ ID NO 80
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=Inp

<400> SEQUENCE: 80

Xaa Leu Xaa Gln Xaa Leu Glu Glu Leu Leu Glu Arg Phe Leu Asp Leu
1               5                   10                  15

Val Xaa
```

```
<210> SEQ ID NO 81
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (12)..(12)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=Inp

<400> SEQUENCE: 81

Lys Leu Xaa Gln Xaa Leu Glu Glu Leu Leu Glu Xaa Phe Leu Asp Leu
1               5                   10                  15

Val Xaa

<210> SEQ ID NO 82
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 82

Lys Leu Arg Gln Arg Phe Glu Glu Leu Leu Asp Lys Phe Leu Glu Leu
1               5                   10                  15

Ala Xaa

<210> SEQ ID NO 83
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 83

Lys Leu Lys Gln Lys Trp Glu Glu Leu Leu Glu Arg Phe Leu Asp Leu
1               5                   10                  15

Val Xaa
```

```
<210> SEQ ID NO 84
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 84

Lys Leu Lys Gln Leu Leu Glu Asn Leu Leu Glu Arg Phe Leu Asp Leu
1               5                   10                  15

Val Xaa

<210> SEQ ID NO 85
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 85

Lys Leu Lys Gln Lys Leu Glu Glu Leu Gly Glu Arg Phe Leu Asp Leu
1               5                   10                  15

Val Xaa

<210> SEQ ID NO 86
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 86

Lys Leu Lys Gln Lys Gly Glu Glu Leu Leu Glu Arg Phe Leu Asp Leu
1               5                   10                  15

Val Xaa

<210> SEQ ID NO 87
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
```

```
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Inp

<400> SEQUENCE: 87

Lys Leu Lys Gln Lys Leu Glu Glu Leu Leu Glu Lys Phe Leu Glu Leu
1               5                   10                  15

Leu Xaa

<210> SEQ ID NO 88
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=Inp

<400> SEQUENCE: 88

Lys Leu Lys Gln Glu Leu Leu Glu Arg Phe Leu Asp Leu Val Xaa
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Inp

<400> SEQUENCE: 89

Lys Gln Lys Leu Glu Glu Leu Leu Glu Arg Phe Leu Asp Leu Val Xaa
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Inp

<400> SEQUENCE: 90

Lys Gln Lys Leu Lys Glu Leu Leu Glu Arg Phe Leu Asp Leu Val Xaa
1               5                   10                  15

<210> SEQ ID NO 91
```

```
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=Inp

<400> SEQUENCE: 91

Lys Gln Leu Lys Glu Leu Leu Glu Arg Phe Leu Asp Leu Val Xaa
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Inp

<400> SEQUENCE: 92

Lys Gln Lys Leu Ala Glu Leu Leu Glu Arg Phe Leu Asp Leu Val Xaa
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Inp

<400> SEQUENCE: 93

Lys Gln Lys Leu Glu Asn Leu Leu Glu Arg Phe Leu Asp Leu Val Xaa
1               5                   10                  15

<210> SEQ ID NO 94
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 94

Lys Leu Lys Gln Lys Leu Trp Glu Leu Leu Glu Asn Leu Leu Glu Arg
1               5                   10                  15

Phe Leu Asp Leu Val Xaa
```

```
                          20

<210> SEQ ID NO 95
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 95

Lys Leu Lys Gln Lys Leu Ala Glu Leu Gly Glu Asn Leu Leu Glu Arg
1               5                   10                  15

Phe Leu Asp Leu Val Xaa
            20

<210> SEQ ID NO 96
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Nip

<400> SEQUENCE: 96

Lys Leu Lys Gln Lys Xaa Ala Glu Leu Gly Glu Asn Leu Leu Glu Arg
1               5                   10                  15

Phe Leu Asp Leu Val Xaa
            20

<210> SEQ ID NO 97
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 97

Lys Leu Lys Gln Lys Leu Trp Glu Leu Gly Glu Asn Leu Leu Glu Arg
1               5                   10                  15

Phe Leu Asp Leu Val Xaa
            20

<210> SEQ ID NO 98
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 98
```

```
Lys Leu Lys Gln Lys Leu Ala Glu Leu Gly Glu Asn Trp Leu Glu Arg
1               5                   10                  15

Phe Leu Asp Leu Val Xaa
            20
```

<210> SEQ ID NO 99
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Nip

<400> SEQUENCE: 99

```
Xaa Leu Xaa Gln Xaa Leu Ala Glu Leu Gly Glu Asn Leu Leu Glu Arg
1               5                   10                  15

Phe Leu Asp Leu Val Xaa
            20
```

<210> SEQ ID NO 100
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 100

```
Lys Leu Lys Gln Lys Leu Ala Glu Leu Gly Glu Asn Leu Leu Glu Arg
1               5                   10                  15

Phe Phe Asp Leu Val Xaa
            20
```

<210> SEQ ID NO 101
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 101

```
Lys Leu Lys Gln Lys Leu Ala Glu Leu Gly Glu Asn Leu Leu Glu Arg
1               5                   10                  15

Phe Leu Glu Leu Val Xaa
            20
```

```
<210> SEQ ID NO 102
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 102

Lys Leu Lys Gln Lys Leu Ala Glu Leu Leu Glu Asn Leu Gly Glu Arg
1               5                   10                  15

Phe Leu Asp Leu Val Xaa
            20

<210> SEQ ID NO 103
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 103

Lys Leu Lys Gln Lys Leu Ala Glu Leu Leu Glu Asn Gly Leu Glu Arg
1               5                   10                  15

Phe Leu Asp Leu Val Xaa
            20

<210> SEQ ID NO 104
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 104

Lys Leu Lys Gln Lys Leu Ala Glu Gly Leu Glu Asn Leu Leu Glu Arg
1               5                   10                  15

Phe Leu Asp Leu Val Xaa
            20

<210> SEQ ID NO 105
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 105

Lys Leu Lys Gln Lys Leu Gly Glu Leu Leu Glu Asn Leu Leu Glu Arg
1               5                   10                  15

Phe Leu Asp Leu Val Xaa
            20
```

<210> SEQ ID NO 106
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 106

Lys Leu Lys Gln Lys Gly Ala Glu Leu Leu Glu Asn Leu Leu Glu Arg
1               5                   10                  15

Phe Leu Asp Leu Val Xaa
            20

<210> SEQ ID NO 107
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (7)..(7)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Nip

<400> SEQUENCE: 107

Lys Leu Lys Gln Lys Leu Xaa Glu Leu Leu Glu Asn Leu Leu Glu Arg
1               5                   10                  15

Phe Leu Asp Leu Val Xaa
            20

<210> SEQ ID NO 108
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 108

Lys Leu Lys Gln Lys Leu Ala Glu Leu Leu Glu Asn Leu Leu Glu Arg
1               5                   10                  15

Phe Leu Asp Leu Val Xaa
            20

<210> SEQ ID NO 109
<211> LENGTH: 23
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (23)..(23)
<223> OTHER INFORMATION: Xaa=Nip

<400> SEQUENCE: 109

Lys Lys Leu Lys Gln Lys Leu Ala Glu Leu Leu Glu Asn Leu Leu Glu
1               5                   10                  15

Arg Phe Leu Asp Leu Val Xaa
            20

<210> SEQ ID NO 110
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=Nip

<400> SEQUENCE: 110

Lys Leu Lys Gln Lys Leu Ala Glu Leu Xaa Glu Asn Leu Leu Glu Arg
1               5                   10                  15

Phe Leu Asp Leu Val Xaa
            20

<210> SEQ ID NO 111
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 111

Lys Leu Lys Gln Lys Leu Ala Glu Leu Leu Glu Asn Leu Leu Glu Lys
1               5                   10                  15

Phe Leu Asp Leu Val Xaa
            20

<210> SEQ ID NO 112
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Nip

<400> SEQUENCE: 112

Lys Leu Lys Gln Lys Xaa Ala Glu Leu Leu Glu Asn Leu Leu Glu Arg
1               5                   10                  15

Phe Leu Asp Leu Val Xaa
            20

<210> SEQ ID NO 113
<211> LENGTH: 22
<212> TYPE: PRT
<213> ORGANISM: Artificial Sequence

```
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 113

Lys Leu Lys Gln Lys Leu Ala Glu Leu Leu Glu Gln Leu Leu Glu Lys
1               5                   10                  15

Phe Leu Asp Leu Val Xaa
            20

<210> SEQ ID NO 114
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Nip

<400> SEQUENCE: 114

Xaa Leu Xaa Gln Xaa Leu Ala Glu Leu Leu Glu Asn Leu Leu Glu Arg
1               5                   10                  15

Phe Leu Asp Leu Val Xaa
            20

<210> SEQ ID NO 115
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 115

Lys Leu Lys Gln Lys Leu Ala Glu Leu Leu Glu Asn Trp Leu Glu Arg
1               5                   10                  15

Phe Leu Asp Leu Val Xaa
            20

<210> SEQ ID NO 116
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip
```

```
<400> SEQUENCE: 116

Lys Leu Lys Gln Lys Leu Ala Glu Leu Leu Glu Asn Leu Leu Glu Arg
1               5                   10                  15

Phe Leu Asp Leu Val Xaa
            20

<210> SEQ ID NO 117
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 117

Lys Leu Lys Gln Lys Leu Ala Glu Leu Leu Glu Gln Leu Leu Glu Lys
1               5                   10                  15

Phe Leu Glu Leu Val Xaa
            20

<210> SEQ ID NO 118
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 118

Lys Leu Lys Gln Lys Leu Ala Glu Leu Leu Glu Gln Leu Leu Glu Lys
1               5                   10                  15

Phe Leu Glu Leu Leu Xaa
            20

<210> SEQ ID NO 119
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 119

Lys Leu Lys Lys Gln Leu Ala Glu Leu Leu Glu Asn Leu Leu Glu Arg
1               5                   10                  15

Phe Leu Asp Leu Val Xaa
            20

<210> SEQ ID NO 120
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
```

```
<220> FEATURE:
<221> NAME/KEY: MISC_FEATURE
<222> LOCATION: (22)..(22)
<223> OTHER INFORMATION: Xaa=Nip

<400> SEQUENCE: 120

Lys Leu Lys Gln Lys Leu Ala Glu Leu Xaa Glu Asn Leu Leu Glu Arg
1               5                   10                  15

Phe Phe Asp Leu Val Xaa
                20

<210> SEQ ID NO 121
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 121

Lys Leu Lys Gln Lys Leu Leu Glu Leu Leu Glu Asn Leu Leu Glu Arg
1               5                   10                  15

Phe Leu Asp Leu Val Xaa
                20

<210> SEQ ID NO 122
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (9)..(9)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Nip

<400> SEQUENCE: 122

Lys Leu Lys Gln Lys Leu Ala Glu Xaa Leu Glu Asn Leu Leu Glu Arg
1               5                   10                  15

Phe Leu Asp Leu Val Xaa
                20

<210> SEQ ID NO 123
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 123

Lys Leu Lys Gln Lys Leu Ala Glu Trp Leu Glu Asn Leu Leu Glu Arg
1               5                   10                  15

Phe Leu Asp Leu Val Xaa
                20

<210> SEQ ID NO 124
```

```
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (16)..(16)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Nip

<400> SEQUENCE: 124

Xaa Leu Xaa Gln Xaa Leu Ala Glu Leu Leu Glu Asn Leu Leu Glu Xaa
1               5                   10                  15

Phe Leu Asp Leu Val Xaa
            20

<210> SEQ ID NO 125
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 125

Lys Leu Lys Gln Lys Leu Phe Glu Leu Leu Glu Asn Leu Leu Glu Arg
1               5                   10                  15

Phe Leu Asp Leu Val Xaa
            20

<210> SEQ ID NO 126
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 126

Lys Leu Lys Lys Gln Leu Ala Glu Leu Leu Glu Arg Leu Leu Asp Asn
1               5                   10                  15

Phe Leu Glu Leu Val Xaa
            20

<210> SEQ ID NO 127
<211> LENGTH: 22
<212> TYPE: PRT
<213> ORGANISM: Artificial Sequence
```

<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 127

Lys Leu Lys Gln Lys Leu Ala Glu Leu Leu Glu Arg Leu Leu Asp Asn
1               5                   10                  15

Phe Leu Glu Leu Val Xaa
            20

<210> SEQ ID NO 128
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 128

Lys Leu Lys Gln Arg Leu Ala Asp Leu Leu Glu Asn Leu Leu Glu Lys
1               5                   10                  15

Phe Leu Glu Leu Val Xaa
            20

<210> SEQ ID NO 129
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 129

Lys Leu Lys Lys Gln Leu Ala Glu Leu Leu Asn Glu Leu Leu Glu Arg
1               5                   10                  15

Phe Leu Asp Leu Val Xaa
            20

<210> SEQ ID NO 130
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 130

Lys Leu Lys Lys Asn Leu Ala Gln Leu Leu Asp Glu Leu Leu Glu Arg
1               5                   10                  15

Phe Leu Glu Leu Val Xaa
            20

<210> SEQ ID NO 131
<211> LENGTH: 22
<212> TYPE: PRT

<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 131

Lys Leu Lys Gln Asn Leu Ala Lys Leu Leu Asp Glu Leu Leu Arg Glu
1               5                   10                  15

Phe Leu Glu Leu Val Xaa
            20

<210> SEQ ID NO 132
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 132

Lys Leu Lys Gln Lys Leu Ala Glu Leu Leu Glu Gln Leu Leu Asp Lys
1               5                   10                  15

Phe Leu Glu Leu Ala Xaa
            20

<210> SEQ ID NO 133
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 133

Lys Leu Lys Gln Lys Leu Ala Glu Leu Leu Glu Gln Leu Leu Glu Lys
1               5                   10                  15

Leu Leu Glu Leu Leu Xaa
            20

<210> SEQ ID NO 134
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=Nip

<400> SEQUENCE: 134

Lys Leu Lys Gln Lys Leu Ala Glu Leu Xaa Glu Asn Leu Leu Glu Arg
1               5                   10                  15

Phe Leu Asp Leu Val Xaa
            20

```
<210> SEQ ID NO 135
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 135

Lys Leu Lys Lys Lys Leu Ala Lys Leu Leu Glu Glu Leu Leu Glu Arg
1               5                   10                  15

Phe Leu Asp Leu Val Xaa
            20

<210> SEQ ID NO 136
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 136

Lys Leu Lys Lys Gln Leu Ala Glu Leu Leu Glu Arg Leu Leu Glu Asn
1               5                   10                  15

Phe Leu Asp Leu Val Xaa
            20

<210> SEQ ID NO 137
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=D-Val
<220> FEATURE:
<221> NAME/KEY: MISC_FEATURE
<222> LOCATION: (22)..(22)
<223> OTHER INFORMATION: Xaa=Nip

<400> SEQUENCE: 137

Lys Leu Lys Gln Lys Leu Ala Glu Leu Leu Glu Asn Leu Leu Glu Arg
1               5                   10                  15

Phe Leu Asp Leu Xaa Xaa
            20

<210> SEQ ID NO 138
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=Nip

<400> SEQUENCE: 138
```

```
Lys Leu Lys Gln Lys Leu Ala Glu Leu Leu Glu Asn Leu Leu Glu Arg
1               5                   10                  15

Phe Leu Xaa
```

<210> SEQ ID NO 139
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 139

```
Lys Lys Lys Gln Lys Leu Ala Glu Leu Leu Glu Asn Leu Leu Glu Arg
1               5                   10                  15

Phe Leu Asp Leu Val Xaa
            20
```

<210> SEQ ID NO 140
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=Nip

<400> SEQUENCE: 140

```
Gln Lys Leu Ala Glu Leu Leu Glu Asn Leu Leu Glu Arg Phe Leu Asp
1               5                   10                  15

Leu Val Xaa
```

<210> SEQ ID NO 141
<211> LENGTH: 21
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=Nip

<400> SEQUENCE: 141

```
Lys Leu Lys Gln Lys Leu Ala Glu Leu Leu Glu Asn Leu Leu Glu Arg
1               5                   10                  15

Phe Leu Asp Leu Xaa
            20
```

<210> SEQ ID NO 142
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 142

```
Lys Leu Lys Lys Gln Leu Ala Asn Leu Leu Glu Asp Leu Leu Arg Glu
```

```
                1               5                   10                  15
Phe Leu Glu Leu Val Xaa
                20
```

<210> SEQ ID NO 143
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=Nip

<400> SEQUENCE: 143

```
Glu Leu Leu Glu Asn Leu Leu Glu Arg Phe Leu Asp Leu Val Xaa
1               5                   10                  15
```

<210> SEQ ID NO 144
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=Nip

<400> SEQUENCE: 144

```
Lys Leu Lys Gln Lys Leu Ala Glu Leu Leu Glu Asn Leu Leu Xaa
1               5                   10                  15
```

<210> SEQ ID NO 145
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 145

```
Lys Leu Lys Gln Leu Leu Glu Asn Leu Leu Glu Arg Phe Leu Asp Leu
1               5                   10                  15

Val Xaa
```

<210> SEQ ID NO 146
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 146

```
Lys Leu Lys Gln Lys Leu Glu Glu Leu Leu Glu Arg Phe Leu Asp Leu
1               5                   10                  15

Val Xaa
```

<210> SEQ ID NO 147

<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 147

Lys Leu Lys Gln Lys Leu Glu Glu Leu Leu Glu Lys Phe Leu Glu Leu
1               5                   10                  15

Val Xaa

<210> SEQ ID NO 148
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 148

Lys Leu Lys Gln Lys Leu Leu Glu Leu Leu Glu Arg Phe Leu Asp Leu
1               5                   10                  15

Val Xaa

<210> SEQ ID NO 149
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 149

Lys Leu Lys Gln Trp Leu Glu Asn Leu Leu Glu Arg Phe Leu Asp Leu
1               5                   10                  15

Val Xaa

<210> SEQ ID NO 150
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 150

Lys Leu Lys Lys Gln Leu Glu Glu Leu Leu Glu Arg Phe Leu Asp Leu
1               5                   10                  15

Val Xaa

<210> SEQ ID NO 151
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 151

Lys Lys Leu Gln Leu Leu Ala Glu Leu Leu Glu Arg Phe Ala Asp Leu
1               5                   10                  15

Val Xaa

<210> SEQ ID NO 152
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 152

Lys Lys Leu Gln Ala Leu Ala Glu Leu Leu Glu Arg Phe Ala Asp Leu
1               5                   10                  15

Val Xaa

<210> SEQ ID NO 153
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 153

Lys Leu Lys Gln Lys Leu Glu Glu Trp Gly Glu Arg Phe Leu Asp Leu
1               5                   10                  15

Val Xaa

<210> SEQ ID NO 154
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Nip

<400> SEQUENCE: 154

Lys Leu Lys Lys Gln Leu Asp Glu Leu Leu Arg Glu Phe Leu Glu Leu
1               5                   10                  15

Val Xaa

<210> SEQ ID NO 155
<211> LENGTH: 18
<212> TYPE: PRT
<213> ORGANISM: Artificial Sequence
<220> FEATURE:
<223> OTHER INFORMATION: ApoA-I mimic
<220> FEATURE:

```
<221> NAME/KEY: MISC_FEATURE
<222> LOCATION: (18)..(18)
<223> OTHER INFORMATION: Xaa=Nip

<400> SEQUENCE: 155

Lys Leu Lys Gln Glu Leu Lys Glu Leu Leu Glu Arg Phe Leu Asp Leu
1               5                   10                  15

Val Xaa

<210> SEQ ID NO 156
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(22)
<223> OTHER INFORMATION: N-terminal acetylated and C-terminal amidated
<220> FEATURE:
<221> NAME/KEY: MISC_FEATURE
<222> LOCATION: (22)..(22)
<223> OTHER INFORMATION: Xaa=Nip

<400> SEQUENCE: 156

Lys Leu Lys Gln Lys Leu Ala Glu Leu Gly Glu Asn Leu Leu Glu Arg
1               5                   10                  15

Phe Leu Asp Leu Val Xaa
            20

<210> SEQ ID NO 157
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 157

Lys Leu Lys Gln Lys Leu Glu Glu Leu Leu Glu Arg Leu Leu Asp Leu
1               5                   10                  15

Val Xaa

<210> SEQ ID NO 158
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 158

Lys Leu Lys Gln Lys Leu Glu Glu Leu Leu Glu Lys Phe Leu Asp Leu
1               5                   10                  15
```

Val Xaa

<210> SEQ ID NO 159
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 159

Lys Leu Lys Gln Lys Leu Glu Glu Leu Leu Glu Arg Phe Leu Asp Leu
1               5                   10                  15

Val Xaa

<210> SEQ ID NO 160
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 160

Lys Leu Lys Gln Lys Leu Glu Glu Leu Leu Glu Arg Phe Leu Glu Leu
1               5                   10                  15

Val Xaa

<210> SEQ ID NO 161
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 161

Lys Leu Lys Gln Lys Leu Glu Glu Leu Leu Glu Lys Phe Leu Glu Leu
1               5                   10                  15

Val Xaa

<210> SEQ ID NO 162
<211> LENGTH: 18
<212> TYPE: PRT
<213> ORGANISM: Artificial Sequence
<220> FEATURE:
<223> OTHER INFORMATION: ApoA-I mimic
<220> FEATURE:

```
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 162

Lys Leu Lys Asn Lys Leu Glu Glu Leu Leu Glu Arg Phe Leu Asp Leu
1               5                   10                  15

Val Xaa

<210> SEQ ID NO 163
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 163

Lys Leu Lys Gln Lys Leu Glu Glu Leu Leu Glu Arg Phe Leu Asp Leu
1               5                   10                  15

Leu Xaa

<210> SEQ ID NO 164
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 164

Lys Leu Lys Gln Lys Leu Glu Glu Trp Leu Glu Arg Phe Leu Asp Leu
1               5                   10                  15

Val Xaa

<210> SEQ ID NO 165
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 165
```

Lys Leu Lys Gln Lys Leu Glu Glu Leu Leu Glu Lys Phe Leu Asp Leu
1               5                   10                  15

Leu Xaa

<210> SEQ ID NO 166
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 166

Arg Leu Lys Gln Arg Leu Glu Glu Leu Leu Asp Lys Phe Leu Glu Leu
1               5                   10                  15

Ala Xaa

<210> SEQ ID NO 167
<211> LENGTH: 18
<212> TYPE: PRT
<213> ORGANISM: Artificial Sequence
<220> FEATURE:
<223> OTHER INFORMATION: ApoA-1 mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 167

Lys Leu Lys Gln Lys Leu Glu Glu Leu Leu Glu Arg Phe Phe Asp Leu
1               5                   10                  15

Val Xaa

<210> SEQ ID NO 168
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 168

Lys Leu Lys Gln Lys Leu Glu Glu Leu Trp Glu Arg Phe Leu Asp Leu
1               5                   10                  15

Val Xaa

<210> SEQ ID NO 169
<211> LENGTH: 18
<212> TYPE: PRT
<213> ORGANISM: Artificial Sequence

```
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 169

Lys Leu Lys Gln Lys Leu Glu Glu Leu Leu Glu Lys Leu Leu Glu Leu
1               5                   10                  15

Leu Xaa

<210> SEQ ID NO 170
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 170

Lys Leu Lys Gln Lys Leu Glu Glu Leu Leu Glu Lys Leu Leu Glu Leu
1               5                   10                  15

Val Xaa

<210> SEQ ID NO 171
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 171

Lys Leu Arg Gln Arg Leu Glu Glu Leu Leu Asp Lys Phe Leu Glu Leu
1               5                   10                  15

Ala Xaa

<210> SEQ ID NO 172
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (1)..(1)
<223> OTHER INFORMATION: Xaa=Orn
```

```
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=Nip

<400> SEQUENCE: 172

Xaa Leu Xaa Gln Xaa Leu Glu Glu Leu Leu Glu Arg Phe Leu Asp Leu
1               5                   10                  15

Val Xaa

<210> SEQ ID NO 173
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (12)..(12)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=Nip

<400> SEQUENCE: 173

Lys Leu Xaa Gln Xaa Leu Glu Glu Leu Leu Glu Xaa Phe Leu Asp Leu
1               5                   10                  15

Val Xaa

<210> SEQ ID NO 174
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 174

Lys Leu Arg Gln Arg Phe Glu Glu Leu Leu Asp Lys Phe Leu Glu Leu
1               5                   10                  15

Ala Xaa
```

```
<210> SEQ ID NO 175
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 175

Lys Leu Lys Gln Lys Trp Glu Glu Leu Leu Glu Arg Phe Leu Asp Leu
1               5                   10                  15

Val Xaa

<210> SEQ ID NO 176
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 176

Lys Leu Lys Gln Leu Leu Glu Asn Leu Leu Glu Arg Phe Leu Asp Leu
1               5                   10                  15

Val Xaa

<210> SEQ ID NO 177
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 177

Lys Leu Lys Gln Lys Leu Glu Glu Leu Gly Glu Arg Phe Leu Asp Leu
1               5                   10                  15

Val Xaa

<210> SEQ ID NO 178
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
```

```
<220> FEATURE:
<221> NAME/KEY: MISC_FEATURE
<222> LOCATION: (18)..(18)
<223> OTHER INFORMATION: Xaa=Nip

<400> SEQUENCE: 178

Lys Leu Lys Gln Lys Gly Glu Glu Leu Leu Glu Arg Phe Leu Asp Leu
1               5                   10                  15

Val Xaa

<210> SEQ ID NO 179
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Nip

<400> SEQUENCE: 179

Lys Leu Lys Gln Lys Leu Glu Glu Leu Leu Glu Lys Phe Leu Glu Leu
1               5                   10                  15

Leu Xaa

<210> SEQ ID NO 180
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=Nip

<400> SEQUENCE: 180

Lys Leu Lys Gln Glu Leu Leu Glu Arg Phe Leu Asp Leu Val Xaa
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Nip

<400> SEQUENCE: 181

Lys Gln Lys Leu Glu Glu Leu Leu Glu Arg Phe Leu Asp Leu Val Xaa
1               5                   10                  15

<210> SEQ ID NO 182
```

```
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Nip

<400> SEQUENCE: 182

Lys Gln Lys Leu Lys Glu Leu Leu Glu Arg Phe Leu Asp Leu Val Xaa
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=Nip

<400> SEQUENCE: 183

Lys Gln Leu Lys Glu Leu Leu Glu Arg Phe Leu Asp Leu Val Xaa
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Nip

<400> SEQUENCE: 184

Lys Gln Lys Leu Ala Glu Leu Leu Glu Arg Phe Leu Asp Leu Val Xaa
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Nip

<400> SEQUENCE: 185
```

-continued

Lys Gln Lys Leu Glu Asn Leu Leu Glu Arg Phe Leu Asp Leu Val Xaa
1               5                   10                  15

<210> SEQ ID NO 186
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 186

Lys Leu Lys Lys Gln Leu Ala Asp Leu Leu Arg Glu Leu Leu Asn Glu
1               5                   10                  15

Phe Leu Glu Phe Val Xaa
            20

<210> SEQ ID NO 187
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 187

Lys Leu Lys Lys Gln Leu Ala Asp Leu Gly Arg Glu Leu Leu Asn Glu
1               5                   10                  15

Phe Leu Glu Leu Val Xaa
            20

<210> SEQ ID NO 188
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 188

Lys Leu Lys Lys Gln Leu Ala Asp Leu Leu Arg Glu Trp Leu Asn Leu
1               5                   10                  15

Phe Leu Glu Leu Val Xaa
            20

<210> SEQ ID NO 189
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 189

Lys Leu Lys Lys Gln Leu Ala Asp Leu Leu Arg Glu Leu Leu Asn Leu
1               5                   10                  15

```
Phe Leu Glu Leu Val Xaa
            20

<210> SEQ ID NO 190
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 190

Lys Leu Lys Lys Gln Leu Trp Asp Leu Leu Arg Glu Leu Leu Asn Leu
1               5                  10                  15

Phe Leu Glu Leu Val Xaa
            20

<210> SEQ ID NO 191
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 191

Lys Leu Lys Lys Gln Leu Trp Asp Leu Leu Arg Glu Leu Leu Asn Glu
1               5                  10                  15

Phe Leu Glu Leu Val Xaa
            20

<210> SEQ ID NO 192
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 192

Lys Leu Lys Lys Gln Trp Ala Asp Leu Leu Arg Glu Leu Leu Asn Glu
1               5                  10                  15

Phe Leu Glu Leu Val Xaa
            20

<210> SEQ ID NO 193
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 193

Lys Leu Lys Lys Gln Leu Leu Asp Leu Leu Arg Glu Leu Leu Asn Glu
```

```
                1               5                  10                 15
Phe Leu Glu Leu Val Xaa
                20

<210> SEQ ID NO 194
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 194

Lys Leu Lys Lys Gln Leu Ala Asp Gly Leu Arg Glu Leu Leu Asn Leu
1               5                   10                  15

Phe Leu Glu Leu Val Xaa
                20

<210> SEQ ID NO 195
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 195

Lys Leu Lys Lys Gln Trp Ala Asp Leu Leu Arg Glu Leu Leu Asn Leu
1               5                   10                  15

Phe Leu Glu Leu Val Xaa
                20

<210> SEQ ID NO 196
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (4)..(4)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Inp

<400> SEQUENCE: 196

Xaa Leu Xaa Xaa Gln Leu Ala Asp Leu Leu Arg Glu Leu Leu Asn Glu
1               5                   10                  15

Phe Leu Glu Leu Val Xaa
                20

<210> SEQ ID NO 197
```

```
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 197

Lys Leu Lys Lys Gln Leu Ala Asp Leu Leu Arg Glu Leu Leu Gln Glu
1               5                   10                  15

Phe Leu Glu Leu Val Xaa
            20

<210> SEQ ID NO 198
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 198

Lys Leu Lys Lys Asn Leu Ala Asp Leu Leu Arg Glu Leu Leu Asn Glu
1               5                   10                  15

Phe Leu Glu Leu Val Xaa
            20

<210> SEQ ID NO 199
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Inp

<400> SEQUENCE: 199

Lys Leu Lys Lys Gln Leu Ala Asp Leu Leu Arg Asp Leu Leu Asn Glu
1               5                   10                  15

Phe Leu Glu Leu Val Xaa
            20

<210> SEQ ID NO 200
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 200

Lys Leu Lys Lys Gln Leu Ala Asp Leu Leu Arg Glu Leu Leu Asn Glu
1               5                   10                  15

Phe Leu Glu Leu Val Xaa
            20
```

```
<210> SEQ ID NO 201
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 201

Lys Leu Lys Lys Gln Leu Ala Asp Leu Gly Arg Glu Leu Leu Asn Glu
1               5                   10                  15

Phe Leu Glu Leu Val Xaa
            20

<210> SEQ ID NO 202
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 202

Lys Leu Lys Lys Gln Leu Ala Asp Leu Leu Arg Glu Trp Leu Asn Leu
1               5                   10                  15

Phe Leu Glu Leu Val Xaa
            20

<210> SEQ ID NO 203
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 203

Lys Leu Lys Lys Gln Leu Ala Asp Leu Leu Arg Glu Leu Leu Asn Leu
1               5                   10                  15

Phe Leu Glu Leu Val Xaa
            20

<210> SEQ ID NO 204
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 204

Lys Leu Lys Lys Gln Leu Trp Asp Leu Leu Arg Glu Leu Leu Asn Leu
1               5                   10                  15

Phe Leu Glu Leu Val Xaa
            20
```

<210> SEQ ID NO 205
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 205

Lys Leu Lys Lys Gln Leu Trp Asp Leu Leu Arg Glu Leu Leu Asn Glu
1               5                   10                  15

Phe Leu Glu Leu Val Xaa
            20

<210> SEQ ID NO 206
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 206

Lys Leu Lys Lys Gln Trp Ala Asp Leu Leu Arg Glu Leu Leu Asn Glu
1               5                   10                  15

Phe Leu Glu Leu Val Xaa
            20

<210> SEQ ID NO 207
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 207

Lys Leu Lys Lys Gln Leu Leu Asp Leu Leu Arg Glu Leu Leu Asn Glu
1               5                   10                  15

Phe Leu Glu Leu Val Xaa
            20

<210> SEQ ID NO 208
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 208

Lys Leu Lys Lys Gln Leu Ala Asp Gly Leu Arg Glu Leu Leu Asn Leu
1               5                   10                  15

Phe Leu Glu Leu Val Xaa
            20

```
<210> SEQ ID NO 209
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 209

Lys Leu Lys Lys Gln Trp Ala Asp Leu Leu Arg Glu Leu Leu Asn Leu
1               5                   10                  15

Phe Leu Glu Leu Val Xaa
            20

<210> SEQ ID NO 210
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (4)..(4)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Nip

<400> SEQUENCE: 210

Xaa Leu Xaa Xaa Gln Leu Ala Asp Leu Leu Arg Glu Leu Leu Asn Glu
1               5                   10                  15

Phe Leu Glu Leu Val Xaa
            20

<210> SEQ ID NO 211
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 211

Lys Leu Lys Lys Gln Leu Ala Asp Leu Leu Arg Glu Leu Leu Gln Glu
1               5                   10                  15

Phe Leu Glu Leu Val Xaa
            20

<210> SEQ ID NO 212
<211> LENGTH: 22
<212> TYPE: PRT
<213> ORGANISM: Artificial Sequence
<220> FEATURE:
```

<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 212

Lys Leu Lys Lys Asn Leu Ala Asp Leu Leu Arg Glu Leu Leu Asn Glu
1               5                   10                  15

Phe Leu Glu Leu Val Xaa
            20

<210> SEQ ID NO 213
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Nip

<400> SEQUENCE: 213

Lys Leu Lys Lys Gln Leu Ala Asp Leu Leu Arg Asp Leu Leu Asn Glu
1               5                   10                  15

Phe Leu Glu Leu Val Xaa
            20

<210> SEQ ID NO 214
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 214

Lys Leu Lys Gln Lys Leu Trp Glu Leu Leu Glu Asn Leu Leu Glu Arg
1               5                   10                  15

Phe Leu Asp Leu Val Xaa
            20

<210> SEQ ID NO 215
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 215

Lys Leu Lys Gln Lys Leu Ala Glu Leu Gly Glu Asn Leu Leu Glu Arg
1               5                   10                  15

Phe Leu Asp Leu Val Xaa
            20

<210> SEQ ID NO 216
<211> LENGTH: 22
<212> TYPE: PRT
<213> ORGANISM: Artificial Sequence

```
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=azPro

<400> SEQUENCE: 216

Lys Leu Lys Gln Lys Xaa Ala Glu Leu Gly Glu Asn Leu Leu Glu Arg
1               5                   10                  15

Phe Leu Asp Leu Val Xaa
            20

<210> SEQ ID NO 217
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 217

Lys Leu Lys Gln Lys Leu Trp Glu Leu Gly Glu Asn Leu Leu Glu Arg
1               5                   10                  15

Phe Leu Asp Leu Val Xaa
            20

<210> SEQ ID NO 218
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 218

Lys Leu Lys Gln Lys Leu Ala Glu Leu Gly Glu Asn Trp Leu Glu Arg
1               5                   10                  15

Phe Leu Asp Leu Val Xaa
            20

<210> SEQ ID NO 219
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(22)
<223> OTHER INFORMATION: N-terminal acetylated and C-terminal amidated
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
```

```
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=azPro

<400> SEQUENCE: 219

Xaa Leu Xaa Gln Xaa Leu Ala Glu Leu Gly Glu Asn Leu Leu Glu Arg
1               5                   10                  15

Phe Leu Asp Leu Val Xaa
            20

<210> SEQ ID NO 220
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 220

Lys Leu Lys Gln Lys Leu Ala Glu Leu Gly Glu Asn Leu Leu Glu Arg
1               5                   10                  15

Phe Phe Asp Leu Val Xaa
            20

<210> SEQ ID NO 221
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 221

Lys Leu Lys Gln Lys Leu Ala Glu Leu Gly Glu Asn Leu Leu Glu Arg
1               5                   10                  15

Phe Leu Glu Leu Val Xaa
            20

<210> SEQ ID NO 222
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 222

Lys Leu Lys Gln Lys Leu Ala Glu Leu Leu Glu Asn Leu Gly Glu Arg
1               5                   10                  15

Phe Leu Asp Leu Val Xaa
            20

<210> SEQ ID NO 223
<211> LENGTH: 22
```

```
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 223

Lys Leu Lys Gln Lys Leu Ala Glu Leu Leu Glu Asn Gly Leu Glu Arg
1               5                   10                  15

Phe Leu Asp Leu Val Xaa
            20

<210> SEQ ID NO 224
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 224

Lys Leu Lys Gln Lys Leu Ala Glu Gly Leu Glu Asn Leu Leu Glu Arg
1               5                   10                  15

Phe Leu Asp Leu Val Xaa
            20

<210> SEQ ID NO 225
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 225

Lys Leu Lys Gln Lys Leu Gly Glu Leu Leu Glu Asn Leu Leu Glu Arg
1               5                   10                  15

Phe Leu Asp Leu Val Xaa
            20

<210> SEQ ID NO 226
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 226

Lys Leu Lys Gln Lys Gly Ala Glu Leu Leu Glu Asn Leu Leu Glu Arg
1               5                   10                  15

Phe Leu Asp Leu Val Xaa
            20

<210> SEQ ID NO 227
```

-continued

```
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (7)..(7)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=azPro

<400> SEQUENCE: 227

Lys Leu Lys Gln Lys Leu Xaa Glu Leu Leu Glu Asn Leu Leu Glu Arg
1               5                   10                  15

Phe Leu Asp Leu Val Xaa
            20

<210> SEQ ID NO 228
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 228

Lys Leu Lys Gln Lys Leu Ala Glu Leu Leu Glu Asn Leu Leu Glu Arg
1               5                   10                  15

Phe Leu Asp Leu Val Xaa
            20

<210> SEQ ID NO 229
<211> LENGTH: 23
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (23)..(23)
<223> OTHER INFORMATION: Xaa=azPro

<400> SEQUENCE: 229

Lys Lys Leu Lys Gln Lys Leu Ala Glu Leu Leu Glu Asn Leu Leu Glu
1               5                   10                  15

Arg Phe Leu Asp Leu Val Xaa
            20

<210> SEQ ID NO 230
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=azPro

<400> SEQUENCE: 230
```

-continued

Lys Leu Lys Gln Lys Leu Ala Glu Leu Xaa Glu Asn Leu Leu Glu Arg
1               5                   10                  15

Phe Leu Asp Leu Val Xaa
            20

<210> SEQ ID NO 231
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 231

Lys Leu Lys Gln Lys Leu Ala Glu Leu Leu Glu Asn Leu Leu Glu Lys
1               5                   10                  15

Phe Leu Asp Leu Val Xaa
            20

<210> SEQ ID NO 232
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=azPro

<400> SEQUENCE: 232

Lys Leu Lys Gln Lys Xaa Ala Glu Leu Leu Glu Asn Leu Leu Glu Arg
1               5                   10                  15

Phe Leu Asp Leu Val Xaa
            20

<210> SEQ ID NO 233
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 233

Lys Leu Lys Gln Lys Leu Ala Glu Leu Leu Glu Gln Leu Leu Glu Lys
1               5                   10                  15

Phe Leu Asp Leu Val Xaa
            20

<210> SEQ ID NO 234
<211> LENGTH: 22
<212> TYPE: PRT
<213> ORGANISM: Artificial Sequence
<220> FEATURE:
<223> OTHER INFORMATION: APO A-1 mimic
<220> FEATURE:

```
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=azPro

<400> SEQUENCE: 234

Xaa Leu Xaa Gln Xaa Leu Ala Glu Leu Leu Glu Asn Leu Leu Glu Arg
1               5                   10                  15

Phe Leu Asp Leu Val Xaa
            20

<210> SEQ ID NO 235
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 235

Lys Leu Lys Gln Lys Leu Ala Glu Leu Leu Glu Asn Trp Leu Glu Arg
1               5                   10                  15

Phe Leu Asp Leu Val Xaa
            20

<210> SEQ ID NO 236
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 236

Lys Leu Lys Gln Lys Leu Ala Glu Leu Leu Glu Asn Leu Leu Glu Arg
1               5                   10                  15

Leu Leu Asp Leu Val Xaa
            20

<210> SEQ ID NO 237
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 237

Lys Leu Lys Gln Lys Leu Ala Glu Leu Leu Glu Gln Leu Leu Glu Lys
```

```
1               5                   10                  15
Phe Leu Glu Leu Val Xaa
            20

<210> SEQ ID NO 238
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 238

Lys Leu Lys Gln Lys Leu Ala Glu Leu Leu Glu Gln Leu Leu Glu Lys
1               5                   10                  15

Phe Leu Glu Leu Leu Xaa
            20

<210> SEQ ID NO 239
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 239

Lys Leu Lys Lys Gln Leu Ala Glu Leu Leu Glu Asn Leu Leu Glu Arg
1               5                   10                  15

Phe Leu Asp Leu Val Xaa
            20

<210> SEQ ID NO 240
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=azPro

<400> SEQUENCE: 240

Lys Leu Lys Gln Lys Leu Ala Glu Leu Xaa Glu Asn Leu Leu Glu Arg
1               5                   10                  15

Phe Phe Asp Leu Val Xaa
            20

<210> SEQ ID NO 241
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
```

<223> OTHER INFORMATION: Xaa=azPro

<400> SEQUENCE: 241

Lys Leu Lys Gln Lys Leu Leu Glu Leu Leu Glu Asn Leu Leu Glu Arg
1               5                   10                  15

Phe Leu Asp Leu Val Xaa
            20

<210> SEQ ID NO 242
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (9)..(9)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=azPro

<400> SEQUENCE: 242

Lys Leu Lys Gln Lys Leu Ala Glu Xaa Leu Glu Asn Leu Leu Glu Arg
1               5                   10                  15

Phe Leu Asp Leu Val Xaa
            20

<210> SEQ ID NO 243
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 243

Lys Leu Lys Gln Lys Leu Ala Glu Trp Leu Glu Asn Leu Leu Glu Arg
1               5                   10                  15

Phe Leu Asp Leu Val Xaa
            20

<210> SEQ ID NO 244
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (16)..(16)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=azPro

<400> SEQUENCE: 244

Xaa Leu Xaa Gln Xaa Leu Ala Glu Leu Leu Glu Asn Leu Leu Glu Xaa
1               5                   10                  15

Phe Leu Asp Leu Val Xaa
            20

<210> SEQ ID NO 245
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa-azPro

<400> SEQUENCE: 245

Lys Leu Lys Gln Lys Leu Phe Glu Leu Leu Glu Asn Leu Leu Glu Arg
1               5                   10                  15

Phe Leu Asp Leu Val Xaa
            20

<210> SEQ ID NO 246
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 246

Lys Leu Lys Lys Gln Leu Ala Glu Leu Leu Glu Arg Leu Leu Asp Asn
1               5                   10                  15

Phe Leu Glu Leu Val Xaa
            20

<210> SEQ ID NO 247
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 247

Lys Leu Lys Gln Lys Leu Ala Glu Leu Leu Glu Arg Leu Leu Asp Asn
1               5                   10                  15

Phe Leu Glu Leu Val Xaa
            20

<210> SEQ ID NO 248
<211> LENGTH: 22
<212> TYPE: PRT
<213> ORGANISM: Artificial Sequence
<220> FEATURE:
<223> OTHER INFORMATION: APO A-1 mimic
<220> FEATURE:

```
<221> NAME/KEY: MISC_FEATURE
<222> LOCATION: (22)..(22)
<223> OTHER INFORMATION: Xaa=azPro

<400> SEQUENCE: 248

Lys Leu Lys Gln Arg Leu Ala Asp Leu Leu Glu Asn Leu Leu Glu Lys
1               5                   10                  15

Phe Leu Glu Leu Val Xaa
            20

<210> SEQ ID NO 249
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 249

Lys Leu Lys Lys Gln Leu Ala Glu Leu Leu Asn Glu Leu Leu Glu Arg
1               5                   10                  15

Phe Leu Asp Leu Val Xaa
            20

<210> SEQ ID NO 250
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 250

Lys Leu Lys Lys Asn Leu Ala Gln Leu Leu Asp Glu Leu Leu Arg Glu
1               5                   10                  15

Phe Leu Glu Leu Val Xaa
            20

<210> SEQ ID NO 251
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 251

Lys Leu Lys Gln Asn Leu Ala Lys Leu Leu Asp Glu Leu Leu Arg Glu
1               5                   10                  15

Phe Leu Glu Leu Val Xaa
            20

<210> SEQ ID NO 252
<211> LENGTH: 22
<212> TYPE: PRT
<213> ORGANISM: Artificial Sequence
<220> FEATURE:
<223> OTHER INFORMATION: APO A-1 mimic
```

```
<220> FEATURE:
<221> NAME/KEY: MISC_FEATURE
<222> LOCATION: (22)..(22)
<223> OTHER INFORMATION: Xaa=azPro

<400> SEQUENCE: 252

Lys Leu Lys Gln Lys Leu Ala Glu Leu Leu Glu Gln Leu Leu Asp Lys
1               5                   10                  15

Phe Leu Glu Leu Ala Xaa
            20

<210> SEQ ID NO 253
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 253

Lys Leu Lys Gln Lys Leu Ala Glu Leu Leu Glu Gln Leu Leu Glu Lys
1               5                   10                  15

Leu Leu Glu Leu Leu Xaa
            20

<210> SEQ ID NO 254
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=azPro

<400> SEQUENCE: 254

Lys Leu Lys Gln Lys Leu Ala Glu Leu Xaa Glu Asn Leu Leu Glu Leu
1               5                   10                  15

Phe Leu Asp Leu Val Xaa
            20

<210> SEQ ID NO 255
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 255

Lys Leu Lys Gln Lys Leu Ala Lys Leu Leu Glu Glu Leu Leu Glu Arg
1               5                   10                  15

Phe Leu Asp Leu Val Xaa
            20

<210> SEQ ID NO 256
```

```
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 256

Lys Leu Lys Lys Gln Leu Ala Glu Leu Leu Glu Arg Leu Leu Glu Asn
1               5                   10                  15

Phe Leu Asp Leu Val Xaa
            20

<210> SEQ ID NO 257
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=D-Val
<220> FEATURE:
<221> NAME/KEY: MISC_FEATURE
<222> LOCATION: (22)..(22)
<223> OTHER INFORMATION: Xaa=azPro

<400> SEQUENCE: 257

Lys Leu Lys Gln Lys Leu Ala Glu Leu Leu Glu Asn Leu Leu Glu Arg
1               5                   10                  15

Phe Leu Asp Leu Xaa Xaa
            20

<210> SEQ ID NO 258
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=azPro

<400> SEQUENCE: 258

Lys Leu Lys Gln Lys Leu Ala Glu Leu Leu Glu Asn Leu Leu Glu Arg
1               5                   10                  15

Phe Leu Xaa

<210> SEQ ID NO 259
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 259

Lys Lys Lys Gln Lys Leu Ala Glu Leu Leu Glu Asn Leu Leu Glu Arg
1               5                   10                  15

Phe Leu Asp Leu Val Xaa
```

20

<210> SEQ ID NO 260
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=azPro

<400> SEQUENCE: 260

Gln Lys Leu Ala Glu Leu Leu Glu Asn Leu Leu Glu Arg Phe Leu Asp
1               5                   10                  15

Leu Val Xaa

<210> SEQ ID NO 261
<211> LENGTH: 21
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=azPro

<400> SEQUENCE: 261

Lys Leu Lys Gln Lys Leu Ala Glu Leu Leu Glu Asn Leu Leu Glu Arg
1               5                   10                  15

Phe Leu Asp Leu Xaa
            20

<210> SEQ ID NO 262
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 262

Lys Leu Lys Lys Gln Leu Ala Asn Leu Leu Glu Asp Leu Leu Arg Glu
1               5                   10                  15

Phe Leu Glu Leu Val Xaa
            20

<210> SEQ ID NO 263
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=azPro

<400> SEQUENCE: 263

Glu Leu Leu Glu Asn Leu Leu Glu Arg Phe Leu Asp Leu Val Xaa
1               5                   10                  15

```
<210> SEQ ID NO 264
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=azPro

<400> SEQUENCE: 264

Lys Leu Lys Gln Lys Leu Ala Glu Leu Leu Glu Asn Leu Leu Xaa
1               5                   10                  15

<210> SEQ ID NO 265
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 265

Lys Leu Lys Gln Leu Leu Glu Asn Leu Leu Glu Arg Phe Leu Asp Leu
1               5                   10                  15

Val Xaa

<210> SEQ ID NO 266
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 266

Lys Leu Lys Gln Lys Leu Glu Glu Leu Leu Glu Arg Phe Leu Asp Leu
1               5                   10                  15

Val Xaa

<210> SEQ ID NO 267
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 267

Lys Leu Lys Gln Lys Leu Glu Glu Leu Leu Glu Lys Phe Leu Glu Leu
1               5                   10                  15

Val Xaa

<210> SEQ ID NO 268
<211> LENGTH: 18
<212> TYPE: PRT
<213> ORGANISM: Artificial Sequence
<220> FEATURE:
```

<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 268

Lys Leu Lys Gln Lys Leu Leu Glu Leu Leu Glu Arg Phe Leu Asp Leu
1               5                   10                  15

Val Xaa

<210> SEQ ID NO 269
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 269

Lys Leu Lys Gln Trp Leu Glu Asn Leu Leu Glu Arg Phe Leu Asp Leu
1               5                   10                  15

Val Xaa

<210> SEQ ID NO 270
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 270

Lys Leu Lys Lys Gln Leu Glu Glu Leu Leu Glu Arg Phe Leu Asp Leu
1               5                   10                  15

Val Xaa

<210> SEQ ID NO 271
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 271

Lys Lys Leu Gln Leu Leu Ala Glu Leu Leu Glu Arg Phe Ala Asp Leu
1               5                   10                  15

Val Xaa

<210> SEQ ID NO 272
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 272

Lys Lys Leu Gln Ala Leu Ala Glu Leu Leu Glu Arg Phe Ala Asp Leu
1               5                   10                  15

Val Xaa

<210> SEQ ID NO 273
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 273

Lys Leu Lys Gln Lys Leu Glu Glu Trp Gly Glu Arg Phe Leu Asp Leu
1               5                   10                  15

Val Xaa

<210> SEQ ID NO 274
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 274

Lys Leu Lys Lys Gln Leu Asp Glu Leu Leu Arg Glu Phe Leu Glu Leu
1               5                   10                  15

Val Xaa

<210> SEQ ID NO 275
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPro

<400> SEQUENCE: 275

Lys Leu Lys Gln Glu Leu Lys Glu Leu Leu Glu Arg Phe Leu Asp Leu
1               5                   10                  15

Val Xaa

<210> SEQ ID NO 276
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(22)
<223> OTHER INFORMATION: N-terminal acetylated and C-terminal amidated
<220> FEATURE:

<221> NAME/KEY: MISC_FEATURE
<222> LOCATION: (22)..(22)
<223> OTHER INFORMATION: Xaa=azPro

<400> SEQUENCE: 276

Lys Leu Lys Gln Lys Leu Ala Glu Leu Gly Glu Asn Leu Leu Glu Arg
1               5                   10                  15

Phe Leu Asp Leu Val Xaa
            20

<210> SEQ ID NO 277
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 277

Lys Leu Lys Gln Lys Leu Glu Glu Leu Leu Glu Arg Leu Leu Asp Leu
1               5                   10                  15

Val Xaa

<210> SEQ ID NO 278
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 278

Lys Leu Lys Gln Lys Leu Glu Glu Leu Leu Glu Lys Phe Leu Asp Leu
1               5                   10                  15

Val Xaa

<210> SEQ ID NO 279
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 279

Lys Leu Lys Gln Lys Leu Glu Glu Leu Leu Glu Arg Phe Leu Asp Leu
1               5                   10                  15

Val Xaa

<210> SEQ ID NO 280
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 280

Lys Leu Lys Gln Lys Leu Glu Glu Leu Leu Glu Arg Phe Leu Glu Leu
1               5                   10                  15

Val Xaa

<210> SEQ ID NO 281
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 281

Lys Leu Lys Gln Lys Leu Glu Glu Leu Leu Glu Lys Phe Leu Glu Leu
1               5                   10                  15

Val Xaa

<210> SEQ ID NO 282
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 282

Lys Leu Lys Asn Lys Leu Glu Glu Leu Leu Glu Arg Phe Leu Asp Leu
1               5                   10                  15

Val Xaa

<210> SEQ ID NO 283
<211> LENGTH: 18
<212> TYPE: PRT
<213> ORGANISM: Artificial Sequence
<220> FEATURE:
<223> OTHER INFORMATION: ApoA-I mimic
<220> FEATURE:

-continued

<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 283

Lys Leu Lys Gln Lys Leu Glu Glu Leu Leu Glu Arg Phe Leu Asp Leu
1               5                   10                  15

Leu Xaa

<210> SEQ ID NO 284
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 284

Lys Leu Lys Gln Lys Leu Glu Glu Trp Leu Glu Arg Phe Leu Asp Leu
1               5                   10                  15

Val Xaa

<210> SEQ ID NO 285
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 285

Lys Leu Lys Gln Lys Leu Glu Glu Leu Leu Glu Lys Phe Leu Asp Leu
1               5                   10                  15

Leu Xaa

<210> SEQ ID NO 286
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 286

Arg Leu Lys Gln Arg Leu Glu Glu Leu Leu Asp Lys Phe Leu Glu Leu
1               5                   10                  15

Ala Xaa

<210> SEQ ID NO 287
<211> LENGTH: 18
<212> TYPE: PRT
<213> ORGANISM: Artificial Sequence
<220> FEATURE:
<223> OTHER INFORMATION: ApoA-1 mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 287

Lys Leu Lys Gln Lys Leu Glu Glu Leu Leu Glu Arg Phe Phe Asp Leu
1               5                   10                  15

Val Xaa

<210> SEQ ID NO 288
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 288

Lys Leu Lys Gln Lys Leu Glu Glu Leu Trp Glu Arg Phe Leu Asp Leu
1               5                   10                  15

Val Xaa

<210> SEQ ID NO 289
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 289

Lys Leu Lys Gln Lys Leu Glu Glu Leu Leu Glu Lys Leu Leu Glu Leu
1               5                   10                  15

Leu Xaa

<210> SEQ ID NO 290
<211> LENGTH: 18
<212> TYPE: PRT
<213> ORGANISM: Artificial Sequence

```
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 290

Lys Leu Lys Gln Lys Leu Glu Glu Leu Leu Glu Lys Leu Leu Glu Leu
1               5                   10                  15

Val Xaa

<210> SEQ ID NO 291
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=1zPro

<400> SEQUENCE: 291

Lys Leu Arg Gln Arg Leu Glu Glu Leu Leu Asp Lys Phe Leu Glu Leu
1               5                   10                  15

Ala Xaa

<210> SEQ ID NO 292
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=azPro

<400> SEQUENCE: 292

Xaa Leu Xaa Gln Xaa Leu Glu Glu Leu Leu Glu Arg Phe Leu Asp Leu
1               5                   10                  15

Val Xaa

<210> SEQ ID NO 293
<211> LENGTH: 18
```

```
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (12)..(12)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=azPro

<400> SEQUENCE: 293

Lys Leu Xaa Gln Xaa Leu Glu Glu Leu Leu Glu Xaa Phe Leu Asp Leu
1               5                   10                  15

Val Xaa

<210> SEQ ID NO 294
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 294

Lys Leu Arg Gln Arg Phe Glu Glu Leu Leu Asp Lys Phe Leu Glu Leu
1               5                   10                  15

Ala Xaa

<210> SEQ ID NO 295
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 295

Lys Leu Lys Gln Lys Trp Glu Glu Leu Leu Glu Arg Phe Leu Asp Leu
1               5                   10                  15

Val Xaa
```

-continued

<210> SEQ ID NO 296
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 296

Lys Leu Lys Gln Leu Leu Glu Asn Leu Leu Glu Arg Phe Leu Asp Leu
1               5                   10                  15

Val Xaa

<210> SEQ ID NO 297
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 297

Lys Leu Lys Gln Lys Leu Glu Glu Leu Gly Glu Arg Phe Leu Asp Leu
1               5                   10                  15

Val Xaa

<210> SEQ ID NO 298
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPro

<400> SEQUENCE: 298

Lys Leu Lys Gln Lys Gly Glu Glu Leu Leu Glu Arg Phe Leu Asp Leu
1               5                   10                  15

Val Xaa

<210> SEQ ID NO 299
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated

```
<220> FEATURE:
<221> NAME/KEY: MISC_FEATURE
<222> LOCATION: (18)..(18)
<223> OTHER INFORMATION: Xaa=azPro

<400> SEQUENCE: 299

Lys Leu Lys Gln Lys Leu Glu Glu Leu Leu Glu Lys Phe Leu Glu Leu
1               5                   10                  15

Leu Xaa

<210> SEQ ID NO 300
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=azPro

<400> SEQUENCE: 300

Lys Leu Lys Gln Glu Leu Leu Glu Arg Phe Leu Asp Leu Val Xaa
1               5                   10                  15

<210> SEQ ID NO 301
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=azPro

<400> SEQUENCE: 301

Lys Gln Lys Leu Glu Glu Leu Leu Glu Arg Phe Leu Asp Leu Val Xaa
1               5                   10                  15

<210> SEQ ID NO 302
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=azPro

<400> SEQUENCE: 302

Lys Gln Lys Leu Lys Glu Leu Leu Glu Arg Phe Leu Asp Leu Val Xaa
1               5                   10                  15

<210> SEQ ID NO 303
<211> LENGTH: 15
<212> TYPE: PRT
```

```
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=azPro

<400> SEQUENCE: 303

Lys Gln Leu Lys Glu Leu Leu Glu Arg Phe Leu Asp Leu Val Xaa
1               5                   10                  15

<210> SEQ ID NO 304
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=azPro

<400> SEQUENCE: 304

Lys Gln Lys Leu Ala Glu Leu Leu Glu Arg Phe Leu Asp Leu Val Xaa
1               5                   10                  15

<210> SEQ ID NO 305
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=azPro

<400> SEQUENCE: 305

Lys Gln Lys Leu Glu Asn Leu Leu Glu Arg Phe Leu Asp Leu Val Xaa
1               5                   10                  15

<210> SEQ ID NO 306
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 306

Lys Leu Lys Gln Lys Leu Trp Glu Leu Leu Glu Asn Leu Leu Glu Arg
1               5                   10                  15

Phe Leu Asp Leu Val Xaa
            20
```

```
<210> SEQ ID NO 307
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 307

Lys Leu Lys Gln Lys Leu Ala Glu Leu Gly Glu Asn Leu Leu Glu Arg
1               5                   10                  15

Phe Leu Asp Leu Val Xaa
            20

<210> SEQ ID NO 308
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Pip

<400> SEQUENCE: 308

Lys Leu Lys Gln Lys Xaa Ala Glu Leu Gly Glu Asn Leu Leu Glu Arg
1               5                   10                  15

Phe Leu Asp Leu Val Xaa
            20

<210> SEQ ID NO 309
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 309

Lys Leu Lys Gln Lys Leu Trp Glu Leu Gly Glu Asn Leu Leu Glu Arg
1               5                   10                  15

Phe Leu Asp Leu Val Xaa
            20

<210> SEQ ID NO 310
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 310

Lys Leu Lys Gln Lys Leu Ala Glu Leu Gly Glu Asn Trp Leu Glu Arg
```

```
                1               5                  10                 15

Phe Leu Asp Leu Val Xaa
                20

<210> SEQ ID NO 311
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Pip

<400> SEQUENCE: 311

Xaa Leu Xaa Gln Xaa Leu Ala Glu Leu Gly Glu Asn Leu Leu Glu Arg
1               5                  10                 15

Phe Leu Asp Leu Val Xaa
                20

<210> SEQ ID NO 312
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 312

Lys Leu Lys Gln Lys Leu Ala Glu Leu Gly Glu Asn Leu Leu Glu Arg
1               5                  10                 15

Phe Phe Asp Leu Val Xaa
                20

<210> SEQ ID NO 313
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 313

Lys Leu Lys Gln Lys Leu Ala Glu Leu Gly Glu Asn Leu Leu Glu Arg
1               5                  10                 15

Phe Leu Glu Leu Val Xaa
                20

<210> SEQ ID NO 314
```

```
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 314

Lys Leu Lys Gln Lys Leu Ala Glu Leu Leu Glu Asn Leu Gly Glu Arg
1               5                   10                  15

Phe Leu Asp Leu Val Xaa
            20

<210> SEQ ID NO 315
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 315

Lys Leu Lys Gln Lys Leu Ala Glu Leu Leu Glu Asn Gly Leu Glu Arg
1               5                   10                  15

Phe Leu Asp Leu Val Xaa
            20

<210> SEQ ID NO 316
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 316

Lys Leu Lys Gln Lys Leu Ala Glu Gly Leu Glu Asn Leu Leu Glu Arg
1               5                   10                  15

Phe Leu Asp Leu Val Xaa
            20

<210> SEQ ID NO 317
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 317

Lys Leu Lys Gln Lys Leu Gly Glu Leu Leu Glu Asn Leu Leu Glu Arg
1               5                   10                  15

Phe Leu Asp Leu Val Xaa
            20
```

-continued

```
<210> SEQ ID NO 318
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 318

Lys Leu Lys Gln Lys Gly Ala Glu Leu Leu Glu Asn Leu Leu Glu Arg
1               5                   10                  15

Phe Leu Asp Leu Val Xaa
            20

<210> SEQ ID NO 319
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (7)..(7)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Pip

<400> SEQUENCE: 319

Lys Leu Lys Gln Lys Leu Xaa Glu Leu Leu Glu Asn Leu Leu Glu Arg
1               5                   10                  15

Phe Leu Asp Leu Val Xaa
            20

<210> SEQ ID NO 320
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 320

Lys Leu Lys Gln Lys Leu Ala Glu Leu Leu Glu Asn Leu Leu Glu Arg
1               5                   10                  15

Phe Leu Asp Leu Val Xaa
            20

<210> SEQ ID NO 321
<211> LENGTH: 23
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (23)..(23)
<223> OTHER INFORMATION: Xaa=Pip

<400> SEQUENCE: 321

Lys Lys Leu Lys Gln Lys Leu Ala Glu Leu Leu Glu Asn Leu Leu Glu
1               5                   10                  15
```

```
Arg Phe Leu Asp Leu Val Xaa
            20

<210> SEQ ID NO 322
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=Pip

<400> SEQUENCE: 322

Lys Leu Lys Gln Lys Leu Ala Glu Leu Xaa Glu Asn Leu Leu Glu Arg
1               5                   10                  15

Phe Leu Asp Leu Val Xaa
            20

<210> SEQ ID NO 323
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 323

Lys Leu Lys Gln Lys Leu Ala Glu Leu Leu Glu Asn Leu Leu Glu Lys
1               5                   10                  15

Phe Leu Asp Leu Val Xaa
            20

<210> SEQ ID NO 324
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Pip

<400> SEQUENCE: 324

Lys Leu Lys Gln Lys Xaa Ala Glu Leu Leu Glu Asn Leu Leu Glu Arg
1               5                   10                  15

Phe Leu Asp Leu Val Xaa
            20

<210> SEQ ID NO 325
<211> LENGTH: 22
<212> TYPE: PRT
<213> ORGANISM: Artificial Sequence
<220> FEATURE:
<223> OTHER INFORMATION: APO A-1 mimic
```

```
<220> FEATURE:
<221> NAME/KEY: MISC_FEATURE
<222> LOCATION: (22)..(22)
<223> OTHER INFORMATION: Xaa=Pip

<400> SEQUENCE: 325

Lys Leu Lys Gln Lys Leu Ala Glu Leu Glu Gln Leu Leu Glu Lys
1               5                   10                  15

Phe Leu Asp Leu Val Xaa
            20

<210> SEQ ID NO 326
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Pip

<400> SEQUENCE: 326

Xaa Leu Xaa Gln Xaa Leu Ala Glu Leu Leu Glu Asn Leu Leu Glu Arg
1               5                   10                  15

Phe Leu Asp Leu Val Xaa
            20

<210> SEQ ID NO 327
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 327

Lys Leu Lys Gln Lys Leu Ala Glu Leu Leu Glu Asn Trp Leu Glu Arg
1               5                   10                  15

Phe Leu Asp Leu Val Xaa
            20

<210> SEQ ID NO 328
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 328
```

Lys Leu Lys Gln Lys Leu Ala Glu Leu Leu Glu Asn Leu Leu Glu Arg
1               5                   10                  15

Leu Leu Asp Leu Val Xaa
            20

<210> SEQ ID NO 329
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 329

Lys Leu Lys Gln Lys Leu Ala Glu Leu Leu Glu Gln Leu Leu Glu Lys
1               5                   10                  15

Phe Leu Glu Leu Val Xaa
            20

<210> SEQ ID NO 330
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 330

Lys Leu Lys Gln Lys Leu Ala Glu Leu Leu Glu Gln Leu Leu Glu Lys
1               5                   10                  15

Phe Leu Glu Leu Leu Xaa
            20

<210> SEQ ID NO 331
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 331

Lys Leu Lys Lys Gln Leu Ala Glu Leu Leu Glu Asn Leu Leu Glu Arg
1               5                   10                  15

Phe Leu Asp Leu Val Xaa
            20

<210> SEQ ID NO 332
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=Pip

<400> SEQUENCE: 332

Lys Leu Lys Gln Lys Leu Ala Glu Leu Xaa Glu Asn Leu Leu Glu Arg
1               5                   10                  15

Phe Phe Asp Leu Val Xaa
            20

<210> SEQ ID NO 333
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 333

Lys Leu Lys Gln Lys Leu Leu Glu Leu Leu Glu Asn Leu Leu Glu Arg
1               5                   10                  15

Phe Leu Asp Leu Val Xaa
            20

<210> SEQ ID NO 334
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (9)..(9)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=Pip

<400> SEQUENCE: 334

Lys Leu Lys Gln Lys Leu Ala Glu Xaa Leu Glu Asn Leu Leu Glu Arg
1               5                   10                  15

Phe Leu Asp Leu Val Xaa
            20

<210> SEQ ID NO 335
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 335

Lys Leu Lys Gln Lys Leu Ala Glu Trp Leu Glu Asn Leu Leu Glu Arg
1               5                   10                  15

Phe Leu Asp Leu Val Xaa
            20

<210> SEQ ID NO 336
<211> LENGTH: 22
<212> TYPE: PRT

<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (16)..(16)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Pip

<400> SEQUENCE: 336

Xaa Leu Xaa Gln Xaa Leu Ala Glu Leu Leu Glu Asn Leu Leu Glu Xaa
1               5                   10                  15

Phe Leu Asp Leu Val Xaa
            20

<210> SEQ ID NO 337
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa-Pip

<400> SEQUENCE: 337

Lys Leu Lys Gln Lys Leu Phe Glu Leu Leu Glu Asn Leu Leu Glu Arg
1               5                   10                  15

Phe Leu Asp Leu Val Xaa
            20

<210> SEQ ID NO 338
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 338

Lys Leu Lys Lys Gln Leu Ala Glu Leu Leu Glu Arg Leu Leu Asp Asn
1               5                   10                  15

Phe Leu Glu Leu Val Xaa
            20

<210> SEQ ID NO 339
<211> LENGTH: 22
<212> TYPE: PRT
<213> ORGANISM: Artificial Sequence
<220> FEATURE:
<223> OTHER INFORMATION: APO A-1 mimic

```
<220> FEATURE:
<221> NAME/KEY: MISC_FEATURE
<222> LOCATION: (22)..(22)
<223> OTHER INFORMATION: Xaa=Pip

<400> SEQUENCE: 339

Lys Leu Lys Gln Lys Leu Ala Glu Leu Leu Glu Arg Leu Leu Asp Asn
1               5                   10                  15

Phe Leu Glu Leu Val Xaa
            20

<210> SEQ ID NO 340
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 340

Lys Leu Lys Gln Arg Leu Ala Asp Leu Leu Glu Asn Leu Leu Glu Lys
1               5                   10                  15

Phe Leu Glu Leu Val Xaa
            20

<210> SEQ ID NO 341
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 341

Lys Leu Lys Lys Gln Leu Ala Glu Leu Leu Asn Glu Leu Leu Glu Arg
1               5                   10                  15

Phe Leu Asp Leu Val Xaa
            20

<210> SEQ ID NO 342
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 342

Lys Leu Lys Lys Asn Leu Ala Gln Leu Leu Asp Glu Leu Leu Arg Glu
1               5                   10                  15

Phe Leu Glu Leu Val Xaa
            20

<210> SEQ ID NO 343
<211> LENGTH: 22
<212> TYPE: PRT
<213> ORGANISM: Artificial Sequence
<220> FEATURE:
```

```
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 343

Lys Leu Lys Gln Asn Leu Ala Lys Leu Leu Asp Glu Leu Leu Arg Glu
1               5                   10                  15

Phe Leu Glu Leu Val Xaa
            20

<210> SEQ ID NO 344
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 344

Lys Leu Lys Gln Lys Leu Ala Glu Leu Leu Glu Gln Leu Leu Asp Lys
1               5                   10                  15

Phe Leu Glu Leu Ala Xaa
            20

<210> SEQ ID NO 345
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 345

Lys Leu Lys Gln Lys Leu Ala Glu Leu Leu Glu Gln Leu Leu Glu Lys
1               5                   10                  15

Leu Leu Glu Leu Leu Xaa
            20

<210> SEQ ID NO 346
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=Pip

<400> SEQUENCE: 346

Lys Leu Lys Gln Lys Leu Ala Glu Leu Xaa Glu Asn Leu Leu Glu Leu
1               5                   10                  15

Phe Leu Asp Leu Val Xaa
            20
```

```
<210> SEQ ID NO 347
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 347

Lys Leu Lys Lys Lys Leu Ala Lys Leu Leu Glu Glu Leu Leu Glu Arg
1               5                   10                  15

Phe Leu Asp Leu Val Xaa
            20

<210> SEQ ID NO 348
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 348

Lys Leu Lys Lys Gln Leu Ala Glu Leu Leu Glu Arg Leu Leu Glu Asn
1               5                   10                  15

Phe Leu Asp Leu Val Xaa
            20

<210> SEQ ID NO 349
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=D-Val
<220> FEATURE:
<221> NAME/KEY: MISC_FEATURE
<222> LOCATION: (22)..(22)
<223> OTHER INFORMATION: Xaa=Pip

<400> SEQUENCE: 349

Lys Leu Lys Gln Lys Leu Ala Glu Leu Leu Glu Asn Leu Leu Glu Arg
1               5                   10                  15

Phe Leu Asp Leu Xaa Xaa
            20

<210> SEQ ID NO 350
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=Pip

<400> SEQUENCE: 350

Lys Leu Lys Gln Lys Leu Ala Glu Leu Leu Glu Asn Leu Leu Glu Arg
1               5                   10                  15
```

Phe Leu Xaa

<210> SEQ ID NO 351
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 351

Lys Lys Lys Gln Lys Leu Ala Glu Leu Leu Glu Asn Leu Leu Glu Arg
1               5                   10                  15

Phe Leu Asp Leu Val Xaa
            20

<210> SEQ ID NO 352
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=Pip

<400> SEQUENCE: 352

Gln Lys Leu Ala Glu Leu Leu Glu Asn Leu Leu Glu Arg Phe Leu Asp
1               5                   10                  15

Leu Val Xaa

<210> SEQ ID NO 353
<211> LENGTH: 21
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=Pip

<400> SEQUENCE: 353

Lys Leu Lys Gln Lys Leu Ala Glu Leu Leu Glu Asn Leu Leu Glu Arg
1               5                   10                  15

Phe Leu Asp Leu Xaa
            20

<210> SEQ ID NO 354
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 354

Lys Leu Lys Lys Gln Leu Ala Asn Leu Leu Glu Asp Leu Leu Arg Glu
1               5                   10                  15

Phe Leu Glu Leu Val Xaa
        20

<210> SEQ ID NO 355
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=Pip

<400> SEQUENCE: 355

Glu Leu Leu Glu Asn Leu Leu Glu Arg Phe Leu Asp Leu Val Xaa
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=Pip

<400> SEQUENCE: 356

Lys Leu Lys Gln Lys Leu Ala Glu Leu Leu Glu Asn Leu Leu Xaa
1               5                   10                  15

<210> SEQ ID NO 357
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Pip

<400> SEQUENCE: 357

Lys Leu Lys Gln Leu Leu Glu Asn Leu Leu Glu Arg Phe Leu Asp Leu
1               5                   10                  15

Val Xaa

<210> SEQ ID NO 358
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Pip

<400> SEQUENCE: 358

Lys Leu Lys Gln Lys Leu Glu Glu Leu Leu Glu Arg Phe Leu Asp Leu
1               5                   10                  15

Val Xaa

<210> SEQ ID NO 359
<211> LENGTH: 18
<212> TYPE: PRT

-continued

<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Pip

<400> SEQUENCE: 359

Lys Leu Lys Gln Lys Leu Glu Glu Leu Leu Glu Lys Phe Leu Glu Leu
1               5                   10                  15

Val Xaa

<210> SEQ ID NO 360
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Pip

<400> SEQUENCE: 360

Lys Leu Lys Gln Lys Leu Leu Glu Leu Leu Glu Arg Phe Leu Asp Leu
1               5                   10                  15

Val Xaa

<210> SEQ ID NO 361
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Pip

<400> SEQUENCE: 361

Lys Leu Lys Gln Trp Leu Glu Asn Leu Leu Glu Arg Phe Leu Asp Leu
1               5                   10                  15

Val Xaa

<210> SEQ ID NO 362
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=Pip

<400> SEQUENCE: 362

Lys Leu Lys Lys Gln Leu Glu Glu Leu Leu Glu Arg Phe Leu Asp Leu
1               5                   10                  15

Val Xaa

<210> SEQ ID NO 363
<211> LENGTH: 18
<212> TYPE: PRT
<213> ORGANISM: Artificial Sequence
<220> FEATURE:
<223> OTHER INFORMATION: APO A-1 mimic

```
<220> FEATURE:
<221> NAME/KEY: MISC_FEATURE
<222> LOCATION: (18)..(18)
<223> OTHER INFORMATION: Xaa=Pip

<400> SEQUENCE: 363

Lys Lys Leu Gln Leu Leu Ala Glu Leu Leu Glu Arg Phe Ala Asp Leu
1               5                   10                  15

Val Xaa

<210> SEQ ID NO 364
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=Pip

<400> SEQUENCE: 364

Lys Lys Leu Gln Ala Leu Ala Glu Leu Leu Glu Arg Phe Ala Asp Leu
1               5                   10                  15

Val Xaa

<210> SEQ ID NO 365
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=Pip

<400> SEQUENCE: 365

Lys Leu Lys Gln Lys Leu Glu Glu Trp Gly Glu Arg Phe Leu Asp Leu
1               5                   10                  15

Val Xaa

<210> SEQ ID NO 366
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=Pip

<400> SEQUENCE: 366

Lys Leu Lys Lys Gln Leu Asp Glu Leu Leu Arg Glu Phe Leu Glu Leu
1               5                   10                  15

Val Xaa

<210> SEQ ID NO 367
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
```

<223> OTHER INFORMATION: Xaa=Pip

<400> SEQUENCE: 367

Lys Leu Lys Gln Glu Leu Lys Glu Leu Leu Glu Arg Phe Leu Asp Leu
1               5                   10                  15

Val Xaa

<210> SEQ ID NO 368
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(22)
<223> OTHER INFORMATION: N-terminal acetylated and C-terminal amidated
<220> FEATURE:
<221> NAME/KEY: MISC_FEATURE
<222> LOCATION: (22)..(22)
<223> OTHER INFORMATION: Xaa=Pip

<400> SEQUENCE: 368

Lys Leu Lys Gln Lys Leu Ala Glu Leu Gly Glu Asn Leu Leu Glu Arg
1               5                   10                  15

Phe Leu Asp Leu Val Xaa
            20

<210> SEQ ID NO 369
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 369

Lys Leu Lys Gln Lys Leu Glu Glu Leu Leu Glu Arg Leu Leu Asp Leu
1               5                   10                  15

Val Xaa

<210> SEQ ID NO 370
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 370

Lys Leu Lys Gln Lys Leu Glu Glu Leu Leu Glu Lys Phe Leu Asp Leu
1               5                   10                  15

Val Xaa

```
<210> SEQ ID NO 371
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 371

Lys Leu Lys Gln Lys Leu Glu Glu Leu Leu Glu Arg Phe Leu Asp Leu
1               5                   10                  15

Val Xaa

<210> SEQ ID NO 372
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 372

Lys Leu Lys Gln Lys Leu Glu Glu Leu Leu Glu Arg Phe Leu Glu Leu
1               5                   10                  15

Val Xaa

<210> SEQ ID NO 373
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 373

Lys Leu Lys Gln Lys Leu Glu Glu Leu Leu Glu Lys Phe Leu Glu Leu
1               5                   10                  15

Val Xaa

<210> SEQ ID NO 374
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
```

<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 374

Lys Leu Lys Asn Lys Leu Glu Glu Leu Leu Glu Arg Phe Leu Asp Leu
1               5                   10                  15

Val Xaa

<210> SEQ ID NO 375
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 375

Lys Leu Lys Gln Lys Leu Glu Glu Leu Leu Glu Arg Phe Leu Asp Leu
1               5                   10                  15

Leu Xaa

<210> SEQ ID NO 376
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 376

Lys Leu Lys Gln Lys Leu Glu Glu Trp Leu Glu Arg Phe Leu Asp Leu
1               5                   10                  15

Val Xaa

<210> SEQ ID NO 377
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 377

Lys Leu Lys Gln Lys Leu Glu Glu Leu Leu Glu Lys Phe Leu Asp Leu
1               5                   10                  15

Leu Xaa

<210> SEQ ID NO 378
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 378

Arg Leu Lys Gln Arg Leu Glu Glu Leu Leu Asp Lys Phe Leu Glu Leu
1               5                   10                  15

Ala Xaa

<210> SEQ ID NO 379
<211> LENGTH: 18
<212> TYPE: PRT
<213> ORGANISM: Artificial Sequence
<220> FEATURE:
<223> OTHER INFORMATION: ApoA-1 mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 379

Lys Leu Lys Gln Lys Leu Glu Glu Leu Leu Glu Arg Phe Phe Asp Leu
1               5                   10                  15

Val Xaa

<210> SEQ ID NO 380
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 380

Lys Leu Lys Gln Lys Leu Glu Glu Leu Trp Glu Arg Phe Leu Asp Leu
1               5                   10                  15

Val Xaa

<210> SEQ ID NO 381
<211> LENGTH: 18
<212> TYPE: PRT
<213> ORGANISM: Artificial Sequence
<220> FEATURE:
<223> OTHER INFORMATION: ApoA-I mimic

```
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 381

Lys Leu Lys Gln Lys Leu Glu Glu Leu Leu Glu Lys Leu Leu Glu Leu
1               5                   10                  15

Leu Xaa

<210> SEQ ID NO 382
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 382

Lys Leu Lys Gln Lys Leu Glu Glu Leu Leu Glu Lys Leu Leu Glu Leu
1               5                   10                  15

Val Xaa

<210> SEQ ID NO 383
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 383

Lys Leu Arg Gln Arg Leu Glu Glu Leu Leu Asp Lys Phe Leu Glu Leu
1               5                   10                  15

Ala Xaa

<210> SEQ ID NO 384
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
```

```
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=Pip

<400> SEQUENCE: 384

Xaa Leu Xaa Gln Xaa Leu Glu Glu Leu Leu Glu Arg Phe Leu Asp Leu
1               5                   10                  15

Val Xaa

<210> SEQ ID NO 385
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (12)..(12)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=Pip

<400> SEQUENCE: 385

Lys Leu Xaa Gln Xaa Leu Glu Glu Leu Leu Glu Xaa Phe Leu Asp Leu
1               5                   10                  15

Val Xaa

<210> SEQ ID NO 386
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 386

Lys Leu Arg Gln Arg Phe Glu Glu Leu Leu Asp Lys Phe Leu Glu Leu
1               5                   10                  15

Ala Xaa

<210> SEQ ID NO 387
<211> LENGTH: 18
```

```
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 387

Lys Leu Lys Gln Lys Trp Glu Glu Leu Leu Glu Arg Phe Leu Asp Leu
1               5                   10                  15

Val Xaa

<210> SEQ ID NO 388
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 388

Lys Leu Lys Gln Leu Leu Glu Asn Leu Leu Glu Arg Phe Leu Asp Leu
1               5                   10                  15

Val Xaa

<210> SEQ ID NO 389
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 389

Lys Leu Lys Gln Lys Leu Glu Glu Leu Gly Glu Arg Phe Leu Asp Leu
1               5                   10                  15

Val Xaa

<210> SEQ ID NO 390
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
```

<222> LOCATION: (18)..(18)
<223> OTHER INFORMATION: Xaa=Pip

<400> SEQUENCE: 390

Lys Leu Lys Gln Lys Gly Glu Glu Leu Leu Glu Arg Phe Leu Asp Leu
1               5                   10                  15
Val Xaa

<210> SEQ ID NO 391
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=Pip

<400> SEQUENCE: 391

Lys Leu Lys Gln Lys Leu Glu Glu Leu Leu Glu Lys Phe Leu Glu Leu
1               5                   10                  15
Leu Xaa

<210> SEQ ID NO 392
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=Pip

<400> SEQUENCE: 392

Lys Leu Lys Gln Glu Leu Leu Glu Arg Phe Leu Asp Leu Val Xaa
1               5                   10                  15

<210> SEQ ID NO 393
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Pip

<400> SEQUENCE: 393

Lys Gln Lys Leu Glu Glu Leu Leu Glu Arg Phe Leu Asp Leu Val Xaa
1               5                   10                  15

<210> SEQ ID NO 394
<211> LENGTH: 16
<212> TYPE: PRT

```
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Pip

<400> SEQUENCE: 394

Lys Gln Lys Leu Lys Glu Leu Leu Glu Arg Phe Leu Asp Leu Val Xaa
1               5                   10                  15

<210> SEQ ID NO 395
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=Pip

<400> SEQUENCE: 395

Lys Gln Leu Lys Glu Leu Leu Glu Arg Phe Leu Asp Leu Val Xaa
1               5                   10                  15

<210> SEQ ID NO 396
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Pip

<400> SEQUENCE: 396

Lys Gln Lys Leu Ala Glu Leu Leu Glu Arg Phe Leu Asp Leu Val Xaa
1               5                   10                  15

<210> SEQ ID NO 397
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=Pip

<400> SEQUENCE: 397

Lys Gln Lys Leu Glu Asn Leu Leu Glu Arg Phe Leu Asp Leu Val Xaa
1               5                   10                  15
```

<210> SEQ ID NO 398
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 398

Lys Leu Lys Gln Lys Leu Trp Glu Leu Leu Glu Asn Leu Leu Glu Arg
1               5                   10                  15

Phe Leu Asp Leu Val Xaa
            20

<210> SEQ ID NO 399
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 399

Lys Leu Lys Gln Lys Leu Ala Glu Leu Gly Glu Asn Leu Leu Glu Arg
1               5                   10                  15

Phe Leu Asp Leu Val Xaa
            20

<210> SEQ ID NO 400
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=azPip

<400> SEQUENCE: 400

Lys Leu Lys Gln Lys Xaa Ala Glu Leu Gly Glu Asn Leu Leu Glu Arg
1               5                   10                  15

Phe Leu Asp Leu Val Xaa
            20

<210> SEQ ID NO 401
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 401

```
Lys Leu Lys Gln Lys Leu Trp Glu Leu Gly Glu Asn Leu Leu Glu Arg
1               5                   10                  15

Phe Leu Asp Leu Val Xaa
            20

<210> SEQ ID NO 402
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 402

Lys Leu Lys Gln Lys Leu Ala Glu Leu Gly Glu Asn Trp Leu Glu Arg
1               5                   10                  15

Phe Leu Asp Leu Val Xaa
            20

<210> SEQ ID NO 403
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=azPip

<400> SEQUENCE: 403

Xaa Leu Xaa Gln Xaa Leu Ala Glu Leu Gly Glu Asn Leu Leu Glu Arg
1               5                   10                  15

Phe Leu Asp Leu Val Xaa
            20

<210> SEQ ID NO 404
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 404

Lys Leu Lys Gln Lys Leu Ala Glu Leu Gly Glu Asn Leu Leu Glu Arg
1               5                   10                  15

Phe Phe Asp Leu Val Xaa
            20
```

```
<210> SEQ ID NO 405
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 405

Lys Leu Lys Gln Lys Leu Ala Glu Leu Gly Glu Asn Leu Leu Glu Arg
1               5                   10                  15

Phe Leu Glu Leu Val Xaa
            20

<210> SEQ ID NO 406
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 406

Lys Leu Lys Gln Lys Leu Ala Glu Leu Leu Glu Asn Leu Gly Glu Arg
1               5                   10                  15

Phe Leu Asp Leu Val Xaa
            20

<210> SEQ ID NO 407
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 407

Lys Leu Lys Gln Lys Leu Ala Glu Leu Leu Glu Asn Gly Leu Glu Arg
1               5                   10                  15

Phe Leu Asp Leu Val Xaa
            20

<210> SEQ ID NO 408
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 408

Lys Leu Lys Gln Lys Leu Ala Glu Gly Leu Glu Asn Leu Leu Glu Arg
1               5                   10                  15

Phe Leu Asp Leu Val Xaa
            20
```

```
<210> SEQ ID NO 409
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 409

Lys Leu Lys Gln Lys Leu Gly Glu Leu Leu Glu Asn Leu Leu Glu Arg
1               5                   10                  15

Phe Leu Asp Leu Val Xaa
            20

<210> SEQ ID NO 410
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 410

Lys Leu Lys Gln Lys Gly Ala Glu Leu Leu Glu Asn Leu Leu Glu Arg
1               5                   10                  15

Phe Leu Asp Leu Val Xaa
            20

<210> SEQ ID NO 411
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (7)..(7)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=azPip

<400> SEQUENCE: 411

Lys Leu Lys Gln Lys Leu Xaa Glu Leu Leu Glu Asn Leu Leu Glu Arg
1               5                   10                  15

Phe Leu Asp Leu Val Xaa
            20

<210> SEQ ID NO 412
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 412

Lys Leu Lys Gln Lys Leu Ala Glu Leu Leu Glu Asn Leu Leu Glu Arg
```

```
                1               5                  10                 15
Phe Leu Asp Leu Val Xaa
            20

<210> SEQ ID NO 413
<211> LENGTH: 23
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (23)..(23)
<223> OTHER INFORMATION: Xaa=azPip

<400> SEQUENCE: 413

Lys Lys Leu Lys Gln Lys Leu Ala Glu Leu Leu Glu Asn Leu Leu Glu
1               5                  10                 15
Arg Phe Leu Asp Leu Val Xaa
            20

<210> SEQ ID NO 414
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=azPip

<400> SEQUENCE: 414

Lys Leu Lys Gln Lys Leu Ala Glu Leu Xaa Glu Asn Leu Leu Glu Arg
1               5                  10                 15
Phe Leu Asp Leu Val Xaa
            20

<210> SEQ ID NO 415
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 415

Lys Leu Lys Gln Lys Leu Ala Glu Leu Leu Glu Asn Leu Leu Glu Lys
1               5                  10                 15
Phe Leu Asp Leu Val Xaa
            20

<210> SEQ ID NO 416
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (6)..(6)
```

```
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=azPip

<400> SEQUENCE: 416

Lys Leu Lys Gln Lys Xaa Ala Glu Leu Leu Glu Asn Leu Leu Glu Arg
1               5                   10                  15

Phe Leu Asp Leu Val Xaa
            20

<210> SEQ ID NO 417
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 417

Lys Leu Lys Gln Lys Leu Ala Glu Leu Leu Glu Gln Leu Leu Glu Lys
1               5                   10                  15

Phe Leu Asp Leu Val Xaa
            20

<210> SEQ ID NO 418
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=azPip

<400> SEQUENCE: 418

Xaa Leu Xaa Gln Xaa Leu Ala Glu Leu Leu Glu Asn Leu Leu Glu Arg
1               5                   10                  15

Phe Leu Asp Leu Val Xaa
            20

<210> SEQ ID NO 419
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 419
```

```
Lys Leu Lys Gln Lys Leu Ala Glu Leu Leu Glu Asn Trp Leu Glu Arg
1               5                   10                  15

Phe Leu Asp Leu Val Xaa
            20

<210> SEQ ID NO 420
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 420

Lys Leu Lys Gln Lys Leu Ala Glu Leu Leu Glu Asn Leu Leu Glu Arg
1               5                   10                  15

Leu Leu Asp Leu Val Xaa
            20

<210> SEQ ID NO 421
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 421

Lys Leu Lys Gln Lys Leu Ala Glu Leu Leu Glu Gln Leu Leu Glu Lys
1               5                   10                  15

Phe Leu Glu Leu Val Xaa
            20

<210> SEQ ID NO 422
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 422

Lys Leu Lys Gln Lys Leu Ala Glu Leu Leu Glu Gln Leu Leu Glu Lys
1               5                   10                  15

Phe Leu Glu Leu Leu Xaa
            20

<210> SEQ ID NO 423
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip
```

<400> SEQUENCE: 423

Lys Leu Lys Lys Gln Leu Ala Glu Leu Leu Glu Asn Leu Leu Glu Arg
1               5                   10                  15

Phe Leu Asp Leu Val Xaa
            20

<210> SEQ ID NO 424
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=azPip

<400> SEQUENCE: 424

Lys Leu Lys Gln Lys Leu Ala Glu Leu Xaa Glu Asn Leu Leu Glu Arg
1               5                   10                  15

Phe Phe Asp Leu Val Xaa
            20

<210> SEQ ID NO 425
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 425

Lys Leu Lys Gln Lys Leu Leu Glu Leu Leu Glu Asn Leu Leu Glu Arg
1               5                   10                  15

Phe Leu Asp Leu Val Xaa
            20

<210> SEQ ID NO 426
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (9)..(9)
<223> OTHER INFORMATION: Xaa=Nal
<220> FEATURE:
<221> NAME/KEY: MISC_FEATURE
<222> LOCATION: (22)..(22)
<223> OTHER INFORMATION: Xaa=azPip

<400> SEQUENCE: 426

Lys Leu Lys Gln Lys Leu Ala Glu Xaa Leu Glu Asn Leu Leu Glu Arg
1               5                   10                  15

Phe Leu Asp Leu Val Xaa
            20

<210> SEQ ID NO 427
<211> LENGTH: 22

```
-continued

<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 427

Lys Leu Lys Gln Lys Leu Ala Glu Trp Leu Glu Asn Leu Leu Glu Arg
1               5                   10                  15

Phe Leu Asp Leu Val Xaa
            20

<210> SEQ ID NO 428
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (16)..(16)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=azPip

<400> SEQUENCE: 428

Xaa Leu Xaa Gln Xaa Leu Ala Glu Leu Leu Glu Asn Leu Leu Glu Xaa
1               5                   10                  15

Phe Leu Asp Leu Val Xaa
            20

<210> SEQ ID NO 429
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 429

Lys Leu Lys Gln Lys Leu Phe Glu Leu Leu Glu Asn Leu Leu Glu Arg
1               5                   10                  15

Phe Leu Asp Leu Val Xaa
            20

<210> SEQ ID NO 430
<211> LENGTH: 22
<212> TYPE: PRT
<213> ORGANISM: Artificial Sequence
<220> FEATURE:
```

```
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 430

Lys Leu Lys Lys Gln Leu Ala Glu Leu Leu Glu Arg Leu Leu Asp Asn
1               5                   10                  15

Phe Leu Glu Leu Val Xaa
            20

<210> SEQ ID NO 431
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 431

Lys Leu Lys Gln Lys Leu Ala Glu Leu Leu Glu Arg Leu Leu Asp Asn
1               5                   10                  15

Phe Leu Glu Leu Val Xaa
            20

<210> SEQ ID NO 432
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 432

Lys Leu Lys Gln Arg Leu Ala Asp Leu Leu Glu Asn Leu Leu Glu Lys
1               5                   10                  15

Phe Leu Glu Leu Val Xaa
            20

<210> SEQ ID NO 433
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 433

Lys Leu Lys Lys Gln Leu Ala Glu Leu Leu Asn Glu Leu Leu Glu Arg
1               5                   10                  15

Phe Leu Asp Leu Val Xaa
            20

<210> SEQ ID NO 434
<211> LENGTH: 22
<212> TYPE: PRT
<213> ORGANISM: Artificial Sequence
```

```
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 434

Lys Leu Lys Lys Asn Leu Ala Gln Leu Leu Asp Glu Leu Leu Arg Glu
1               5                   10                  15

Phe Leu Glu Leu Val Xaa
            20

<210> SEQ ID NO 435
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 435

Lys Leu Lys Gln Asn Leu Ala Lys Leu Leu Asp Glu Leu Leu Arg Glu
1               5                   10                  15

Phe Leu Glu Leu Val Xaa
            20

<210> SEQ ID NO 436
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 436

Lys Leu Lys Gln Lys Leu Ala Glu Leu Leu Gln Leu Leu Asp Lys
1               5                   10                  15

Phe Leu Glu Leu Ala Xaa
            20

<210> SEQ ID NO 437
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 437

Lys Leu Lys Gln Lys Leu Ala Glu Leu Leu Glu Gln Leu Leu Glu Lys
1               5                   10                  15

Leu Leu Glu Leu Leu Xaa
            20

<210> SEQ ID NO 438
<211> LENGTH: 22
<212> TYPE: PRT
```

```
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (10)..(10)
<223> OTHER INFORMATION: Xaa=Aib
<220> FEATURE:
<221> NAME/KEY: MISC_FEATURE
<222> LOCATION: (22)..(22)
<223> OTHER INFORMATION: Xaa=azPip

<400> SEQUENCE: 438

Lys Leu Lys Gln Lys Leu Ala Glu Leu Xaa Glu Asn Leu Leu Glu Leu
1               5                   10                  15

Phe Leu Asp Leu Val Xaa
            20

<210> SEQ ID NO 439
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 439

Lys Leu Lys Lys Lys Leu Ala Lys Leu Leu Glu Glu Leu Leu Glu Arg
1               5                   10                  15

Phe Leu Asp Leu Val Xaa
            20

<210> SEQ ID NO 440
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 440

Lys Leu Lys Lys Gln Leu Ala Glu Leu Leu Glu Arg Leu Leu Glu Asn
1               5                   10                  15

Phe Leu Asp Leu Val Xaa
            20

<210> SEQ ID NO 441
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=D-Val
<220> FEATURE:
<221> NAME/KEY: MISC_FEATURE
<222> LOCATION: (22)..(22)
<223> OTHER INFORMATION: Xaa=azPip

<400> SEQUENCE: 441

Lys Leu Lys Gln Lys Leu Ala Glu Leu Leu Glu Asn Leu Leu Glu Arg
```

```
1               5                   10                  15
Phe Leu Asp Leu Xaa Xaa
            20

<210> SEQ ID NO 442
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=azPip

<400> SEQUENCE: 442

Lys Leu Lys Gln Lys Leu Ala Glu Leu Leu Glu Asn Leu Leu Glu Arg
1               5                   10                  15

Phe Leu Xaa

<210> SEQ ID NO 443
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 443

Lys Lys Lys Gln Lys Leu Ala Glu Leu Leu Glu Asn Leu Leu Glu Arg
1               5                   10                  15

Phe Leu Asp Leu Val Xaa
            20

<210> SEQ ID NO 444
<211> LENGTH: 19
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (19)..(19)
<223> OTHER INFORMATION: Xaa=azPip

<400> SEQUENCE: 444

Gln Lys Leu Ala Glu Leu Leu Glu Asn Leu Leu Glu Arg Phe Leu Asp
1               5                   10                  15

Leu Val Xaa

<210> SEQ ID NO 445
<211> LENGTH: 21
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (21)..(21)
<223> OTHER INFORMATION: Xaa=azPip

<400> SEQUENCE: 445

Lys Leu Lys Gln Lys Leu Ala Glu Leu Leu Glu Asn Leu Leu Glu Arg
1               5                   10                  15
```

Phe Leu Asp Leu Xaa
            20

<210> SEQ ID NO 446
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 446

Lys Leu Lys Lys Gln Leu Ala Asn Leu Leu Glu Asp Leu Leu Arg Glu
1               5                   10                  15

Phe Leu Glu Leu Val Xaa
            20

<210> SEQ ID NO 447
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=azPip

<400> SEQUENCE: 447

Glu Leu Leu Glu Asn Leu Leu Glu Arg Phe Leu Asp Leu Val Xaa
1               5                   10                  15

<210> SEQ ID NO 448
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (15)..(15)
<223> OTHER INFORMATION: Xaa=azPip

<400> SEQUENCE: 448

Lys Leu Lys Gln Lys Leu Ala Glu Leu Leu Glu Asn Leu Leu Xaa
1               5                   10                  15

<210> SEQ ID NO 449
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPip

<400> SEQUENCE: 449

Lys Leu Lys Gln Leu Leu Glu Asn Leu Leu Glu Arg Phe Leu Asp Leu
1               5                   10                  15

Val Xaa

<210> SEQ ID NO 450

```
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPip

<400> SEQUENCE: 450

Lys Leu Lys Gln Lys Leu Glu Glu Leu Leu Glu Arg Phe Leu Asp Leu
1               5                   10                  15

Val Xaa

<210> SEQ ID NO 451
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPip

<400> SEQUENCE: 451

Lys Leu Lys Gln Lys Leu Glu Glu Leu Leu Glu Lys Phe Leu Glu Leu
1               5                   10                  15

Val Xaa

<210> SEQ ID NO 452
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPip

<400> SEQUENCE: 452

Lys Leu Lys Gln Lys Leu Leu Glu Leu Leu Glu Arg Phe Leu Asp Leu
1               5                   10                  15

Val Xaa

<210> SEQ ID NO 453
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPip

<400> SEQUENCE: 453

Lys Leu Lys Gln Trp Leu Glu Asn Leu Leu Glu Arg Phe Leu Asp Leu
1               5                   10                  15

Val Xaa

<210> SEQ ID NO 454
<211> LENGTH: 18
<212> TYPE: PRT
<213> ORGANISM: Artificial Sequence
```

```
<220> FEATURE:
<223> OTHER INFORMATION: ApoA-I mimic
<220> FEATURE:
<221> NAME/KEY: MISC_FEATURE
<222> LOCATION: (18)..(18)
<223> OTHER INFORMATION: Xaa=azPip

<400> SEQUENCE: 454

Lys Leu Lys Lys Gln Leu Glu Glu Leu Leu Glu Arg Phe Leu Asp Leu
1               5                   10                  15

Val Xaa

<210> SEQ ID NO 455
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=azPip

<400> SEQUENCE: 455

Lys Lys Leu Gln Leu Leu Ala Glu Leu Leu Glu Arg Phe Ala Asp Leu
1               5                   10                  15

Val Xaa

<210> SEQ ID NO 456
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=azPip

<400> SEQUENCE: 456

Lys Lys Leu Gln Ala Leu Ala Glu Leu Leu Glu Arg Phe Ala Asp Leu
1               5                   10                  15

Val Xaa

<210> SEQ ID NO 457
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=azPip

<400> SEQUENCE: 457

Lys Leu Lys Gln Lys Leu Glu Glu Trp Gly Glu Arg Phe Leu Asp Leu
1               5                   10                  15

Val Xaa

<210> SEQ ID NO 458
<211> LENGTH: 18
<212> TYPE: PRT
<213> ORGANISM: Artificial Sequence
<220> FEATURE:
<223> OTHER INFORMATION: APO A-1 mimic
<220> FEATURE:
```

```
<221> NAME/KEY: MISC_FEATURE
<222> LOCATION: (18)..(18)
<223> OTHER INFORMATION: Xaa=azPip

<400> SEQUENCE: 458

Lys Leu Lys Lys Gln Leu Asp Glu Leu Leu Arg Glu Phe Leu Glu Leu
1               5                   10                  15

Val Xaa

<210> SEQ ID NO 459
<211> LENGTH: 18
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (18)..(18)
<223> OTHER INFORMATION: Xaa=azPip

<400> SEQUENCE: 459

Lys Leu Lys Gln Glu Leu Lys Glu Leu Leu Glu Arg Phe Leu Asp Leu
1               5                   10                  15

Val Xaa

<210> SEQ ID NO 460
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(22)
<223> OTHER INFORMATION: N-terminal acetylated and C-terminal amidated
<220> FEATURE:
<221> NAME/KEY: MISC_FEATURE
<222> LOCATION: (22)..(22)
<223> OTHER INFORMATION: Xaa=azPip

<400> SEQUENCE: 460

Lys Leu Lys Gln Lys Leu Ala Glu Leu Gly Glu Asn Leu Leu Glu Arg
1               5                   10                  15

Phe Leu Asp Leu Val Xaa
            20

<210> SEQ ID NO 461
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 461

Lys Leu Lys Gln Lys Leu Glu Glu Leu Leu Glu Arg Leu Leu Asp Leu
1               5                   10                  15

Val Xaa

<210> SEQ ID NO 462
```

```
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 462

Lys Leu Lys Gln Lys Leu Glu Glu Leu Leu Glu Lys Phe Leu Asp Leu
1               5                   10                  15

Val Xaa

<210> SEQ ID NO 463
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 463

Lys Leu Lys Gln Lys Leu Glu Glu Leu Leu Glu Arg Phe Leu Asp Leu
1               5                   10                  15

Val Xaa

<210> SEQ ID NO 464
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 464

Lys Leu Lys Gln Lys Leu Glu Glu Leu Leu Glu Arg Phe Leu Glu Leu
1               5                   10                  15

Val Xaa

<210> SEQ ID NO 465
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
```

```
<221> NAME/KEY: MISC_FEATURE
<222> LOCATION: (18)..(18)
<223> OTHER INFORMATION: Xaa=azPip

<400> SEQUENCE: 465

Lys Leu Lys Gln Lys Leu Glu Glu Leu Leu Glu Lys Phe Leu Glu Leu
1               5                   10                  15

Val Xaa

<210> SEQ ID NO 466
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 466

Lys Leu Lys Asn Lys Leu Glu Glu Leu Leu Glu Arg Phe Leu Asp Leu
1               5                   10                  15

Val Xaa

<210> SEQ ID NO 467
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 467

Lys Leu Lys Gln Lys Leu Glu Glu Leu Leu Glu Arg Phe Leu Asp Leu
1               5                   10                  15

Leu Xaa

<210> SEQ ID NO 468
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 468

Lys Leu Lys Gln Lys Leu Glu Glu Trp Leu Glu Arg Phe Leu Asp Leu
1               5                   10                  15

Val Xaa
```

<210> SEQ ID NO 469
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 469

Lys Leu Lys Gln Lys Leu Glu Glu Leu Leu Glu Lys Phe Leu Asp Leu
1               5                   10                  15

Leu Xaa

<210> SEQ ID NO 470
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 470

Arg Leu Lys Gln Arg Leu Glu Glu Leu Leu Asp Lys Phe Leu Glu Leu
1               5                   10                  15

Ala Xaa

<210> SEQ ID NO 471
<211> LENGTH: 18
<212> TYPE: PRT
<213> ORGANISM: Artificial Sequence
<220> FEATURE:
<223> OTHER INFORMATION: ApoA-1 mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 471

Lys Leu Lys Gln Lys Leu Glu Glu Leu Leu Glu Arg Phe Phe Asp Leu
1               5                   10                  15

Val Xaa

<210> SEQ ID NO 472
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE

```
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 472

Lys Leu Lys Gln Lys Leu Glu Glu Leu Trp Glu Arg Phe Leu Asp Leu
1               5                   10                  15

Val Xaa

<210> SEQ ID NO 473
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 473

Lys Leu Lys Gln Lys Leu Glu Glu Leu Leu Glu Lys Leu Leu Glu Leu
1               5                   10                  15

Leu Xaa

<210> SEQ ID NO 474
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 474

Lys Leu Lys Gln Lys Leu Glu Glu Leu Leu Glu Lys Leu Leu Glu Leu
1               5                   10                  15

Val Xaa

<210> SEQ ID NO 475
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 475

Lys Leu Arg Gln Arg Leu Glu Glu Leu Leu Asp Lys Phe Leu Glu Leu
```

1               5                   10                  15

Ala Xaa

<210> SEQ ID NO 476
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=azPip

<400> SEQUENCE: 476

Xaa Leu Xaa Gln Xaa Leu Glu Glu Leu Leu Glu Arg Phe Leu Asp Leu
1               5                   10                  15

Val Xaa

<210> SEQ ID NO 477
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (5)..(5)
<223> OTHER INFORMATION: Xaa=Orn
<220> FEATURE:
<221> NAME/KEY: MISC_FEATURE
<222> LOCATION: (12)..(12)
<223> OTHER INFORMATION: Xaa=Orn
<220> FEATURE:
<221> NAME/KEY: MISC_FEATURE
<222> LOCATION: (18)..(18)
<223> OTHER INFORMATION: Xaa=azPip

<400> SEQUENCE: 477

Lys Leu Xaa Gln Xaa Leu Glu Glu Leu Leu Glu Xaa Phe Leu Asp Leu
1               5                   10                  15

Val Xaa

<210> SEQ ID NO 478
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 478

Lys Leu Arg Gln Arg Phe Glu Glu Leu Leu Asp Lys Phe Leu Glu Leu
1               5                   10                  15

Ala Xaa

<210> SEQ ID NO 479
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 479

Lys Leu Lys Gln Lys Trp Glu Glu Leu Leu Glu Arg Phe Leu Asp Leu
1               5                   10                  15

Val Xaa

<210> SEQ ID NO 480
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 480

Lys Leu Lys Gln Leu Leu Glu Asn Leu Leu Glu Arg Phe Leu Asp Leu
1               5                   10                  15

Val Xaa

<210> SEQ ID NO 481
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

```
<400> SEQUENCE: 481

Lys Leu Lys Gln Lys Leu Glu Glu Leu Gly Glu Arg Phe Leu Asp Leu
1               5                   10                  15

Val Xaa

<210> SEQ ID NO 482
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 482

Lys Leu Lys Gln Lys Gly Glu Glu Leu Leu Glu Arg Phe Leu Asp Leu
1               5                   10                  15

Val Xaa

<210> SEQ ID NO 483
<211> LENGTH: 18
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(18)
<223> OTHER INFORMATION: N-terminal acetylated and C-terminal amidated
<220> FEATURE:
<221> NAME/KEY: MISC_FEATURE
<222> LOCATION: (18)..(18)
<223> OTHER INFORMATION: Xaa=azPip

<400> SEQUENCE: 483

Lys Leu Lys Gln Lys Leu Glu Glu Leu Glu Lys Phe Leu Glu Leu
1               5                   10                  15

Leu Xaa

<210> SEQ ID NO 484
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=azPip

<400> SEQUENCE: 484

Lys Leu Lys Gln Glu Leu Leu Glu Arg Phe Leu Asp Leu Val Xaa
1               5                   10                  15

<210> SEQ ID NO 485
<211> LENGTH: 16
<212> TYPE: PRT
```

```
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=azPip

<400> SEQUENCE: 485

Lys Gln Lys Leu Glu Glu Leu Leu Glu Arg Phe Leu Asp Leu Val Xaa
1               5                   10                  15

<210> SEQ ID NO 486
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=azPip

<400> SEQUENCE: 486

Lys Gln Lys Leu Lys Glu Leu Leu Glu Arg Phe Leu Asp Leu Val Xaa
1               5                   10                  15

<210> SEQ ID NO 487
<211> LENGTH: 15
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(15)
<223> OTHER INFORMATION: N-terminal acetylated and C-terminal amidated
<220> FEATURE:
<221> NAME/KEY: MISC_FEATURE
<222> LOCATION: (15)..(15)
<223> OTHER INFORMATION: Xaa=azPip

<400> SEQUENCE: 487

Lys Gln Leu Lys Glu Leu Leu Glu Arg Phe Leu Asp Leu Val Xaa
1               5                   10                  15

<210> SEQ ID NO 488
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=azPip

<400> SEQUENCE: 488

Lys Gln Lys Leu Ala Glu Leu Leu Glu Arg Phe Leu Asp Leu Val Xaa
1               5                   10                  15
```

```
<210> SEQ ID NO 489
<211> LENGTH: 16
<212> TYPE: PRT
<213> ORGANISM: Artificial Sequence
<220> FEATURE:
<223> OTHER INFORMATION: ApoA-I mimic
<220> FEATURE:
<221> NAME/KEY: MISC_FEATURE
<222> LOCATION: (1)..(16)
<223> OTHER INFORMATION: N-terminal acetylated and C-terminal amidated
<220> FEATURE:
<221> NAME/KEY: MISC_FEATURE
<222> LOCATION: (16)..(16)
<223> OTHER INFORMATION: Xaa=azPip

<400> SEQUENCE: 489

Lys Gln Lys Leu Glu Asn Leu Leu Glu Arg Phe Leu Asp Leu Val Xaa
1               5                   10                  15

<210> SEQ ID NO 490
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 490

Lys Leu Lys Lys Gln Leu Ala Asp Leu Leu Arg Glu Leu Leu Asn Glu
1               5                   10                  15

Phe Leu Glu Phe Val Xaa
            20

<210> SEQ ID NO 491
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 491

Lys Leu Lys Lys Gln Leu Ala Asp Leu Gly Arg Glu Leu Leu Asn Glu
1               5                   10                  15

Phe Leu Glu Leu Val Xaa
            20

<210> SEQ ID NO 492
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 492

Lys Leu Lys Lys Gln Leu Ala Asp Leu Leu Arg Glu Trp Leu Asn Leu
1               5                   10                  15
```

Phe Leu Glu Leu Val Xaa
            20

<210> SEQ ID NO 493
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 493

Lys Leu Lys Lys Gln Leu Ala Asp Leu Leu Arg Glu Leu Leu Asn Leu
1               5                   10                  15

Phe Leu Glu Leu Val Xaa
            20

<210> SEQ ID NO 494
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 494

Lys Leu Lys Lys Gln Leu Trp Asp Leu Leu Arg Glu Leu Leu Asn Leu
1               5                   10                  15

Phe Leu Glu Leu Val Xaa
            20

<210> SEQ ID NO 495
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 495

Lys Leu Lys Lys Gln Leu Trp Asp Leu Leu Arg Glu Leu Leu Asn Glu
1               5                   10                  15

Phe Leu Glu Leu Val Xaa
            20

<210> SEQ ID NO 496
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 496

Lys Leu Lys Lys Gln Trp Ala Asp Leu Leu Arg Glu Leu Leu Asn Glu
1               5                   10                  15

Phe Leu Glu Leu Val Xaa
            20

<210> SEQ ID NO 497
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 497

Lys Leu Lys Lys Gln Leu Leu Asp Leu Leu Arg Glu Leu Leu Asn Glu
1               5                   10                  15

Phe Leu Glu Leu Val Xaa
            20

<210> SEQ ID NO 498
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 498

Lys Leu Lys Lys Gln Leu Ala Asp Gly Leu Arg Glu Leu Leu Asn Leu
1               5                   10                  15

Phe Leu Glu Leu Val Xaa
            20

<210> SEQ ID NO 499
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 499

Lys Leu Lys Lys Gln Trp Ala Asp Leu Leu Arg Glu Leu Leu Asn Leu
1               5                   10                  15

Phe Leu Glu Leu Val Xaa
            20

<210> SEQ ID NO 500
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (4)..(4)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=azPro

<400> SEQUENCE: 500

Xaa Leu Xaa Xaa Gln Leu Ala Asp Leu Leu Arg Glu Leu Leu Asn Glu
1               5                   10                  15

Phe Leu Glu Leu Val Xaa
            20

<210> SEQ ID NO 501
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 501

Lys Leu Lys Lys Gln Leu Ala Asp Leu Leu Arg Glu Leu Leu Gln Glu
1               5                   10                  15

Phe Leu Glu Leu Val Xaa
            20

<210> SEQ ID NO 502
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 502

Lys Leu Lys Lys Asn Leu Ala Asp Leu Leu Arg Glu Leu Leu Asn Glu
1               5                   10                  15

Phe Leu Glu Leu Val Xaa
            20

<210> SEQ ID NO 503
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPro

<400> SEQUENCE: 503

Lys Leu Lys Lys Gln Leu Ala Asp Leu Leu Arg Asp Leu Leu Asn Glu
1               5                   10                  15

Phe Leu Glu Leu Val Xaa
            20

<210> SEQ ID NO 504

```
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 504

Lys Leu Lys Lys Gln Leu Ala Asp Leu Leu Arg Glu Leu Leu Asn Glu
1               5                   10                  15

Phe Leu Glu Leu Val Xaa
            20

<210> SEQ ID NO 505
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 505

Lys Leu Lys Lys Gln Leu Ala Asp Leu Gly Arg Glu Leu Leu Asn Glu
1               5                   10                  15

Phe Leu Glu Leu Val Xaa
            20

<210> SEQ ID NO 506
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 506

Lys Leu Lys Lys Gln Leu Ala Asp Leu Leu Arg Glu Trp Leu Asn Leu
1               5                   10                  15

Phe Leu Glu Leu Val Xaa
            20

<210> SEQ ID NO 507
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 507

Lys Leu Lys Lys Gln Leu Ala Asp Leu Leu Arg Glu Leu Leu Asn Leu
1               5                   10                  15

Phe Leu Glu Leu Val Xaa
            20
```

```
<210> SEQ ID NO 508
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 508

Lys Leu Lys Lys Gln Leu Trp Asp Leu Leu Arg Glu Leu Leu Asn Leu
1               5                   10                  15

Phe Leu Glu Leu Val Xaa
            20

<210> SEQ ID NO 509
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 509

Lys Leu Lys Lys Gln Leu Trp Asp Leu Leu Arg Glu Leu Leu Asn Glu
1               5                   10                  15

Phe Leu Glu Leu Val Xaa
            20

<210> SEQ ID NO 510
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 510

Lys Leu Lys Lys Gln Trp Ala Asp Leu Leu Arg Glu Leu Leu Asn Glu
1               5                   10                  15

Phe Leu Glu Leu Val Xaa
            20

<210> SEQ ID NO 511
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 511

Lys Leu Lys Lys Gln Leu Leu Asp Leu Leu Arg Glu Leu Leu Asn Glu
1               5                   10                  15

Phe Leu Glu Leu Val Xaa
            20
```

<210> SEQ ID NO 512
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 512

Lys Leu Lys Lys Gln Leu Ala Asp Gly Leu Arg Glu Leu Leu Asn Leu
1               5                   10                  15

Phe Leu Glu Leu Val Xaa
            20

<210> SEQ ID NO 513
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 513

Lys Leu Lys Lys Gln Trp Ala Asp Leu Leu Arg Glu Leu Leu Asn Leu
1               5                   10                  15

Phe Leu Glu Leu Val Xaa
            20

<210> SEQ ID NO 514
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (4)..(4)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=Pip

<400> SEQUENCE: 514

Xaa Leu Xaa Xaa Gln Leu Ala Asp Leu Leu Arg Glu Leu Leu Asn Glu
1               5                   10                  15

Phe Leu Glu Leu Val Xaa
            20

<210> SEQ ID NO 515
<211> LENGTH: 22
<212> TYPE: PRT
<213> ORGANISM: Artificial Sequence
<220> FEATURE:
<223> OTHER INFORMATION: APO A-1 mimic

```
<220> FEATURE:
<221> NAME/KEY: MISC_FEATURE
<222> LOCATION: (22)..(22)
<223> OTHER INFORMATION: Xaa=Pip

<400> SEQUENCE: 515

Lys Leu Lys Lys Gln Leu Ala Asp Leu Leu Arg Glu Leu Leu Gln Glu
1               5                   10                  15

Phe Leu Glu Leu Val Xaa
            20

<210> SEQ ID NO 516
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 516

Lys Leu Lys Lys Asn Leu Ala Asp Leu Leu Arg Glu Leu Leu Asn Glu
1               5                   10                  15

Phe Leu Glu Leu Val Xaa
            20

<210> SEQ ID NO 517
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=Pip

<400> SEQUENCE: 517

Lys Leu Lys Lys Gln Leu Ala Asp Leu Leu Arg Asp Leu Leu Asn Glu
1               5                   10                  15

Phe Leu Glu Leu Val Xaa
            20

<210> SEQ ID NO 518
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 518

Lys Leu Lys Lys Gln Leu Ala Asp Leu Leu Arg Glu Leu Leu Asn Glu
1               5                   10                  15

Phe Leu Glu Phe Val Xaa
            20

<210> SEQ ID NO 519
<211> LENGTH: 22
<212> TYPE: PRT
<213> ORGANISM: Artificial Sequence
<220> FEATURE:
```

<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 519

Lys Leu Lys Lys Gln Leu Ala Asp Leu Gly Arg Glu Leu Leu Asn Glu
1               5                   10                  15

Phe Leu Glu Leu Val Xaa
            20

<210> SEQ ID NO 520
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 520

Lys Leu Lys Lys Gln Leu Ala Asp Leu Leu Arg Glu Trp Leu Asn Leu
1               5                   10                  15

Phe Leu Glu Leu Val Xaa
            20

<210> SEQ ID NO 521
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 521

Lys Leu Lys Lys Gln Leu Ala Asp Leu Leu Arg Glu Leu Leu Asn Leu
1               5                   10                  15

Phe Leu Glu Leu Val Xaa
            20

<210> SEQ ID NO 522
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 522

Lys Leu Lys Lys Gln Leu Trp Asp Leu Leu Arg Glu Leu Leu Asn Leu
1               5                   10                  15

Phe Leu Glu Leu Val Xaa
            20

<210> SEQ ID NO 523
<211> LENGTH: 22
<212> TYPE: PRT
<213> ORGANISM: Artificial Sequence

```
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 523

Lys Leu Lys Lys Gln Leu Trp Asp Leu Leu Arg Glu Leu Leu Asn Glu
1               5                   10                  15

Phe Leu Glu Leu Val Xaa
            20

<210> SEQ ID NO 524
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 524

Lys Leu Lys Lys Gln Trp Ala Asp Leu Leu Arg Glu Leu Leu Asn Glu
1               5                   10                  15

Phe Leu Glu Leu Val Xaa
            20

<210> SEQ ID NO 525
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 525

Lys Leu Lys Lys Gln Leu Leu Asp Leu Leu Arg Glu Leu Leu Asn Glu
1               5                   10                  15

Phe Leu Glu Leu Val Xaa
            20

<210> SEQ ID NO 526
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 526

Lys Leu Lys Lys Gln Leu Ala Asp Gly Leu Arg Glu Leu Leu Asn Leu
1               5                   10                  15

Phe Leu Glu Leu Val Xaa
            20

<210> SEQ ID NO 527
<211> LENGTH: 22
<212> TYPE: PRT
```

<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 527

Lys Leu Lys Lys Gln Trp Ala Asp Leu Leu Arg Glu Leu Leu Asn Leu
1               5                   10                  15

Phe Leu Glu Leu Val Xaa
            20

<210> SEQ ID NO 528
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (1)..(1)
<223> OTHER INFORMATION: Xaa=Orn
<220> FEATURE:
<221> NAME/KEY: MISC_FEATURE
<222> LOCATION: (3)..(3)
<223> OTHER INFORMATION: Xaa=Orn
<220> FEATURE:
<221> NAME/KEY: MISC_FEATURE
<222> LOCATION: (4)..(4)
<223> OTHER INFORMATION: Xaa=Orn
<220> FEATURE:
<221> NAME/KEY: MISC_FEATURE
<222> LOCATION: (22)..(22)
<223> OTHER INFORMATION: Xaa=azPip

<400> SEQUENCE: 528

Xaa Leu Xaa Xaa Gln Leu Ala Asp Leu Leu Arg Glu Leu Leu Asn Glu
1               5                   10                  15

Phe Leu Glu Leu Val Xaa
            20

<210> SEQ ID NO 529
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 529

Lys Leu Lys Lys Gln Leu Ala Asp Leu Leu Arg Glu Leu Leu Gln Glu
1               5                   10                  15

Phe Leu Glu Leu Val Xaa
            20

<210> SEQ ID NO 530
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

```
<400> SEQUENCE: 530

Lys Leu Lys Lys Asn Leu Ala Asp Leu Leu Arg Glu Leu Leu Asn Glu
1               5                   10                  15

Phe Leu Glu Leu Val Xaa
            20

<210> SEQ ID NO 531
<211> LENGTH: 22
<212> TYPE: PRT
<213> ORGANISM: Artificial Sequence
<220> FEATURE:
<223> OTHER INFORMATION: APO A-1 mimic
<220> FEATURE:
<221> NAME/KEY: MISC_FEATURE
<222> LOCATION: (22)..(22)
<223> OTHER INFORMATION: Xaa=azPip

<400> SEQUENCE: 531

Lys Leu Lys Lys Gln Leu Ala Asp Leu Leu Arg Asp Leu Leu Asn Glu
1               5                   10                  15

Phe Leu Glu Leu Val Xaa
            20
```

APOLIPOPROTEIN A-I MIMICS

CROSS-REFERENCE TO RELATED APPLICATIONS

This application is a division of U.S. application Ser. No. 13/766,561, filed Feb. 13, 2013, which is a continuation of U.S. application Ser. No. 12/705,094, now U.S. Pat. No. 8,378,068, filed Feb. 12, 2010, which claims the benefit of U.S. Provisional Application Serial Nos. 61/152,962, filed Feb. 16, 2009, 61/152,966, filed Feb. 16, 2009, and 61/152,960, filed Feb. 16, 2009, each of which is incorporated by reference herein in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CERE_002_08US_SeqList.txt, date recorded: Feb. 5, 2015, file size 201 kilobytes).

FIELD OF THE INVENTION

The invention provides peptides, compositions thereof, and methods for treating or preventing dyslipidemia, a cardiovascular disease, endothelial dysfunction, a macrovascular disorder, or a microvascular disorder.

BACKGROUND OF THE INVENTION

Cholesterol circulating in the human body is carried by plasma lipoproteins, which are particles of complex lipid and protein composition that transport lipids in the blood. Two types of plasma lipoproteins that carry cholesterol are low density lipoproteins ("LDL") and high density lipoproteins ("HDL"). LDL particles are believed to be responsible for the delivery of cholesterol from the liver (where it is synthesized or obtained from dietary sources) to extrahepatic tissues in the body. HDL particles, on the other hand, are believed to aid in the transport of cholesterol from the extrahepatic tissues to the liver, where the cholesterol is catabolized and eliminated. Such transport of cholesterol from the extrahepatic tissues to the liver is referred to as "reverse cholesterol transport."

The reverse cholesterol transport ("RCT") pathway has three main steps: (i) cholesterol efflux, i.e., the initial removal of cholesterol from various pools of peripheral cells; (ii) cholesterol esterification by the action of lecithin:cholesterol acyltransferase ("LCAT"), thereby preventing a re-entry of effluxed cholesterol into cells; and (iii) uptake of the cholesteryl ester by HDL and delivery of the HDL-cholesteryl ester complex to liver cells.

The RCT pathway is mediated by HDL particles. Each HDL particle has a lipid component and a protein component. The lipid component of HDL can be a phospholipid, cholesterol (or a cholesterol ester), or a triglyceride. The protein component of HDL is primarily made up of ApoA-I. ApoA-I is synthesized by the liver and small intestine as preproapolipoprotein which is secreted as a proprotein that is rapidly cleaved to generate a mature polypeptide having 243 amino acid residues. ApoA-I is primarily made up of 6 to 8 different repeat units made up of 22 amino acid residues spaced by a linker moiety which is often proline, and in some cases is a moiety made up of several residues. ApoA-I forms three types of stable complexes with lipids: small, lipid-poor complexes referred to as pre-β-1 HDL; flattened discoidal particles containing polar lipids (phospholipid and cholesterol) referred to as pre-β-2 HDL; and spherical particles containing both polar and nonpolar lipids, referred to as spherical or mature HDL ($HDL_3$ and $HDL_2$).

Attempts have been made to recombinantly produce and administer ApoA-I to patients to protect against atherosclerotic disease. However, there are many pitfalls associated with the production and use of ApoA-I, making it less than ideal as a drug; e.g., ApoA-I is a large protein that is difficult and expensive to produce, and significant manufacturing and reproducibility problems must be overcome with respect to stability during storage, delivery of an active product and half-life in vivo.

In view of these drawbacks, attempts have been made to produce peptides that can mimic the activity of ApoA-I in vivo. There is a need in the art for the development of additional peptides that can mimic the activity of ApoA-I in vivo, which are simple and cost-effective to produce.

SUMMARY OF THE INVENTION

In one embodiment, the invention provides 22- to 29-residue peptides having the following Formula I $$R^1\text{-}Y^1\text{-}X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13}\text{-}X^{14}\text{-}X^{15}\text{-}X^{16}\text{-}X^{17}\text{-}X^{18}\text{-}X^{19}\text{-}X^{20}\text{-}X^{21}\text{-}X^{22}\text{-}X^{23}\text{-}Y^2\text{-}R^2$$

Formula I and pharmaceutically acceptable salts thereof, wherein:

$X^1$ is absent or an achiral, D-, or L-basic amino acid residue;

$X^2$ is an achiral, D-, or L-basic amino acid residue;

$X^3$ is an achiral, D-, or L-aliphatic amino acid residue;

$X^4$ is an achiral, D-, or L-basic amino acid residue;

$X^5$ is Gln, Asn, D-Gln, D-Asn, or an achiral, D-, or L-basic amino acid residue;

$X^6$ is an achiral, D-, or L-basic amino acid residue;

$X^7$ is an achiral, D-, or L-hydrophobic amino acid residue;

$X^8$ is an achiral, D-, or L-hydrophobic amino acid residue;

$X^9$ is an achiral, D-, or L-hydrophilic amino acid residue;

$X^{10}$ is Leu, Trp, Gly, Nal, D-Leu, D-Trp, or D-Nal;

$X^{11}$ is Gly or an achiral, D-, or L-aliphatic amino acid residue;

$X^{12}$ is an achiral, D-, or L-hydrophilic amino acid residue;

$X^{13}$ is an achiral, D-, or L-hydrophilic amino acid residue;

$X^{14}$ is Leu, Trp, Gly, D-Leu, or D-Trp;

$X^{15}$ is Leu, Gly, or D-Leu;

$X^{16}$ is an achiral, D-, or L-acidic amino acid residue;

$X^{17}$ is an achiral, D-, or L-hydrophilic amino acid residue;

$X^{18}$ is Leu, Phe, D-Leu, or D-Phe;

$X^{19}$ is Leu, Phe, D-Leu, or D-Phe;

$X^{20}$ is an achiral, D-, or L-acidic amino acid residue;

$X^{21}$ is Leu, Phe, D-Leu, or D-Phe;

$X^{22}$ is an achiral, D-, or L-aliphatic amino acid residue; and $X^{23}$ is Inp, Nip, azPro, Pip, azPip, D-Nip, or D-Pip;

$Y^1$ is absent or an amino acid sequence having from 1 to 7 residues;

$Y^2$ is absent or an amino acid sequence having from 1 to 7 residues;

$R^1$ is H or an amino protecting group;

$R^2$ is OH or a carboxyl protecting group;

wherein:

a) each chiral amino acid residue is an L-amino acid residue;

b) each chiral amino acid residue is a D-amino acid residue;

c) each chiral amino acid residue is an L-amino acid residue, except that one or more of each chiral terminal amino acid residue and each chiral amino acid residue immediately adjacent thereto is a D-amino acid residue; or d) each chiral amino acid residue is an D-amino acid residue, except that one or more of each chiral terminal amino acid residue and each chiral amino acid residue immediately adjacent thereto is an L-amino acid residue.

In another embodiment, the invention provides 15- to 22-residue peptides having the following Formula II

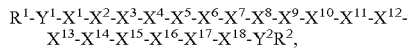
$$R^1\text{-}Y^1\text{-}X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13}\text{-}X^{14}\text{-}X^{15}\text{-}X^{16}\text{-}X^{17}\text{-}X^{18}\text{-}Y^2R^2, \quad \text{Formula II}$$

and pharmaceutically acceptable salts thereof, wherein:
$X^1$ is an achiral, D-, or L-basic amino acid residue;
$X^2$ is Leu or D-Leu;
$X^3$ is an achiral, D-, or L-basic amino acid residue;
$X^4$ is Gln, Asn, D-Gln, or D-Asn;
$X^5$ is Leu, D-Leu, or an achiral, D-, or L-basic amino acid residue;
$X^6$ is Leu, Trp, Phe, D-Leu, D-Trp, or D-Phe;
$X^7$ is an achiral, D-, or L-acidic amino acid residue;
$X^8$ is Asn, D-Asn, or an achiral, D-, or L-acidic amino acid residue;
$X^9$ is Leu, Trp, D-Leu, or D-Trp;
$X^{10}$ is Leu, Trp, D-Leu, or D-Trp;
$X^{11}$ is an achiral, D-, or L-acidic amino acid residue;
$X^{12}$ is an achiral, D-, or L-basic amino acid residue;
$X^{13}$ is Leu, Phe, D-Leu, or D-Phe;
$X^{14}$ is Leu, Phe, D-Leu, or D-Phe;
$X^{15}$ is an achiral, D-, or L-acidic amino acid residue;
$X^{16}$ is Leu or D-Leu;
$X^{17}$ is an achiral, D-, or L-aliphatic amino acid residue;
$X^{18}$ is Inp, Nip, azPro, Pip, azPip, D-Nip, or D-Pip;
$Y^1$ is absent or an amino acid sequence having from 1 to 4 residues;
$Y^2$ is absent;
$R^1$ is H or an amino protecting group;
$R^2$ is OH or a carboxyl protecting group;
wherein zero to three of residues $X^1$ to $X^{17}$ are absent; and wherein:

a) each chiral amino acid residue is an L-amino acid residue;

b) each chiral amino acid residue is a D-amino acid residue;

c) each chiral amino acid residue is an L-amino acid residue, except that one or more of each chiral terminal amino acid residue and each chiral amino acid residue immediately adjacent thereto is a D-amino acid residue; or d) each chiral amino acid residue is an D-amino acid residue, except that one or more of each chiral terminal amino acid residue and each chiral amino acid residue immediately adjacent thereto is an L-amino acid residue In another embodiment, the invention provides 22- to 29-residue peptides having the following Formula III

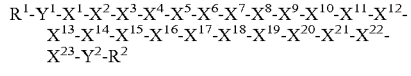
$$R^1\text{-}Y^1\text{-}X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13}\text{-}X^{14}\text{-}X^{15}\text{-}X^{16}\text{-}X^{17}\text{-}X^{18}\text{-}X^{19}\text{-}X^{20}\text{-}X^{21}\text{-}X^{22}\text{-}X^{23}\text{-}Y^2\text{-}R^2 \quad \text{Formula III}$$

or a pharmaceutically acceptable salt thereof, wherein:
$X^1$ is absent or an achiral, D-, or L-basic amino acid residue;
$X^2$ is an achiral, D-, or L-basic amino acid residue;
$X^3$ is Leu or D-Leu;
$X^4$ is an achiral, D-, or L-basic amino acid residue;
$X^5$ is an achiral, D-, or L-basic amino acid residue;
$X^6$ is Gln, Asn, D-Gln, or D-Asn;
$X^7$ is Leu or D-Leu;
$X^8$ is Ala or D-Ala;
$X^9$ is Asp or D-Asp;
$X^{10}$ is Leu, Phe, Gly, D-Leu, or D-Phe;
$X^{11}$ is Gly, Leu, or D-Leu;
$X^{12}$ is Arg or D-Arg;
$X^{13}$ is an achiral, D-, or L-acidic amino acid residue;
$X^{14}$ is Leu, Trp, Gly, D-Leu, or D-Trp;
$X^{15}$ is Leu or D-Leu;
$X^{16}$ is Gln or D-Gln;
$X^{17}$ is Glu, Leu, D-Glu, or D-Leu;
$X^{18}$ is Leu, Phe, D-Leu, or D-Phe;
$X^{19}$ is an achiral, D-, or L-aliphatic amino acid residue; $X^{20}$ is Glu or D-Glu;
$X^{21}$ is Leu, Phe, D-Leu, or D-Phe;
$X^{22}$ is an achiral, D-, or L-aliphatic amino acid residue;
$X^{23}$ is Inp, Nip, azPro, Pip, azPip, D-Nip, or D-Pip;
$Y^1$ is absent or an amino acid sequence having from 1 to 7 residues;
$Y^2$ is absent or an amino acid sequence having from 1 to 7 residues;
$R^1$ is H or an amino protecting group;
$R^2$ is OH or a carboxyl protecting group;
wherein:

a) each chiral amino acid residue is an L-amino acid residue;

b) each chiral amino acid residue is a D-amino acid residue;

c) each chiral amino acid residue is an L-amino acid residue, except that one or more of each chiral terminal amino acid residue and each chiral amino acid residue immediately adjacent thereto is a D-amino acid residue; or d) each chiral amino acid residue is a D-amino acid residue, except that one or more of each chiral terminal amino acid residue and each chiral amino acid residue immediately adjacent thereto is an L-amino acid residue.

A peptide of Formula I, II, or III, or a pharmaceutically acceptable salt thereof (an "ApoA-I Mimic") is useful for treating or preventing dyslipidemia, a cardiovascular disease, endothelial dysfunction, a macrovascular disorder, or a microvascular disorder (each being a "Condition").

In another embodiment, the invention provides compositions comprising an effective amount of an ApoA-1 Mimic and a pharmaceutically acceptable carrier or vehicle.

In another embodiment, the invention provides methods for treating or preventing a Condition, comprising administering an effective amount of an ApoA-I Mimic to a mammal in need thereof.

16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma VLDL total cholesterol was measured. Baseline values were subtracted to determine the increase in cholesterol levels. Baseline VLDL total cholesterol ranged from 0.04 to 0.11 g/L. There were 3 animals per group. By 30-34 hours post dose the values had returned to a value at or below baseline.

Figure 11A:
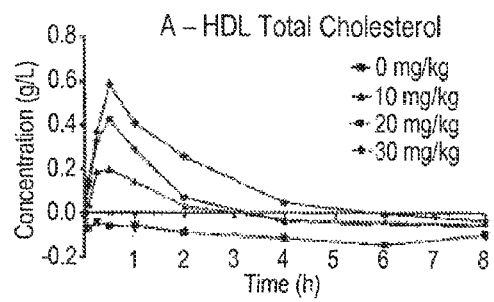
FIG. 11A is a plot of increase in plasma HDL total cholesterol following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma HDL total cholesterol was measured. Baseline values were subtracted to determine the increase in cholesterol levels. Baseline HDL total cholesterol ranged from 0.33 to 0.38 g/L. There were 3 animals per group. By 30-34 hours post dose the values had returned to a value at or below baseline.
Figure 11B:
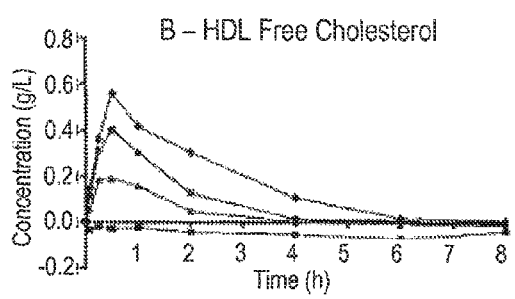
FIG. 11B is a plot of increase in plasma HDL free cholesterol following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma HDL free cholesterol was measured. Baseline values were subtracted to determine the increase in cholesterol levels. Baseline HDL free cholesterol ranged from 0.11 to 0.13 g/L. There were 3 animals per group. By 30-34 hours post dose the values had returned to a value at or below baseline.
Figure 11C:
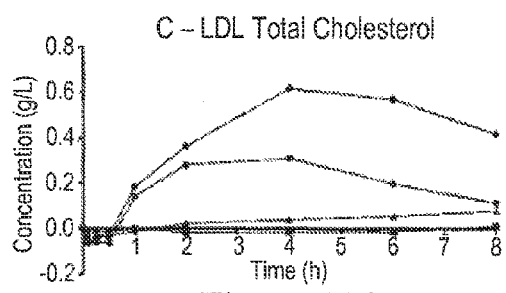
FIG. 11C is a plot of increase in plasma LDL total cholesterol following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma LDL total cholesterol was measured. Baseline values were subtracted to determine the increase in cholesterol levels. Baseline LDL total cholesterol ranged from 0.17 to 0.33 g/L. There were 3 animals per group. By 30-34 hours post dose the values had returned to a value at or below baseline.
Figure 11D:
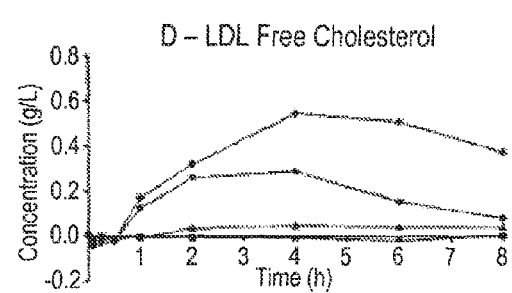
FIG. 11D is a plot of increase in plasma LDL free cholesterol following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma LDL free cholesterol was measured. Baseline values were subtracted to determine the increase in cholesterol levels. Baseline LDL free cholesterol ranged from 0.06 to 0.11 g/L. There were 3 animals per group. By 30-34 hours post dose the values had returned to a value at or below baseline.
Figure 11E:
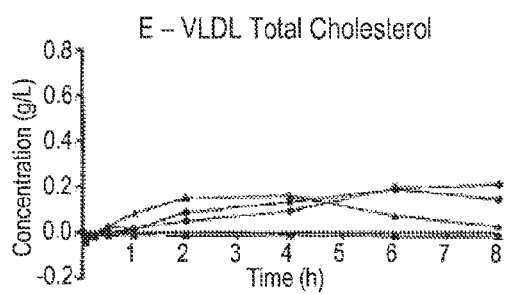
FIG. 11E is a plot of increase in plasma VLDL total cholesterol following infusion of a Peptide 16 (SEQ ID NO.
Figure 11F:
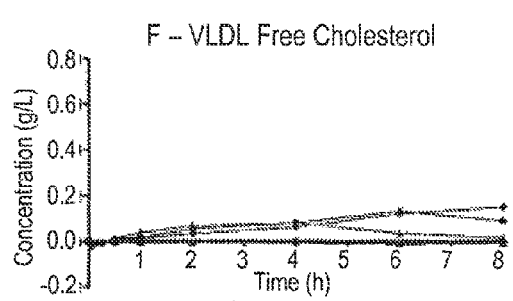

FIG. 11F is a plot of increase in plasma VLDL free cholesterol following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma VLDL free cholesterol was measured. Baseline values were subtracted to determine the increase in cholesterol levels. Baseline VLDL free cholesterol ranged from 0.02 to 0.04 g/L. There were 3 animals per group. By 30-34 hours post dose the values had returned to a value at or below baseline.

Figure 12:
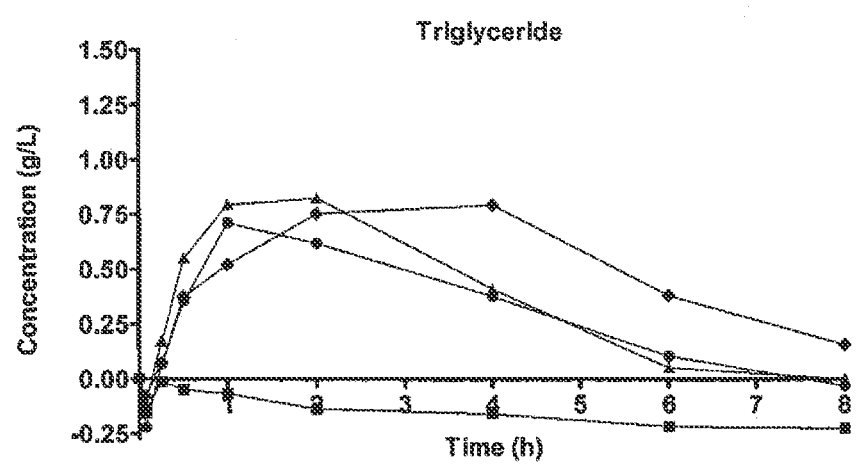

FIG. 12 is a plot of the increase in plasma triglyceride levels following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma triglyceride levels were measured. Baseline values (ranging from 0.40 to 0.80 g/L for the four groups) were subtracted to determine the increase in plasma triglyceride levels. There were 3 animals per group.

Figure 13:
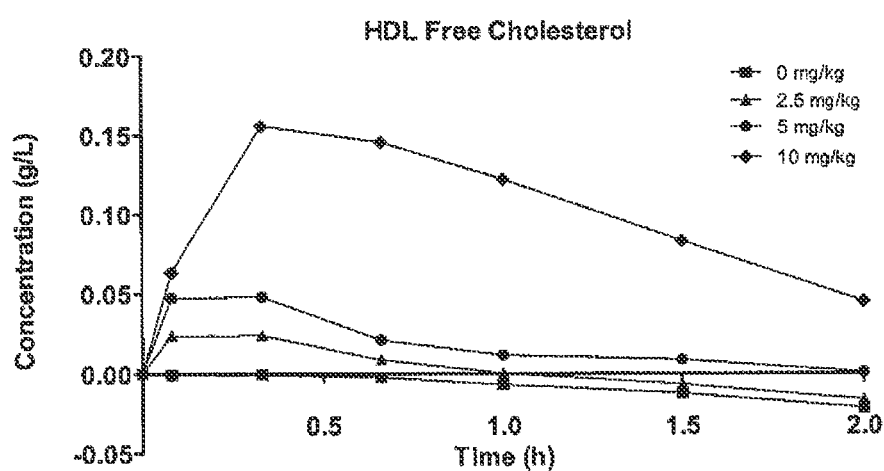

FIG. 13 is a plot of the increase in plasma HDL free cholesterol levels following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 2.5 (triangle), 5 (circle) or 10 (diamond) mg/kg. At baseline and 5, 20, 40, 60, 90 and 120 minutes after initiating the infusion, plasma HDL free cholesterol levels were measured. Baseline values were subtracted to determine the increase in plasma HDL free cholesterol levels. There were 4 animals per group.

Figure 14A:
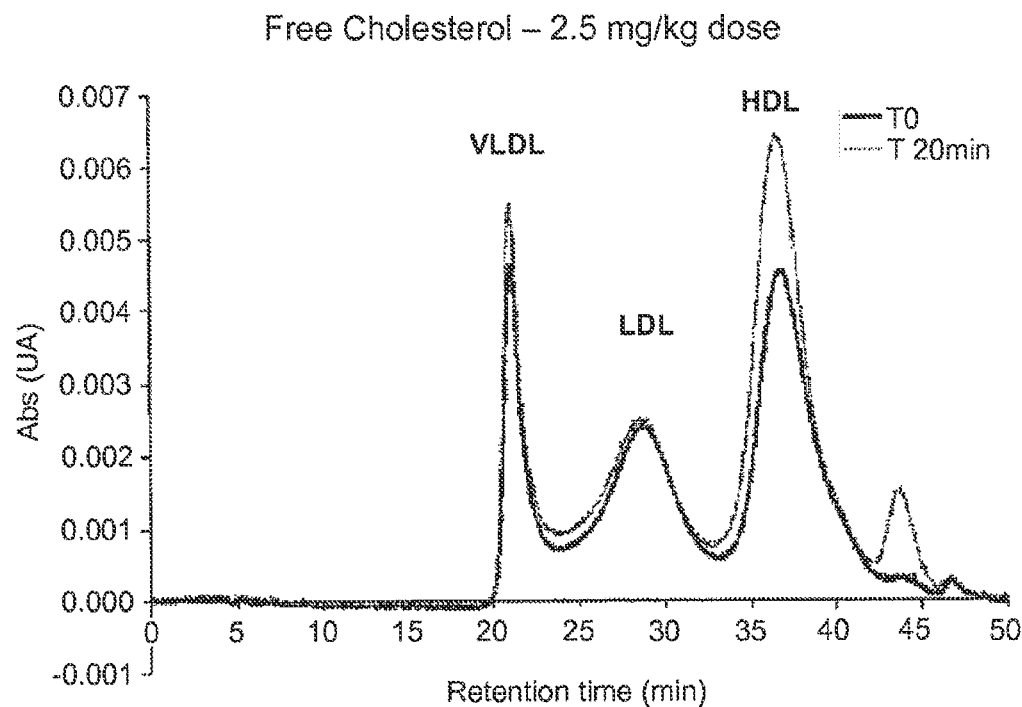

FIG. 14A is a plot of an HPLC gel permeation chromatography elution profile at baseline (dark line) and 20 min after infusion of 2.5 mg/kg Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5). Shown on the Y-axis is the absorption from the inline free cholesterol assay of the lipoprotein fractions eluting from the HPLC gel permeation chromatography. The peaks from left to right correspond to the VLDL, LDL and HDL fractions.

Figure 14B:
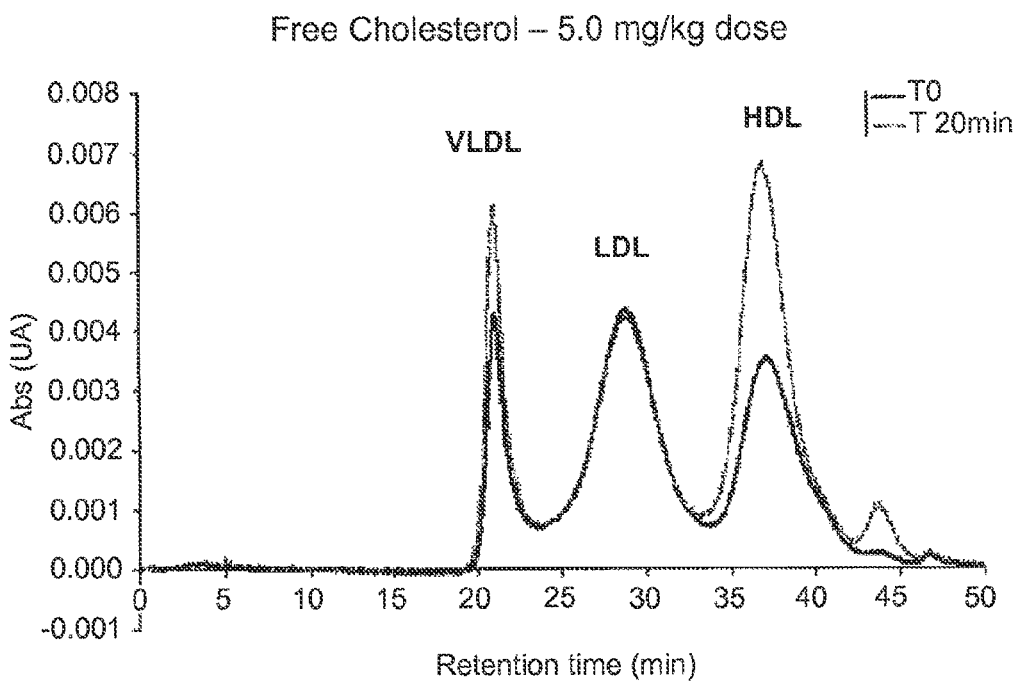

FIG. 14B is a plot of an HPLC gel permeation chromatography elution profile at baseline (dark line) and 20 min after infusion of 5.0 mg/kg Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5). Shown on the Y-axis is the absorption from the inline free cholesterol assay of the lipoprotein fractions eluting from the HPLC gel permeation chromatography. The peaks from left to right correspond to the VLDL, LDL and HDL fractions.

Figure 15:
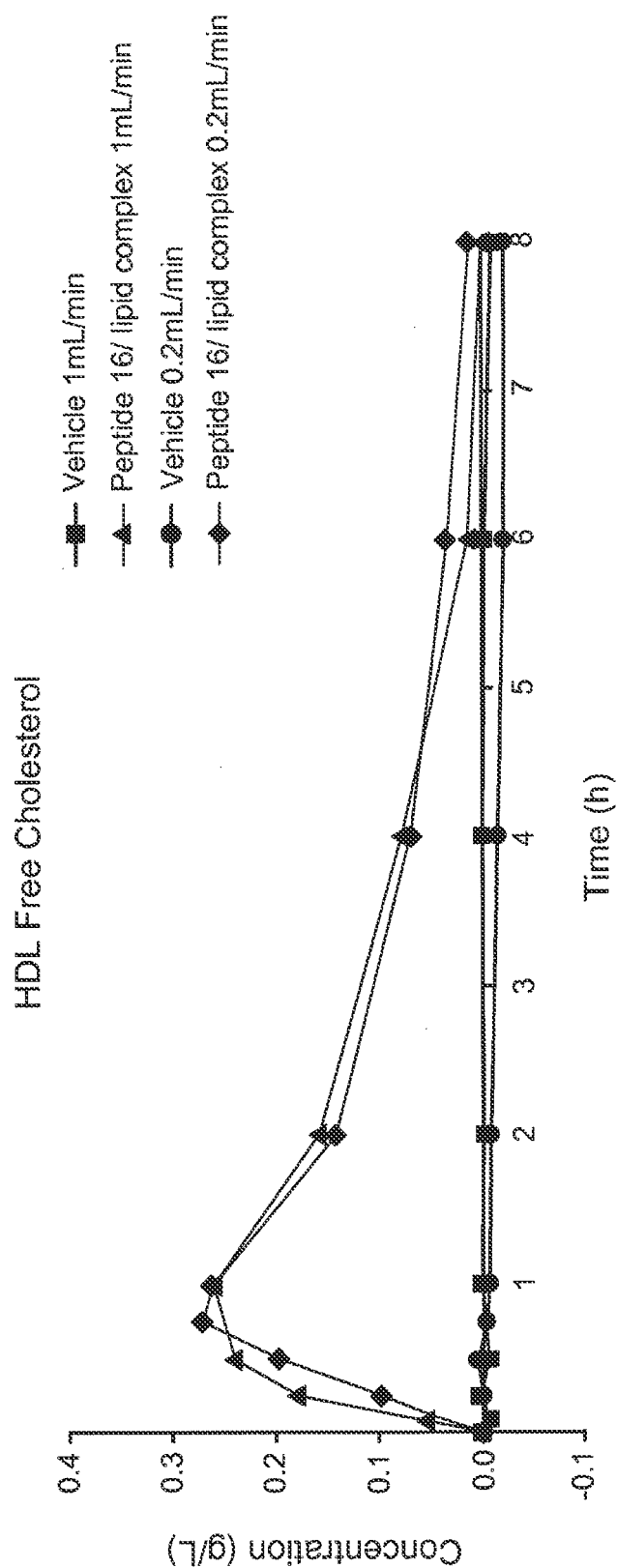

FIG. 15 is a plot of the increase in plasma HDL free cholesterol levels following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at a dose of 20 mg/kg at a rate of 1 mL/min (triangles) or 0.2 mL/min (diamonds). At various times post dose, plasma HDL free cholesterol levels were measured. Baseline values were subtracted to determine the increase in plasma HDL free cholesterol levels. There were 4 animals per Peptide 16 (SEQ ID NO: 16)/lipid complex treatment group, while there were 2 animals per vehicle treatment group.

Figure 16:
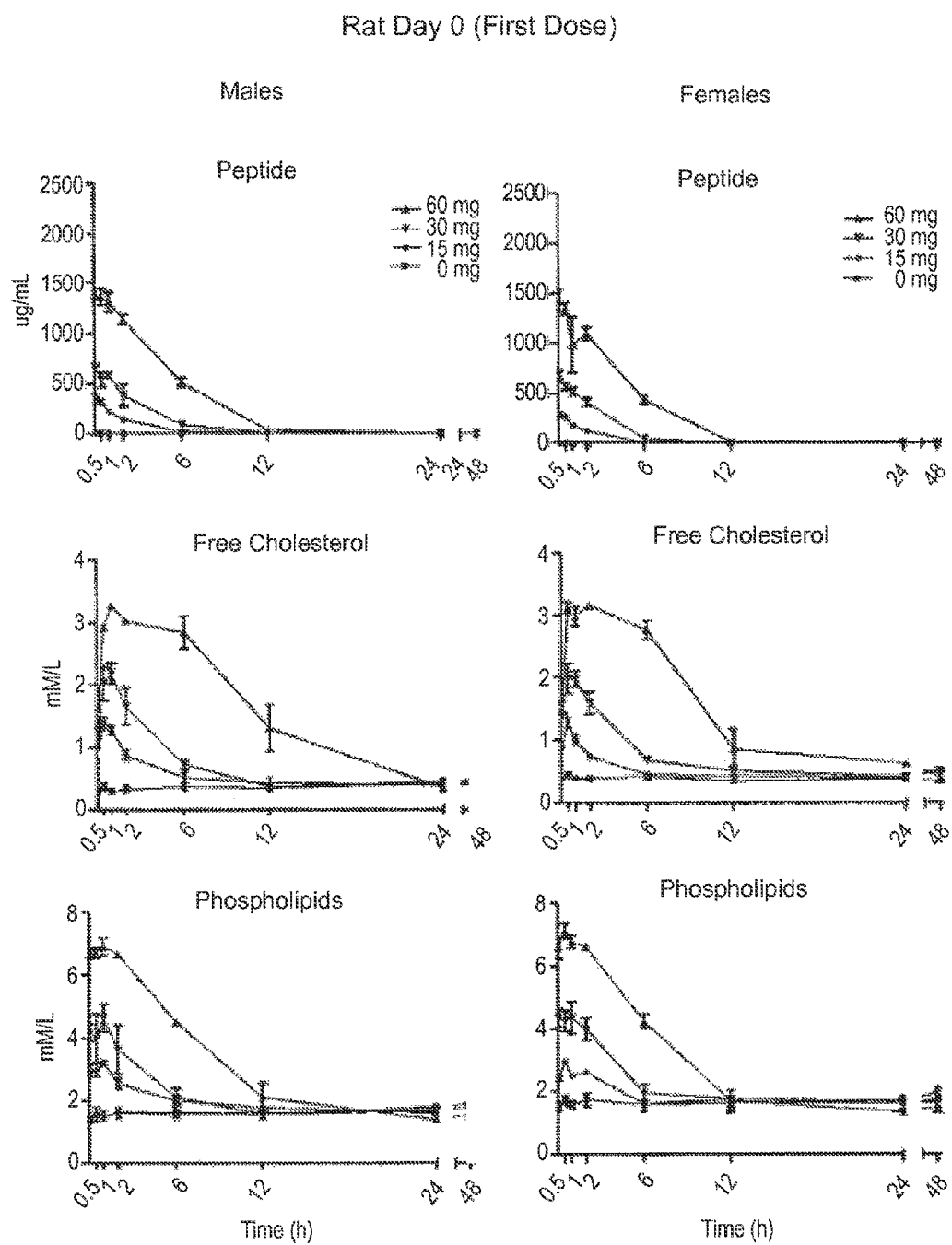

FIG. 16 illustrates plots of the kinetic profiles of Peptide 16 (SEQ ID NO: 16) (upper panels), free cholesterol (middle panels) and phospholipid (lower panels) in male and female rats following first dose administration of Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) on Day 0. The decrease of Peptide 16 (SEQ ID NO: 16) and phospholipid levels in plasma over time indicate the clearance of Peptide 16 (SEQ ID NO: 16)/lipid complex. The kinetics of free cholesterol are presented. Each data point represents the average ±SD (N=3 rats/group).

Figure 17:
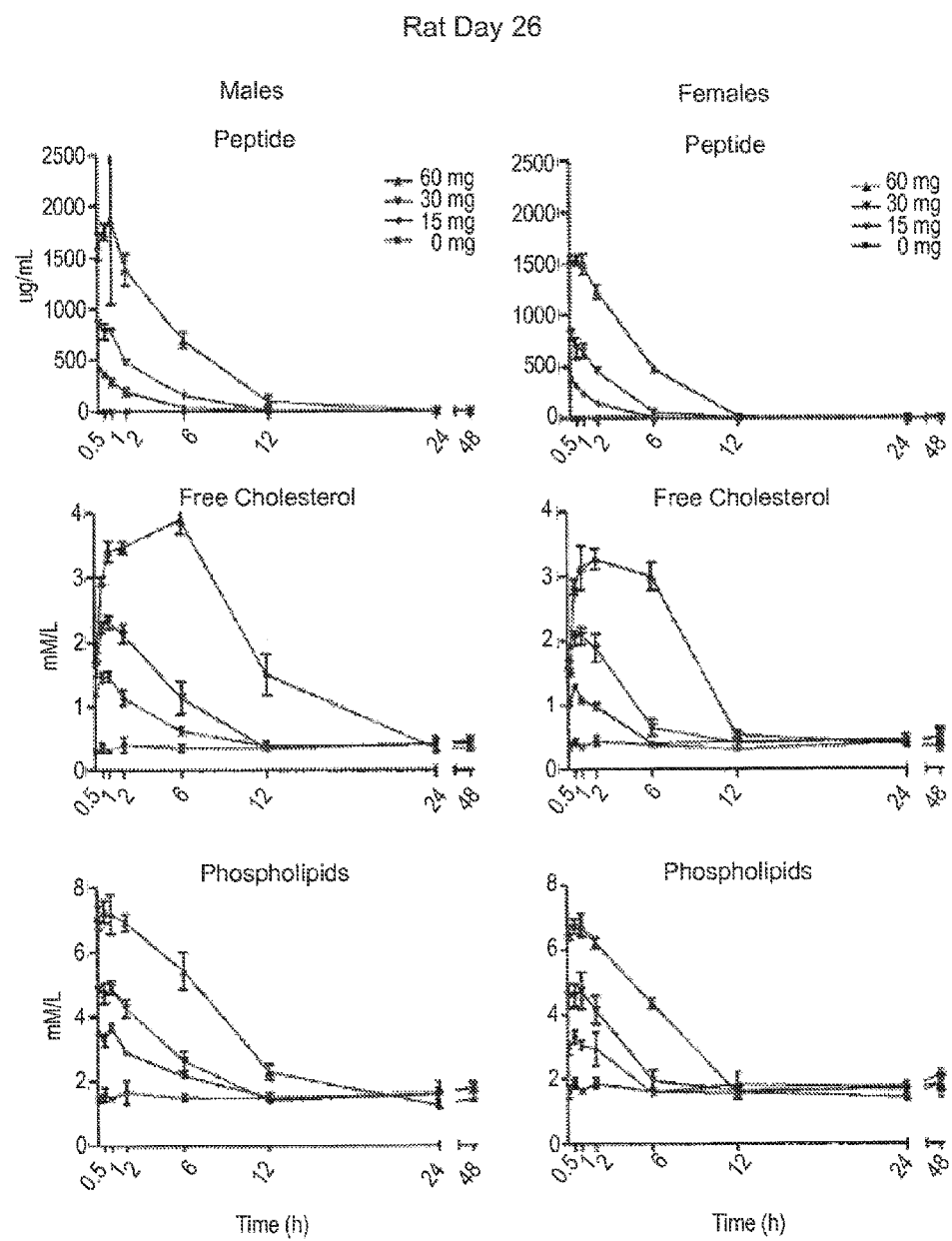

FIG. 17 illustrates plots of the kinetic profiles of Peptide 16 (SEQ ID NO: 16) (upper panels), free cholesterol (middle panels) and phospholipid (lower panels) in male and female rats following multiple dose administration of Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) on Day 26. These animals received Peptide 16 (SEQ ID NO: 16)/lipid complex every second day for 4 weeks. The decrease of Peptide 16 (SEQ ID NO: 16) and phospholipid levels in plasma over time indicate the clearance of Peptide 16 (SEQ ID NO: 16)/lipid complex. The kinetics of free cholesterol are presented. Each data point represents the average ±SD (N=3 rats/group).

Figure 18:
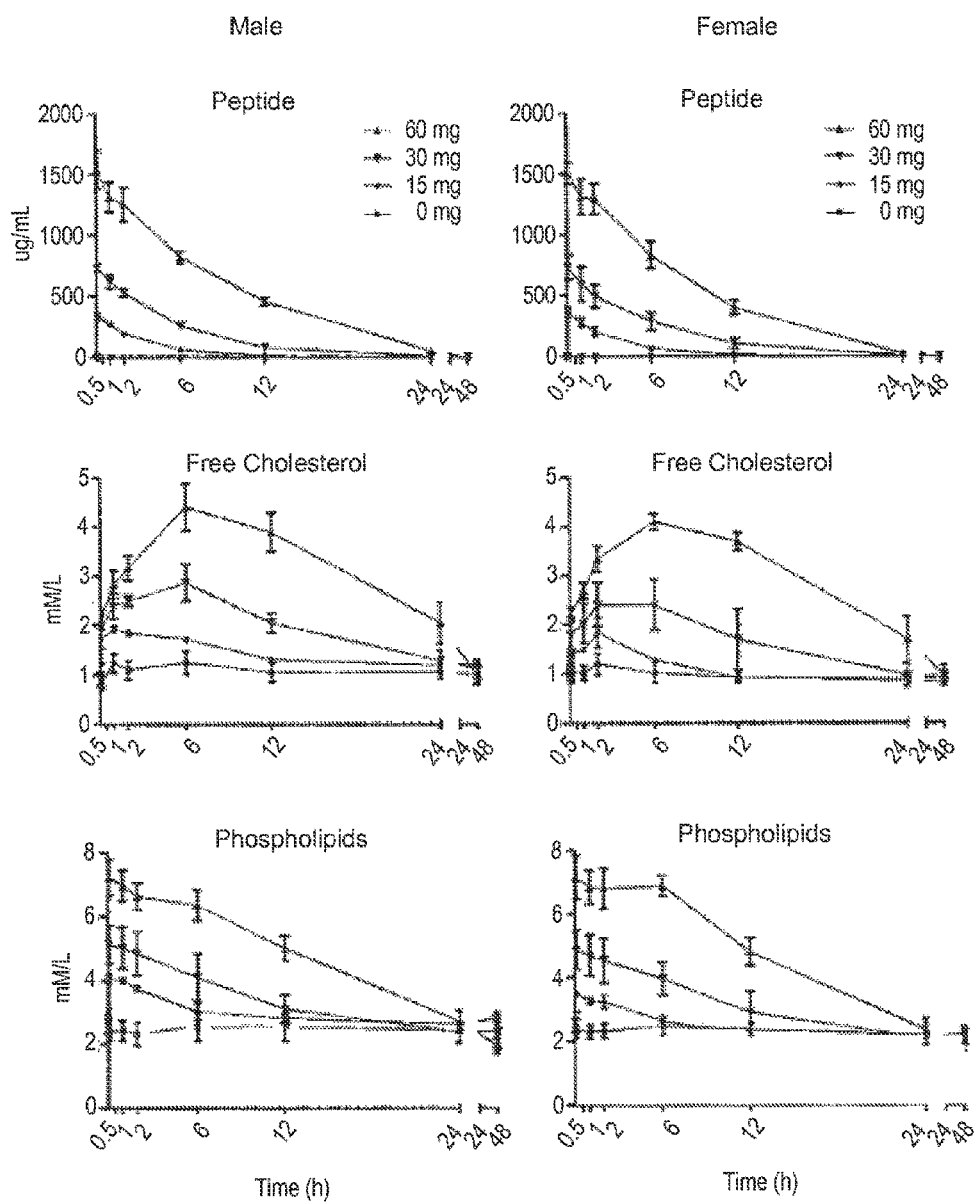

FIG. 18 illustrates plots of the kinetic profiles of Peptide 16 (SEQ ID NO: 16) (upper panels), free cholesterol (middle panels) and phospholipid (lower panels) in male and female cynomolgus monkeys following first dose administration of Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) on Day 0. The decrease of Peptide 16 (SEQ ID NO: 16) and phospholipid levels in plasma over time indicate the clearance of Peptide 16 (SEQ ID NO: 16)/lipid complex. The kinetics of free cholesterol are presented. Each data point represents the average ±SD (N=3 monkeys/group).

Figure 19:
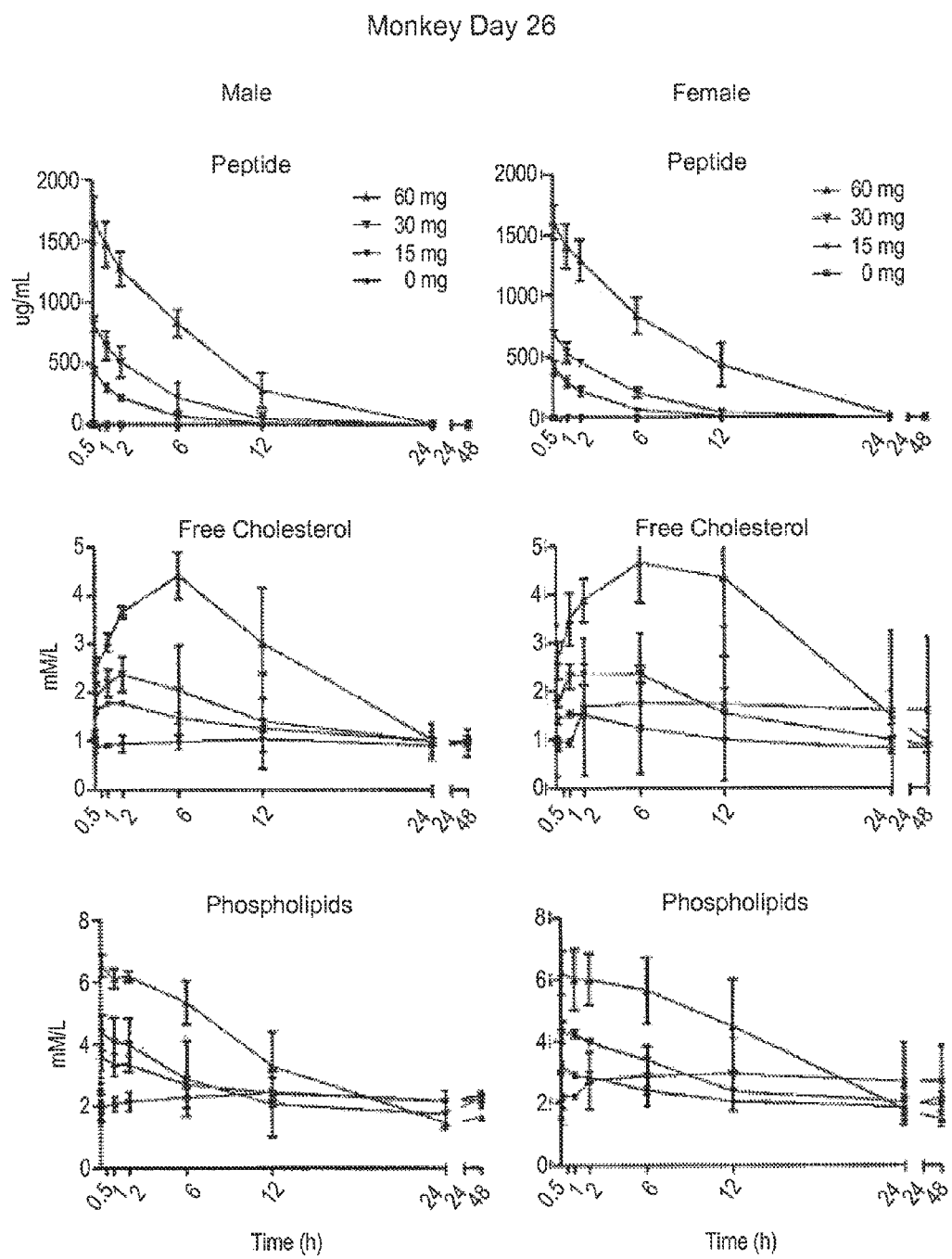

FIG. 19 illustrates plots of the kinetic profiles of Peptide 16 (SEQ ID NO: 16) (upper panels), free cholesterol (middle panels) and phospholipid (lower panels) in male and female cynomolgus monkeys following multiple dose administration of Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) on Day 26. These animals received Peptide 16 (SEQ ID NO: 16)/lipid complex every second day for 4 weeks. The decrease of Peptide 16 (SEQ ID NO: 16) and phospholipid levels in plasma over time indicate the clearance of Peptide 16 (SEQ ID NO: 16)/lipid complex. The kinetics of free cholesterol are presented. Each data point represents the average ±SD (N=3 monkeys/group).

Figure 20A:
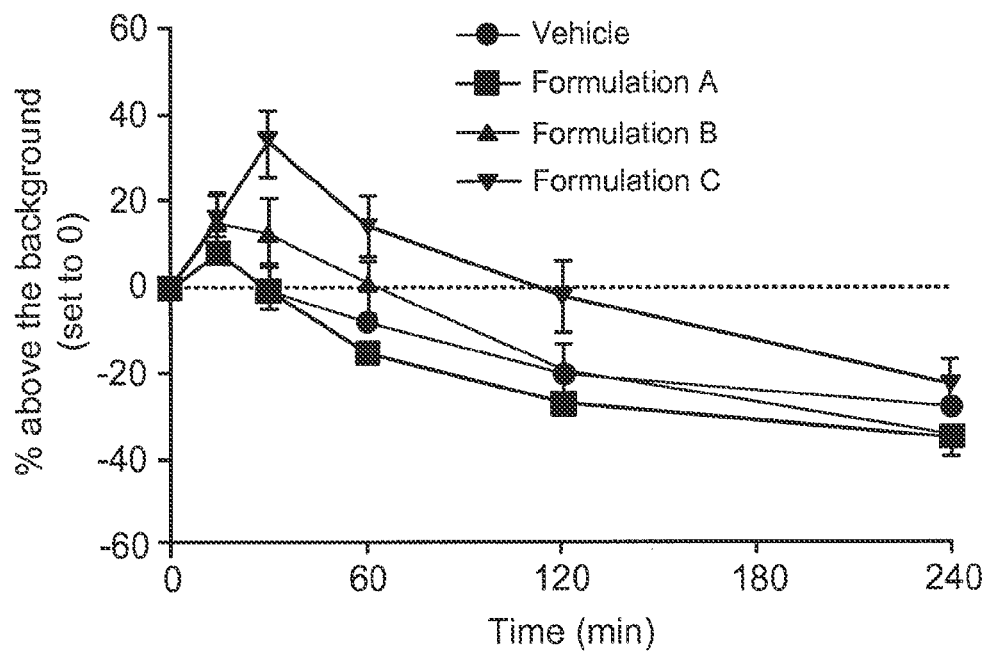

FIG. 20A is a plot of the % of increase from the pre-dose value of plasma total cholesterol in C57Bl/6 J mice after treatment with the Formulation A, B, or C. 6 animals/per group were sequentially sampled at different time points.

Figure 20B:
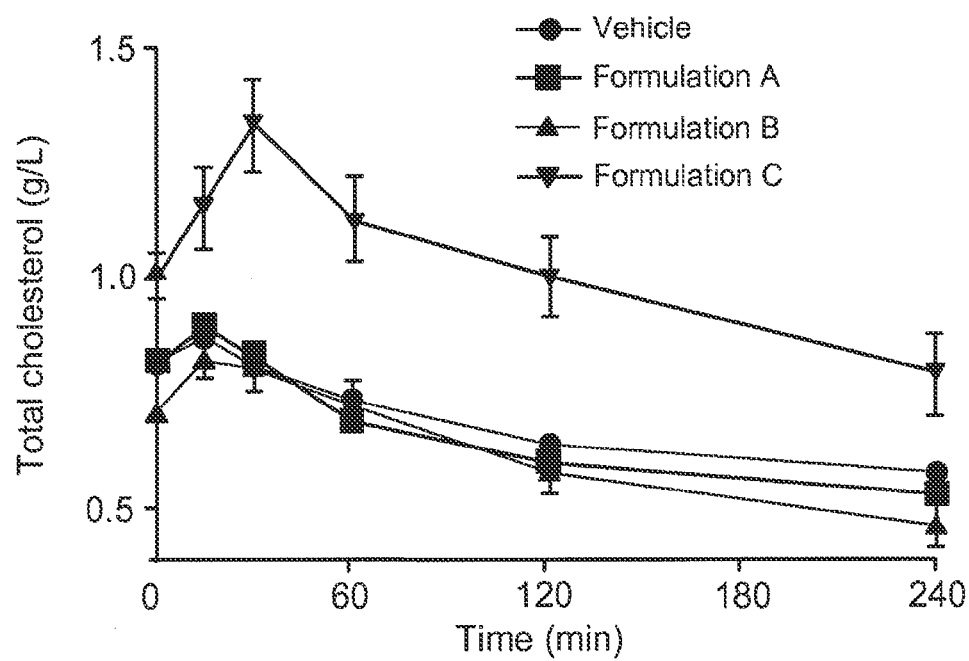

FIG. 20B is a plot of the increase in plasma total cholesterol in C57Bl/6J mice after treatment with the Formulation A, B, or C. 6 animals/per group were sequentially sampled at different time points.

Figure 21A:
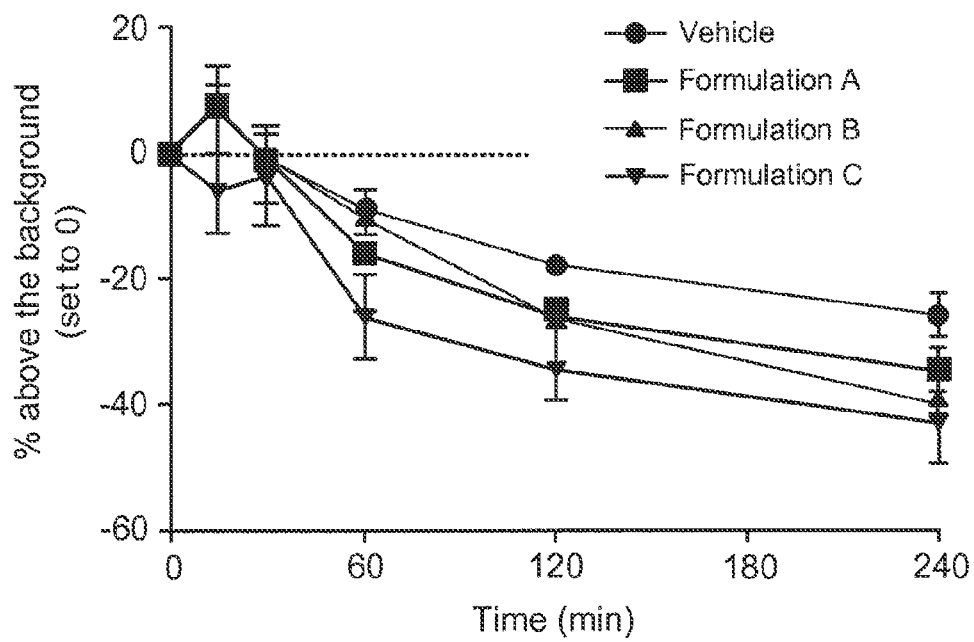

FIG. 21A is a plot of the % of increase from the pre-dose value of plasma esterified cholesterol in C57Bl/6J mice after treatment with the Formulation A, B, or C. 6 animals/per group were sequentially sampled at different time points.

Figure 21B:
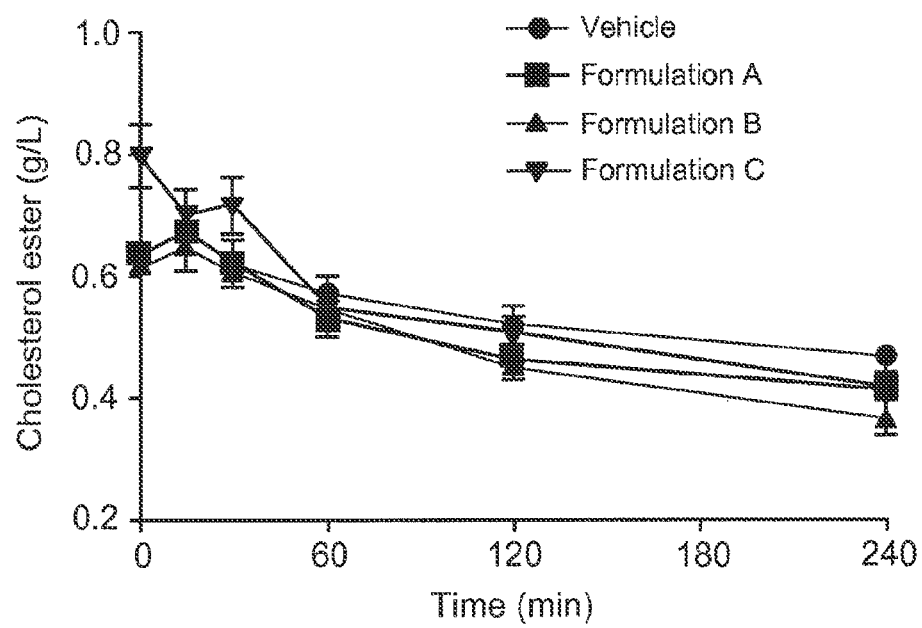

FIG. 21B is a plot of the increase in plasma esterified cholesterol in C57Bl/6J mice after treatment with the Formulation A, B, or C. 6 animals/per group were sequentially sampled at different time points.

DETAILED DESCRIPTION OF THE INVENTION

I. Definitions

"About," when immediately preceding a number or numeral means that the number or numeral ranges plus or minus 10%. For example, "about 1:1" ranges from 0.9:1 to 1.1:1.

"Alkyl," as used herein unless otherwise defined, refers to an optionally substituted saturated branched, straight chain or cyclic hydrocarbon radical. Typical alkyl groups are ($C_1$-$C_6$) alkyl groups that include, but are not limited to, methyl, ethyl, propyl, isopropyl, butyl, isobutyl, t-butyl, pentyl, isopentyl, hexyl, and the like. In some embodiments, the alkyl groups are ($C_1$-$C_4$) alkyl. Unless specified otherwise, the alkyl is unsubstituted.

"Alkenyl," as used herein unless otherwise defined, refers to an unsaturated branched, straight chain or cyclic non-aromatic hydrocarbon radical having one or more carbon-carbon double bonds. The one or more double bonds can be in either the cis or trans conformation. Typical alkenyl groups include, but are not limited to, ethenyl, propenyl, isopropenyl, butenyl, isobutenyl, tert-butenyl, pentenyl, hexenyl and the like. In some embodiments, the alkenyl group is ($C_2$-$C_6$) alkenyl.

"Alkynyl," as used herein unless otherwise defined, refers to an unsaturated branched or straight chain hydrocarbon radical having at least one carbon-carbon triple bond. Typical alkynyl groups include, but are not limited to, ethynyl, propynyl, butynyl, isobutynyl, pentynyl, hexynyl and the like. In some embodiments, the alkynyl group is ($C_2$-$C_6$) alkynyl.

"Aryl," as used herein unless otherwise defined, refers to an optionally substituted aromatic ring system in which each atom within the ring is C, O, N, or S, thus encompassing heterocyclic aromatic rings. Typical aryl groups include, but are not limited to benzyl, phenyl, naphthyl, anthracyl, furan, imidazole, indazole, indole, isoquinoline, isothiazole, isoxazole, pyran, pyrazine, pyrazole, pyridazine, pyridine, pyrimidine, pyrrole, pyrrolizine, quinazoline, quinoline, quinolizine, quinoxaline, thiazole, and thiophene. In some embodiments, the aryl group is ($C_5$-$C_{26}$ aryl). In some embodiments, a heteroaryl group is a 5-20-membered heteroaryl. In other embodiments, a heteroaryl group is 5-10-membered heteroaryl. Unless specified otherwise, the aryl is unsubstituted.

"Aralkyl," as used herein unless otherwise defined, refers to an alkyl group substituted with an aryl group.

"Substituted Alkyl or Aryl," as used herein unless otherwise defined, refers to an alkyl or aryl group in which one or more of its hydrogen atoms are replaced with another substituent. Typical substituents include —$OR^a$, —$SR^a$, —$NR^aR^a$, —$NO_2$, —CN, halogen, —$SO_2R^a$, —$C(O)R^a$, —$C(O)OR^a$ and —$C(O)NR^aR^a$, where each $R^a$ is independently hydrogen, alkyl, or aryl.

"Hydrophilic face," as used herein unless otherwise defined, refers to a face of the helix having overall net hydrophilic character.

"Hydrophobic face," as used herein unless otherwise defined, refers to a face of the peptide having overall net hydrophobic character.

As used herein when referring to an ApoA-I Mimic, the number of terminal —$NH_2$ groups is zero where $R^1$ is an amino protecting group and is 1 where $R^1$ is H.

As used herein when referring to an ApoA-1 Mimic, the number of terminal-COOH groups is zero where $R^2$ is a carboxyl protecting group and is 1 where $R^2$ is OH.

A "mammal," as used herein unless otherwise defined, refers to a human, mouse, rat, guinea pig, dog, cat, horse, cow, pig, or non-human primate, such as a monkey, chimpanzee, or baboon. In one embodiment, the mammal is a human.

An "effective amount," when used in connection with an ApoA-I Mimic is an amount that is effective for treating or preventing a Condition.

"HDL free cholesterol," as used herein means the amount of cholesterol having a free hydroxyl group ("free cholesterol") that is contained within HDL particles in the serum. The HDL particles can be formed from an ApoA-I Mimic/ lipid complex.

"HDL total cholesterol," as used herein means the amount of free cholesterol plus the amount of cholesterol having a hydroxyl group that has been esterified ("esterified cholesterol") that is contained within HDL particles in the serum. The HDL particles can be formed from an ApoA-I Mimic/ lipid complex.

"Amino acid residue," as used herein unless otherwise defined, includes genetically encoded amino acid residues and non-genetically encoded amino acid residues.

Abbreviations for the genetically encoded amino acid residues as used herein are set forth in Table 1 below.

TABLE 1

| Amino Acid | One-Letter Abbreviation | Three-Letter Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | p | Pro |
| Serine | S | Ser |
| Threonine | T | Thr |
| Tryptophan | W | Trp |
| Tyrosine | Y | Tyr |
| Valine | V | Val |

Non-genetically encoded amino acid residues include, but are not limited to, β-alanine (β-Ala); 2,3-diaminopropionic acid (Dpr); nipecotic acid (Nip); pipecolic acid (Pip); ornithine (Orn); citrulline (Cit); t-butylalanine (t-BuA); 2-t-butylglycine (t-BuG); N-methylisoleucine (MeIle); phenylglycine (PhG); cyclohexylalanine (ChA); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH$_2$)); N-methyl valine (MeVal); homocysteine (hCys), homophenylalanine (hPhe); homoserine (hSer); hydroxyproline (Hyp); homoproline (hPro); and the corresponding D-enantiomer of each of the foregoing, e.g., D- -Ala, D-Dpr, D-Nip, D-Orn, D-Cit, D-t-BuA, D-t-BuG, D-MeIle, D-PhG, D-ChA, D-Nle, D-Nal, D-Phe(4-Cl), D-Phe(2-F), D-Phe(3-F), D-Phe(4-F), D-Pen, D-Tic, D-Thi, D-MSO, D-hArg, D-AcLys, D-Dbu, D-Dab, D-Phe(pNH$_2$), D-MeVal, D-hCys, D-hPhe, D-hSer, D-Hyp, and D-hPro. Other non-genetically encoded amino acid residues include 3-aminopropionic acid; 4-aminobutyric acid; isonipecotic acid (Inp); aza-pipecolic acid (azPip); aza-proline (azPro); α-aminoisobutyric acid (Aib); ε-aminohexanoic acid (Aha); δ-aminovaleric acid (Ava); N-methylglycine (MeGly).

"Chiral," as used herein to refer to an amino acid residue, means an amino acid residue having at least one chiral center. In one embodiment, the chiral amino acid residue is an L-amino acid residue. Examples of L-amino acid residues include, but are not limited to, Ala, Arg, Asn, Asp, Cys, Gln, Glu, His, Ile, Leu, Lys, Met, Phe, Pro, Ser, Thr, Trp, Tyr, Val, β-Ala, Dpr, Nip, Orn, Cit, t-BuA, t-BuG, MeIle, PhG, ChA, Nle, Nal, Phe(4-Cl), Phe(2-F), Phe(3-F), Phe(4-F), Pen, Tic, Thi, MSO, hArg, AcLys, Dbu, Dab, Phe(pNH$_2$), MeVal, hCys, hPhe, hSer, Hyp, and hPro. In one embodiment, the chiral amino acid residue is a D-amino acid residue. Examples of D-amino acid residues include, but are not limited to D-Ala, D-Arg, D-Asn, D-Asp, D-Cys, D-Gln, D-Glu, D-His, D-Ile, D-Leu, D-Lys, D-Met, D-Phe, D-Pro, D-Ser, D-Thr, D-Trp, D-Tyr, D-Val, D-β-Ala, D-Dpr, D-Nip, D-Pip, D-Orn, D-Cit, D-t-BuA, D-t-BuG, D-MeIle, D-PhG, D-ChA, D-Nle, D-Nal, D-Phe(4-Cl), D-Phe(2-F), D-Phe(3-F), D-Phe (4-F), D-Pen, D-Tic, D-Thi, D-MSO, D-hArg, D-AcLys, D-Dbu, D-Dab, D-Phe (pNH$_2$), D-MeVal, D-hCys, D-hPhe, D-hSer, D-Hyp, and D-hPro.

"Achiral," as used herein to refer to an amino acid residue, means an amino acid residue that does not have a chiral center. Examples of achiral amino acid residues include, but are not limited to, Gly, Inp, Aib, Aha, Ava, MeGly, azPip, and azPro.

"Aliphatic amino acid residue," as used herein unless otherwise defined, refers to an amino acid residue having an aliphatic hydrocarbon side chain. Aliphatic amino acid residues include, but are not limited to, Ala (A), Val (V), Leu (L), Ile (I), Pro (P), azPro, Pip, azPip, β-Ala, Aib, t-BuA, t-BuG, MeIle, ChA, Nle, MeVal, Inp, Nip, hPro, D-Ala, D-Val, D-Leu, D-Ile, D-Pro, D-β-Ala, D-t-BuA, D-t-BuG, D-MeIle, D-Nle, D-MeVal, D-Nip, D-Pip, D-ChA, and D-hPro. In one embodiment, the aliphatic amino acid residue is an L-amino acid residue. In another embodiment, the aliphatic amino acid residue is a D-amino acid residue. In another embodiment, the aliphatic amino acid residue is an achiral amino acid residue.

"Hydrophilic amino acid residue," as used herein unless otherwise defined, refers to an amino acid residue exhibiting a hydrophobicity of less than zero according to the normalized consensus hydrophobicity scale of Eisenberg et al., 1984, *J. Mol. Biol.* 179:125-142. Hydrophilic amino acid residues include, but are not limited to, Pro (P), Gly (G), Thr (T), Ser (S), His (H), Glu (E), Asn (N), Gln (Q), Asp (D), Lys (K) Arg (R), Dpr, Orn, Cit, Pen, MSO, hArg, AcLys, Dbu, Dab, Phe(p-NH$_2$), hCys, hSer, Hyp, D-Pro, D-Thr, D-Ser, D-His, D-Glu, D-Asn, D-Gln, D-Asp, D-Lys, D-Arg, D-Dpr, D-Orn, D-Cit, D-Pen, D-MSO, D-hArg, D-AcLys, D-Dbu, D-Dab, D-Phe(p-NH$_2$), D-hCys, D-hSer, and D-Hyp. Other hydrophilic amino acid residues include, but are not limited to, $C_{1-4}$ lateral chain analogs having the following formulas:

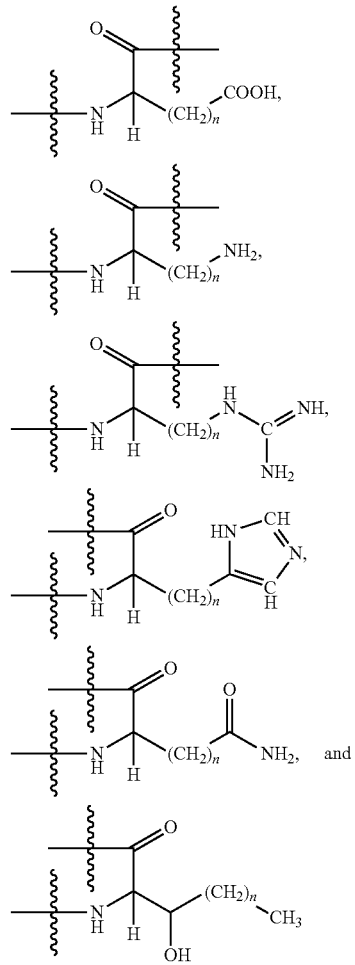

wherein n is an integer from 1 to 4. In one embodiment, the hydrophilic amino acid residue is an L-amino acid residue. In another embodiment, the hydrophilic amino acid residue is a D-amino acid residue. In another embodiment, the hydrophilic amino acid residue is an achiral amino acid residue. In another embodiment, the hydrophilic amino acid residue is an acidic L-amino acid residue, an acidic D-amino acid residue, or an acidic achiral amino acid residue. In another embodiment, the hydrophilic amino acid residue is a basic L-amino acid residue, a basic D-amino acid residue, or a basic achiral amino acid residue.

"Hydrophobic amino acid residue," as used herein unless otherwise defined, refers to an amino acid residue exhibiting a hydrophobicity of greater than zero according to the normalized consensus hydrophobicity scale of Eisenberg, 1984, *J. Mol. Biol.* 179:125-142. Hydrophobic amino acid residues include, but are not limited to, Ile (I), Phe (F), Val (V), Leu (L), Trp (W), Met (M), Ala (A), Gly (G), Tyr (Y), β-Ala, Nip, t-BuA, t-BuG, MeIle, PhG, ChA, Nle, Nal, Phe(4-Cl), Phe(2-F), Phe(3-F), Phe(4-F), Tic, Thi, MeVal, hPhe, hPro, 3-aminopropionic acid, 4 aminobutryic acid, Inp, Aib, Aha, Ava, MeGly, D-Pro, D-Ile, D-Phe, D-Val, D-Leu, D-Trp, D-Met, D-Ala, D-Tyr, D- -Ala, D-Nip, D-t-BuA, D-t-BuG, D-MeIle, D-PhG, D-ChA, D-Nle, D-Nal, D-Phe(4-Cl), D-Phe(2-F), D-Phe(3-F), D-Phe(4-F), D-Tic, D-Thi, D-MeVal, D-hPhe, and D-hPro. Other hydrophobic amino acids include, but are not limited to, $C_{1-4}$ lateral chain analogs having the following formulas:

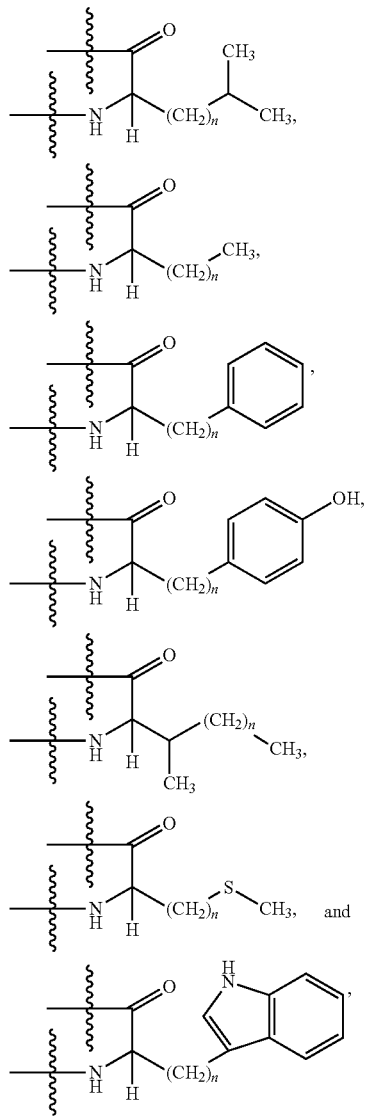

wherein n is an integer from 1 to 4. In one embodiment, the hydrophobic amino acid residue is an L-amino acid residue. In another embodiment, the hydrophobic amino acid residue is a D-amino acid residue. In another embodiment, the hydrophobic amino acid residue is an achiral amino acid residue.

"Polar amino acid residue," as used herein unless otherwise defined, refers to a hydrophilic amino acid residue having a side chain that is uncharged at physiological pH, but which has at least one bond in which the pair of electrons shared in common by two atoms is held more closely by one of the atoms. Polar amino acid residues include, but are not limited to, Asn (N), Gln (Q), Ser (S), Thr (T), Cit, Pen, MSO, AcLys, hCys, hSer, Hyp, D-Asn, D-Gln, D-Ser, D-Thr, D-Cit, D-Pen, D-MSO, D-AcLys, D-hCys, D-hSer, and D-Hyp. Other polar amino acids include, but are not limited to, $C_{1-4}$ lateral chain analogs having the following formulas:

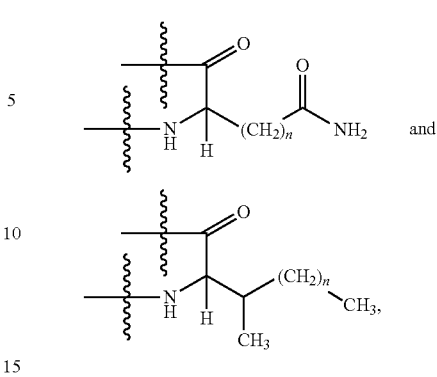

wherein n is an integer from 1 to 4. In one embodiment, the polar amino acid residue is an L-amino acid residue. In another embodiment, the polar amino acid residue is a D-amino acid residue. In another embodiment, the polar amino acid residue is an achiral amino acid residue.

"Acidic amino acid residue," as used herein unless otherwise defined, refers to a hydrophilic amino acid residue having a side chain pK value of less than 7. Acidic amino acid residues typically have negatively charged side chains at physiological pH due to loss of a hydrogen ion. Acidic amino acid residues include, but are not limited to, Glu (E), Asp (D), D-Glu, and D-Asp. Other acidic amino acids include, but are not limited to, $C_{1-4}$ lateral chain analogs having the following formula:

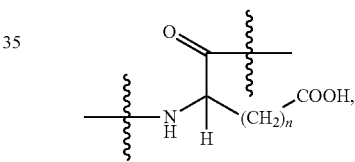

wherein n is an integer from 1 to 4. In one embodiment, the acidic amino acid residue is an L-amino acid residue. In another embodiment, the acidic amino acid residue is a D-amino acid residue. In another embodiment, the acidic amino acid residue is an achiral amino acid residue.

"Basic amino acid residue," as used herein unless otherwise defined, refers to a hydrophilic amino acid residue having a side chain pK value of greater than 7. Basic amino acid residues typically have positively charged side chains at physiological pH due to association with a hydronium ion. Basic amino acid residues include, but are not limited to, His (H), Arg (R), Lys (K), Dpr, Orn, hArg, Dbu, Dab, Phe(p-$NH_2$), D-His, D-Arg, D-Lys, D-Dpr, D-Orn, D-hArg, D-Dbu, D-Dab, and D-Phe(p-$NH_2$). Other basic amino acid residues include, but are not limited to, $C_{1-4}$ lateral chain analogs having the following formulas:

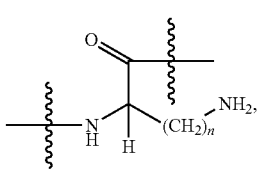

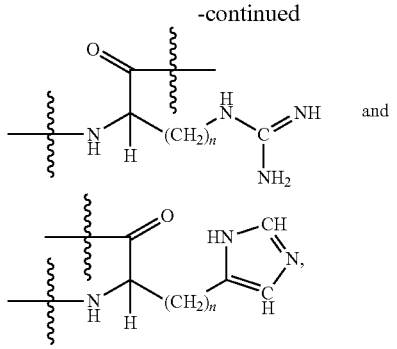

wherein n is an integer from 1 to 4. In one embodiment, the basic amino acid residue is an L-amino acid residue. In another embodiment, the basic amino acid residue is a D-amino acid residue. In another embodiment, the basic amino acid residue is an achiral amino acid residue.

"Nonpolar amino acid residue," as used herein unless otherwise defined, refers to a hydrophobic amino acid residue having a side chain that is uncharged at physiological pH and which has bonds in which the pair of electrons shared in common by two atoms is held substantially equally by each of the two atoms (i.e., the side chain is not polar). Non-polar amino acid residues include, but are not limited to, Leu (L), Val (V), Ile (I), Met (M), Gly (G), Ala (A), Pro (P), azPro, Pip, azPip, β-Ala, Nip, t-BuG, MeIle, ChA, Nle, MeVal, hPro, 3-aminopropionic acid, 4-aminobutyric acid, Inp, Aib, Aha, Ava, MeGly, D-Leu, D-Val, D-Ile, D-Met, D-Ala, D-Pro, D-β-Ala, D-Inp, D-t-BuG, D-MeIle, D-ChA, D-Nle, D-MeVal, D-Nip, D-Pip, and D-hPro. Other non-polar amino acid residues include, but are not limited to, $C_{1-4}$ lateral chain analogs having the following formulas:

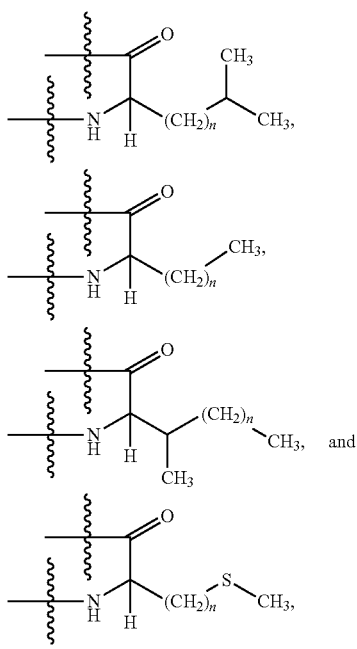

wherein n is an integer from 1 to 4. In one embodiment, the non-polar amino acid residue is an L-amino acid residue. In another embodiment, the non-polar amino acid residue is a D-amino acid residue. In another embodiment, the non-polar amino acid residue is an achiral amino acid residue.

"Aromatic amino acid residue," as used herein unless otherwise defined, refers to a hydrophobic amino acid residue with a side chain having at least one aromatic or heteroaromatic ring. The aromatic or heteroaromatic ring can contain one or more substituents such as —OH, —SH, —CN, —F, —Cl, —Br, —I, —NO₂, —NO, —NH₂, —NHR, —NRR, —C(O)R, —C(O)OH, —C(O)OR, —C(O)NH₂, —C(O) NHR, —C(O)NRR where each R is independently ($C_1$-$C_6$) alkyl, substituted ($C_1$-$C_6$) alkyl, 5-26-membered aryl, and substituted 5-26-membered aryl. Aromatic amino acid residues include, but are not limited to, Phe (F), Tyr (Y), Trp (W), PhG, Nal, Phe(4-Cl), Phe(2-F), Phe(3-F), Phe(4-F), Tic, Thi, hPhe, D-Phe, D-Tyr and D-Trp, D-PhG, D-Nal, D-Phe(4-Cl), D-Phe(2-F), D-Phe(3-F), D-Phe(4-F), D-Tic, D-Thi, and D-hPhe. Other aromatic amino acid residues include, but are not limited to, $C_{1-4}$ lateral chain analogs having the following formulas:

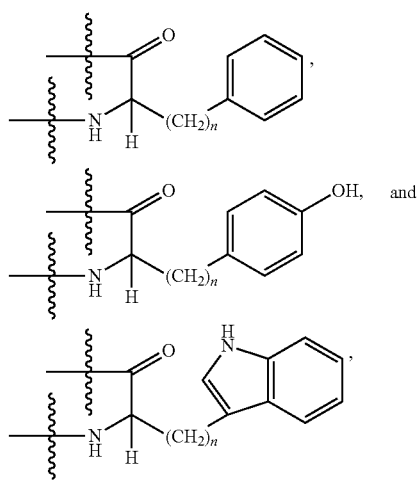

wherein n is an integer from 1 to 4. In one embodiment, the aromatic amino acid residue is an L-amino acid residue. In another embodiment, the aromatic amino acid residue is a D-amino acid residue. In another embodiment, the aromatic amino acid residue is an achiral amino acid residue.

The classifications of the genetically encoded and non-genetically encoded amino acid residues according to the categories defined above are summarized in the table below. It is to be understood that the following table is included for illustrative purposes only and does not purport to be an exhaustive list of amino acid residues that can be used in the ApoA-I Mimics described herein. Other amino acid residues not specifically disclosed herein can be readily categorized based on their observed physical and chemical properties in view of the definitions provided herein. Some classifications of amino acid residues are included in Table 2 below.

TABLE 2

| Classifications of Some Amino Acid Residues | | |
|---|---|---|
| Classification | Genetically Encoded | Non-Genetically Encoded |
| Hydrophobic | | |
| Aromatic | F, Y, W | PhG, Nal, Thi, Tic, Phe(4-Cl), Phe(2-F), Phe(3-F), Phe(4-F), hPhe |

TABLE 2-continued

Classifications of Some Amino Acid Residues

| Classification | Genetically Encoded | Non-Genetically Encoded |
|---|---|---|
| Nonpolar | L, V, I, M, G, A, P | -Ala, t-BuA, t-BuG, Melle, Nle, MeVal, ChA, MeGly, Aib, Nip, hPro, |
| Aliphatic | A, V, L, I, P | -Ala, Aib, t-BuA, t-BuG, Melle, ChA, Nle, MeVal, Nip, hPro, Inp, azPro, Pip, |
| Hydrophilic | | |
| Acidic | D, E | |
| Basic | H, K, R | Dpr, Orn, hArg, Phe(p—NH$_2$), Dbu, Dab, hArg |
| Polar | C, Q, N, S, T | Cit, Pen, AcLys, MSO, bAla, hSer, hCys, hSer, Hyp |
| Helix-Breaking | P, G | MeGly, L-amino acids (in D-peptides), D-Pro and other D-amino acids (in L-peptides), |

As will be appreciated by those of skill in the art, the above-defined categories are not mutually exclusive. Thus, amino acid residues having side chains exhibiting two or more physical-chemical properties can be included in multiple categories. For example, amino acid side chains having aromatic moieties that are further substituted with polar substituents, such as Tyr (Y) or its corresponding D-enantiomer, can exhibit both aromatic hydrophobic properties and polar or hydrophilic properties, and can therefore be included in both the aromatic and polar categories. The appropriate categorization of any amino acid residue will be apparent to those of skill in the art, especially in view of the disclosure provided herein.

In addition, the amino acid residue Cys (C) or its corresponding D-enantiomer can form disulfide bridges with other Cys (C) residues or their corresponding D-enantiomers or with other sulfanyl-containing amino acids. The ability of Cys (C) residues (and other amino acids with —SH containing side chains) to exist in a peptide in either the reduced free —SH or oxidized disulfide-bridged form affects whether Cys (C) residues or their corresponding D-enantiomers contribute net hydrophobic or hydrophilic character to a peptide. While Cys (C) or its corresponding D-enantiomer exhibits a hydrophobicity of 0.29 according to the normalized consensus scale of Eisenberg (Eisenberg, 1984, supra), it is to be understood that for purposes of the present invention Cys (C) and its corresponding D-enantiomer are categorized as polar hydrophilic amino acids, notwithstanding the general classifications defined above.

II. ApoA-I Mimics

A. Peptides of Formula I

In one embodiment, the invention provides 15- to 29-residue peptides having the following Formula I

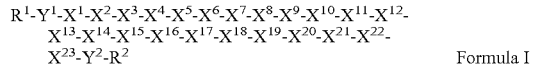
Formula I and pharmaceutically acceptable salts thereof, wherein:
$X^1$ is absent or an achiral, D-, or L-basic amino acid residue;
$X^2$ is an achiral, D-, or L-basic amino acid residue;
$X^3$ is an achiral, D-, or L-aliphatic amino acid residue;
$X^4$ is an achiral, D-, or L-basic amino acid residue;
$X^5$ is Gln, Asn, D-Gln, D-Asn, or an achiral, D-, or L-basic amino acid residue;
$X^6$ is Gln, Asn, D-Gln, D-Asn, or an achiral, D-, or L-basic amino acid residue;
$X^7$ is an achiral, D-, or L-hydrophobic amino acid residue;
$X^8$ is an achiral, D-, or L-hydrophobic amino acid residue;
$X^9$ is an achiral, D-, or L-hydrophilic amino acid residue;
$X^{10}$ is Leu, Trp, Gly, Nal, D-Leu, D-Trp, or D-Nal;
$X^{11}$ is Gly or an achiral, D-, or L-aliphatic amino acid residue;
$X^{12}$ is an achiral, D-, or L-hydrophilic amino acid residue;
$X^{13}$ is an achiral, D-, or L-hydrophilic amino acid residue;
$X^{14}$ is Leu, Trp, Gly, D-Leu, or D-Trp;
$X^{15}$ is Leu, Gly, or D-Leu;
$X^{16}$ is an achiral, D-, or L-acidic amino acid residue or an achiral, D-, or L-basic amino acid residue;
$X^{17}$ is an achiral, D-, or L-hydrophilic amino acid residue;
$X^{18}$ is Leu, Phe, D-Leu, or D-Phe;
$X^{19}$ is Leu, Phe, D-Leu, or D-Phe;
$X^{20}$ is an achiral, D-, or L-acidic amino acid residue;
$X^{21}$ is Leu, Phe, D-Leu, or D-Phe;
$X^{22}$ is an achiral, D-, or L-aliphatic amino acid residue; and
$X^{23}$ is Inp, Nip, azPro, Pip, azPip, D-Nip, or D-Pip;
$Y^1$ is absent or an amino acid sequence having from 1 to 7 residues;
$Y^2$ is absent or an amino acid sequence having from 1 to 7 residues;
$R^1$ is H or an amino protecting group;
$R^2$ is OH or a carboxyl protecting group;
wherein zero to eight of residues $X^2$ to $X^{22}$ are absent; and wherein:
 a) each chiral amino acid residue is an L-amino acid residue;
 b) each chiral amino acid residue is a D-amino acid residue;
 c) each chiral amino acid residue is an L-amino acid residue, except that one or more of each chiral terminal amino acid residue and each chiral amino acid residue immediately adjacent thereto is a D-amino acid residue; or
 d) each chiral amino acid residue is an D-amino acid residue, except that one or more of each chiral terminal amino acid residue and each chiral amino acid residue immediately adjacent thereto is an L-amino acid residue.

In another embodiment, the invention provides 22- to 29-residue peptides having the following Formula I

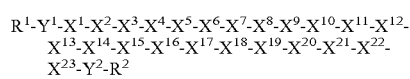
Formula I and pharmaceutically acceptable salts thereof, wherein:
$X^1$ is absent or an achiral, D-, or L-basic amino acid residue;
$X^2$ is an achiral, D-, or L-basic amino acid residue;
$X^3$ is an achiral, D-, or L-aliphatic amino acid residue;
$X^4$ is an achiral, D-, or L-basic amino acid residue;
$X^5$ is Gln, Asn, D-Gln, D-Asn, or an achiral, D-, or L-basic amino acid residue;
$X^6$ is an achiral, D-, or L-basic amino acid residue;
$X^7$ is an achiral, D-, or L-hydrophobic amino acid residue;
$X^8$ is an achiral, D-, or L-hydrophobic amino acid residue;
$X^9$ is an achiral, D-, or L-hydrophilic amino acid residue;
$X^{10}$ is Leu, Trp, Gly, Nal, D-Leu, D-Trp, or D-Nal;
$X^{11}$ is Gly or an achiral, D-, or L-aliphatic amino acid residue;
$X^{12}$ is an achiral, D-, or L-hydrophilic amino acid residue;
$X^{13}$ is an achiral, D-, or L-hydrophilic amino acid residue;
$X^{14}$ is Leu, Trp, Gly, D-Leu, or D-Trp;
$X^{15}$ is Leu, Gly, or D-Leu;
$X^{16}$ is an achiral, D-, or L-acidic amino acid residue;
$X^{17}$ is an achiral, D-, or L-hydrophilic amino acid residue;

$X^{18}$ is Leu, Phe, D-Leu, or D-Phe;
$X^{19}$ is Leu, Phe, D-Leu, or D-Phe;
$X^{20}$ is an achiral, D-, or L-acidic amino acid residue;
$X^{21}$ is Leu, Phe, D-Leu, or D-Phe;
$X^{22}$ is an achiral, D-, or L-aliphatic amino acid residue; and
$X^{23}$ is Inp, Nip, azPro, Pip, azPip, D-Nip, or D-Pip;
$Y^1$ is absent or an amino acid sequence having from 1 to 7 residues;
$Y^2$ is absent or an amino acid sequence having from 1 to 7 residues;
$R^1$ is H or an amino protecting group;
$R^2$ is OH or a carboxyl protecting group;
wherein:
 a) each chiral amino acid residue is an L-amino acid residue;
 b) each chiral amino acid residue is a D-amino acid residue;
 c) each chiral amino acid residue is an L-amino acid residue, except that one or more of each chiral terminal amino acid residue and each chiral amino acid residue immediately adjacent thereto is a D-amino acid residue; or
 d) each chiral amino acid residue is an D-amino acid residue, except that one or more of each chiral terminal amino acid residue and each chiral amino acid residue immediately adjacent thereto is an L-amino acid residue.

In another embodiment, the invention provides 15- to 21-residue peptides having the following Formula I

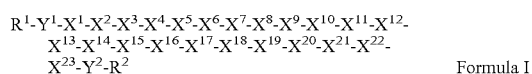

$$R^1\text{-}Y^1\text{-}X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13}\text{-}X^{14}\text{-}X^{15}\text{-}X^{16}\text{-}X^{17}\text{-}X^{18}\text{-}X^{19}\text{-}X^{20}\text{-}X^{21}\text{-}X^{22}\text{-}X^{23}\text{-}Y^2\text{-}R^2$$ Formula I and pharmaceutically acceptable salts thereof, wherein:
$X^1$ is absent or an achiral, D-, or L-basic amino acid residue;
$X^2$ is an achiral, D-, or L-basic amino acid residue;
$X^3$ is an achiral, D-, or L-aliphatic amino acid residue;
$X^4$ is an achiral, D-, or L-basic amino acid residue;
$X^5$ is Gln, Asn, D-Gln, D-Asn, or an achiral, D-, or L-basic amino acid residue;
$X^6$ is an achiral, D-, or L-basic amino acid residue;
$X^7$ is an achiral, D-, or L-hydrophobic amino acid residue;
$X^8$ is an achiral, D-, or L-hydrophobic amino acid residue;
$X^9$ is an achiral, D-, or L-hydrophilic amino acid residue;
$X^{10}$ is Leu, Trp, Gly, Nal, D-Leu, D-Trp, or D-Nal;
$X^{11}$ is Gly or an achiral, D-, or L-aliphatic amino acid residue;
$X^{12}$ is an achiral, D-, or L-hydrophilic amino acid residue;
$X^{13}$ is an achiral, D-, or L-hydrophilic amino acid residue;
$X^{14}$ is Leu, Trp, Gly, D-Leu, or D-Trp;
$X^{15}$ is Leu, Gly, or D-Leu;
$X^{16}$ is an achiral, D-, or L-acidic amino acid residue;
$X^{17}$ is an achiral, D-, or L-hydrophilic amino acid residue;
$X^{18}$ is Leu, Phe, D-Leu, or D-Phe;
$X^{19}$ is Leu, Phe, D-Leu, or D-Phe;
$X^{20}$ is an achiral, D-, or L-acidic amino acid residue;
$X^{21}$ is Leu, Phe, D-Leu, or D-Phe;
$X^{22}$ is an achiral, D-, or L-aliphatic amino acid residue; and
$X^{23}$ is Inp, Nip, azPro, Pip, azPip, D-Nip, or D-Pip;
$Y^1$ is absent or an amino acid sequence having from 1 to 7 residues;
$Y^2$ is absent or an amino acid sequence having from 1 to 7 residues;
$R^1$ is H or an amino protecting group;
$R^2$ is OH or a carboxyl protecting group;
wherein one to eight of residues $X^2$ to $X^{22}$ are absent; and
wherein:
 a) each chiral amino acid residue is an L-amino acid residue;
 b) each chiral amino acid residue is a D-amino acid residue;
 c) each chiral amino acid residue is an L-amino acid residue, except that one or more of each chiral terminal amino acid residue and each chiral amino acid residue immediately adjacent thereto is a D-amino acid residue; or
 d) each chiral amino acid residue is an D-amino acid residue, except that one or more of each chiral terminal amino acid residue and each chiral amino acid residue immediately adjacent thereto is an L-amino acid residue.

In another embodiment, the peptide of Formula I or pharmaceutically acceptable salt thereof is 22 amino acid residues in length and $X^1$ is absent.

The following embodiments relate to the ApoA-1 Mimics of Formula I, unless otherwise specified.

In one embodiment, $X^2$ and $X^4$ are both Lys, Orn, D-Lys, or D-Orn. In another embodiment, $X^5$ is Gln, Lys, D-Gln, or D-Lys. In another embodiment, $X^9$ is an acidic amino acid residue. In another embodiment, $X^{12}$ is Glu, Asn, Gln, Arg, D-Glu, D-Asn, D-Gln, or D-Arg. In another embodiment, $X^{13}$ is Glu, Asn, Gln, Arg, D-Glu, D-Asn, D-Gln, or D-Arg. In another embodiment, $X^{16}$ is an acidic amino acid residue. In another embodiment, $X^{17}$ is Arg, Lys, Orn, D-Arg, D-Lys, or D-Orn. In another embodiment, $X^{21}$ is Leu or D-Leu. In another embodiment, $X^{22}$ is Ala, Val, Leu, D-Ala, D-Val, or D-Leu.

In another embodiment, $X^1$ is absent; $X^{13}$ is an acidic amino acid residue, Arg, or D-Arg; $X^{14}$ is a basic amino acid residue, Asn, Glu, D-Asn, or D-Glu; and $X^2$ to $X^{12}$ and $X^{15}$ to $X^{23}$ are as defined above in Formula I.

In another embodiment, $X^1$ is absent; $X^2$ is Lys, Orn, D-Lys, or D-Orn; $X^3$ is Leu or D-Leu; $X^4$ is Lys, Orn, D-Lys, or D-Orn; $X^5$ is Lys, Orn, Gln, Asn, D-Lys, D-Orn, D-Gln, or D-Asn; $X^6$ is Lys, Orn, Gln, Asn, D-Lys, D-Orn, D-Gln, or D-Asn; $X^7$ is Leu, Gly, Nal, D-Leu, or D-Nal; $X^8$ is Ala, Trp, Gly, Leu, Phe, Nal, D-Ala, D-Trp, D-Leu, D-Phe, or D-Nal; $X^9$ is Asp, Glu, Gln, Lys, D-Asp, D-Glu, D-Gln, or D-Lys; $X^{11}$ is Leu, Gly, D-Leu, or Aib; $X^{12}$ is Asp, Glu, Asn, D-Asp, D-Glu, or D-Asn; $X^{13}$ is Asn, Gln, Glu, Arg, D-Asn, D-Gln, D-Glu, or D-Arg; $X^{16}$ is Asp, Arg, Glu, D-Asp, D-Arg, or D-Glu; $X^{17}$ is Lys, Arg, Orn, Asn, Glu, D-Lys, D-Arg, D-Orn, D-Asn, or D-Glu; $X^{20}$ is Asp, Glu, D-Asp, or D-Glu; and/or $X^{22}$ is Ala, Val, Leu, D-Ala, D-Val, or D-Leu; and $X^{10}$, $X^{14}$, $X^{15}$, $X^{19}$, $X^{21}$, and $X^2$ are as defined above in Formula I.

In another embodiment, $X^1$ is absent; $X^9$ is Glu or D-Glu; $X^{12}$ is Glu or D-Glu; $X^{13}$ is Asn, Glu, D-Asn, or D-Glu; $X^{14}$ is Leu or D-Leu; $X^{15}$ is Leu or D-Leu; $X^{16}$ is Glu or D-Glu; $X^{17}$ is Arg, Lys, D-Arg, or D-Lys; $X^{18}$ is Phe or D-Phe; $X^{19}$ is Leu or D-Leu; $X^{21}$ is Leu or D-Leu; and/or $X^{22}$ is Val or D-Val; and $X^2$ to $X^8$, $X^{10}$, $X^{11}$, $X^{20}$, and $X^{23}$ are as defined above in Formula I.

In another embodiment, $X^1$ is absent; $X^2$ is Lys, Orn, D-Lys, or D-Orn; $X^3$ is Leu or D-Leu; $X^4$ is Lys, Orn, D-Lys, or D-Orn; $X^5$ is Lys, Orn, Gln, Asn, D-Lys, D-Orn, D-Gln, or D-Asn; $X^6$ is Lys, Orn, Gln, Asn, D-Lys, D-Orn, D-Gln, or D-Asn; $X^7$ is Leu, Gly, Nal, D-Leu, or D-Nal; $X^8$ is Ala, Trp, Gly, Leu, Phe, Nal, D-Ala, D-Trp, D-Leu, D-Phe, or D-Nal; $X^9$ is Glu or D-Glu; $X^{11}$ is Leu, D-Leu, Gly, or Aib; $X^{12}$ is Glu or D-Glu; $X^{13}$ is Asn, Glu, D-Asn, or D-Glu; $X^{14}$ is Leu or D-Leu; $X^{15}$ is Leu or D-Leu; $X^{16}$ is Glu or D-Glu; $X^{17}$ is Arg, Lys, D-Arg, or D-Lys; $X^{18}$ is Phe or D-Phe; $X^{19}$ is Leu or D-Leu; $X^{20}$ is Asp, Glu, D-Asp, or D-Glu; $X^{21}$ is Leu or D-Leu; and/or $X^{22}$ is Val or D-Val; and $X^{10}$ and $X^{23}$ are as defined above in Formula I.

In another embodiment, $X^1$ is absent, only one of $X^5$ and $X^6$ is a basic amino acid residue, and the other of $X^5$ and $X^6$ is Gln, Asn, D-Gln, or D-Asn.

In another embodiment, Y1 or Y2 is absent or is a sequence having from one to seven amino acid residues. In another embodiment, one or more of the amino acid residues of the amino acid sequence is an acidic amino acid residue. In another embodiment, one or more of the amino acid residues of the amino acid sequence is a basic amino acid residue.

In another embodiment, one of $X^5$ and $X^6$ is Lys, Orn, D-Lys, or D-Orn, and the other of $X^5$ and $X^6$ is Gln, Asn, D-Gln, or D-Asn.

In another embodiment, each chiral amino acid residue is an L-amino acid residue.

In another embodiment, each chiral amino acid residue is a D-amino acid residue.

In another embodiment, $X^1$ is absent; one of $X^7$, $X^8$, $X^{10}$, $X^{11}$, $X^{14}$ and $X^{15}$ is Gly; and $X^1$ to $X^6$, $X^9$, $X^{12}$, $X^{13}$, and $X^{16}$ to $X^{23}$ are other than Gly.

In another embodiment, $X^1$ is absent; $X^{11}$ is Gly; and each of $X^7$, $X^8$, $X^{10}$, $X^{14}$, and $X^{15}$ is other than Gly.

In another embodiment, $X^1$ is absent; $X^2$ is Lys, Orn, D-Lys, or D-Orn; $X^3$ is Leu or D-Leu; $X^4$ is Lys, Orn, D-Lys, or D-Orn; $X^5$ is Gln or D-Gln; $X^6$ is Lys, Orn, D-Lys, or D-Orn; $X^7$ is Leu, Nal, D-Leu, or D-Nal; $X^8$ is Ala, Trp, D-Ala, or D-Trp; $X^9$ is Glu or D-Glu; $X^{10}$ is Leu or D-Leu; $X^{11}$ is Gly; $X^{12}$ is Glu or D-Glu; $X^{13}$ is Asn or D-Asn; $X^{14}$ is Leu, Tip, D-Leu, or D-Trp; $X^{15}$ is Leu or D-Leu; $X^{16}$ is Glu or D-Glu; $X^{17}$ is Arg or D-Arg; $X^{18}$ is Phe or D-Phe; $X^{19}$ is Leu, Phe, D-Leu, or D-Phe; $X^{20}$ is Asp, Glu, D-Asp, or D-Glu; $X^{21}$ is Leu or D-Leu; $X^{22}$ is Val or D-Val; and $X^{23}$ is Inp. In one embodiment, the peptide of Formula I is a peptide set forth in Table 3 below:

TABLE 3

| | |
|---|---|
| Peptide 2 | Lys-Leu-Lys-Gln-Lys-Leu-Trp-Glu-Leu-Leu-Glu-Asn-Leu-Leu-Glu-Arg-Phe-Leu-Asp-Leu-Val-Inp (SEQ. ID. NO. 2) |
| Peptide 3 | Lys-Leu-Lys-Gln-Lys-Leu-Ala-Glu-Leu-Gly-Glu-Asn-Leu-Leu-Glu-Arg-Phe-Leu-Asp-Leu-Val-Inp (SEQ. ID. NO. 3) |
| Peptide 4 | Lys-Leu-Lys-Gln-Lys-Nal-Ala-Glu-Leu-Gly-Glu-Asn-Leu-Leu-Glu-Arg-Phe-Leu-Asp-Leu-Val-Inp (SEQ. ID. NO. 4) |
| Peptide 5 | Lys-Leu-Lys-Gln-Lys-Leu-Trp-Glu-Leu-Gly-Glu-Asn-Leu-Leu-Glu-Arg-Phe-Leu-Asp-Leu-Val-Inp (SEQ. ID. NO. 5) |
| Peptide 6 | Lys-Leu-Lys-Gln-Lys-Leu-Ala-Glu-Leu-Gly-Glu-Asn-Trp-Leu-Glu-Arg-Phe-Leu-Asp-Leu-Val-Inp (SEQ. ID. NO. 6) |
| Peptide 7 | Orn-Leu-Orn-Gln-Orn-Leu-Ala-Glu-Leu-Gly-Glu-Asn-Leu-Leu-Glu-Arg-Phe-Leu-Asp-Leu-Val-Inp (SEQ. ID. NO. 7) |
| Peptide 8 | Lys-Leu-Lys-Gln-Lys-Leu-Ala-Glu-Leu-Gly-Glu-Asn-Leu-Leu-Glu-Arg-Phe-Phe-Asp-Leu-Val-Inp (SEQ. ID. NO. 8) |
| Peptide 9 | Lys-Leu-Lys-Gln-Lys-Leu-Ala-Glu-Leu-Gly-Glu-Asn-Leu-Leu-Glu-Arg-Phe-Leu-Glu-Leu-Val-Inp (SEQ. ID. NO. 9) |

TABLE 3-continued

| | |
|---|---|
| Peptide 94 | Lys-Leu-Lys-Gln-Lys-Leu-Trp-Glu-Leu-Leu-Glu-Asn-Leu-Leu-Glu-Arg-Phe-Leu-Asp-Leu-Val-Nip (SEQ. ID. NO. 94) |
| Peptide 95 | Lys-Leu-Lys-Gln-Lys-Leu-Ala-Glu-Leu-Gly-Glu-Asn-Leu-Leu-Glu-Arg-Phe-Leu-Asp-Leu-Val-Nip (SEQ. ID. NO. 95) |
| Peptide 96 | Lys-Leu-Lys-Gln-Lys-Nal-Ala-Glu-Leu-Gly-Glu-Asn-Leu-Leu-Glu-Arg-Phe-Leu-Asp-Leu-Val-Nip (SEQ. ID. NO. 96) |
| Peptide 97 | Lys-Leu-Lys-Gln-Lys-Leu-Trp-Glu-Leu-Gly-Glu-Asn-Leu-Leu-Glu-Arg-Phe-Leu-Asp-Leu-Val-Nip (SEQ. ID. NO. 97) |
| Peptide 98 | Lys-Leu-Lys-Gln-Lys-Leu-Ala-Glu-Leu-Gly-Glu-Asn-Trp-Leu-Glu-Arg-Phe-Leu-Asp-Leu-Val-Nip (SEQ. ID. NO. 98) |
| Peptide 99 | Orn-Leu-Orn-Gln-Orn-Leu-Ala-Glu-Leu-Gly-Glu-Asn-Leu-Leu-Glu-Arg-Phe-Leu-Asp-Leu-Val-Nip (SEQ. ID. NO. 99) |
| Peptide 100 | Lys-Leu-Lys-Gln-Lys-Leu-Ala-Glu-Leu-Gly-Glu-Asn-Leu-Leu-Glu-Arg-Phe-Phe-Asp-Leu-Val-Nip (SEQ. ID. NO. 100) |
| Peptide 101 | Lys-Leu-Lys-Gln-Lys-Leu-Ala-Glu-Leu-Gly-Glu-Asn-Leu-Leu-Glu-Arg-Phe-Leu-Glu-Leu-Val-Nip (SEQ. ID. NO. 101) |
| Peptide 214 | Lys-Leu-Lys-Gln-Lys-Leu-Trp-Glu-Leu-Gly-Glu-Asn-Leu-Leu-Glu-Arg-Phe-Leu-Asp-Leu-Val-azPro (SEQ. ID. NO. 214) |
| Peptide 215 | Lys-Leu-Lys-Gln-Lys-Leu-Ala-Glu-Leu-Gly-Glu-Asn-Leu-Leu-Glu-Arg-Phe-Leu-Asp-Leu-Val-azPro (SEQ. ID. NO. 215) |
| Peptide 216 | Lys-Leu-Lys-Gln-Lys-Nal-Ala-Glu-Leu-Gly-Glu-Asn-Leu-Leu-Glu-Arg-Phe-Leu-Asp-Leu-Val-azPro (SEQ. ID. NO. 216) |
| Peptide 217 | Lys-Leu-Lys-Gln-Lys-Leu-Trp-Glu-Leu-Gly-Glu-Asn-Leu-Leu-Glu-Arg-Phe-Leu-Asp-Leu-Val-azPro (SEQ. ID. NO. 217) |
| Peptide 218 | Lys-Leu-Lys-Gln-Lys-Leu-Ala-Glu-Leu-Gly-Glu-Asn-Trp-Leu-Glu-Arg-Phe-Leu-Asp-Leu-Val-azPro (SEQ. ID. NO. 218) |
| Peptide 219 | Orn-Leu-Orn-Gln-Orn-Leu-Ala-Glu-Leu-Gly-Glu-Asn-Leu-Leu-Glu-Arg-Phe-Leu-Asp-Leu-Val-azPro (SEQ. ID. NO. 219) |
| Peptide 220 | Lys-Leu-Lys-Gln-Lys-Leu-Ala-Glu-Leu-Gly-Glu-Asn-Leu-Leu-Glu-Arg-Phe-Phe-Asp-Leu-Val-azPro (SEQ. ID. NO. 220) |
| Peptide 221 | Lys-Leu-Lys-Gln-Lys-Leu-Ala-Glu-Leu-Gly-Glu-Asn-Leu-Leu-Glu-Arg-Phe-Leu-Glu-Leu-Val-azPro (SEQ. ID. NO. 221) |

TABLE 3-continued

| Peptide 306 | Lys-Leu-Lys-Gln-Lys-Leu-Trp-Glu-Leu-Leu-Glu-Asn-Leu-Leu-Glu-Arg-Phe-Leu-Asp-Leu-Val-Pip (SEQ. ID. NO. 306) |
| --- | --- |
| Peptide 307 | Lys-Leu-Lys-Gln-Lys-Leu-Ala-Glu-Leu-Gly-Glu-Asn-Leu-Leu-Glu-Arg-Phe-Leu-Asp-Leu-Val-Pip (SEQ. ID. NO. 307) |
| Peptide 308 | Lys-Leu-Lys-Gln-Lys-Nal-Ala-Glu-Leu-Gly-Glu-Asn-Leu-Leu-Glu-Arg-Phe-Leu-Asp-Leu-Val-Pip (SEQ. ID. NO. 308) |
| Peptide 309 | Lys-Leu-Lys-Gln-Lys-Leu-Trp-Glu-Leu-Gly-Glu-Asn-Leu-Leu-Glu-Arg-Phe-Leu-Asp-Leu-Val-Pip (SEQ. ID. NO. 309) |
| Peptide 310 | Lys-Leu-Lys-Gln-Lys-Leu-Ala-Glu-Leu-Gly-Glu-Asn-Trp-Leu-Glu-Arg-Phe-Leu-Asp-Leu-Val-Pip (SEQ. ID. NO. 310) |
| Peptide 311 | Orn-Leu-Orn-Gln-Orn-Leu-Ala-Glu-Leu-Gly-Glu-Asn-Leu-Leu-Glu-Arg-Phe-Leu-Asp-Leu-Val-Pip (SEQ. ID. NO. 311) |
| Peptide 312 | Lys-Leu-Lys-Gln-Lys-Leu-Ala-Glu-Leu-Gly-Glu-Asn-Leu-Leu-Glu-Arg-Phe-Phe-Asp-Leu-Val-Pip (SEQ. ID. NO. 312) |
| Peptide 313 | Lys-Leu-Lys-Gln-Lys-Leu-Ala-Glu-Leu-Gly-Glu-Asn-Leu-Leu-Glu-Arg-Phe-Leu-Glu-Leu-Val-Pip (SEQ. ID. NO. 313) |
| Peptide 398 | Lys-Leu-Lys-Gln-Lys-Leu-Trp-Glu-Leu-Leu-Glu-Asn-Leu-Leu-Glu-Arg-Phe-Leu-Asp-Leu-Val-azPip (SEQ. ID. NO. 398) |
| Peptide 399 | Lys-Leu-Lys-Gln-Lys-Leu-Ala-Glu-Leu-Gly-Glu-Asn-Leu-Leu-Glu-Arg-Phe-Leu-Asp-Leu-Val-azPip (SEQ. ID. NO. 399) |
| Peptide 400 | Lys-Leu-Lys-Gln-Lys-Nal-Ala-Glu-Leu-Gly-Glu-Asn-Leu-Leu-Glu-Arg-Phe-Leu-Asp-Leu-Val-azPip (SEQ. ID. NO. 400) |
| Peptide 401 | Lys-Leu-Lys-Gln-Lys-Leu-Trp-Glu-Leu-Gly-Glu-Asn-Leu-Leu-Glu-Arg-Phe-Leu-Asp-Leu-Val-azPip (SEQ. ID. NO. 401) |
| Peptide 402 | Lys-Leu-Lys-Gln-Lys-Leu-Ala-Glu-Leu-Gly-Glu-Asn-Trp-Leu-Glu-Arg-Phe-Leu-Asp-Leu-Val-azPip (SEQ. ID. NO. 402) |
| Peptide 403 | Orn-Leu-Orn-Gln-Orn-Leu-Ala-Glu-Leu-Gly-Glu-Asn-Leu-Leu-Glu-Arg-Phe-Leu-Asp-Leu-Val-azPip (SEQ. ID. NO. 403) |
| Peptide 404 | Lys-Leu-Lys-Gln-Lys-Leu-Ala-Glu-Leu-Gly-Glu-Asn-Leu-Leu-Glu-Arg-Phe-Phe-Asp-Leu-Val-azPip (SEQ. ID. NO. 404) |
| Peptide 405 | Lys-Leu-Lys-Gln-Lys-Leu-Ala-Glu-Leu-Gly-Glu-Asn-Leu-Leu-Glu-Arg-Phe-Leu-Glu-Leu-Val-azPip (SEQ. ID. NO. 405) | or a pharmaceutically acceptable salt thereof.

In another embodiment, $X^1$ is absent; $X^{15}$ is Gly; and each of $X^7, X^8, X^{10}, X^{11}$, and $X^{14}$ is other than Gly. In one embodiment, the peptide of Formula I is:

Peptide 10
(SEQ. ID. NO. 10)
Lys-Leu-Lys-Gln-Lys-Leu-Ala-Glu-Leu-Leu-Glu-Asn-Leu-Gly-Glu-Arg-Phe-Leu-Asp-Leu-Val-Inp;
or Peptide 102
(SEQ. ID. NO. 102)
Lys-Leu-Lys-Gln-Lys-Leu-Ala-Glu-Leu-Leu-Glu-Asn-Leu-Gly-Glu-Arg-Phe-Leu-Asp-Leu-Val-Nip Peptide 222
(SEQ. ID. NO. 222)
Lys-Leu-Lys-Gln-Lys-Leu-Ala-Glu-Leu-Leu-Glu-Asn-Leu-Gly-Glu-Arg-Phe-Leu-Asp-Leu-Val-azPro Peptide 314
(SEQ. ID. NO. 314)
Lys-Leu-Lys-Gln-Lys-Leu-Ala-Glu-Leu-Leu-Glu-Asn-Leu-Gly-Glu-Arg-Phe-Leu-Asp-Leu-Val-Pip Peptide 406
(SEQ. ID. NO. 406)
Lys-Leu-Lys-Gln-Lys-Leu-Ala-Glu-Leu-Leu-Glu-Asn-Leu-Gly-Glu-Arg-Phe-Leu-Asp-Leu-Val-azPip or a pharmaceutically acceptable salt thereof In another embodiment, $X^1$ is absent; $X^{14}$ is Gly; and each of $X^7, X^8, X^{10}, X^{11}$, and $X^{15}$ is other than Gly. In one embodiment, the peptide of Formula I is:

Peptide 11
(SEQ. ID. NO. 11)
Lys-Leu-Lys-Gln-Lys-Leu-Ala-Glu-Leu-Leu-Glu-Asn-Gly-Leu-Glu-Arg-Phe-Leu-Asp-Leu-Val-Inp;
or Peptide 103
(SEQ. ID. NO. 103)
Lys-Leu-Lys-Gln-Lys-Leu-Ala-Glu-Leu-Leu-Glu-Asn-Gly-Leu-Glu-Arg-Phe-Leu-Asp-Leu-Val-Nip Peptide 223
(SEQ. ID. NO. 223)
Lys-Leu-Lys-Gln-Lys-Leu-Ala-Glu-Leu-Leu-Glu-Asn-Gly-Leu-Glu-Arg-Phe-Leu-Asp-Leu-Val-azPro Peptide 315
(SEQ. ID. NO. 315)
Lys-Leu-Lys-Gln-Lys-Leu-Ala-Glu-Leu-Leu-Glu-Asn-Gly-Leu-Glu-Arg-Phe-Leu-Asp-Leu-Val-Pip Peptide 407
(SEQ. ID. NO. 407)
Lys-Leu-Lys-Gln-Lys-Leu-Ala-Glu-Leu-Leu-Glu-Asn-Gly-Leu-Glu-Arg-Phe-Leu-Asp-Leu-Val-azPip or a pharmaceutically acceptable salt thereof In another embodiment, $X^1$ is absent; $X^{10}$ is Gly; and each of $X^7, X^8, X^{11}, X^{14}$, and $X^{15}$ is other than Gly. In one embodiment, the peptide of Formula I is:

Peptide 12
(SEQ. ID. NO. 12)
Lys-Leu-Lys-Gln-Lys-Leu-Ala-Glu-Gly-Leu-Glu-Asn-Leu-Leu-Glu-Arg-Phe-Leu-Asp-Leu-Val-Inp;
or Peptide 104
(SEQ. ID. NO. 104)
Lys-Leu-Lys-Gln-Lys-Leu-Ala-Glu-Gly-Leu-Glu-Asn-
Leu-Leu-Glu-Arg-Phe-Leu-Asp-Leu-Val-Nip Peptide 224
(SEQ. ID. NO. 224)
Lys-Leu-Lys-Gln-Lys-Leu-Ala-Glu-Gly-Leu-Glu-Asn-
Leu-Leu-Glu-Arg-Phe-Leu-Asp-Leu-Val-azPro Peptide 316
(SEQ. ID. NO. 316)
Lys-Leu-Lys-Gln-Lys-Leu-Ala-Glu-Gly-Leu-Glu-Asn-
Leu-Leu-Glu-Arg-Phe-Leu-Asp-Leu-Val-Pip Peptide 408
(SEQ. ID. NO. 408)
Lys-Leu-Lys-Gln-Lys-Leu-Ala-Glu-Gly-Leu-Glu-Asn-
Leu-Leu-Glu-Arg-Phe-Leu-Asp-Leu-Val-azPip or a pharmaceutically acceptable salt thereof In another embodiment, $X^1$ is absent; $X^8$ is Gly; and each of $X^7$, $X^{10}$, $X^{11}$, $X^{14}$, and $X^{15}$ is other than Gly. In one embodiment, the peptide of Formula I is:

Peptide 13
(SEQ. ID. NO. 13)
Lys-Leu-Lys-Gln-Lys-Leu-Gly-Glu-Leu-Leu-Glu-Asn-
Leu-Leu-Glu-Arg-Phe-Leu-Asp-Leu-Val-Inp;
or Peptide 105
(SEQ. ID. NO. 105)
Lys-Leu-Lys-Gln-Lys-Leu-Gly-Glu-Leu-Leu-Glu-Asn-
Leu-Leu-Glu-Arg-Phe-Leu-Asp-Leu-Val-Nip Peptide 225
(SEQ. ID. NO. 225)
Lys-Leu-Lys-Gln-Lys-Leu-Gly-Glu-Leu-Leu-Glu-Asn-
Leu-Leu-Glu-Arg-Phe-Leu-Asp-Leu-Val-azPro Peptide 317
(SEQ. ID. NO. 317)
Lys-Leu-Lys-Gln-Lys-Leu-Gly-Glu-Leu-Leu-Glu-Asn-
Leu-Leu-Glu-Arg-Phe-Leu-Asp-Leu-Val-Pip Peptide 409
(SEQ. ID. NO. 409)
Lys-Leu-Lys-Gln-Lys-Leu-Gly-Glu-Leu-Leu-Glu-Asn-
Leu-Leu-Glu-Arg-Phe-Leu-Asp-Leu-Val-azPip or a pharmaceutically acceptable salt thereof In another embodiment, $X^1$ is absent; $X^7$ is Gly; and each of $X^8$, $X^{10}$, $X^{11}$, $X^{14}$, and $X^{15}$ is other than Gly. In one embodiment, the peptide of Formula I is:

Peptide 14
(SEQ. ID. NO. 14)
Lys-Leu-Lys-Gln-Lys-Gly-Ala-Glu-Leu-Leu-Glu-Asn-
Leu-Leu-Glu-Arg-Phe-Leu-Asp-Leu-Val-Inp;
or Peptide 106
(SEQ. ID. NO. 106)
Lys-Leu-Lys-Gln-Lys-Gly-Ala-Glu-Leu-Leu-Glu-Asn-
Leu-Leu-Glu-Arg-Phe-Leu-Asp-Leu-Val-Nip Peptide 226
(SEQ. ID. NO. 226)
Lys-Leu-Lys-Gln-Lys-Gly-Ala-Glu-Leu-Leu-Glu-Asn-
Leu-Leu-Glu-Arg-Phe-Leu-Asp-Leu-Val-azPro Peptide 318
(SEQ. ID. NO. 318)
Lys-Leu-Lys-Gln-Lys-Gly-Ala-Glu-Leu-Leu-Glu-Asn-
Leu-Leu-Glu-Arg-Phe-Leu-Asp-Leu-Val-Pip Peptide 410
(SEQ. ID. NO. 410)
Lys-Leu-Lys-Gln-Lys-Gly-Ala-Glu-Leu-Leu-Glu-Asn-
Leu-Leu-Glu-Arg-Phe-Leu-Asp-Leu-Val-azPip or a pharmaceutically acceptable salt thereof In another embodiment, $X^1$ is absent; and each of $X^7$, $X^8$, $X^{10}$, $X^{11}$, $X^{14}$, and $X^{15}$ is other than Gly.

In another embodiment, $X^1$ is absent; $X^2$ is Lys, Orn, D-Lys, or D-Orn; $X^3$ is Leu or D-Leu; $X^4$ is Lys, Orn, D-Lys, or D-Orn; one of $X^5$ or $X^6$ is Gln or D-Gln and the other of $X^5$ or $X^6$ is Lys, Orn, D-Lys, or D-Orn; $X^7$ is Leu, Nal, D-Leu, or D-Nal; $X^8$ is Ala, Leu, Trp, Nal, D-Ala, D-Leu, D-Trp, or D-Nal; $X^9$ is Glu or D-Glu; $X^{10}$ is Leu, Trp, Nal, D-Leu, D-Trp, or D-Nal; $X^{11}$ is Leu, D-Leu or Aib; $X^{12}$ is Glu or D-Glu; $X^{13}$ is Asn, Gln, D-Asn, or D-Gln; $X^{14}$ is Leu, Trp, D-Leu, or D-Trp; $X^{15}$ is Leu or D-Leu; $X^{16}$ is Glu or D-Glu; $X^{17}$ is Arg, Lys, D-Arg, or D-Lys; $X^{18}$ is Leu, Phe, D-Leu, or D-Phe; $X^{19}$ is Leu, Phe, D-Leu, or D-Phe; $X^{20}$ is Asp, Glu, D-Asp, or D-Glu; $X^{21}$ is Leu or D-Leu; $X^{22}$ is Val, Leu, D-Val, or D-Leu; and $X^{23}$ is Inp.

In another embodiment, $X^1$ is absent; $X^2$ is Lys or D-Lys; $X^3$ is Leu or D-Leu; $X^4$ is Lys or D-Lys; $X^5$ is Glu or D-Glu; $X^6$ is Lys or D-Lys; $X^7$ is Leu or D-Leu; $X^8$ is Ala or D-Ala; $X^9$ is Glu or D-Glu; $X^{10}$ is Leu or D-Leu; $X^{11}$ is Leu or D-Leu; $X^{12}$ is Glu or D-Glu; $X^{13}$ is Asn or D-Asn; $X^{14}$ is Leu or D-Leu; $X^{15}$ is Leu or D-Leu; $X^{16}$ is Glu or D-Glu; $X^{17}$ is Arg or D-Arg; $X^{18}$ is Phe or D-Phe; $X^{19}$ is Leu or D-Leu; $X^{20}$ is Asp or D-Asp; $X^{21}$ is Leu or D-Leu; $X^{22}$ is Val or D-Val; and/or $X^{23}$ is Inp.

In another embodiment, $X^3$ is other than Lys or D-Lys; $X^9$ is other than Trp or D-Trp; $X^{11}$ is other than Glu, Trp, D-Glu, or D-Trp; $X^{12}$ is other than Trp, Leu, D-Trp, or D-Leu; $X^{13}$ is other than Trp or D-Trp; $X^{15}$ is other than Lys, Trp, D-Lys, or D-Trp; $X^{16}$ is other than Trp or D-Trp; $X^{17}$ is other than Trp, Leu, D-Trp, or D-Leu; $X^{18}$ is other than Trp or D-Trp; $X^{19}$ is other than Lys, Glu, Trp, Nal, D-Lys, D-Glu, D-Trp, or D-Nal; and/or $X^{22}$ is other than Val or D-Val.

In another embodiment, the peptide of Formula I is one of the peptides set forth in Table 4 below:

TABLE 4

| Peptide 15 | Lys-Leu-Lys-Gln-Lys-Leu-Nal-Glu-Leu-Leu-Glu-Asn-Leu-Leu-Glu-Arg-Phe-Leu-Asp-Leu-Val-Inp (SEQ. ID. NO. 15) |
|---|---|
| Peptide 16 | Lys-Leu-Lys-Gln-Lys-Leu-Ala-Glu-Leu-Glu-Asn-Leu-Leu-Glu-Arg-Phe-Leu-Asp-Leu-Val-Inp (SEQ. ID. NO. 16) |
| Peptide 17 | Lys-Lys-Leu-Lys-Gln-Lys-Leu-Ala-Glu-Leu-Glu-Asn-Leu-Leu-Glu-Arg-Phe-Leu-Asp-Leu-Val-Inp (SEQ. ID. NO. 17) |
| Peptide 18 | Lys-Leu-Lys-Gln-Lys-Leu-Ala-Glu-Leu-Aib-Glu-Asn-Leu-Leu-Glu-Arg-Phe-Leu-Asp-Leu-Val-Inp (SEQ. ID. NO. 18) |
| Peptide 19 | Lys-Leu-Lys-Gln-Lys-Leu-Ala-Glu-Leu-Leu-Glu-Asn-Leu-Leu-Glu-Lys-Phe-Leu-Asp-Leu-Val-Inp (SEQ. ID. NO. 19) |

TABLE 4-continued

| Peptide 20 | Lys-Leu-Lys-Gln-Lys-Nal-Ala-Glu-Leu-Leu-Glu-Asn-Leu-Leu-Glu-Arg-Phe-Leu-Asp-Leu-Val-Inp (SEQ. ID. NO. 20) |
| --- | --- |
| Peptide 21 | Lys-Leu-Lys-Gln-Lys-Leu-Ala-Glu-Leu-Leu-Glu-Gln-Leu-Leu-Glu-Lys-Phe-Leu-Asp-Leu-Val-Inp (SEQ. ID. NO. 21) |
| Peptide 22 | Orn-Leu-Orn-Gln-Orn-Leu-Ala-Glu-Leu-Leu-Glu-Asn-Leu-Leu-Glu-Arg-Phe-Leu-Asp-Leu-Val-Inp (SEQ. ID. NO. 22) |
| Peptide 23 | Lys-Leu-Lys-Gln-Lys-Leu-Ala-Glu-Leu-Leu-Glu-Asn-Trp-Leu-Glu-Arg-Phe-Leu-Asp-Leu-Val-Inp (SEQ. ID. NO. 23) |
| Peptide 24 | Lys-Leu-Lys-Gln-Lys-Leu-Ala-Glu-Leu-Leu-Glu-Asn-Leu-Leu-Glu-Arg-Leu-Leu-Asp-Leu-Val-Inp (SEQ. ID. NO. 24) |
| Peptide 25 | Lys-Leu-Lys-Gln-Lys-Leu-Ala-Glu-Leu-Leu-Glu-Gln-Leu-Leu-Glu-Lys-Phe-Leu-Glu-Leu-Val-Inp (SEQ. ID. NO. 25) |
| Peptide 26 | Lys-Leu-Lys-Gln-Lys-Leu-Ala-Glu-Leu-Leu-Glu-Gln-Leu-Leu-Glu-Lys-Phe-Leu-Glu-Leu-Leu-Inp (SEQ. ID. NO. 26) |
| Peptide 27 | Lys-Leu-Lys-Lys-Gln-Leu-Ala-Glu-Leu-Leu-Glu-Asn-Leu-Leu-Glu-Arg-Phe-Leu-Asp-Leu-Val-Inp (SEQ. ID. NO. 27) |
| Peptide 28 | Lys-Leu-Lys-Gln-Lys-Leu-Ala-Glu-Leu-Aib-Glu-Asn-Leu-Leu-Glu-Arg-Phe-Phe-Asp-Leu-Val-Inp (SEQ. ID. NO. 28) |
| Peptide 29 | Lys-Leu-Lys-Gln-Lys-Leu-Leu-Glu-Leu-Leu-Glu-Asn-Leu-Leu-Glu-Arg-Phe-Leu-Asp-Leu-Val-Inp (SEQ. ID. NO. 29) |
| Peptide 30 | Lys-Leu-Lys-Gln-Lys-Leu-Ala-Glu-Nal-Leu-Glu-Asn-Leu-Leu-Glu-Arg-Phe-Leu-Asp-Leu-Val-Inp (SEQ. ID. NO. 30) |
| Peptide 31 | Lys-Leu-Lys-Gln-Lys-Leu-Ala-Glu-Trp-Leu-Glu-Asn-Leu-Leu-Glu-Arg-Phe-Leu-Asp-Leu-Val-Inp (SEQ. ID. NO. 31) |
| Peptide 32 | Orn-Leu-Orn-Gln-Orn-Leu-Ala-Glu-Leu-Leu-Glu-Asn-Leu-Leu-Glu-Orn-Phe-Leu-Asp-Leu-Val-Inp (SEQ. ID. NO. 32) |
| Peptide 33 | Lys-Leu-Lys-Gln-Lys-Leu-Phe-Glu-Leu-Leu-Glu-Asn-Leu-Leu-Glu-Arg-Phe-Leu-Asp-Leu-Val-Inp (SEQ. ID. NO. 33) |
| Peptide 34 | Lys-Leu-Lys-Lys-Gln-Leu-Ala-Glu-Leu-Leu-Glu-Arg-Leu-Leu-Asp-Asn-Phe-Leu-Glu-Leu-Val-Inp (SEQ. ID. NO. 34) |
| Peptide 35 | Lys-Leu-Lys-Gln-Lys-Leu-Ala-Glu-Leu-Leu-Glu-Arg-Leu-Leu-Asp-Asn-Phe-Leu-Glu-Leu-Val-Inp (SEQ. ID. NO. 35) |
| Peptide 36 | Lys-Leu-Lys-Gln-Arg-Leu-Ala-Asp-Leu-Leu-Glu-Asn-Leu-Leu-Glu-Lys-Phe-Leu-Glu-Leu-Val-Inp (SEQ. ID. NO. 36) |
| Peptide 37 | Lys-Leu-Lys-Lys-Gln-Leu-Ala-Glu-Leu-Leu-Asn-Glu-Leu-Leu-Glu-Arg-Phe-Leu-Asp-Leu-Val-Inp (SEQ. ID. NO. 37) |
| Peptide 38 | Lys-Leu-Lys-Lys-Asn-Ala-Ala-Gln-Leu-Leu-Asp-Glu-Leu-Leu-Glu-Arg-Glu-Phe-Leu-Glu-Leu-Val-Inp (SEQ. ID. NO. 38) |
| Peptide 39 | Lys-Leu-Lys-Gln-Asn-Leu-Ala-Lys-Leu-Leu-Asp-Glu-Leu-Leu-Arg-Glu-Phe-Leu-Glu-Leu-Val-Inp (SEQ. ID. NO. 39) |
| Peptide 40 | Lys-Leu-Lys-Gln-Lys-Leu-Ala-Glu-Leu-Leu-Glu-Gln-Leu-Leu-Asp-Lys-Phe-Leu-Glu-Leu-Ala-Inp (SEQ. ID. NO. 40) |
| Peptide 107 | Lys-Leu-Lys-Gln-Lys-Leu-Nal-Glu-Leu-Leu-Glu-Asn-Leu-Leu-Glu-Arg-Phe-Leu-Asp-Leu-Val-Nip (SEQ. ID. NO. 107) |
| Peptide 108 | Lys-Leu-Lys-Gln-Lys-Leu-Ala-Glu-Leu-Leu-Glu-Asn-Leu-Leu-Glu-Arg-Phe-Leu-Asp-Leu-Val-Nip (SEQ. ID. NO. 108) |
| Peptide 109 | Lys-Lys-Leu-Lys-Gln-Lys-Leu-Ala-Glu-Leu-Leu-Glu-Asn-Leu-Leu-Glu-Arg-Phe-Leu-Asp-Leu-Val-Nip (SEQ. ID. NO. 109) |
| Peptide 110 | Lys-Leu-Lys-Gln-Lys-Leu-Ala-Glu-Leu-Aib-Glu-Asn-Leu-Leu-Glu-Arg-Phe-Leu-Asp-Leu-Val-Nip (SEQ. ID. NO. 110) |
| Peptide 111 | Lys-Leu-Lys-Gln-Lys-Leu-Ala-Glu-Leu-Leu-Glu-Asn-Leu-Leu-Glu-Lys-Phe-Leu-Asp-Leu-Val-Nip (SEQ. ID. NO. 111) |
| Peptide 112 | Lys-Leu-Lys-Gln-Lys-Nal-Ala-Glu-Leu-Leu-Glu-Asn-Leu-Leu-Glu-Arg-Phe-Leu-Asp-Leu-Val-Nip (SEQ. ID. NO. 112) |
| Peptide 113 | Lys-Leu-Lys-Gln-Lys-Leu-Ala-Glu-Leu-Leu-Glu-Gln-Leu-Leu-Glu-Lys-Phe-Leu-Asp-Leu-Val-Nip (SEQ. ID. NO. 113) |
| Peptide 114 | Orn-Leu-Orn-Gln-Orn-Leu-Ala-Glu-Leu-Leu-Glu-Asn-Leu-Leu-Glu-Arg-Phe-Leu-Asp-Leu-Val-Nip (SEQ. ID. NO. 114) |
| Peptide 115 | Lys-Leu-Lys-Gln-Lys-Leu-Ala-Glu-Leu-Leu-Glu-Asn-Trp-Leu-Glu-Arg-Phe-Leu-Asp-Leu-Val-Nip (SEQ. ID. NO. 115) |
| Peptide 116 | Lys-Leu-Lys-Gln-Lys-Leu-Ala-Glu-Leu-Leu-Glu-Asn-Leu-Leu-Glu-Arg-Leu-Leu-Asp-Leu-Val-Nip (SEQ. ID. NO. 116) |
| Peptide 117 | Lys-Leu-Lys-Gln-Lys-Leu-Ala-Glu-Leu-Leu-Glu-Gln-Leu-Leu-Glu-Lys-Phe-Leu-Glu-Leu-Val-Nip (SEQ. ID. NO. 117) |

TABLE 4-continued

| Peptide 118 | Lys-Leu-Lys-Gln-Lys-Leu-Ala-Glu-Leu-Leu-Glu-Gln-Leu-Leu-Glu-Lys-Phe-Leu-Glu-Leu-Leu-Nip (SEQ. ID. NO. 118) |
| --- | --- |
| Peptide 119 | Lys-Leu-Lys-Lys-Gln-Leu-Ala-Glu-Leu-Leu-Glu-Asn-Leu-Leu-Glu-Arg-Phe-Leu-Asp-Leu-Val-Nip (SEQ. ID. NO. 119) |
| Peptide 120 | Lys-Leu-Lys-Gln-Lys-Leu-Ala-Glu-Leu-Aib-Glu-Asn-Leu-Leu-Glu-Arg-Phe-Phe-Asp-Leu-Val-Nip (SEQ. ID. NO. 120) |
| Peptide 121 | Lys-Leu-Lys-Gln-Lys-Leu-Leu-Glu-Leu-Leu-Glu-Asn-Leu-Leu-Glu-Arg-Phe-Leu-Asp-Leu-Val-Nip (SEQ. ID. NO. 121) |
| Peptide 122 | Lys-Leu-Lys-Gln-Lys-Leu-Ala-Glu-Nal-Leu-Glu-Asn-Leu-Leu-Glu-Arg-Phe-Leu-Asp-Leu-Val-Nip (SEQ. ID. NO. 122) |
| Peptide 123 | Lys-Leu-Lys-Gln-Lys-Leu-Ala-Glu-Trp-Leu-Glu-Asn-Leu-Leu-Glu-Arg-Phe-Leu-Asp-Leu-Val-Nip (SEQ. ID. NO. 123) |
| Peptide 124 | Orn-Leu-Orn-Gln-Orn-Leu-Ala-Glu-Leu-Leu-Glu-Asn-Leu-Leu-Glu-Orn-Phe-Leu-Asp-Leu-Val-Nip (SEQ. ID. NO. 124) |
| Peptide 125 | Lys-Leu-Lys-Gln-Lys-Leu-Phe-Glu-Leu-Leu-Glu-Asn-Leu-Leu-Glu-Arg-Phe-Leu-Asp-Leu-Val-Nip (SEQ. ID. NO. 125) |
| Peptide 126 | Lys-Leu-Lys-Lys-Gln-Leu-Ala-Glu-Leu-Leu-Glu-Arg-Leu-Leu-Asp-Asn-Phe-Leu-Glu-Leu-Val-Nip (SEQ. ID. NO. 126) |
| Peptide 127 | Lys-Leu-Lys-Gln-Lys-Leu-Ala-Glu-Leu-Leu-Glu-Arg-Leu-Leu-Asp-Asn-Phe-Leu-Glu-Leu-Val-Nip (SEQ. ID. NO. 127) |
| Peptide 128 | Lys-Leu-Lys-Gln-Arg-Leu-Ala-Asp-Leu-Leu-Glu-Asn-Leu-Leu-Glu-Lys-Phe-Leu-Glu-Leu-Val-Nip (SEQ. ID. NO. 128) |
| Peptide 129 | Lys-Leu-Lys-Lys-Gln-Leu-Ala-Glu-Leu-Leu-Asn-Glu-Leu-Leu-Glu-Arg-Phe-Leu-Asp-Leu-Val-Nip (SEQ. ID. NO. 129) |
| Peptide 130 | Lys-Leu-Lys-Lys-Asn-Leu-Ala-Gln-Leu-Leu-Asp-Glu-Leu-Leu-Arg-Glu-Phe-Leu-Glu-Leu-Val-Nip (SEQ. ID. NO. 130) |
| Peptide 131 | Lys-Leu-Lys-Gln-Asn-Leu-Ala-Lys-Leu-Leu-Asp-Glu-Leu-Leu-Arg-Glu-Phe-Leu-Glu-Leu-Val-Nip (SEQ. ID. NO. 131) |
| Peptide 132 | Lys-Leu-Lys-Gln-Lys-Leu-Ala-Glu-Leu-Leu-Glu-Gln-Leu-Leu-Asp-Lys-Phe-Leu-Glu-Leu-Ala-Nip (SEQ. ID. NO. 132) |
| Peptide 227 | Lys-Leu-Lys-Gln-Lys-Leu-Nal-Glu-Leu-Leu-Glu-Asn-Leu-Leu-Glu-Arg-Phe-Leu-Asp-Leu-Val-azPro (SEQ. ID. NO. 227) |
| Peptide 228 | Lys-Leu-Lys-Gln-Lys-Leu-Ala-Glu-Leu-Leu-Glu-Asn-Leu-Leu-Glu-Arg-Phe-Leu-Asp-Leu-Val-azPro (SEQ. ID. NO. 228) |
| Peptide 229 | Lys-Lys-Leu-Lys-Gln-Lys-Leu-Ala-Glu-Leu-Leu-Glu-Asn-Leu-Leu-Glu-Arg-Phe-Leu-Asp-Leu-Val-azPro (SEQ. ID. NO. 229) |
| Peptide 230 | Lys-Leu-Lys-Gln-Lys-Leu-Ala-Glu-Leu-Aib-Glu-Asn-Leu-Leu-Glu-Arg-Phe-Leu-Asp-Leu-Val-azPro (SEQ. ID. NO. 230) |
| Peptide 231 | Lys-Leu-Lys-Gln-Lys-Leu-Ala-Glu-Leu-Leu-Glu-Asn-Leu-Leu-Glu-Lys-Phe-Leu-Asp-Leu-Val-azPro (SEQ. ID. NO. 231) |
| Peptide 232 | Lys-Leu-Lys-Gln-Lys-Nal-Ala-Glu-Leu-Leu-Glu-Asn-Leu-Leu-Glu-Arg-Phe-Leu-Asp-Leu-Val-azPro (SEQ. ID. NO. 232) |
| Peptide 233 | Lys-Leu-Lys-Gln-Lys-Leu-Ala-Glu-Leu-Leu-Glu-Gln-Leu-Leu-Glu-Lys-Phe-Leu-Asp-Leu-Val-azPro (SEQ. ID. NO. 233) |
| Peptide 234 | Orn-Leu-Orn-Gln-Orn-Leu-Ala-Glu-Leu-Leu-Glu-Asn-Leu-Leu-Glu-Arg-Phe-Leu-Asp-Leu-Val-azPro (SEQ. ID. NO. 234) |
| Peptide 235 | Lys-Leu-Lys-Gln-Lys-Leu-Ala-Glu-Leu-Leu-Glu-Asn-Trp-Leu-Glu-Arg-Phe-Leu-Asp-Leu-Val-azPro (SEQ. ID. NO. 235) |
| Peptide 236 | Lys-Leu-Lys-Gln-Lys-Leu-Ala-Glu-Leu-Leu-Glu-Asn-Leu-Leu-Glu-Arg-Leu-Leu-Asp-Leu-Val-azPro (SEQ. ID. NO. 236) |
| Peptide 237 | Lys-Leu-Lys-Gln-Lys-Leu-Ala-Glu-Leu-Leu-Glu-Gln-Leu-Leu-Glu-Lys-Phe-Leu-Glu-Leu-Val-azPro (SEQ. ID. NO. 237) |
| Peptide 238 | Lys-Leu-Lys-Gln-Lys-Leu-Ala-Glu-Leu-Leu-Glu-Gln-Leu-Leu-Glu-Lys-Phe-Leu-Glu-Leu-Leu-azPro (SEQ. ID. NO. 238) |
| Peptide 239 | Lys-Leu-Lys-Lys-Gln-Leu-Ala-Glu-Leu-Leu-Glu-Asn-Leu-Leu-Glu-Arg-Phe-Leu-Asp-Leu-Val-azPro (SEQ. ID. NO. 239) |
| Peptide 240 | Lys-Leu-Lys-Gln-Lys-Leu-Ala-Glu-Leu-Aib-Glu-Asn-Leu-Leu-Glu-Arg-Phe-Phe-Asp-Leu-Val-azPro (SEQ. ID. NO. 240) |
| Peptide 241 | Lys-Leu-Lys-Gln-Lys-Leu-Leu-Glu-Leu-Leu-Glu-Asn-Leu-Leu-Glu-Arg-Phe-Leu-Asp-Leu-Val-azPro (SEQ. ID. NO. 241) |
| Peptide 242 | Lys-Leu-Lys-Gln-Lys-Leu-Ala-Glu-Nal-Leu-Glu-Asn-Leu-Leu-Glu-Arg-Phe-Leu-Asp-Leu-Val-azPro (SEQ. ID. NO. 242) |
| Peptide 243 | Lys-Leu-Lys-Gln-Lys-Leu-Ala-Glu-Trp-Leu-Glu-Asn-Leu-Leu-Glu-Arg-Phe-Leu-Asp-Leu-Val-azPro (SEQ. ID. NO. 243) |

TABLE 4-continued

| | |
|---|---|
| Peptide 244 | Orn-Leu-Orn-Gln-Orn-Leu-Ala-Glu-Leu-Leu-Glu-Asn-Leu-Leu-Glu-Orn-Phe-Leu-Asp-Leu-Val-azPro (SEQ. ID. NO. 244) |
| Peptide 245 | Lys-Leu-Lys-Gln-Lys-Leu-Phe-Glu-Leu-Leu-Glu-Asn-Leu-Leu-Glu-Arg-Phe-Leu-Asp-Leu-Val-azPro (SEQ. ID. NO. 245) |
| Peptide 246 | Lys-Leu-Lys-Gln-Lys-Leu-Ala-Glu-Leu-Leu-Glu-Arg-Leu-Leu-Asp-Asn-Phe-Leu-Glu-Leu-Val-azPro (SEQ. ID. NO. 246) |
| Peptide 247 | Lys-Leu-Lys-Gln-Lys-Leu-Ala-Glu-Leu-Leu-Glu-Arg-Leu-Leu-Asp-Asn-Phe-Leu-Glu-Leu-Val-azPro (SEQ. ID. NO. 247) |
| Peptide 248 | Lys-Leu-Lys-Gln-Arg-Leu-Ala-Asp-Leu-Leu-Glu-Asn-Leu-Leu-Glu-Lys-Phe-Leu-Glu-Leu-Val-azPro (SEQ. ID. NO. 248) |
| Peptide 249 | Lys-Leu-Lys-Lys-Gln-Leu-Ala-Glu-Leu-Leu-Asn-Glu-Leu-Leu-Glu-Arg-Phe-Leu-Asp-Leu-Val-azPro (SEQ. ID. NO. 249) |
| Peptide 250 | Lys-Leu-Lys-Lys-Asn-Leu-Ala-Gln-Leu-Leu-Asp-Glu-Leu-Leu-Arg-Glu-Phe-Leu-Glu-Leu-Val-azPro (SEQ. ID. NO. 250) |
| Peptide 251 | Lys-Leu-Lys-Gln-Asn-Leu-Ala-Lys-Leu-Leu-Asp-Glu-Leu-Leu-Arg-Glu-Phe-Leu-Glu-Leu-Val-azPro (SEQ. ID. NO. 251) |
| Peptide 252 | Lys-Leu-Lys-Gln-Lys-Leu-Ala-Glu-Leu-Leu-Glu-Gln-Leu-Leu-Asp-Lys-Phe-Leu-Glu-Leu-Ala-azPro (SEQ. ID. NO. 252) |
| Peptide 319 | Lys-Leu-Lys-Gln-Lys-Leu-Nal-Glu-Leu-Leu-Glu-Asn-Leu-Leu-Glu-Arg-Phe-Leu-Asp-Leu-Val-Pip (SEQ. ID. NO. 319) |
| Peptide 320 | Lys-Leu-Lys-Gln-Lys-Leu-Ala-Glu-Leu-Leu-Glu-Asn-Leu-Leu-Glu-Arg-Phe-Leu-Asp-Leu-Val-Pip (SEQ. ID. NO. 320) |
| Peptide 321 | Lys-Lys-Leu-Lys-Gln-Lys-Leu-Ala-Glu-Leu-Leu-Glu-Asn-Leu-Leu-Glu-Arg-Phe-Leu-Asp-Leu-Val-Pip (SEQ. ID. NO. 321) |
| Peptide 322 | Lys-Leu-Lys-Gln-Lys-Leu-Ala-Glu-Leu-Aib-Glu-Leu-Asn-Leu-Leu-Glu-Arg-Phe-Leu-Asp-Leu-Val-Pip (SEQ. ID. NO. 322) |
| Peptide 323 | Lys-Leu-Lys-Gln-Lys-Leu-Ala-Glu-Leu-Leu-Glu-Asn-Leu-Leu-Glu-Lys-Phe-Leu-Asp-Leu-Val-Pip (SEQ. ID. NO. 323) |
| Peptide 324 | Lys-Leu-Lys-Gln-Lys-Nal-Ala-Glu-Leu-Leu-Glu-Asn-Leu-Leu-Glu-Arg-Phe-Leu-Asp-Leu-Val-Pip (SEQ. ID. NO. 324) |
| Peptide 325 | Lys-Leu-Lys-Gln-Lys-Leu-Ala-Glu-Leu-Leu-Glu-Gln-Leu-Leu-Glu-Lys-Phe-Leu-Asp-Leu-Val-Pip (SEQ. ID. NO. 325) |
| Peptide 326 | Orn-Leu-Orn-Gln-Orn-Leu-Ala-Glu-Leu-Leu-Glu-Asn-Leu-Leu-Glu-Arg-Phe-Leu-Asp-Leu-Val-Pip (SEQ. ID. NO. 326) |
| Peptide 327 | Lys-Leu-Lys-Gln-Lys-Leu-Ala-Glu-Leu-Leu-Glu-Asn-Trp-Leu-Glu-Arg-Phe-Leu-Asp-Leu-Val-Pip (SEQ. ID. NO. 327) |
| Peptide 328 | Lys-Leu-Lys-Gln-Lys-Leu-Ala-Glu-Leu-Leu-Glu-Asn-Leu-Leu-Glu-Arg-Phe-Leu-Asp-Leu-Val-Pip (SEQ. ID. NO. 328) |
| Peptide 329 | Lys-Leu-Lys-Gln-Lys-Leu-Ala-Glu-Leu-Leu-Glu-Gln-Leu-Leu-Glu-Lys-Phe-Leu-Glu-Leu-Val-Pip (SEQ. ID. NO. 329) |
| Peptide 330 | Lys-Leu-Lys-Gln-Lys-Leu-Ala-Glu-Leu-Leu-Glu-Gln-Leu-Leu-Glu-Lys-Phe-Leu-Glu-Leu-Leu-Pip (SEQ. ID. NO. 330) |
| Peptide 331 | Lys-Leu-Lys-Lys-Gln-Leu-Ala-Glu-Leu-Leu-Asn-Glu-Leu-Leu-Glu-Arg-Phe-Leu-Asp-Leu-Val-Pip (SEQ. ID. NO. 331) |
| Peptide 332 | Lys-Leu-Lys-Gln-Lys-Leu-Ala-Glu-Leu-Aib-Glu-Asn-Leu-Leu-Glu-Arg-Phe-Phe-Asp-Leu-Val-Pip (SEQ. ID. NO. 332) |
| Peptide 333 | Lys-Leu-Lys-Gln-Lys-Leu-Leu-Glu-Leu-Leu-Glu-Asn-Leu-Leu-Glu-Arg-Phe-Leu-Asp-Leu-Val-Pip (SEQ. ID. NO. 333) |
| Peptide 334 | Lys-Leu-Lys-Gln-Lys-Leu-Ala-Glu-Nal-Leu-Glu-Asn-Leu-Leu-Glu-Arg-Phe-Leu-Asp-Leu-Val-Pip (SEQ. ID. NO. 334) |
| Peptide 335 | Lys-Leu-Lys-Gln-Lys-Leu-Ala-Glu-Trp-Leu-Glu-Asn-Leu-Leu-Glu-Arg-Phe-Leu-Asp-Leu-Val-Pip (SEQ. ID. NO. 335) |
| Peptide 336 | Orn-Leu-Orn-Gln-Orn-Leu-Ala-Glu-Leu-Leu-Glu-Asn-Leu-Leu-Glu-Orn-Phe-Leu-Asp-Leu-Val-Pip (SEQ. ID. NO. 336) |
| Peptide 337 | Lys-Leu-Lys-Gln-Lys-Leu-Phe-Glu-Leu-Leu-Glu-Asn-Leu-Leu-Glu-Arg-Phe-Leu-Asp-Leu-Val-Pip (SEQ. ID. NO. 337) |
| Peptide 338 | Lys-Leu-Lys-Lys-Gln-Leu-Ala-Glu-Leu-Leu-Glu-Arg-Leu-Leu-Asp-Asn-Phe-Leu-Glu-Leu-Val-Pip (SEQ. ID. NO. 338) |
| Peptide 339 | Lys-Leu-Lys-Gln-Lys-Leu-Ala-Glu-Leu-Leu-Glu-Arg-Leu-Leu-Asp-Asn-Phe-Leu-Glu-Leu-Val-Pip (SEQ. ID. NO. 339) |
| Peptide 340 | Lys-Leu-Lys-Gln-Arg-Leu-Ala-Asp-Leu-Leu-Glu-Asn-Leu-Leu-Glu-Lys-Phe-Leu-Glu-Leu-Val-Pip (SEQ. ID. NO. 340) |
| Peptide 341 | Lys-Leu-Lys-Lys-Gln-Leu-Ala-Glu-Leu-Leu-Asn-Glu-Leu-Leu-Glu-Arg-Phe-Leu-Asp-Leu-Val-Pip (SEQ. ID. NO. 341) |

TABLE 4-continued

Peptide 342  Lys-Leu-Lys-Lys-Asn-Leu-Ala-Gln-
Leu-Leu-Asp-Glu-Leu-Leu-Arg-Glu-
Phe-Leu-Glu-Leu-Val-Pip
(SEQ. ID. NO. 342)

Peptide 343  Lys-Leu-Lys-Gln-Asn-Leu-Ala-Lys-
Leu-Leu-Asp-Glu-Leu-Leu-Arg-Glu-
Phe-Leu-Glu-Leu-Val-Pip
(SEQ. ID. NO. 343)

Peptide 344  Lys-Leu-Lys-Gln-Lys-Leu-Ala-Glu-
Leu-Leu-Glu-Gln-Leu-Leu-Asp-Lys-
Phe-Leu-Glu-Leu-Ala-Pip
(SEQ. ID. NO. 344)

Peptide 411  Lys-Leu-Lys-Gln-Lys-Leu-Nal-Glu-
Leu-Leu-Glu-Asn-Leu-Leu-Glu-Arg-
Phe-Leu-Asp-Leu-Val-azPip
(SEQ. ID. NO. 411)

Peptide 412  Lys-Leu-Lys-Gln-Lys-Leu-Ala-Glu-
Leu-Leu-Glu-Asn-Leu-Leu-Glu-Arg-
Phe-Leu-Asp-Leu-Val-azPip
(SEQ. ID. NO. 412)

Peptide 413  Lys-Lys-Leu-Lys-Gln-Lys-Leu-Ala-
Glu-Leu-Leu-Glu-Asn-Leu-Leu-Glu-
Arg-Phe-Leu-Asp-Leu-Val-azPip
(SEQ. ID. NO. 413)

Peptide 414  Lys-Leu-Lys-Gln-Lys-Leu-Ala-Glu-
Leu-Aib-Glu-Asn-Leu-Leu-Glu-Arg-
Phe-Leu-Asp-Leu-Val-azPip
(SEQ. ID. NO. 414)

Peptide 415  Lys-Leu-Lys-Gln-Lys-Leu-Ala-Glu-
Leu-Leu-Glu-Asn-Leu-Leu-Glu-Lys-
Phe-Leu-Asp-Leu-Val-azPip
(SEQ. ID. NO. 415)

Peptide 416  Lys-Leu-Lys-Gln-Lys-Nal-Ala-Glu-
Leu-Leu-Glu-Asn-Leu-Leu-Glu-Arg-
Phe-Leu-Asp-Leu-Val-azPip
(SEQ. ID. NO. 416)

Peptide 417  Lys-Leu-Lys-Gln-Lys-Leu-Ala-Glu-
Leu-Leu-Glu-Gln-Leu-Leu-Glu-Lys-
Phe-Leu-Asp-Leu-Val-azPip
(SEQ. ID. NO. 417)

Peptide 418  Orn-Leu-Orn-Gln-Orn-Leu-Ala-Glu-
Leu-Leu-Glu-Asn-Leu-Leu-Glu-Arg-
Phe-Leu-Asp-Leu-Val-azPip
(SEQ. ID. NO. 418)

Peptide 419  Lys-Leu-Lys-Gln-Lys-Leu-Ala-Glu-
Leu-Leu-Glu-Asn-Trp-Leu-Glu-Arg-
Phe-Leu-Asp-Leu-Val-azPip
(SEQ. ID. NO. 419)

Peptide 420  Lys-Leu-Lys-Gln-Lys-Leu-Ala-Glu-
Leu-Leu-Glu-Asn-Leu-Leu-Glu-Arg-
Leu-Leu-Asp-Leu-Val-azPip
(SEQ. ID. NO. 420)

Peptide 421  Lys-Leu-Lys-Gln-Lys-Leu-Ala-Glu-
Leu-Leu-Glu-Gln-Leu-Leu-Glu-Lys-
Phe-Leu-Glu-Leu-Val-azPip
(SEQ. ID. NO. 421)

Peptide 422  Lys-Leu-Lys-Gln-Lys-Leu-Ala-Glu-
Leu-Leu-Glu-Gln-Leu-Leu-Glu-Lys-
Phe-Leu-Glu-Leu-Leu-azPip
(SEQ. ID. NO. 422)

Peptide 423  Lys-Leu-Lys-Lys-Gln-Leu-Ala-Glu-
Leu-Leu-Glu-Asn-Leu-Leu-Glu-Arg-
Phe-Leu-Asp-Leu-Val-azPip
(SEQ. ID. NO. 423)

TABLE 4-continued

Peptide 424  Lys-Leu-Lys-Gln-Lys-Leu-Ala-Glu-
Leu-Aib-Glu-Asn-Leu-Leu-Glu-Arg-
Phe-Phe-Asp-Leu-Val-azPip
(SEQ. ID. NO. 424)

Peptide 425  Lys-Leu-Lys-Gln-Lys-Leu-Leu-Glu-
Leu-Leu-Glu-Asn-Leu-Leu-Glu-Arg-
Phe-Leu-Asp-Leu-Val-azPip
(SEQ. ID. NO. 425)

Peptide 426  Lys-Leu-Lys-Gln-Lys-Leu-Ala-Glu-
Nal-Leu-Glu-Asn-Leu-Leu-Glu-Arg-
Phe-Leu-Asp-Leu-Val-azPip
(SEQ. ID. NO. 426)

Peptide 427  Lys-Leu-Lys-Gln-Lys-Leu-Ala-Glu-
Trp-Leu-Glu-Asn-Leu-Leu-Glu-Arg-
Phe-Leu-Asp-Leu-Val-azPip
(SEQ. ID. NO. 427)

Peptide 428  Orn-Leu-Orn-Gln-Orn-Leu-Ala-Glu-
Leu-Leu-Glu-Asn-Leu-Leu-Glu-Orn-
Phe-Leu-Asp-Leu-Val-azPip
(SEQ. ID. NO. 428)

Peptide 429  Lys-Leu-Lys-Gln-Lys-Leu-Phe-Glu-
Leu-Leu-Glu-Asn-Leu-Leu-Glu-Arg-
Phe-Leu-Asp-Leu-Val-azPip
(SEQ. ID. NO. 429)

Peptide 430  Lys-Leu-Lys-Lys-Gln-Leu-Ala-Glu-
Leu-Leu-Glu-Arg-Leu-Leu-Asp-Asn-
Phe-Leu-Glu-Leu-Val-azPip
(SEQ. ID. NO. 430)

Peptide 431  Lys-Leu-Lys-Gln-Lys-Leu-Ala-Glu-
Leu-Leu-Glu-Arg-Leu-Leu-Asp-Asn-
Phe-Leu-Glu-Leu-Val-azPip
(SEQ. ID. NO. 431)

Peptide 432  Lys-Leu-Lys-Gln-Arg-Leu-Ala-Asp-
Leu-Leu-Glu-Asn-Leu-Leu-Glu-Lys-
Phe-Leu-Glu-Leu-Val-azPip
(SEQ. ID. NO. 432)

Peptide 433  Lys-Leu-Lys-Lys-Gln-Leu-Ala-Glu-
Leu-Leu-Asn-Glu-Leu-Leu-Glu-Arg-
Phe-Leu-Asp-Leu-Val-azPip
(SEQ. ID. NO. 433)

Peptide 434  Lys-Leu-Lys-Lys-Asn-Leu-Ala-Gln-
Leu-Leu-Asp-Glu-Leu-Leu-Arg-Glu-
Phe-Leu-Glu-Leu-Val-azPip
(SEQ. ID. NO. 434)

Peptide 435  Lys-Leu-Lys-Gln-Asn-Leu-Ala-Lys-
Leu-Leu-Asp-Glu-Leu-Leu-Arg-Glu-
Phe-Leu-Glu-Leu-Val-azPip
(SEQ. ID. NO. 435)

Peptide 436  Lys-Leu-Lys-Gln-Lys-Leu-Ala-Glu-
Leu-Leu-Glu-Gln-Leu-Leu-Asp-Lys-
Phe-Leu-Glu-Leu-Ala-azPip
(SEQ. ID. NO. 436)

or a pharmaceutically acceptable salt thereof.

B. Peptides of Formula II

In one embodiment, the invention encompasses 14- to 22-residue peptides having the following Formula II $$R^1\text{-}Y^1\text{-}X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13}\text{-}X^{14}\text{-}X^{15}\text{-}X^{16}\text{-}X^{17}\text{-}X^{18}\text{-}Y^2\text{-}R^2,$$ 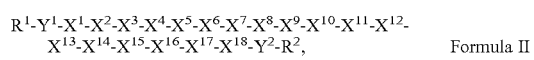

and pharmaceutically acceptable salts thereof, wherein:
$X^1$ is an achiral, D-, or L-basic amino acid residue;
$X^2$ is Leu or D-Leu;
$X^3$ is an achiral, D-, or L-basic amino acid residue;
$X^4$ is Gln, Asn, D-Gln, or D-Asn;

$X^5$ is Leu, D-Leu, or an achiral, D-, or L-basic amino acid amino acid residue;
$X^6$ is Leu, Trp, Phe, D-Leu, D-Trp, or D-Phe;
$X^7$ is an achiral, D-, or L-acidic amino acid residue;
$X^8$ is Asn, D-Asn, or an achiral, D-, or L-acidic amino acid residue;
$X^9$ is Leu, Trp, D-Leu, or D-Trp;
$X^{10}$ is Leu, Trp, D-Leu, or D-Trp;
$X^{11}$ is an achiral, D-, or L-acidic amino acid residue;
$X^{12}$ is an achiral, D-, or L-basic amino acid residue;
$X^{13}$ is Leu, Phe, D-Leu, or D-Phe;
$X^{14}$ is Leu, Phe, D-Leu, or D-Phe;
$X^{15}$ is an achiral, D-, or L-acidic amino acid residue;
$X^{16}$ is Leu or D-Leu;
$X^{17}$ is an achiral, D-, or L-aliphatic amino acid residue;
$X^{18}$ is Inp, Nip, azPro, Pip, azPip, D-Nip, or D-Pip;
$Y^1$ is absent or an amino acid sequence having from 1 to 4 residues;
$Y^2$ is absent or an amino acid sequence having from 1 to 4 residues;
$R^1$ is H or an amino protecting group;
$R^2$ is OH or a carboxyl protecting group;
wherein zero to eight of residues $X^1$ to $X^{17}$ are absent; and
wherein:
a) each chiral amino acid residue is an L-amino acid residue;
b) each chiral amino acid residue is a D-amino acid residue;
c) each chiral amino acid residue is an L-amino acid residue, except that one or more of each chiral terminal amino acid residue and each chiral amino acid residue immediately adjacent thereto is a D-amino acid residue; or
d) each chiral amino acid residue is an D-amino acid residue, except that one or more of each chiral terminal amino acid residue and each chiral amino acid residue immediately adjacent thereto is an L-amino acid residue.

In another embodiment, the invention encompasses 15- to 22-residue peptides having the following Formula II

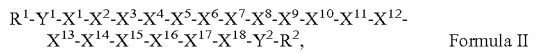

$$R^1-Y^1-X^1-X^2-X^3-X^4-X^5-X^6-X^7-X^8-X^9-X^{10}-X^{11}-X^{12}-X^{13}-X^{14}-X^{15}-X^{16}-X^{17}-X^{18}-Y^2-R^2, \quad \text{Formula II}$$

and pharmaceutically acceptable salts thereof, wherein:
$X^1$ is an achiral, D-, or L-basic amino acid residue;
$X^2$ is Leu or D-Leu;
$X^3$ is an achiral, D-, or L-basic amino acid residue;
$X^4$ is Gln, Asn, D-Gln, or D-Asn;
$X^5$ is Leu, D-Leu, or an achiral, D-, or L-basic amino acid amino acid residue;
$X^6$ is Leu, Trp, Phe, D-Leu, D-Trp, or D-Phe;
$X^7$ is an achiral, D-, or L-acidic amino acid residue;
$X^8$ is Asn, D-Asn, or an achiral, D-, or L-acidic amino acid residue;
$X^9$ is Leu, Trp, D-Leu, or D-Trp;
$X^{10}$ is Leu, Trp, D-Leu, or D-Trp;
$X^{11}$ is an achiral, D-, or L-acidic amino acid residue;
$X^{12}$ is an achiral, D-, or L-basic amino acid residue;
$X^{13}$ is Leu, Phe, D-Leu, or D-Phe;
$X^{14}$ is Leu, Phe, D-Leu, or D-Phe;
$X^{15}$ is an achiral, D-, or L-acidic amino acid residue;
$X^{16}$ is Leu or D-Leu;
$X^{17}$ is an achiral, D-, or L-aliphatic amino acid residue;
$X^{18}$ is Inp, Nip, azPro, Pip, azPip, D-Nip, or D-Pip;
$Y^1$ is absent or an amino acid sequence having from 1 to 4 residues;
$Y^2$ is absent;
$R^1$ is H or an amino protecting group;
$R^2$ is OH or a carboxyl protecting group;
wherein zero to three of residues $X^1$ to $X^{17}$ are absent; and
wherein:
a) each chiral amino acid residue is an L-amino acid residue;
b) each chiral amino acid residue is a D-amino acid residue;
c) each chiral amino acid residue is an L-amino acid residue, except that one or more of each chiral terminal amino acid residue and each chiral amino acid residue immediately adjacent thereto is a D-amino acid residue; or
d) each chiral amino acid residue is an D-amino acid residue, except that one or more of each chiral terminal amino acid residue and each chiral amino acid residue immediately adjacent thereto is an L-amino acid residue.

In another embodiment, the invention encompasses 14-residue peptides having the following Formula II

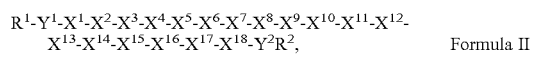

$$R^1-Y^1-X^1-X^2-X^3-X^4-X^5-X^6-X^7-X^8-X^9-X^{10}-X^{11}-X^{12}-X^{13}-X^{14}-X^{15}-X^{16}-X^{17}-X^{18}-Y^2-R^2, \quad \text{Formula II}$$

and pharmaceutically acceptable salts thereof, wherein:
$X^1$ is an achiral, D-, or L-basic amino acid residue;
$X^2$ is Leu or D-Leu;
$X^3$ is an achiral, D-, or L-basic amino acid residue;
$X^4$ is Gln, Asn, D-Gln, or D-Asn;
$X^5$ is Leu, D-Leu, or an achiral, D-, or L-basic amino acid amino acid residue;
$X^6$ is Leu, Trp, Phe, D-Leu, D-Trp, or D-Phe;
$X^7$ is an achiral, D-, or L-acidic amino acid residue;
$X^8$ is Asn, D-Asn, or an achiral, D-, or L-acidic amino acid residue;
$X^9$ is Leu, Trp, D-Leu, or D-Trp;
$X^{10}$ is Leu, Trp, D-Leu, or D-Trp;
$X^{11}$ is an achiral, D-, or L-acidic amino acid residue;
$X^{12}$ is an achiral, D-, or L-basic amino acid residue;
$X^{13}$ is Leu, Phe, D-Leu, or D-Phe;
$X^{14}$ is Leu, Phe, D-Leu, or D-Phe;
$X^{15}$ is an achiral, D-, or L-acidic amino acid residue;
$X^{16}$ is Leu or D-Leu;
$X^{17}$ is an achiral, D-, or L-aliphatic amino acid residue;
$X^{18}$ is Inp, Nip, azPro, Pip, azPip, D-Nip, or D-Pip;
$Y^1$ is absent or an amino acid sequence having from 1 to 4 residues;
$Y^2$ is absent;
$R^1$ is H or an amino protecting group;
$R^2$ is OH or a carboxyl protecting group;
wherein four to eight of residues $X^1$ to $X^{17}$ are absent; and
wherein:
a) each chiral amino acid residue is an L-amino acid residue;
b) each chiral amino acid residue is a D-amino acid residue;
c) each chiral amino acid residue is an L-amino acid residue, except that one or more of each chiral terminal amino acid residue and each chiral amino acid residue immediately adjacent thereto is a D-amino acid residue; or
d) each chiral amino acid residue is an D-amino acid residue, except that one or more of each chiral terminal amino acid residue and each chiral amino acid residue immediately adjacent thereto is an L-amino acid residue.

In one embodiment, the peptide of Formula II is an 18-residue peptide.

In one embodiment, the peptide of Formula II is a peptide set forth in Table 5 below.

TABLE 5

| Peptide 51 | Glu-Leu-Leu-Glu-Asn-Leu-Leu-Glu-Arg-Phe-Leu-Asp-Leu-Val-Inp (SEQ. ID. NO. 51) |

TABLE 5-continued

| | |
|---|---|
| Peptide 53 | Lys-Leu-Lys-Gln-Leu-Leu-Glu-Asn-Leu-Leu-Glu-Arg-Phe-Leu-Asp-Leu-Val-Inp (SEQ. ID. NO. 53) |
| Peptide 54 | Lys-Leu-Lys-Gln-Lys-Leu-Glu-Glu-Leu-Leu-Glu-Arg-Phe-Leu-Asp-Leu-Val-Inp (SEQ. ID. NO. 54) |
| Peptide 55 | Lys-Leu-Lys-Gln-Lys-Leu-Glu-Glu-Leu-Leu-Glu-Lys-Phe-Leu-Glu-Leu-Val-Inp (SEQ. ID. NO. 55) |
| Peptide 56 | Lys-Leu-Lys-Gln-Lys-Leu-Leu-Glu-Leu-Leu-Glu-Arg-Phe-Leu-Asp-Leu-Val-Inp (SEQ. ID. NO. 56) |
| Peptide 58 | Lys-Leu-Lys-Lys-Gln-Leu-Glu-Glu-Leu-Leu-Glu-Arg-Phe-Leu-Asp-Leu-Val-Inp (SEQ. ID. NO. 58) |
| Peptide 143 | Glu-Leu-Leu-Glu-Asn-Leu-Leu-Glu-Arg-Phe-Leu-Asp-Leu-Val-Nip (SEQ. ID. NO. 143) |
| Peptide 145 | Lys-Leu-Lys-Gln-Leu-Leu-Glu-Asn-Leu-Leu-Glu-Arg-Phe-Leu-Asp-Leu-Val-Nip (SEQ. ID. NO. 145) |
| Peptide 146 | Lys-Leu-Lys-Gln-Lys-Leu-Glu-Glu-Leu-Leu-Glu-Arg-Phe-Leu-Asp-Leu-Val-Nip (SEQ. ID. NO. 146) |
| Peptide 147 | Lys-Leu-Lys-Gln-Lys-Leu-Glu-Glu-Leu-Leu-Glu-Lys-Phe-Leu-Glu-Leu-Val-Nip (SEQ. ID. NO. 147) |
| Peptide 148 | Lys-Leu-Lys-Gln-Lys-Leu-Leu-Glu-Leu-Leu-Glu-Arg-Phe-Leu-Asp-Leu-Val-Nip (SEQ. ID. NO. 148) |
| Peptide 150 | Lys-Leu-Lys-Lys-Gln-Leu-Glu-Glu-Leu-Leu-Glu-Arg-Phe-Leu-Asp-Leu-Val-Nip (SEQ. ID. NO. 150) |
| Peptide 263 | Glu-Leu-Leu-Glu-Asn-Leu-Leu-Glu-Arg-Phe-Leu-Asp-Leu-Val-azPro (SEQ. ID. NO. 263) |
| Peptide 265 | Lys-Leu-Lys-Gln-Leu-Leu-Glu-Asn-Leu-Leu-Glu-Arg-Phe-Leu-Asp-Leu-Val-azPro (SEQ. ID. NO. 265) |
| Peptide 266 | Lys-Leu-Lys-Gln-Lys-Leu-Glu-Glu-Leu-Leu-Glu-Arg-Phe-Leu-Asp-Leu-Val-azPro (SEQ. ID. NO. 266) |
| Peptide 267 | Lys-Leu-Lys-Gln-Lys-Leu-Glu-Glu-Leu-Leu-Glu-Lys-Phe-Leu-Glu-Leu-Val-azPro (SEQ. ID. NO. 267) |
| Peptide 268 | Lys-Leu-Lys-Gln-Lys-Leu-Leu-Glu-Leu-Leu-Glu-Arg-Phe-Leu-Asp-Leu-Val-azPro (SEQ. ID. NO. 268) |
| Peptide 270 | Lys-Leu-Lys-Lys-Gln-Leu-Glu-Glu-Leu-Leu-Glu-Arg-Phe-Leu-Asp-Leu-Val-azPro (SEQ. ID. NO. 270) |
| Peptide 355 | Glu-Leu-Leu-Glu-Asn-Leu-Leu-Glu-Arg-Phe-Leu-Asp-Leu-Val-Pip (SEQ. ID. NO. 355) |
| Peptide 357 | Lys-Leu-Lys-Gln-Leu-Leu-Glu-Asn-Leu-Leu-Glu-Arg-Phe-Leu-Asp-Leu-Val-Pip (SEQ. ID. NO. 357) |
| Peptide 358 | Lys-Leu-Lys-Gln-Lys-Leu-Glu-Glu-Leu-Leu-Glu-Arg-Phe-Leu-Asp-Leu-Val-Pip (SEQ. ID. NO. 358) |
| Peptide 359 | Lys-Leu-Lys-Gln-Lys-Leu-Glu-Glu-Leu-Leu-Glu-Lys-Phe-Leu-Glu-Leu-Val-Pip (SEQ. ID. NO. 359) |
| Peptide 360 | Lys-Leu-Lys-Gln-Lys-Leu-Leu-Glu-Leu-Leu-Glu-Arg-Phe-Leu-Asp-Leu-Val-Pip (SEQ. ID. NO. 360) |
| Peptide 362 | Lys-Leu-Lys-Lys-Gln-Leu-Glu-Glu-Leu-Leu-Glu-Arg-Phe-Leu-Asp-Leu-Val-Pip (SEQ. ID. NO. 362) |
| Peptide 447 | Glu-Leu-Leu-Glu-Asn-Leu-Leu-Glu-Arg-Phe-Leu-Asp-Leu-Val-azPip (SEQ. ID. NO. 447) |
| Peptide 449 | Lys-Leu-Lys-Gln-Leu-Leu-Glu-Asn-Leu-Leu-Glu-Arg-Phe-Leu-Asp-Leu-Val-azPip (SEQ. ID. NO. 449) |
| Peptide 450 | Lys-Leu-Lys-Gln-Lys-Leu-Glu-Glu-Leu-Leu-Glu-Arg-Phe-Leu-Asp-Leu-Val-azPip (SEQ. ID. NO. 450) |
| Peptide 451 | Lys-Leu-Lys-Gln-Lys-Leu-Glu-Glu-Leu-Leu-Glu-Lys-Phe-Leu-Glu-Leu-Val-azPip (SEQ. ID. NO. 451) |
| Peptide 452 | Lys-Leu-Lys-Gln-Lys-Leu-Leu-Glu-Leu-Leu-Glu-Arg-Phe-Leu-Asp-Leu-Val-azPip (SEQ. ID. NO. 452) |
| Peptide 454 | Lys-Leu-Lys-Lys-Gln-Leu-Glu-Glu-Leu-Leu-Glu-Arg-Phe-Leu-Asp-Leu-Val-azPip (SEQ. ID. NO. 454) | or a pharmaceutically acceptable salt thereof.

C. Peptides of Formula III

In one embodiment, the invention provides 15- to 29-residue peptides having the following Formula III $$R^1\text{-}Y^1\text{-}X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13}\text{-}X^{14}\text{-}X^{15}\text{-}X^{16}\text{-}X^{17}\text{-}X^{18}\text{-}X^{19}\text{-}X^{20}\text{-}X^{21}\text{-}X^{22}\text{-}X^{23}\text{-}Y^2\text{-}R^2 \quad \text{Formula III}$$

or a pharmaceutically acceptable salt thereof, wherein:

$X^1$ is absent or an achiral, D-, or L-basic amino acid residue;

$X^2$ is an achiral, D-, or L-basic amino acid residue;

$X^3$ is an achiral, D-, or L-aliphatic amino acid residue;

$X^4$ is an achiral, D-, or L-basic amino acid residue;

$X^5$ is Gln, Asn, D-Gln, D-Asn, or an achiral, D-, or L-basic amino acid residue;

$X^6$ is Gln, Asn, D-Gln, D-Asn, or an achiral, D-, or L-basic amino acid residue;

$X^7$ is an achiral, D-, or L-hydrophobic amino acid residue;

$X^8$ is an achiral, D-, or L-hydrophobic amino acid residue;

$X^9$ is an achiral, D-, or L-hydrophilic amino acid residue;

$X^{10}$ is Leu, Trp, Gly, Nal, D-Leu, D-Trp, or D-Nal;

$X^{11}$ is Gly or an achiral, D-, L-aliphatic amino acid residue;

$X^{12}$ is an achiral, D-, or L-hydrophilic amino acid residue;

$X^{13}$ is an achiral, D-, or L-hydrophilic amino acid residue;

$X^{14}$ is Leu, Trp, Gly, D-Leu, or D-Trp;

$X^{15}$ is Leu, Gly, or D-Leu;

$X^{16}$ is an achiral, D-, or L-acidic amino acid residue or an achiral, D-, or L-basic amino acid residue;

$X^{17}$ is an achiral, D-, or L-hydrophilic amino acid residue;

$X^{18}$ is Leu, Phe, D-Leu, or D-Phe;

$X^{19}$ is Leu, Phe, D-Leu, or D-Phe;

$X^{20}$ is an achiral, D-, or L-acidic amino acid residue;

$X^{21}$ is Leu, Phe, D-Leu, or D-Phe;

$X^{22}$ is an achiral, D-, or L-aliphatic amino acid residue; and $X^{23}$ is Inp, Nip, azPro, Pip, azPip, D-Nip, or D-Pip;

Y¹ is absent or an amino acid sequence having from 1 to 7 residues;
Y² is absent or an amino acid sequence having from 1 to 7 residues;
R¹ is H or an amino protecting group;
R² is OH or a carboxyl protecting group;
wherein zero to eight of residues $X^2$ to $X^{22}$ are absent; and
wherein:
 a) each chiral amino acid residue is an L-amino acid residue;
 b) each chiral amino acid residue is a D-amino acid residue;
 c) each chiral amino acid residue is an L-amino acid residue, except that one or more of each chiral terminal amino acid residue and each chiral amino acid residue immediately adjacent thereto is a D-amino acid residue; or
 d) each chiral amino acid residue is an D-amino acid residue, except that one or more of each chiral terminal amino acid residue and each chiral amino acid residue immediately adjacent thereto is an L-amino acid residue.

In another embodiment, the invention provides 22- to 29-residue peptides having the following Formula III

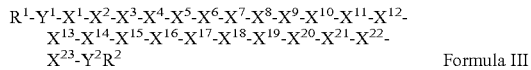
Formula III and pharmaceutically acceptable salts thereof, wherein:
 $X^1$ is absent or an achiral, D-, or L-basic amino acid residue;
 $X^2$ is an achiral, D-, or L-basic amino acid residue;
 $X^3$ is an achiral, D-, or L-aliphatic amino acid residue;
 $X^4$ is an achiral, D-, or L-basic amino acid residue;
 $X^5$ is Gln, Asn, D-Gln, D-Asn, or an achiral D-, or L-basic amino acid residue;
 $X^6$ is an achiral, D-, or L-basic amino acid residue;
 $X^7$ is an achiral, D-, or L-hydrophobic amino acid residue;
 $X^8$ is an achiral, D-, or L-hydrophobic amino acid residue;
 $X^9$ is an achiral, D-, or L-hydrophilic amino acid residue;
 $X^{10}$ is Leu, Trp, Gly, Nal, D-Leu, D-Trp, or D-Nal;
 $X^{11}$ is Gly or an achiral, D-, or L-aliphatic amino acid residue;
 $X^{12}$ is an achiral, D-, or L-hydrophilic amino acid residue;
 $X^{13}$ is an achiral, D-, or L-hydrophilic amino acid residue;
 $X^{14}$ is Leu, Trp, Gly, D-Leu, or D-Trp;
 $X^{15}$ is Leu, Gly, or D-Leu;
 $X^{16}$ is an achiral, D-, or L-acidic amino acid residue;
 $X^{17}$ is an achiral, D-, or L-hydrophilic amino acid residue;
 $X^{18}$ is Leu, Phe, D-Leu, or D-Phe;
 $X^{19}$ is Leu, Phe, D-Leu, or D-Phe;
 $X^{20}$ is an achiral, D-, or L-acidic amino acid residue;
 $X^{21}$ is Leu, Phe, D-Leu, or D-Phe;
 $X^{22}$ is an achiral, D-, or L-aliphatic amino acid residue; and
 $X^{23}$ is Inp, Nip, azPro, Pip, azPip, D-Nip, or D-Pip;
 Y¹ is absent or an amino acid sequence having from 1 to 7 residues;
 Y² is absent or an amino acid sequence having from 1 to 7 residues;
 R¹ is H or an amino protecting group;
 R² is OH or a carboxyl protecting group;
wherein:
 a) each chiral amino acid residue is an L-amino acid residue;
 b) each chiral amino acid residue is a D-amino acid residue;
 c) each chiral amino acid residue is an L-amino acid residue, except that one or more of each chiral terminal amino acid residue and each chiral amino acid residue immediately adjacent thereto is a D-amino acid residue; or
 d) each chiral amino acid residue is an D-amino acid residue, except that one or more of each chiral terminal amino acid residue and each chiral amino acid residue immediately adjacent thereto is an L-amino acid residue.

In another embodiment, the invention provides 15- to 21-residue peptides having the following Formula III

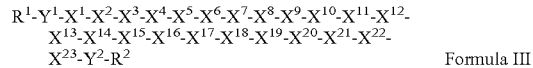
Formula III and pharmaceutically acceptable salts thereof, wherein:
 $X^1$ is absent or an achiral, D-, or L-basic amino acid residue;
 $X^2$ is an achiral, D-, or L-basic amino acid residue;
 $X^3$ is an achiral, D-, or L-aliphatic amino acid residue;
 $X^4$ is an achiral, D-, or L-basic amino acid residue;
 $X^5$ is Gln, Asn, D-Gln, D-Asn, or an achiral, D-, or L-basic amino acid residue;
 $X^6$ is an achiral, D-, or L-basic amino acid residue;
 $X^7$ is an achiral, D-, or L-hydrophobic amino acid residue;
 $X^8$ is an achiral, D-, or L-hydrophobic amino acid residue;
 $X^9$ is an achiral, D-, or L-hydrophilic amino acid residue;
 $X^{10}$ is Leu, Trp, Gly, Nal, D-Leu, D-Trp, or D-Nal;
 $X^{11}$ is Gly or an achiral, D-, or L-aliphatic amino acid residue;
 $X^{12}$ is an achiral, D-, or L-hydrophilic amino acid residue;
 $X^{13}$ is an achiral, D-, or L-hydrophilic amino acid residue;
 $X^{14}$ is Leu, Trp, Gly, D-Leu, or D-Trp;
 $X^{15}$ is Leu, Gly, or D-Leu;
 $X^{16}$ is an achiral, D-, or L-acidic amino acid residue;
 $X^{17}$ is an achiral, D-, or L-hydrophibic amino acid residue;
 $X^{18}$ is Leu, Phe, D-Leu, or D-Phe;
 $X^{19}$ is an Leu, Phe, D-Leu, or D-Phe;
 $X^{20}$ is an achiral, D-, or L-acidic amino acid residue;
 $X^{21}$ is Leu, Phe, D-Leu, or D-Phe;
 $X^{22}$ is an achiral, D-, or L-aliphatic amino acid residue; and
 $X^{23}$ is Inp, Nip, azPro, Pip, azPip, D-Nip, or D-Pip;
 Y¹ is absent or an amino acid sequence having from 1 to 7 residues;
 Y² is absent or an amino acid sequence having from 1 to 7 residues;
 R¹ is H or an amino protecting group;
 R² is OH or a carboxyl protecting group;
wherein one to eight of residues $X^2$ to $X^{22}$ are absent; and
wherein:
 a) each chiral amino acid residue is an L-amino acid residue;
 b) each chiral amino acid residue is a D-amino acid residue;
 c) each chiral amino acid residue is an L-amino acid residue, except that one or more of each chiral terminal amino acid residue and each chiral amino acid residue immediately adjacent thereto is a D-amino acid residue; or
 d) each chiral amino acid residue is an D-amino acid residue, except that one or more of each chiral terminal amino acid residue and each chiral amino acid residue immediately adjacent thereto is an L-amino acid residue.

In another embodiment, the peptide of Formula III is 22 amino acid residues in length and $X^1$ is absent.

In one embodiment, the peptide of Formula III is a peptide set forth in Table 6 below.

TABLE 6

| Peptide 186 | Lys-Leu-Lys-Lys-Gln-Leu-Ala-Asp-Leu-Leu-Arg-Glu-Leu-Leu-Asn-Glu-Phe-Leu-Glu-Phe-Val-Inp (SEQ. ID. NO. 186) |

TABLE 6-continued

| Peptide 187 | Lys-Leu-Lys-Lys-Gln-Leu-Ala-Asp-Leu-Gly-Arg-Glu-Leu-Leu-Asn-Glu-Phe-Leu-Glu-Leu-Val-Inp (SEQ. ID. NO. 187) |
| --- | --- |
| Peptide 188 | Lys-Leu-Lys-Lys-Gln-Leu-Ala-Asp-Leu-Leu-Arg-Glu-Trp-Leu-Asn-Leu-Phe-Leu-Glu-Leu-Val-Inp (SEQ. ID. NO. 188) |
| Peptide 189 | Lys-Leu-Lys-Lys-Gln-Leu-Ala-Asp-Leu-Leu-Arg-Glu-Leu-Leu-Asn-Leu-Phe-Leu-Glu-Leu-Val-Inp (SEQ. ID. NO. 189) |
| Peptide 190 | Lys-Leu-Lys-Lys-Gln-Leu-Trp-Asp-Leu-Leu-Arg-Glu-Leu-Leu-Asn-Leu-Phe-Leu-Glu-Leu-Val-Inp (SEQ. ID. NO. 190) |
| Peptide 191 | Lys-Leu-Lys-Lys-Gln-Leu-Trp-Asp-Leu-Leu-Arg-Glu-Leu-Leu-Asn-Glu-Phe-Leu-Glu-Leu-Val-Inp (SEQ. ID. NO. 191) |
| Peptide 192 | Lys-Leu-Lys-Lys-Gln-Trp-Ala-Asp-Leu-Leu-Arg-Glu-Leu-Leu-Asn-Glu-Phe-Leu-Glu-Leu-Val-Inp (SEQ. ID. NO. 192) |
| Peptide 193 | Lys-Leu-Lys-Lys-Gln-Leu-Ala-Asp-Leu-Leu-Arg-Glu-Leu-Leu-Asn-Glu-Phe-Leu-Glu-Leu-Val-Inp (SEQ. ID. NO. 193) |
| Peptide 194 | Lys-Leu-Lys-Lys-Gln-Leu-Ala-Asp-Gly-Leu-Arg-Glu-Leu-Leu-Asn-Leu-Phe-Leu-Glu-Leu-Val-Inp (SEQ. ID. NO. 194) |
| Peptide 195 | Lys-Leu-Lys-Lys-Gln-Trp-Ala-Asp-Leu-Leu-Arg-Glu-Leu-Leu-Asn-Leu-Phe-Leu-Glu-Leu-Val-Inp (SEQ. ID. NO. 195) |
| Peptide 196 | Orn-Leu-Orn-Orn-Gln-Leu-Ala-Asp-Leu-Leu-Arg-Glu-Leu-Leu-Asn-Glu-Phe-Leu-Glu-Leu-Val-Inp (SEQ. ID. NO. 196) |
| Peptide 197 | Lys-Leu-Lys-Lys-Gln-Leu-Ala-Asp-Leu-Leu-Arg-Glu-Leu-Leu-Gln-Glu-Phe-Leu-Glu-Leu-Val-Inp (SEQ. ID. NO. 197) |
| Peptide 198 | Lys-Leu-Lys-Lys-Asn-Leu-Ala-Asp-Leu-Leu-Arg-Glu-Leu-Leu-Asn-Glu-Phe-Leu-Glu-Leu-Val-Inp (SEQ. ID. NO. 198) |
| Peptide 199 | Lys-Leu-Lys-Lys-Gln-Leu-Ala-Asp-Leu-Leu-Arg-Asp-Leu-Leu-Asn-Glu-Phe-Leu-Glu-Leu-Val-Inp (SEQ. ID. NO. 199) |
| Peptide 200 | Lys-Leu-Lys-Lys-Gln-Leu-Ala-Asp-Leu-Leu-Arg-Glu-Leu-Leu-Asn-Glu-Phe-Leu-Glu-Phe-Val-Nip (SEQ. ID. NO. 200) |
| Peptide 201 | Lys-Leu-Lys-Lys-Gln-Leu-Ala-Asp-Leu-Gly-Arg-Glu-Leu-Leu-Asn-Glu-Phe-Leu-Glu-Leu-Val-Nip (SEQ. ID. NO. 201) |
| Peptide 202 | Lys-Leu-Lys-Lys-Gln-Leu-Ala-Asp-Leu-Leu-Arg-Glu-Trp-Leu-Asn-Leu-Phe-Leu-Glu-Leu-Val-Nip (SEQ. ID. NO. 202) |
| Peptide 203 | Lys-Leu-Lys-Lys-Gln-Leu-Ala-Asp-Leu-Leu-Arg-Glu-Leu-Leu-Asn-Leu-Phe-Leu-Glu-Leu-Val-Nip (SEQ. ID. NO. 203) |
| Peptide 204 | Lys-Leu-Lys-Lys-Gln-Leu-Trp-Asp-Leu-Leu-Arg-Glu-Leu-Leu-Asn-Leu-Phe-Leu-Glu-Leu-Val-Nip (SEQ. ID. NO. 204) |
| Peptide 205 | Lys-Leu-Lys-Lys-Gln-Leu-Trp-Asp-Leu-Leu-Arg-Glu-Leu-Leu-Asn-Glu-Phe-Leu-Glu-Leu-Val-Nip (SEQ. ID. NO. 205) |
| Peptide 206 | Lys-Leu-Lys-Lys-Gln-Trp-Ala-Asp-Leu-Leu-Arg-Glu-Leu-Leu-Asn-Glu-Phe-Leu-Glu-Leu-Val-Nip (SEQ. ID. NO. 206) |
| Peptide 207 | Lys-Leu-Lys-Lys-Gln-Leu-Leu-Asp-Leu-Leu-Arg-Glu-Leu-Leu-Asn-Glu-Phe-Leu-Glu-Leu-Val-Nip (SEQ. ID. NO. 207) |
| Peptide 208 | Lys-Leu-Lys-Lys-Gln-Leu-Ala-Asp-Gly-Leu-Arg-Glu-Leu-Leu-Asn-Leu-Phe-Leu-Glu-Leu-Val-Nip (SEQ. ID. NO. 208) |
| Peptide 209 | Lys-Leu-Lys-Lys-Gln-Trp-Ala-Asp-Leu-Leu-Arg-Glu-Leu-Leu-Asn-Leu-Phe-Leu-Glu-Leu-Val-Nip (SEQ. ID. NO. 209) |
| Peptide 210 | Orn-Leu-Orn-Orn-Gln-Leu-Ala-Asp-Leu-Leu-Arg-Glu-Leu-Leu-Asn-Leu-Phe-Leu-Glu-Leu-Val-Nip (SEQ. ID. NO. 210) |
| Peptide 211 | Lys-Leu-Lys-Lys-Gln-Leu-Ala-Asp-Leu-Leu-Arg-Glu-Leu-Leu-Gln-Glu-Phe-Leu-Glu-Leu-Val-Nip (SEQ. ID. NO. 211) |
| Peptide 212 | Lys-Leu-Lys-Lys-Asn-Leu-Ala-Asp-Leu-Leu-Arg-Glu-Leu-Leu-Asn-Glu-Phe-Leu-Glu-Leu-Val-Nip (SEQ. ID. NO. 212) |
| Peptide 213 | Lys-Leu-Lys-Lys-Gln-Leu-Ala-Asp-Leu-Leu-Arg-Asp-Leu-Leu-Asn-Glu-Phe-Leu-Glu-Leu-Val-Nip (SEQ. ID. NO. 213) |
| Peptide 490 | Lys-Leu-Lys-Lys-Gln-Leu-Ala-Asp-Leu-Leu-Arg-Glu-Leu-Leu-Asn-Glu-Phe-Leu-Glu-Phe-Val-azPro (SEQ. ID. NO. 490) |
| Peptide 491 | Lys-Leu-Lys-Lys-Gln-Leu-Ala-Asp-Leu-Gly-Arg-Glu-Leu-Leu-Asn-Glu-Phe-Leu-Glu-Leu-Val-azPro (SEQ. ID. NO. 491) |
| Peptide 492 | Lys-Leu-Lys-Lys-Gln-Leu-Ala-Asp-Leu-Leu-Arg-Glu-Trp-Leu-Asn-Leu-Phe-Leu-Glu-Leu-Val-azPro (SEQ. ID. NO. 492) |
| Peptide 493 | Lys-Leu-Lys-Lys-Gln-Leu-Ala-Asp-Leu-Leu-Arg-Glu-Leu-Leu-Asn-Leu-Phe-Leu-Glu-Leu-Val-azPro (SEQ. ID. NO. 493) |
| Peptide 494 | Lys-Leu-Lys-Lys-Gln-Leu-Trp-Asp-Leu-Leu-Arg-Glu-Leu-Leu-Asn-Leu-Phe-Leu-Glu-Leu-Val-azPro (SEQ. ID. NO. 494) |

TABLE 6-continued

| | |
|---|---|
| Peptide 495 | Lys-Leu-Lys-Lys-Gln-Leu-Trp-Asp-Leu-Leu-Arg-Glu-Leu-Leu-Asn-Glu-Phe-Leu-Glu-Leu-Val-azPro (SEQ. ID. NO. 495) |
| Peptide 496 | Lys-Leu-Lys-Lys-Gln-Trp-Ala-Asp-Leu-Leu-Arg-Glu-Leu-Leu-Asn-Glu-Phe-Leu-Glu-Leu-Val-azPro (SEQ. ID. NO. 496) |
| Peptide 497 | Lys-Leu-Lys-Lys-Gln-Leu-Leu-Asp-Leu-Leu-Arg-Glu-Leu-Leu-Asn-Glu-Phe-Leu-Glu-Leu-Val-azPro (SEQ. ID. NO. 497) |
| Peptide 498 | Lys-Leu-Lys-Lys-Gln-Leu-Ala-Asp-Gly-Leu-Arg-Glu-Leu-Leu-Asn-Leu-Phe-Leu-Glu-Leu-Val-azPro (SEQ. ID. NO. 498) |
| Peptide 499 | Lys-Leu-Lys-Lys-Gln-Trp-Ala-Asp-Leu-Leu-Arg-Glu-Leu-Leu-Asn-Leu-Phe-Leu-Glu-Leu-Val-azPro (SEQ. ID. NO. 499) |
| Peptide 500 | Orn-Leu-Orn-Orn-Gln-Leu-Ala-Asp-Leu-Leu-Arg-Glu-Leu-Leu-Asn-Glu-Phe-Leu-Glu-Leu-Val-azPro (SEQ. ID. NO. 500) |
| Peptide 501 | Lys-Leu-Lys-Lys-Gln-Leu-Ala-Asp-Leu-Leu-Arg-Glu-Leu-Leu-Gln-Glu-Phe-Leu-Glu-Leu-Val-azPro (SEQ. ID. NO. 501) |
| Peptide 502 | Lys-Leu-Lys-Lys-Asn-Leu-Ala-Asp-Leu-Leu-Arg-Glu-Leu-Leu-Asn-Glu-Phe-Leu-Glu-Leu-Val-azPro (SEQ. ID. NO. 502) |
| Peptide 503 | Lys-Leu-Lys-Lys-Gln-Leu-Ala-Asp-Leu-Leu-Arg-Asp-Leu-Leu-Asn-Glu-Phe-Leu-Glu-Leu-Val-azPro (SEQ. ID. NO. 503) |
| Peptide 504 | Lys-Leu-Lys-Lys-Gln-Leu-Ala-Asp-Leu-Leu-Arg-Glu-Leu-Leu-Asn-Glu-Phe-Leu-Glu-Phe-Val-Pip (SEQ. ID. NO. 504) |
| Peptide 505 | Lys-Leu-Lys-Lys-Gln-Leu-Ala-Asp-Leu-Gly-Arg-Glu-Leu-Leu-Asn-Glu-Phe-Leu-Glu-Leu-Val-Pip (SEQ. ID. NO. 505) |
| Peptide 506 | Lys-Leu-Lys-Lys-Gln-Leu-Ala-Asp-Leu-Leu-Arg-Glu-Trp-Leu-Asn-Leu-Phe-Leu-Glu-Leu-Val-Pip (SEQ. ID. NO. 506) |
| Peptide 507 | Lys-Leu-Lys-Lys-Gln-Leu-Ala-Asp-Leu-Leu-Arg-Glu-Leu-Leu-Asn-Leu-Phe-Leu-Glu-Leu-Val-Pip (SEQ. ID. NO. 507) |
| Peptide 508 | Lys-Leu-Lys-Lys-Gln-Leu-Trp-Asp-Leu-Leu-Arg-Glu-Leu-Leu-Asn-Leu-Phe-Leu-Glu-Leu-Val-Pip (SEQ. ID. NO. 508) |
| Peptide 509 | Lys-Leu-Lys-Lys-Gln-Leu-Trp-Asp-Leu-Leu-Arg-Glu-Leu-Leu-Asn-Glu-Phe-Leu-Glu-Leu-Val-Pip (SEQ. ID. NO. 509) |
| Peptide 510 | Lys-Leu-Lys-Lys-Gln-Trp-Ala-Asp-Leu-Leu-Arg-Glu-Leu-Leu-Asn-Glu-Phe-Leu-Glu-Leu-Val-Pip (SEQ. ID. NO. 510) |
| Peptide 511 | Lys-Leu-Lys-Lys-Gln-Leu-Leu-Asp-Leu-Leu-Arg-Glu-Leu-Leu-Asn-Glu-Phe-Leu-Glu-Leu-Val-Pip (SEQ. ID. NO. 511) |
| Peptide 512 | Lys-Leu-Lys-Lys-Gln-Leu-Ala-Asp-Gly-Leu-Arg-Glu-Leu-Leu-Asn-Leu-Phe-Leu-Glu-Leu-Val-Pip (SEQ. ID. NO. 512) |
| Peptide 513 | Lys-Leu-Lys-Lys-Gln-Trp-Ala-Asp-Leu-Leu-Arg-Glu-Leu-Leu-Asn-Leu-Phe-Leu-Glu-Leu-Val-Pip (SEQ. ID. NO. 513) |
| Peptide 514 | Orn-Leu-Orn-Orn-Gln-Leu-Ala-Asp-Leu-Leu-Arg-Glu-Leu-Leu-Asn-Glu-Phe-Leu-Glu-Leu-Val-Pip (SEQ. ID. NO. 514) |
| Peptide 515 | Lys-Leu-Lys-Lys-Gln-Leu-Ala-Asp-Leu-Leu-Arg-Glu-Leu-Leu-Gln-Glu-Phe-Leu-Glu-Leu-Val-Pip (SEQ. ID. NO. 515) |
| Peptide 516 | Lys-Leu-Lys-Lys-Asn-Leu-Ala-Asp-Leu-Leu-Arg-Glu-Leu-Leu-Asn-Glu-Phe-Leu-Glu-Leu-Val-Pip (SEQ. ID. NO. 516) |
| Peptide 517 | Lys-Leu-Lys-Lys-Gln-Leu-Ala-Asp-Leu-Leu-Arg-Asp-Leu-Leu-Asn-Glu-Phe-Leu-Glu-Leu-Val-Pip (SEQ. ID. NO. 517) |
| Peptide 518 | Lys-Leu-Lys-Lys-Gln-Leu-Ala-Asp-Leu-Leu-Arg-Glu-Leu-Leu-Asn-Glu-Phe-Leu-Glu-Phe-Val-azPip (SEQ. ID. NO. 518) |
| Peptide 519 | Lys-Leu-Lys-Lys-Gln-Leu-Ala-Asp-Leu-Gly-Arg-Glu-Leu-Leu-Asn-Glu-Phe-Leu-Glu-Leu-Val-azPip (SEQ. ID. NO. 519) |
| Peptide 520 | Lys-Leu-Lys-Lys-Gln-Leu-Ala-Asp-Leu-Leu-Arg-Glu-Trp-Leu-Asn-Leu-Phe-Leu-Glu-Leu-Val-azPip (SEQ. ID. NO. 520) |
| Peptide 521 | Lys-Leu-Lys-Lys-Gln-Leu-Ala-Asp-Leu-Leu-Arg-Glu-Leu-Leu-Asn-Leu-Phe-Leu-Glu-Leu-Val-azPip (SEQ. ID. NO. 521) |
| Peptide 522 | Lys-Leu-Lys-Lys-Gln-Leu-Trp-Asp-Leu-Leu-Arg-Glu-Leu-Leu-Asn-Leu-Phe-Leu-Glu-Leu-Val-azPip (SEQ. ID. NO. 522) |
| Peptide 523 | Lys-Leu-Lys-Lys-Gln-Leu-Trp-Asp-Leu-Leu-Arg-Glu-Leu-Leu-Asn-Glu-Phe-Leu-Glu-Leu-Val-azPip (SEQ. ID. NO. 523) |
| Peptide 524 | Lys-Leu-Lys-Lys-Gln-Trp-Ala-Asp-Leu-Leu-Arg-Glu-Leu-Leu-Asn-Glu-Phe-Leu-Glu-Leu-Val-azPip (SEQ. ID. NO. 524) |
| Peptide 525 | Lys-Leu-Lys-Lys-Gln-Leu-Leu-Asp-Leu-Leu-Arg-Glu-Leu-Leu-Asn-Glu-Phe-Leu-Glu-Leu-Val-azPip (SEQ. ID. NO. 525) |
| Peptide 526 | Lys-Leu-Lys-Lys-Gln-Leu-Ala-Asp-Gly-Leu-Arg-Glu-Leu-Leu-Asn-Leu-Phe-Leu-Glu-Leu-Val-azPip (SEQ. ID. NO. 526) |

TABLE 6-continued

| Peptide 527 | Lys-Leu-Lys-Lys-Gln-Trp-Ala-Asp-Leu-Leu-Arg-Glu-Leu-Leu-Asn-Leu-Phe-Leu-Glu-Leu-Val-azPip (SEQ. ID. NO. 527) |
| --- | --- |
| Peptide 528 | Orn-Leu-Orn-Orn-Gln-Leu-Ala-Asp-Leu-Leu-Arg-Glu-Leu-Leu-Asn-Glu-Phe-Leu-Glu-Leu-Val-azPip (SEQ. ID. NO. 528) |
| Peptide 529 | Lys-Leu-Lys-Lys-Gln-Leu-Ala-Asp-Leu-Leu-Arg-Glu-Leu-Leu-Gln-Glu-Phe-Leu-Glu-Leu-Val-azPip (SEQ. ID. NO. 529) |
| Peptide 530 | Lys-Leu-Lys-Lys-Asn-Leu-Ala-Asp-Leu-Leu-Arg-Glu-Leu-Leu-Asn-Glu-Phe-Leu-Glu-Leu-Val-azPip (SEQ. ID. NO. 530) |
| Peptide 531 | Lys-Leu-Lys-Lys-Gln-Leu-Ala-Asp-Leu-Leu-Arg-Asp-Leu-Leu-Asn-Glu-Phe-Leu-Glu-Leu-Val-azPip (SEQ. ID. NO. 531) | or a pharmaceutically acceptable salt thereof

In other embodiments, the present invention includes ApoA-I Mimics wherein one or more of its amide linkages is optionally replaced with a linkage other than amide, including, but not limited to, a substituted amide or an isostere of amide. Thus, while the various $X^1$ to $X^{23}$, $Y^1$ and $Y^2$ residues within Formulas I, II, and III are described in terms of amino acids, in particular embodiments of the invention, a non-amide linkage is present in place of one or more amide linkages.

In another embodiment, the nitrogen atom of one or more of the ApoA-I Mimics' amide linkages is substituted, such that the substituted amide linkage has the formula —C(O)NR'—, where R' is ($C_1$-$C_6$) alkyl, ($C_2$-$C_6$) alkenyl, ($C_2$-$C_6$) alkynyl, ($C_5$-$C_{20}$) aryl, ($C_6$-$C_{26}$) alkaryl, 5-20 membered heteroaryl, or 6-26 membered alkheteroaryl. In another embodiment, R' is substituted with —OR, —SR, —NRR, —NO$_2$, —CN, halogen, —SO$_2$R, —C(O)R, —C(O)OR and —C(O)NRR, where each R is independently hydrogen, alkyl, or aryl.

In another embodiment, a non-amide linkage replaces one or more of the ApoA-I Mimics' amide linkages and includes, but is not limited to, —CH$_2$NH—, —CH$_2$S—, —CH$_2$CH$_2$—, —CH=CH— (cis and trans), —C(O)CH$_2$—, —CH(OH)CH$_2$— and —CH$_2$SO—. Compounds having such non-amide linkages and methods for preparing such compounds are well-known in the art (see, e.g., Spatola, March 1983, Vega Data Vol. 1, Issue 3; Spatola, 1983, "Peptide Backbone Modifications" In: Chemistry and Biochemistry of Amino Acids Peptides and Proteins, Weinstein, ed., Marcel Dekker, New York, p. 267 (general review); Morley, 1980, Trends Pharm. Sci. 1:463-468; Hudson et al., 1979, Int. J. Prot. Res. 14:177-185 (—CH$_2$NH—, —CH$_2$CH$_2$—); Spatola et al., 1986, Life Sci. 38:1243-1249 (—CH$_2$—S); Hann, 1982, J. Chem. Soc. Perkin Trans. I. 1:307-314 (—CH=CH—, cis and trans); Almquist et al., 1980, J. Med. Chem. 23:1392-1398 (—COCH$_2$—); Jennings-White et al., Tetrahedron. Lett. 23:2533 (—COCH$_2$—); European Patent Application EP 45665 (1982) CA 97:39405 (—CH(OH)CH$_2$—); Holladay et al., 1983, Tetrahedron Lett. 24:4401-4404 (—C(OH)CH$_2$—); and Hruby, 1982, Life Sci. 31:189-199 (—CH$_2$—S—).

Additionally, one or more of the ApoA-I Mimics' amide linkages can be replaced with one or more peptidomimetic or amide mimetic moieties that do not significantly interfere with the structure or activity of the peptides. Suitable amide mimetic moieties are described, for example, in Olson et al., 1993, J. Med. Chem. 36:3039-3049.

In some embodiments, the ApoA-I Mimic is in the form of a pharmaceutically acceptable salt. The salt can be formed at the C-terminus or N-terminus or at an acidic or basic amino acid residue side chain.

In some embodiments, the pharmaceutically acceptable salt is a metal salt, organic amine salt, or acid addition salt.

Metal salts can arise from the addition of an inorganic base to the peptide of Formula I, II, or III. The inorganic base consists of a metal cation paired with a basic couterion such as, for example, hydroxide, carbonate, bicarbonate, or phosphate. The metal may be an alkali metal, alkaline earth metal, transition metal, or main group metal. In some embodiments, the metal is lithium, sodium, potassium, cerium, magnesium, manganese, iron, calcium, aluminum, or zinc.

Organic amine salts can arise from the addition of an organic amine to the peptide of Formula I, II, or III. In some embodiments, the organic amine is triethylamine, ethanolamine, diethanolamine, triethanolamine, morpholine, piperidine, N-methylpiperidine, N-ethylpiperidine, dibenzylamine, piperazine, pyridine, pyrazine, or pipyrazine.

Acid addition salts arise from the addition of an acid to the peptide of Formula I, II, or III. In some embodiments, the acid is organic. In some embodiments, the acid is inorganic. In other embodiments, the acid is hydrochloric acid, hydrobromic acid, hydroiodic acid, nitric acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, fumaric acid, succinic acid, methanesulfonic acid, ethanesulfonic acid, benzenesulfonic acid, p-toluenesulfonic acid, citric acid, or maleic acid. In still other embodiments, the acid addition salt is a hydrochloride, hydrobromide, hydroiodide, nitrate, sulfate, sulfite, bisulfate, phosphate, acid phosphate, isonicotinate, lactate, salicylate, tartrate, bitartrate, ascorbate, gentisinate, gluconate, glucaronate, saccarate, formate, benzoate, glutamate, pantothenate, acetate, fumarate, succinate, methanesulfonate, ethanesulfonate, benzenesulfonate, p-toluylsulfonate, citrate, or maleate salt.

In some embodiments, $R^1$ is an amino protecting group. In some embodiments, the amino protecting group is: ($C_1$-$C_6$) alkyl, ($C_2$-$C_6$) alkenyl, ($C_2$-$C_6$) alkynyl, ($C_5$-$C_{26}$) aryl, ($C_6$-$C_{26}$ aralkyl), 5- to 20-membered heteroaryl, or 6- to 26-membered alkheteroaryl; —C(O)R; —C(O)OR; —SO$_2$R; or —SR, wherein R is H or ($C_1$-$C_6$) alkyl, ($C_2$-$C_6$) alkenyl, ($C_2$-$C_6$) alkynyl, ($C_5$-$C_{26}$) aryl, ($C_6$-$C_{26}$ aralkyl), 5- to 20-membered heteroaryl, or 6- to 26-membered alkheteroaryl. In other embodiments, the ($C_1$-$C_6$) alkyl, ($C_2$-$C_6$) alkenyl, ($C_2$-$C_6$) alkynyl, ($C_5$-$C_{26}$) aryl, ($C_6$-$C_{26}$ aralkyl), 5- to 20-membered heteroaryl, or 6- to 26-membered alkheteroaryl is substituted with one or more of —OR$^a$, —SR$^a$, —NR$^a$R$^a$, —NO$_2$, —CN, halogen, —SO$_2$R$^a$, —C(O)R$^a$, —C(O)OR$^a$ and —C(O)NR$^a$R$^a$, where each R$^a$ is independently hydrogen, alkyl, or aryl. When $R^1$ is H, the number of amino protecting groups in the ApoA-I Mimic is zero; and when $R^1$ is an amino protecting group, the number of amino protecting groups in the ApoA-I Mimic is 1.

In other embodiments, the amino protecting group is: dansyl; methoxycarbonyl; ethoxycarbonyl; 9-fluorenylmethoxycarbonyl; 2-chloroethoxycarbonyl; 2,2,2-trichloroethoxycarbonyl; 2-phenylethoxycarbonyl; t-butoxycarbonyl; benzyloxycarbonyl; p-methoxybenzyloxycarbonyl; p-nitrobenzyloxycarbonyl; o-nitrobenzyloxycarbonyl; p-bromobenzyloxycarbonyl; p-chlorobenzyloxycarbonyl; p-iodobenzyloxycarbonyl; 2,4-dichlorobenzyloxycarbonyl; diphenylmethoxycarbonyl; 3,5-dimethoxybenzyloxycarbonyl; phenoxycarbonyl; 2,4,6-tri-t-butylpenoxycarbonyl; 2,4,6-trimethylbenzyloxycarbonyl; formyl; acetyl; chloroacetyl; trichloroacetyl; trifluoroacetyl; phenylacetyl; picolinoyl; benzoyl; p-phenylbenzoyl; phthaloyl; methyl; t-butyl; allyl; [2-(trimethylsilyl)ethoxy]methyl; 2,4-dimethoxybenzyl; 2,4-dinitrophenyl; benzyl; 4-methoxybenzyl; diphenylmethyl; triphenylmethyl; benzenesulfenyl; o-nitrobenzenesulfenyl; 2,4-dinitrobenzenesulfenyl; p-toluenesulfonyl; benzenesulfonyl; 2,3,6-trimethyl-4-methoxybenzenesulfonyl; 2,4,6-trimethoxybenzenesulfonyl; 2,6-dimethyl-4-methoxybenzenesulfonyl; pentamethylbenzenesulfonyl; 4-methoxybenzenesulfonyl; 2,4,6-trimethylbenzenesulfonyl; or benzylsulfonyl. In other embodiments, the amino protecting group is acetyl, formyl, or dansyl.

In some embodiments, $R^2$ is a carboxyl protecting group. In some embodiments, the carboxyl protecting group is: O—($C_1$-$C_6$) alkyl, O—($C_2$-$C_6$) alkenyl, O—($C_2$-$C_6$) alkynyl, O—($C_5$-$C_{26}$) aryl, O—($C_6$-$C_{26}$) aralkyl), O-(5- to 20-membered heteroaryl), or O-(6- to 26-membered alkheteroaryl); or —NRR, wherein R is H or ($C_1$-$C_6$) alkyl, ($C_2$-$C_6$) alkenyl, ($C_2$-$C_6$) alkynyl, ($C_5$-$C_{26}$) aryl, ($C_6$-$C_{26}$) aralkyl), 5- to 20-membered heteroaryl, or 6- to 26-membered alkheteroaryl. In other embodiments, the ($C_1$-$C_6$) alkyl, ($C_2$-$C_6$) alkenyl, ($C_2$-$C_6$) alkynyl, ($C_5$-$C_{26}$) aryl, ($C_6$-$C_{26}$) aralkyl), 5- to 20-membered heteroaryl, or 6- to 26-membered alkheteroaryl is substituted with one or more of —$OR^a$, —$SR^a$, —$NR^aR^a$, —$NO_2$, —CN, halogen, —$SO_2R^a$, —$C(O)R^a$, —$C(O)OR^a$ and —$C(O)NR^aR^a$, where each $R^a$ is independently hydrogen, alkyl, or aryl. When $R^1$ is H, the number of carboxyl protecting groups in the ApoA-I Mimic is zero; and when $R^1$ is a carboxyl protecting group, the number of carboxyl protecting groups in the ApoA-I Mimic is 1.

In other embodiments, the carboxyl protecting group is methoxy; ethoxy; 9-fluorenylmethoxy; methoxymethoxy; methylthiomethoxy; tetrahydropyranoxy; tetrahydrofuranoxy; methoxyethoxymethoxy; benzyloxymethoxy; phenacyloxy; p-bromophenacyloxy; α-methylphenacyloxy; p-methoxyphenacyloxy; desyloxy; 2-chloroethoxy; 2,2,2-thrichloroethoxy, 2-methylthioethoxy; 2-(p-toluenesulfonyl)methoxy; t-butoxy; cyclopentoxy; cyclohexoxy; allyloxy; methallyloxy; cinnamoxy; α-methylcinnamoxy; phenoxy; 2,6-dimethylphenoxy; 2,6-diisopropylphenoxy; benzyloxy; triphenylmethoxy; diphenylmethoxy; 2,4,6-trimethylbenzyloxy; p-bromobenzyloxy; o-nitrobenzyloxy; N,N-dimethylamido; pyrrolidinyl; or piperidinyl.

Also included within the scope of the invention are protected forms of the ApoA-I Mimic, i.e., forms of the ApoA-I Mimic in which one or more of its —$NH_2$ or —COOH groups are protected with a protecting group. In one embodiment, one or more —$NH_2$ groups are protected with an amino protecting group as described above. In another embodiment, one or more —COOH groups are protected with a carboxyl protecting group as described above.

Figure 1C:
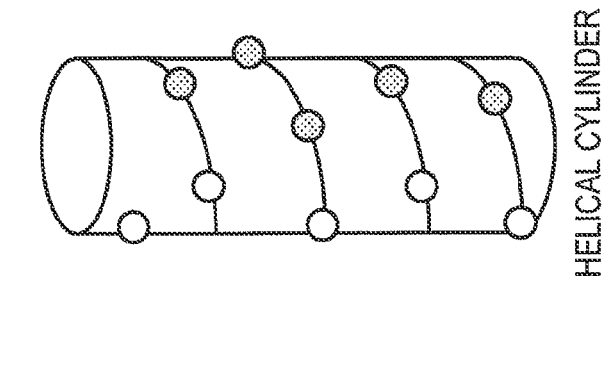
FIG. 1C is a helical cylinder diagram of the idealized amphipathic helix of FIG. 1A.
Figure 1B:
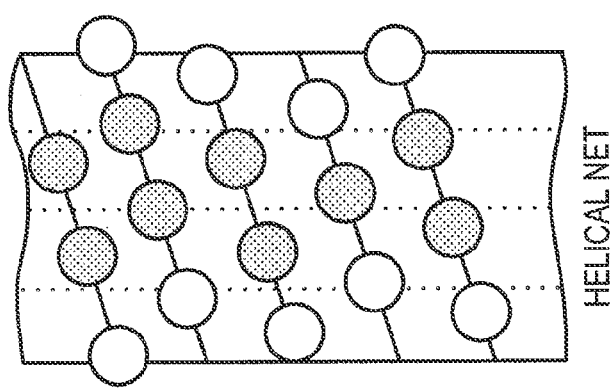
FIG. 1B is a helical net diagram of the idealized amphipathic helix of FIG. 1A.
Figure 1A:
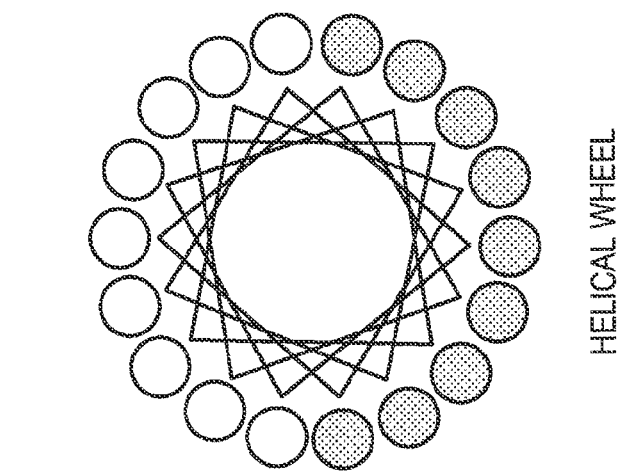
FIG. 1A is a Schiffer-Edmundson helical wheel diagram of an idealized amphipathic α-helix in which open circles represent hydrophilic amino acid residues and shaded circles represent hydrophobic amino acid residues.

In one embodiment, the ApoA-I Mimics have the ability to form an amphipathic α-helix in the presence of one or more lipids. By "amphipathic" is meant that the α-helix has opposing hydrophilic and hydrophobic faces oriented along its long axis, i.e., one face of the helix projects mainly hydrophilic side chains while the opposite face projects mainly hydrophobic side chains. FIGS. 1A and 1B present two illustrative views of the opposing hydrophilic and hydrophobic faces of an exemplary idealized amphipathic α-helix. FIG. 1A is a Schiffer-Edmundson helical wheel diagram (Schiffer and Edmundson, 1967, Biophys. J. 7:121-135). In the wheel, the long axis of the helix is perpendicular to the page. Starting with the N-terminus, successive amino acid residues (represented by circles) are radially distributed about the perimeter of a circle at 100° intervals. Thus, amino acid residue n+1 is positioned 100° from residue n, residue n+2 is positioned 100° from residue n+1, and so forth. The 100° placement accounts for the 3.6 amino acid residues per turn that are typically observed in an idealized α-helix. In FIG. 1A, the opposing hydrophilic and hydrophobic faces of the helix are clearly visible; hydrophilic amino acid residues are represented as open circles and hydrophobic amino acid residues are represented as shaded circles.

FIG. 1B presents a helical net diagram of the idealized amphipathic helix of FIG. 1A. (Lim, 1978, FEBS Lett. 89:10-14). In a typical helical net diagram, the α-helix is presented as a cylinder that has been cut along the center of its hydrophilic face and flattened. Thus, the center of the hydrophobic face, determined by the hydrophobic moment of the helix (Eisenberg et al., 1982, Nature 299:371-374), lies in the center of the figure and is oriented so as to rise out of the plane of the page. An illustration of the helical cylinder prior to being cut and flattened is depicted in FIG. 1C. By cutting the cylinder along different planes, different views of the same amphipathic helix can be observed, and different information about the properties of the helix obtained.

While not being bound by any particular theory, it is believed that certain structural and/or physical properties of the amphipathic helix formed by the ApoA-I Mimics, can be important for activity. These properties include the degree of amphipathicity, overall hydrophobicity, mean hydrophobicity, hydrophobic and hydrophilic angles, hydrophobic moment, mean hydrophobic moment, and net charge of the α-helix.

The degree of amphipathicity (degree of asymmetry of hydrophobicity) of the amphiphatic helix formed by the ApoA-I Mimics can be conveniently quantified by calculating the hydrophobic moment ($\mu_H$) of the helix. Methods for calculating $\mu_H$ for a particular peptide sequence are well-known in the art, and are described, for example in Eisenberg, 1984, Ann. Rev. Biochem. 53:595-623. The actual $\mu_H$ obtained for a particular peptide will depend on the total number of amino acid residues composing the peptide. Thus, it is generally not informative to directly compare $\mu_H$ for peptides of different lengths.

The amphipathicities of peptides of different lengths can be directly compared by way of the mean hydrophobic moment ($<\mu_H>$). The mean hydrophobic moment can be obtained by dividing $\mu_H$ by the number of residues in the helix (i.e., $<\mu_H>=\mu_H/N$). Generally, ApoA-I Mimics which exhibit a $<\mu_H>$ in the range of 0.45 to 0.65, as determined using the normalized consensus hydrophobicity scale of Eisenberg (Eisenberg, 1984, J. Mol. Biol. 179:125-142) are considered to be within the scope of the present invention. In one embodiment, $<\mu_H>$ is in the range of 0.50 to 0.60.

The overall or total hydrophobicity ($H_o$) of a peptide can be conveniently calculated by taking the algebraic sum of the hydrophobicities of each amino acid residue in the peptide (i.e., $$H_o = \sum_{i=1}^{N} H_i),$$

where N is the number of amino acid residues in the peptide and $H_i$ is the hydrophobicity of the ith amino acid residue).

The mean hydrophobicity ($<H_o>$) is the hydrophobicity divided by the number of amino acid residues (i.e., $<H_o>=H_o/N$). Generally, ApoA-I Mimics that exhibit a mean hydrophobicity in the range of −0.050 to −0.070, as determined using the normalized consensus hydrophobicity scale of Eisenberg (Eisenberg, 1984, J. Mol. Biol. 179:125-142) are considered to be within the scope of the present invention. In one embodiment, the mean hydrophobicity is in the range of −0.030 to −0.055.

The total hydrophobicity of the hydrophobic face)($H_o^{pho}$) of an amphipathic helix can be obtained by taking the sum of the hydrophobicities of the hydrophobic amino acid residues which fall into the hydrophobic angle as defined below (i.e., $$H_o^{pho} = \sum_{i=1}^{N} H_i$$

where $H_i$, is as previously defined and $N_H$ is the total number of hydrophobic amino acid residues in the hydrophobic face). The mean hydrophobicity of the hydrophobic face ($<H_o^{pho}>$) is $H_o^{pho}/N_H$ where $N_H$ is as defined above. Generally, ApoA-I Mimics which exhibit a $<H_o^{pho}>$ in the range of 0.90 to 1.20, as determined using the consensus hydrophobicity scale of Eisenberg (Eisenberg, 1984, supra; Eisenberg et al., 1982, supra) are considered to be within the scope of the present invention. In one embodiment, the $<H_o^{pho}>$ is in the range of 0.94 to 1.10.

Figure 2:
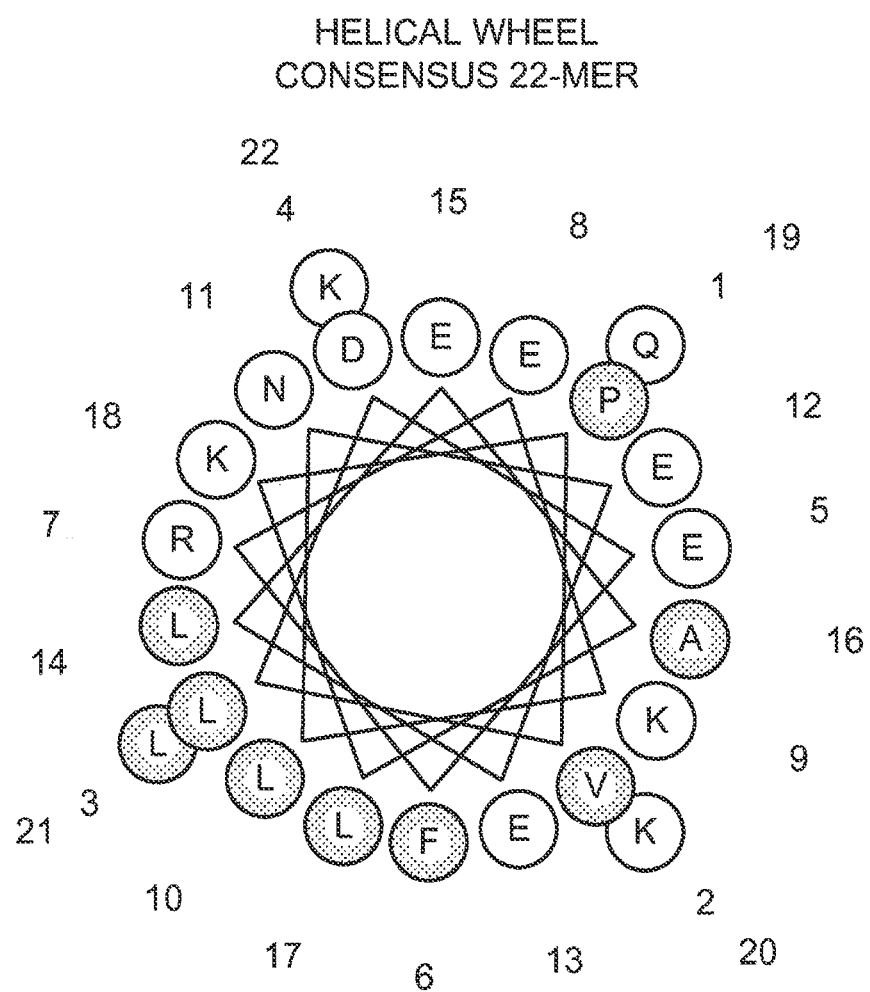
FIG. 2 is a Schiffer-Edmundson helical wheel diagram of Segrest's consensus 22-mer peptide (SEQ ID NO. 1)

The hydrophobic angle (pho angle) is generally defined as the angle or arc covered by the longest continuous stretch of hydrophobic amino acid residues when the peptide is arranged in the Schiffer-Edmundson helical wheel representation (i.e., the number of contiguous hydrophobic residues on the wheel multiplied by 20°). The hydrophilic angle (phi angle) is the difference between 360° and the pho angle (i.e., 360°-pho angle). Those of skill in the art will recognize that the pho and phi angles can depend, in part, on the number of amino acid residues in the peptide. For example, referring to FIG. 2, it can be seen that only 18 amino acid residues fit around one rotation of the Schiffer-Edmundson helical wheel for Segrest's consensus 22-mer peptide Pro-Val-Leu-Asp-Glu-Phe-Arg-Glu-Lys-Leu-Asn-Glu-Glu-Leu-Glu-Ala-Leu-Lys-Gln-Lys-Leu-Lys (SEQ ID NO: 1). Fewer amino acid residues leave a gap in the wheel; more amino acid residues cause certain positions of the wheel to be occupied by more than one amino acid residue.

In the case of peptides having 15 or more amino acid residues, such as an ApoA-I Mimic having from 15 to 29 residues, a "continuous" stretch of hydrophobic amino acid residues is meant that at least one amino acid residue at positions along the wheel containing two or more amino acid residues is a hydrophobic amino acid residue. Thus, referring to FIG. 2, the pho angle is the arc covered by residues 16, 2, 6, 17, 10, 3, and 14 despite the occurrence of a hydrophilic residue at position 20, as the residue at position 2, which shares the same position on the wheel, is a hydrophobic residue. Typically, ApoA-I Mimics having a pho angle in the range of 160° to 220° are considered to be within the scope of the invention. In some embodiments, the pho angle is in the range of 180° to 200°.

In Peptide 16 (Lys-Leu-Lys-Gln-Lys-Leu-Ala-Glu-Leu-Leu-Glu-Asn Leu-Leu-Glu-Arg-Phe-Leu-Asp-Ala-Leu-Val-Inp (SEQ. ID. NO. 16)) or a pharmaceutically acceptable salt thereof, an illustrative ApoA-I Mimic, positively-charged amino acid residues are clustered at the last N-terminal turn of the helix. While not being bound by any particular theory, it is believed that the cluster of basic residues at the N-terminus stabilizes the helix through charge ($NH_3^+$)-helix dipole electrostatic interactions. It is also thought that stabilization occurs through hydrophobic interactions between lysine side chains and the helix core (see, Groebke et al., 1996, Proc. Natl. Acad. Sci. U.S.A. 93:4025-4029; Esposito et al., 1997, Biopolymers 41:27-35).

With the exception of the positively-charged N-terminal cluster, negative charges in Peptide 16 (SEQ ID NO: 16) or a pharmaceutically acceptable salt thereof are distributed on the rest of the hydrophilic face, with at least one negatively charged (acidic) amino acid residue per turn, resulting in a continuous stretch of negative charges along the hydrophilic face of the helix. One positive charge is located at residue 16, which potentially contributes to helix stability by forming a salt bridge with an acidic residue one turn away on the helix.

It is believed that NMR studies of Peptide 16 (SEQ ID NO: 16) or a pharmaceutically acceptable salt thereof would indicate that amino acid residues 13, 14, 17, and 20 of the peptide form a hydrophobic cluster near the C-terminus of the helix. Phe-17 is centered in this cluster and is believed to play an important role in stabilizing the hydrophobic cluster.

While not being bound by any particular theory, it is believed that the hydrophobic cluster formed by residues 13, 14, 17, and 20 of Peptide 16 (SEQ ID NO: 16) or a pharmaceutically acceptable salt thereof is significant in effecting lipid binding and LCAT activation. Amphipathic peptides are expected to bind phospholipids by pointing their hydrophobic faces towards the alkyl chains of the lipid moieties. Thus, it is believed that this highly hydrophobic cluster contributes to the strong lipid affinities observed for the ApoA-I Mimics of the invention. Since lipid binding is a prerequisite for LCAT activation, it is believed that this hydrophobic cluster is also essential for LCAT activation.

Aromatic residues can be important in anchoring peptides and proteins to lipids (De Kruijff, 1990, Biosci. Rep. 10:127-130; O'Neil and De Grado, 1990, Science 250:645-651; Blondelle et al., 1993, Biochim. Biophys. Acta 1202:331-336). Thus, it is further believed that Phe-17, which is positioned at the center of the hydrophobic cluster, may also play a key role in anchoring Peptide 16 (SEQ ID NO: 16) or a pharmaceutically acceptable salt thereof to a lipid.

The long axis of the α-helix formed by the ApoA-I Mimics typically has an overall curved shape. In typical amphipathic helices, it has been found that the lengths of the hydrogen bonds of the hydrophilic and hydrophobic faces vary such that the hydrophobic side of the helix is concave (Barlow and Thornton, 1988, J. Mol. Biol. 201:601-619; Zhou et al., 1992, J. Am. Chem. Soc. 33:11174-11183; Gesell et al., 1997, J. Biomol. NMR 9:127-135). While not being bound by theory, it is believed that the overall curvature of the hydrophobic face of the helix might be important in binding discoidal complexes—a curved helix permits the peptide to "fit" better around the edges of discoidal particles, thereby increasing the stability of the peptide-disc complex.

Figure 4A:
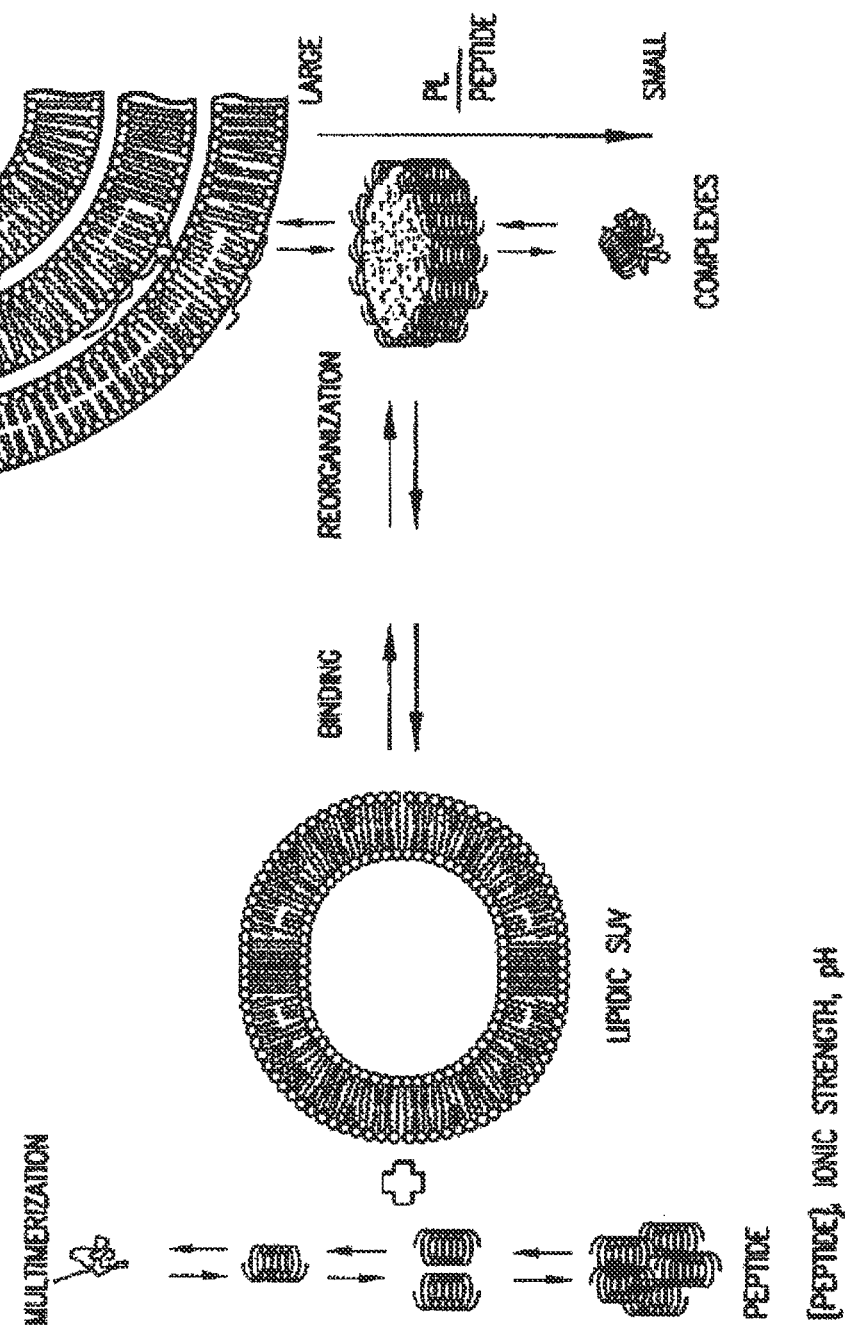
FIG. 4A is a cartoon depicting the various aggregation states and peptide-lipid complexes that can be obtained with the ApoA-I Mimics of the invention. Left: Multimerization process of the peptides resulting from the interaction of several peptide helices and leading to the formation of oligomers in conditions of defined peptide concentration, pH and ionic strength. Center: The interaction of the ApoA-I Mimics (in any of these states of aggregation) with lipidic entities (such as small unilamellar vesicles ("SUVs")) leads to lipid reorganization. Right: By changing the lipid:peptide molar ratio, different types of peptide-lipid complexes can be obtained, from lipid-peptide comicelles at low lipid-peptide ratios, to discoidal particles and finally to large multilamellar complexes at increasingly higher lipid:peptide ratios.
Figure 4B:
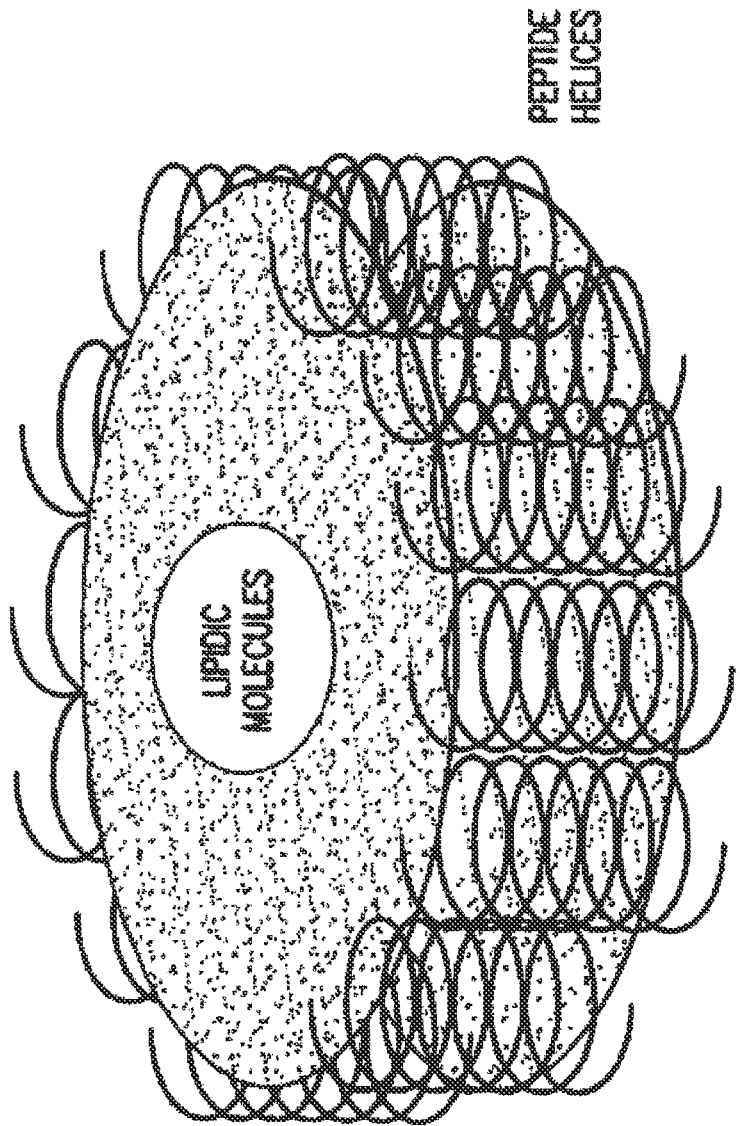
FIG. 4B illustrates the generally-accepted model for discoidal ApoA-I Mimic-lipid complexes formed in a defined range of lipid:ApoA-I Mimic ratios. Each ApoA-I Mimic surrounding the disc edge is in close contact with its two nearest neighbors.

In the generally accepted structural model of ApoA-I, the amphipathic α-helices are packed around the edge of the discoidal HDL (see, FIG. 4B). In this model, the helices are assumed to be aligned with their hydrophobic faces pointing towards the lipid acyl chains (Brasseur et al., 1990, Biochim. Biophys. Acta 1043:245-252). The helices are arranged in an antiparallel fashion, and a cooperative effect between the helices is thought to contribute to the stability of the discoidal HDL complex (Brasseur et al., supra). It has been proposed that one factor that contributes to the stability of the HDL discoidal complex is the existence of ionic interactions between acidic and basic residues resulting in the formation of intermolecular salt bridges or hydrogen bonds between residues on adjacent anti-parallel helices. In this model, the peptides are considered not as a single entity, but as in interaction with at least two other neighboring peptide molecules (FIG. 4B).

It is also generally accepted that intramolecular hydrogen bond or salt bridge formation between acidic and basic residues, respectively, at positions i and i+3 of the helix stabilize the helical structure (Marqusee et al: 1985, Proc. Natl. Acad. Sci. USA 84(24):8898-8902).

Thus, the ApoA-I Mimics have the ability to form intermolecular hydrogen-bonds with one another when aligned in an antiparallel fashion with their hydrophobic faces pointing in the same direction, such as would be the case when the peptides are bound to lipids. The ApoA-I Mimics also have the ability to form intramolecular hydrogen bonds or salt bridges near the N- and C-termini of the helix.

Furthermore, when arranged in this anti-parallel fashion, the helices are closely packed; there is no steric hindrance preventing close contact between the helices. The ApoA-I Mimics have the ability to closely pack and ionically interact to form intra- and/or intermolecular salt bridges and/or hydrogen bonds when bound to lipids in an antiparallel fashion.

The ApoA-I Mimics can self-associate. The self-association phenomenon depends on the conditions of pH, peptide concentration and ionic strength, and can result in several states of association, from monomeric to several multimeric forms (FIG. 4A). The hydrophobic core of peptide aggregates favors hydrophobic interactions with lipids. The ability of the peptides to aggregate even at very low concentrations may favor their binding to lipids. It is thought that in the core of the peptide aggregates peptide-peptide interactions also occur and may compete with lipid-peptide interactions.

The hydrophobic core of the aggregates of the ApoA-I Mimics favors hydrophobic interactions with lipids. The ability of the ApoA-I Mimics to aggregate even at very low concentrations can favor their binding to lipids. Interactions between the ApoA-I Mimics and lipids lead to the formation of peptide-lipid complexes. As illustrated in FIG. 4A, the type of complex obtained (comicelles, discs, vesicles or multilayers) can depend on the lipid:peptide molar ratio, with comicelles generally being formed at low lipid:peptide molar ratios and discoidal and vesicular or multilayer complexes being formed with increasing lipid:peptide molar ratios. Micelles are typically formed at ratios of about 2 moles of lipid: about 1 mole of ApoA-I or about 2 moles of lipid: about 6 to about 10 moles of ApoA-I Mimic. Discoidal complexes are typically formed at ratios of about 50-100 moles of lipid: about 1 mole of ApoA-I or about 6 to about 10 moles of ApoA-I Mimic. Vesicular complexes are typically formed at ratios of about 200 to about 300 moles of lipid: about 1 mole of ApoA-I or about 6 to about 10 moles of ApoA-I Mimic. This characteristic has been described for amphipathic peptides (Epand, The Amphipathic Helix, 1993) and for ApoA-I (Jones, 1992, Structure and Function of Apolipoproteins, Chapter 8, pp. 217-250). The lipid:peptide molar ratio also determines the size and composition of the complexes.

D. Altered Forms of the Peptides of Formula I, II, and III and Pharmaceutically Acceptable Salts Thereof In other embodiments, the ApoA-I Mimics have 22 amino acid residues or fewer. Indeed, truncated or internally deleted forms of Formula I, II, or III containing 21, 20, 19, 18, 17, 16, or even 15 amino acid residues that substantially retain the overall characteristics and properties of the amphipathic helix formed by the ApoA-I Mimics are considered to be within the scope of the present invention.

In one embodiment of the invention, truncated forms of the ApoA-I Mimics are obtained by deleting one or more amino acid residues from the N- and/or C-terminus. Internally deleted forms of the ApoA-I Mimics are obtained by deleting one or more amino acid residues from internal positions within the ApoA-I Mimics. The internal amino acid residues deleted can be consecutive residues or non-consecutive residues.

Those of skill in the art will recognize that deleting an internal amino acid residue from an ApoA-I Mimic can cause the plane of the hydrophilic-hydrophobic interface of the helix to rotate by 100° at the point of the deletion. As such rotations can significantly alter the amphipathic properties of the resultant helix, in one embodiment of the invention one or more amino acid residues are deleted so as to substantially retain the alignment of the plane of the hydrophilic-hydrophobic interface along the entire long axis of the helix.

This can be conveniently achieved by deleting a sufficient number of consecutive or non-consecutive amino acid residues such that one complete helical turn is deleted. An idealized α-helix has 3.6 residues per turn. Thus, in one embodiment, groups of 3-4 consecutive or non-consecutive amino acid residues are deleted. Whether 3 amino acid residues or 4 amino acid residues are deleted can depend upon the position within the helix of the first residue to be deleted. Determining the appropriate number of consecutive or non-consecutive amino acid residues that constitute one complete helical turn from any particular starting point within an amphipathic helix is well within the capabilities of those of skill in the art.

The ApoA-I Mimics can also be extended at one or both termini or internally with additional amino acid residues that do not substantially interfere with, and in some embodiments even enhance, the structural and/or functional properties of the peptides. Indeed, extended ApoA-I Mimics containing as many as 23, 24, 25, 26, 27, 28, or 29 amino acid residues are also within the scope of the invention. Such extended ApoA-I Mimics may substantially retain the net amphipathicity and other properties of the ApoA-I Mimics. Of course, it will be recognized that adding amino acid residues internally can rotate the plane of the hydrophobic-hydrophilic interface at the point of the insertion in a manner similar to that described above for internal deletions. Thus, the considerations discussed above in connection with internal deletions apply to internal additions, as well.

In one embodiment, the ApoA-I Mimics are extended at their N- and/or C-terminus by an amino acid sequence having from 1 to 7 residues.

In one embodiment, the ApoA-I Mimics are extended at their N- and/or C-terminus by least one helical turn. Such extensions stabilize the helical secondary structure in the presence of lipids, such as the end-cap amino acid residues and segments previously described.

In another embodiment, the ApoA-I Mimics are extended at the N-terminus by a single basic amino acid residue, such as Lys (K). In one embodiment, $X^1$ is Lys, $X^2$ is Lys, $X^3$ is Leu, $X^4$ is Lys, $X^5$ is Gln, $X^6$ is Lys, $X^7$ is Leu, $X^8$ is Ala, $X^9$ is Glu, $X^{10}$ is Leu, $X^{11}$ is Leu, $X^{12}$ is Glu, $X^{13}$ is Asn, $X^{14}$ is Leu, $X^{15}$ is Leu, $X^{16}$ is Glu, $X^{17}$ is Arg, $X^{18}$ is Phe, $X^{19}$ is Leu, $X^{20}$ is Asp, $X^{21}$ is Leu, $X^{22}$ is Val, and $X^{23}$ is Inp.

Also included within the scope of the present invention are "protected" forms of the ApoA-I Mimics, i.e., forms of the ApoA-I Mimics in which the $R^1$ is an amino protecting group and/or $R^2$ is a carboxy protecting group. It is believed that removing the N- and/or C-terminal charges of the ApoA-I Mimics having 18 or fewer amino acid residues (by synthesizing N-acylated peptide amides/ester/hydrazides/alcohols and substitutions thereof) can result in mimics which approach, and in some embodiments even exceed, the activity of the unprotected form of the mimic. In some embodiments having 22 or more amino acid residues, it is believed that blocking the N- or C-terminus can result in ApoA-I Mimics that exhibit lower activity than the unblocked forms. However, protecting both the N- and C-termini of ApoA-I Mimics of 22 or more amino acid residues can restore activity. Thus, in one embodiment of the invention, either the N- and/or C-terminus (in another embodiment, both termini) of ApoA-I Mimics having 18 or fewer amino acid residues are protected, whereas the N- and C-termini of peptides having 22 or more amino acid residues are either both protected or both unprotected. Typical N-terminal blocking groups include RC(O)—, where R is —H, ($C_1$-$C_6$) alkyl, ($C_2$-$C_6$) alkenyl, ($C_2$-$C_6$) alkynyl, ($C_5$-$C_{20}$) aryl, ($C_6$-$C_{26}$) alkaryl, 5-20 membered heteroaryl or 6-26 membered alkheteroaryl. Particular N-terminal blocking groups include acetyl, formyl and dansyl. Typical C-terminal blocking groups include —C(O)NRR and —C(O)OR, where each R is independently defined as above. Particular C-terminal blocking groups include those where each R is independently methyl. While not being bound by any particular theory, it is believed that such terminal blocking groups stabilize the α-helix in the presence of lipids (see, e.g., Venkatachelapathi et al., 1993, PROTEINS: Structure, Function and Genetics 15:349-359).

E. Dimers, Trimers, Tetramers, and Multimers of the Peptides of Formula I, II, or III and Pharmaceutically Acceptable Salts Thereof The structure of native ApoA-I contains eight helical units that are thought to act in concert to bind lipids (Nakagawa et al., 1985, J. Am. Chem. Soc. 107:7087-7092; Anantharamaiah et al., 1985, J. Biol. Chem. 260:10248-10262; Vanloo et al., 1991, J. Lipid Res. 32:1253-1264; Mendez et al., 1994, J. Clin. Invest. 94:1698-1705; Palgunari et al., 1996, Arterioscler. Thromb. Vasc. Biol. 16:328-338; Demoor et al., 1996, Eur. J. Biochem. 239:74-84). Thus, also included in the present invention are dimers, trimers, tetramers and even higher order polymers ("multimers") of the ApoA-I Mimics. Such multimers may be in the form of tandem repeats, branched networks or combinations thereof. The ApoA-I Mimics may be directly attached to one another or separated by one or more linkers.

The ApoA-I Mimics that comprise the multimers may be the peptides of Formula I, II, or III, analogs of Formula I, II, or III, altered forms of Formula I, II, or III, truncated or internally deleted forms of Formula I, II, or III, extended forms of Formula I, II, or III, and/or combinations thereof. The ApoA-I Mimics can be connected in a head-to-tail fashion (i.e., N-terminus to C-terminus), a head-to-head fashion, (i.e., N-terminus to N-terminus), a tail-to-tail fashion (i.e., C-terminus to C-terminus), or combinations thereof and pharmaceutically acceptable salts thereof.

In one embodiment of the invention, the multimers are tandem repeats of two, three, four and up to about ten ApoA-I Mimics. In one embodiment, the multimers are tandem repeats of from 2 to 8 peptides. Thus, in one embodiment, the invention provides multimers having the following structural formula:

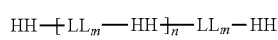

(IV)

wherein:
each m is independently an integer from 0 to 1, and in one embodiment m is 1;
n is an integer from 0 to 10, and in one embodiment n is an integer from 0 to 8;
each "HH" is independently a radical derived from an ApoA-I Mimic; and
each "LL" independently represents a linker.

In structure (IV), the linker LL can be any bifunctional molecule capable of covalently linking two peptides to one another. Thus, suitable linkers are bifunctional molecules in which the functional groups are capable of being covalently attached to the N- and/or C-terminus of a peptide. Functional groups suitable for attachment to the N- or C-terminus of peptides are well known in the art, as are suitable chemistries for effecting such covalent bond formation.

The linker can be flexible, rigid or semi-rigid, depending on the desired properties of the multimer. Suitable linkers include, for example, amino acid residues such as Pro, azPro, Pip, azPip, or Gly or peptide segments containing from about 2 to about 5, 10, 15 or 20 or even more amino acid residues, bifunctional organic compounds such as $H_2N(CH_2)$—COOH, $HO(CH_2)nCOOH$, and $HO(CH_2CH_2O)nCH_2CH_2COOH$, where n is an integer from 1 to 12, and the like. Examples of such linkers, as well as methods of making such linkers and compounds incorporating such linkers are well-known in the art (see, e.g., Hunig et al., 1974, Chem. Ber. 100:3039-3044; Basak et al., 1994, Bioconjug. Chem. 5(4): 301-305).

In one embodiment of the invention, the tandem repeats are internally punctuated by a single proline residue. In those instances where the ApoA-I Mimics do not contain an N- or C-terminal proline residue, LL can be Pro, D-Pro, azPro, Pip, D-Pip, or azPip and m is 1.

In some embodiments of the invention, it can be desirable to employ cleavable linkers that permit the release of one or more helical segments (HH) under certain conditions. Suitable cleavable linkers include peptides having sequences of amino acid residues that are recognized by proteases, oligonucleotides that can be cleaved by endonucleases and organic compounds that can be cleaved via chemical means, such as under acidic, basic or other conditions. Typically, the cleavage conditions will be relatively mild so as not to denature or otherwise degrade the helical segments and/or non-cleaved linkers composing the multimers.

Peptide and oligonucleotide linkers that can be selectively cleaved, as well as means for cleaving the linkers are well known and will be readily apparent to those of skill in the art. Suitable organic compound linkers that can be selectively cleaved will be apparent to those of skill in the art, and include those described, for example, in WO 94/08051, as well as the references cited therein.

In one embodiment, the linkers employed are peptides that are substrates for endogenous circulatory enzymes, thereby permitting the multimers to be selectively cleaved in vivo. An endogenous enzyme suitable for cleaving the linkers is, for example, proapolipoprotein A-I propeptidase. Appropriate enzymes, as well as peptide segments that act as substrates for such enzymes, are well-known in the art (see, e.g., Edelstein et al., 1983, J. Biol. Chem. 258:11430-11433; Zanis, 1983, Proc. Natl. Acad. Sci. USA 80:2574-2578).

In one embodiment, linkers of sufficient length and flexibility are used so as to permit the helical segments (HH) of structure (II) to align in an antiparallel fashion and form intermolecular hydrogen-bonds or salt bridges in the presence of lipids. Linkers of sufficient length and flexibility include, but are not limited to, a residue or radical of Pro, D-Pro, azPro, Pip, D-Pip, azPip, Gly, Cys-Cys, $H_2N(CH_2)_n$ COOH, $HO(CH_2)nCOOH$, or $HO(CH_2CH_2O)nCH_2CH_2COOH$ where n is 1 to 12, or 4 to 6; $H_2N$-aryl-COOH and carbohydrates.

Alternatively, as the native apolipoproteins permit cooperative binding between antiparallel helical segments, peptide linkers which correspond in primary sequence to the peptide segments connecting adjacent helices of the native apolipoproteins, including, for example, ApoA-I, ApoA-II, ApoA-IV, ApoC-I, ApoC-II, ApoC-III, ApoD, ApoE and ApoJ can be conveniently used to link the ApoA-I Mimics of Formula I. These sequences are well known in the art (see, e.g., Rosseneu et al., "Analysis of the Primary and of the Secondary Structure of the Apolipoproteins," In: Structure and Function of Lipoproteins, Ch. 6, 159-183, CRC Press, Inc., 1992).

Other linkers which permit the formation of intermolecular hydrogen bonds or salt bridges between tandem repeats of antiparallel helical segments include peptide reverse turns such as β-turns and γ-turns, as well as organic molecules that mimic the structures of peptide β-turns and/or γ-turns. Generally, reverse turns are segments of peptide that reverse the direction of the polypeptide chain so as to allow a single polypeptide chain to adopt regions of antiparallel β-sheet or antiparallel α-helical structure. β-Turns generally are composed of four amino acid residues and γ-turns are generally composed of three amino acid residues.

The conformations and sequences of many peptide β-turns have been well-described in the art and include, by way of example and not limitation, type-I, type-I', type-II, type-II', type-III, type-III', type-IV, type-V, type-V', type-VIa, type-VIb, type-VII and type-VIII (see, Richardson, 1981, Adv. Protein Chem. 34:167-339; Rose et al., 1985, Adv. Protein Chem. 37:1-109; Wilmot et al., 1988, J. Mol. Biol. 203:221-232; Sibanda et al., 1989, J. Mol. Biol. 206:759-777; Tramontano et al., 1989, Proteins: Struct. Funct. Genet. 6:382-394).

The specific conformations of short peptide turns such as β-turns depend primarily on the positions of certain amino acid residues in the turn (usually Gly, Asn or Pro). Generally, the type-I β-turn is compatible with any amino acid residue at positions 1 through 4 of the turn, except that Pro cannot occur at position 3. Gly predominates at position 4 and Pro predominates at position 2 of both type-I and type-II turns. Asp, Asn, Ser and Cys residues frequently occur at position 1, where their side chains often hydrogen-bond to the NH of residue 3.

In type-II turns, Gly and Asn occur most frequently at position 3, as they adopt the required backbone angles most easily. Ideally, type-I' turns have Gly at positions 2 and 3, and type-IF turns have Gly at position 2. Type-III turns generally can have most amino acid residues, but type-III' turns usually require Gly at positions 2 and 3. Type-VIa and VIb turns generally have a cis peptide bond and Pro as an internal residue. For a review of the different types and sequences of β-turns in proteins and peptides the reader is referred to Wilmot et al., 1988, J. Mol. Biol. 203:221-232.

The conformation and sequences of many peptide γ-turns have also been well-described in the art (see, e.g., Rose et al., 1985, Adv. Protein Chem. 37:1-109; Wilmer-White et al., 1987, Trends Biochem. Sci. 12:189-192; Wilmot et al., 1988, J. Mol. Biol. 203:221-232; Sibanda et al., 1989, J. Mol. Biol. 206:759-777; Tramontano et al., 1989, Proteins: Struct. Funct. Genet. 6:382-394). All of these types of β-turns and γ-turn structures and their corresponding sequences, as well as later discovered peptide β-turns and γ-turn structures and sequences, are specifically included in the invention.

Alternatively, the linker (LL) can comprise an organic molecule or moiety that mimics the structure of a peptide β-turn or γ-turn. Such β-turn and/or γ-turn mimetic moieties, as well as methods for synthesizing peptides containing such moieties, are well known in the art, and include, among others, those described in Giannis and Kolter, 1993 Angew. Chem. Intl. Ed. Eng. 32:1244-1267; Kahn et al., 1988, J. Molecular Recognition 1:75-79; and Kahn et al., 1987, Tetrahedron Lett. 28:1623-1626.

In still another embodiment of the invention, the multimers are in the form of branched networks (see, e.g., FIG. 3). Such networks are conveniently obtained through the use of multifunction linking moieties that permit more than two helical units to be attached to a simple linking moiety. Thus, branched networks employ molecules having three, four or even more functional groups that are capable of covalently attaching to the N- and/or C-terminus of a peptide. Suitable linking moieties include, for example, residues of amino acids having side chains bearing hydroxyl, sulfanyl, amino, carboxyl, amide and/or ester functionalities, such as, for example, Ser (S), Thr (T), Cys (C), Tyr (Y), Asn (N), Gln (Q), Lys (K), Arg (R), Orn, Asp (D) and Glu (E); as well as the corresponding D-enantiomer of each of the foregoing; or residues of other organic molecules containing such functional groups.

The helical segments attached to a single linking moiety need not be attached via like termini. Indeed, in some embodiments the helical segments are attached to a single linking moiety so as to be arranged in an antiparallel fashion, i.e., some of the helices are attached via their N-termini, others via their C-termini.

The helical segments can be attached directly to the linking moiety, or can be spaced from the linking moiety by way of one or more bifunctional linkers (LL), as previously described.

Figure 3A:
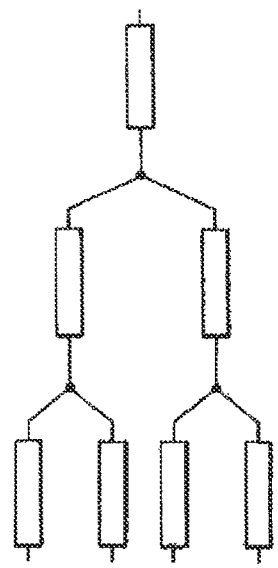
FIG. 3A illustrates a tertiary-order branched network of the ApoA-I Mimics.
Figure 3B:
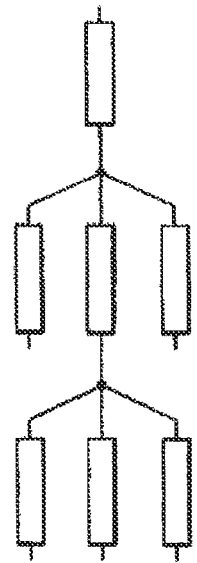
FIG. 3B illustrates a quaternary-order branched network of the ApoA-I Mimics.

Referring to FIGS. 3A and 3B, it can be seen that a branched network can be described in terms of the number of "nodes" comprising the network, where each multifunctional linking moiety constitutes a node. In FIGS. 3A and 3B, helical segments (i.e., ApoA-I Mimics) are illustrated as cylinders, and multifunctional linking moieties (or nodes) as circles (●), where the number of lines emanating from the circle indicates the "order" (or number of functional groups) of the multifunctional linking moiety.

The number of nodes in the network will generally depend on the total desired number of helical segments, and will typically be from about 1 to 2. Of course, it will be appreciated that for a given number of desired helical segments, networks having higher order linking moieties will have fewer nodes. For example, referring to FIGS. 3A and 3B, a tertiary-order network (i.e., a network having trifunctional linking moieties) of seven helical units has three nodes (FIG. 3A), whereas a quaternary order network (i.e., a network having tetrafunctional linking moieties) of seven helical units has only two nodes (FIG. 3B).

The networks can be of uniform order, i.e., networks in which all nodes are, for example, trifunctional or tetrafunctional linking moieties, or can be of mixed order, e.g., networks in which the nodes are mixtures of, for example, trifunctional and tetrafunctional linking moieties. Of course, it is to be understood that even in uniform order networks the linking moieties need not be identical. A tertiary order network can employ, for example, two, three, four or even more different trifunctional linking moieties.

Like the linear multimers, the helical segments comprising the branched network can be, but need not be, identical.

Figure 3C:
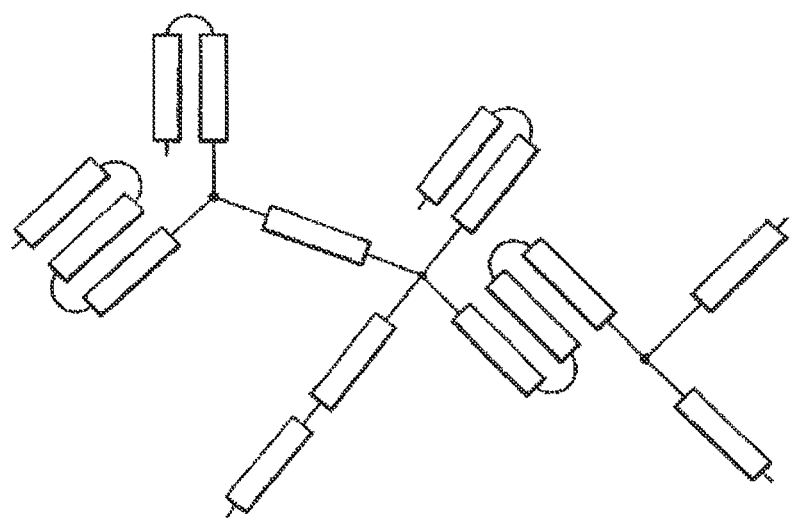
FIG. 3C illustrates a mixed-order branched network of the ApoA-I Mimics.

An example of such a mixed order branched network is illustrated in FIG. 3C. In FIG. 3C, helical segments (i.e., ApoA-I Mimics) are illustrated as cylinders and multifunctional linking moieties as circles (●), where the number of lines emanating from the circle indicates the "order" (or number of functional groups) of the multifunctional linking moiety. Lines connecting helical segments represent bifunctional linkers LL, as previously described. Helical segments which comprise the branched networks can be tandem repeats of ApoA-I Mimics, as previously described.

In one illustrative embodiment, the branched networks of the invention are described by the formula:

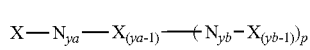
(V)

wherein:
each X is independently a radical derived from a multimer of the formula:

(VI)

wherein:
each HH is independently a radical derived from an ApoA-I Mimic;
each LL is independently a bifunctional linker;
each m is independently an integer from 0 to 1;
each n is independently an integer from 0 to 8;
$N_{ya}$ and $N_{yb}$ are each independently a multifunctional linking moiety where $y_a$ and $y_b$ represent the number of functional groups on $N_{ya}$ and $N_{yb}$, respectively;
each $y_a$ or $y_b$ is independently an integer from 3 to 8; and
p is an integer from 0 to 7.

Figure 3D:
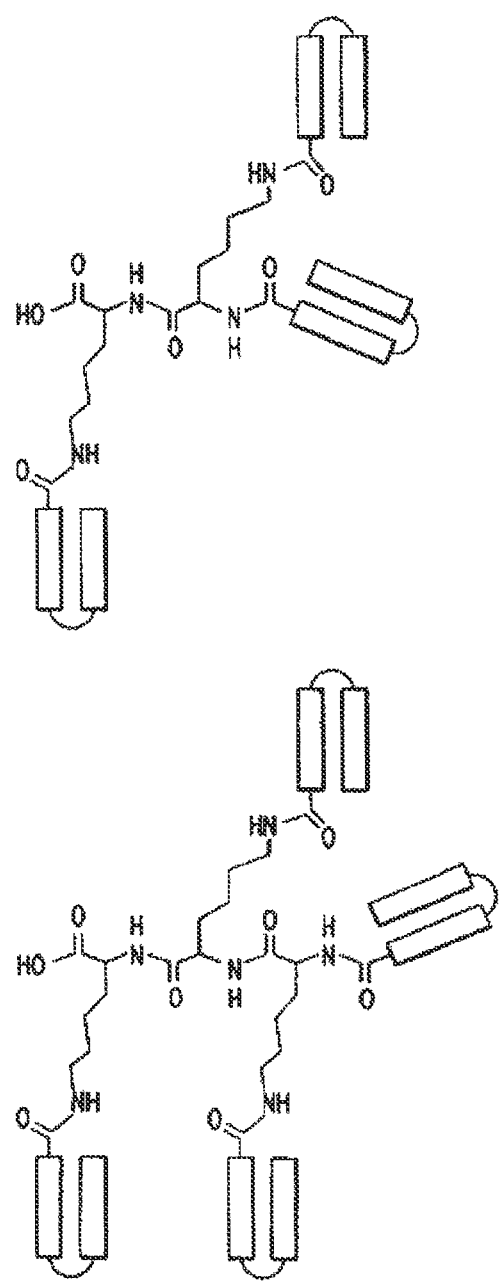
FIG. 3D illustrates exemplary "Lys-tree" branched networks of the ApoA-I Mimics.

In one embodiment, the branched network comprises a "Lys tree," i.e., a network wherein the multifunctional linking moiety is one or more Lys (K) residues (see, e.g., FIG. 3D).

In one illustrative embodiment, the "Lys tree" branched networks of the invention are described by the formulae:

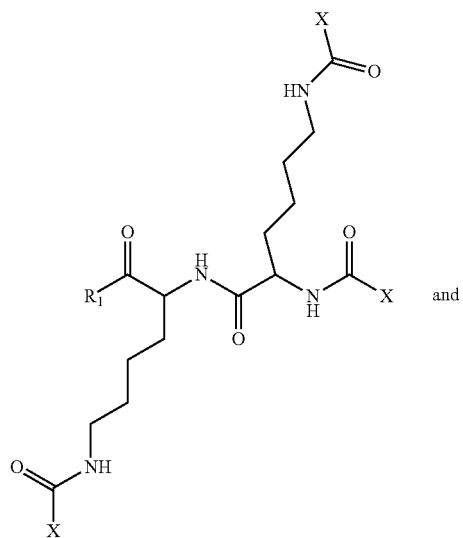
(VII)

and

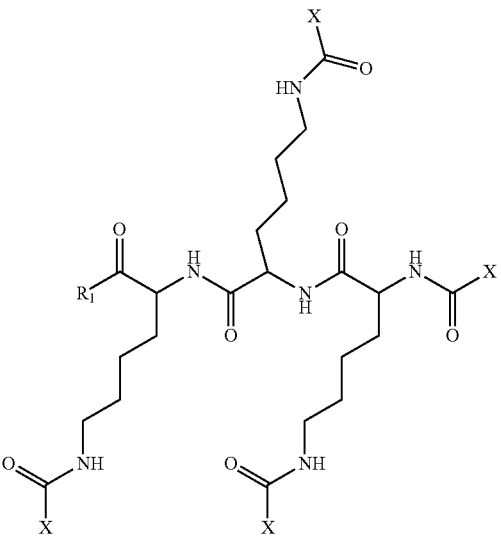
(VIII)

wherein:
each X is independently a radical derived from a multimer of the formula:

(VI)

each HH is independently a radical derived from an ApoA-I Mimic of Formula I;
each LL is independently a bifunctional linker;
each n is independently an integer from 0 to 8;
each m is independently an integer from 0 to 1;
$R_1$ is —OR or —NRR; and
each R is independently —H, $(C_1-C_6)$ alkyl, $(C_2-C_6)$ alkenyl, $(C_2-C_6)$ alkynyl; or $(C_5-C_{26})$ aryl.

Some additional illustrative ApoA-I Mimics are set forth in Table 7 below:

TABLE 7

| | |
|---|---|
| Peptide 41 | Lys-Leu-Lys-Gln-Lys-Leu-Ala-Glu-Leu-Leu-Glu-Gln-Leu-Leu-Glu-Lys-Leu-Leu-Glu-Leu-Leu-Inp (SEQ. ID. NO. 41) |
| Peptide 42 | Lys-Leu-Lys-Gln-Lys-Trp-Ala-Glu-Leu-Aib-Glu-Asn-Leu-Leu-Glu-Arg-Phe-Leu-Asp-Leu-Val-Inp (SEQ. ID. NO. 42) |
| Peptide 43 | Lys-Leu-Lys-Lys-Lys-Leu-Ala-Lys-Leu-Leu-Glu-Glu-Leu-Leu-Glu-Arg-Phe-Leu-Asp-Leu-Val-Inp (SEQ. ID. NO. 43) |
| Peptide 44 | Lys-Leu-Lys-Lys-Gln-Leu-Ala-Glu-Leu-Leu-Glu-Arg-Leu-Leu-Glu-Asn-Phe-Leu-Asp-Leu-Val-Inp (SEQ. ID. NO. 44) |
| Peptide 45 | Lys-Leu-Lys-Gln-Lys-Leu-Ala-Glu-Leu-Leu-Glu-Asn-Leu-Leu-Glu-Arg-Phe-Leu-Asp-Leu-(D-Val)-Inp (SEQ. ID. NO. 45) |

TABLE 7-continued

| | |
|---|---|
| Peptide 46 | Lys-Leu-Lys-Gln-Lys-Leu-Ala-Glu-Leu-Leu-Glu-Asn-Leu-Leu-Glu-Arg-Phe-Leu-Inp (SEQ. ID. NO. 46) |
| Peptide 47 | Lys-Lys-Lys-Gln-Lys-Leu-Ala-Glu-Leu-Leu-Glu-Asn-Leu-Leu-Glu-Arg-Phe-Leu-Asp-Leu-Val-Inp (SEQ. ID. NO. 47) |
| Peptide 48 | Gln-Lys-Leu-Ala-Glu-Leu-Leu-Glu-Asn-Leu-Leu-Glu-Arg-Phe-Leu-Asp-Leu-Val-Inp (SEQ. ID. NO. 48) |
| Peptide 49 | Lys-Leu-Lys-Gln-Lys-Leu-Ala-Glu-Leu-Leu-Glu-Asn-Leu-Leu-Glu-Arg-Phe-Leu-Asp-Leu-Inp (SEQ. ID. NO. 49) |
| Peptide 50 | Lys-Leu-Lys-Lys-Gln-Leu-Ala-Asn-Leu-Leu-Glu-Asp-Leu-Leu-Arg-Glu-Phe-Leu-Glu-Leu-Val-Inp (SEQ. ID. NO. 50) |
| Peptide 51 | Glu-Leu-Leu-Glu-Asn-Leu-Leu-Glu-Arg-Phe-Leu-Asp-Leu-Val-Inp (SEQ. ID. NO. 51) |
| Peptide 52 | Lys-Leu-Lys-Gln-Lys-Leu-Ala-Glu-Leu-Glu-Asn-Leu-Leu-Inp (SEQ. ID. NO. 52) |
| Peptide 53 | Lys-Leu-Lys-Gln-Leu-Leu-Glu-Asn-Leu-Leu-Glu-Arg-Phe-Leu-Asp-Leu-Val-Inp (SEQ. ID. NO. 53) |
| Peptide 54 | Lys-Leu-Lys-Gln-Lys-Leu-Glu-Glu-Leu-Leu-Glu-Arg-Phe-Leu-Asp-Leu-Val-Inp (SEQ. ID. NO. 54) |
| Peptide 55 | Lys-Leu-Lys-Gln-Lys-Leu-Glu-Glu-Leu-Leu-Glu-Lys-Phe-Leu-Glu-Leu-Val-Inp (SEQ. ID. NO. 55) |
| Peptide 56 | Lys-Leu-Lys-Gln-Lys-Leu-Leu-Glu-Leu-Leu-Glu-Arg-Phe-Leu-Asp-Leu-Val-Inp (SEQ. ID. NO. 56) |
| Peptide 57 | Lys-Leu-Lys-Gln-Trp-Leu-Glu-Asn-Leu-Leu-Glu-Arg-Phe-Leu-Asp-Leu-Val-Inp (SEQ. ID. NO. 57) |
| Peptide 58 | Lys-Leu-Lys-Lys-Gln-Leu-Glu-Glu-Leu-Leu-Glu-Arg-Phe-Leu-Asp-Leu-Val-Inp (SEQ. ID. NO. 58) |
| Peptide 59 | Lys-Lys-Leu-Gln-Leu-Leu-Ala-Glu-Leu-Leu-Glu-Arg-Phe-Ala-Asp-Leu-Val-Inp (SEQ. ID. NO. 59) |
| Peptide 60 | Lys-Lys-Leu-Gln-Ala-Leu-Ala-Glu-Leu-Leu-Glu-Arg-Phe-Ala-Asp-Leu-Val-Inp (SEQ. ID. NO. 60) |
| Peptide 61 | Lys-Leu-Lys-Gln-Lys-Leu-Glu-Glu-Trp-Gly-Glu-Arg-Phe-Leu-Asp-Leu-Val-Inp (SEQ. ID. NO. 61) |
| Peptide 62 | Lys-Leu-Lys-Lys-Gln-Leu-Asp-Glu-Leu-Leu-Arg-Glu-Phe-Leu-Glu-Leu-Val-Inp (SEQ. ID. NO. 62) |
| Peptide 63 | Lys-Leu-Lys-Gln-Glu-Leu-Lys-Glu-Leu-Leu-Glu-Arg-Phe-Leu-Asp-Leu-Val-Inp (SEQ. ID. NO. 63) |
| Peptide 133 | Lys-Leu-Lys-Gln-Lys-Leu-Ala-Glu-Leu-Leu-Glu-Gln-Leu-Leu-Glu-Lys-Leu-Leu-Glu-Leu-Leu-Nip (SEQ. ID. NO. 133) |
| Peptide 134 | Lys-Leu-Lys-Gln-Lys-Trp-Ala-Glu-Leu-Aib-Glu-Asn-Leu-Leu-Glu-Arg-Phe-Leu-Asp-Leu-Val-Nip (SEQ. ID. NO. 134) |
| Peptide 135 | Lys-Leu-Lys-Lys-Lys-Leu-Ala-Lys-Leu-Leu-Glu-Glu-Leu-Leu-Glu-Arg-Phe-Leu-Asp-Leu-Val-Nip (SEQ. ID. NO. 135) |
| Peptide 136 | Lys-Leu-Lys-Lys-Gln-Ala-Glu-Leu-Leu-Glu-Arg-Leu-Leu-Glu-Asn-Phe-Leu-Asp-Leu-Val-Nip (SEQ. ID. NO. 136) |
| Peptide 137 | Lys-Leu-Lys-Gln-Lys-Leu-Ala-Glu-Leu-Leu-Glu-Asn-Leu-Leu-Glu-Arg-Phe-Leu-Asp-Leu-(D-Val)-Nip (SEQ. ID. NO. 137) |
| Peptide 138 | Lys-Leu-Lys-Gln-Lys-Leu-Ala-Glu-Leu-Leu-Glu-Asn-Leu-Leu-Glu-Arg-Phe-Leu-Nip (SEQ. ID. NO. 138) |
| Peptide 139 | Lys-Lys-Lys-Gln-Lys-Leu-Ala-Glu-Leu-Leu-Glu-Asn-Leu-Leu-Glu-Arg-Phe-Leu-Asp-Leu-Val-Nip (SEQ. ID. NO. 139) |
| Peptide 140 | Gln-Lys-Leu-Ala-Glu-Leu-Leu-Glu-Asn-Leu-Leu-Glu-Arg-Phe-Leu-Asp-Leu-Val-Nip (SEQ. ID. NO. 140) |
| Peptide 141 | Lys-Leu-Lys-Gln-Lys-Leu-Ala-Glu-Leu-Leu-Glu-Asn-Leu-Leu-Glu-Arg-Phe-Leu-Asp-Leu-Nip (SEQ. ID. NO. 141) |
| Peptide 142 | Lys-Leu-Lys-Lys-Gln-Leu-Ala-Asn-Leu-Leu-Glu-Asp-Leu-Leu-Arg-Glu-Phe-Leu-Glu-Leu-Val-Nip (SEQ. ID. NO. 142) |
| Peptide 143 | Glu-Leu-Leu-Glu-Asn-Leu-Leu-Glu-Arg-Phe-Leu-Asp-Leu-Val-Nip (SEQ. ID. NO. 143) |
| Peptide 144 | Lys-Leu-Lys-Gln-Lys-Leu-Ala-Glu-Leu-Leu-Glu-Asn-Leu-Leu-Nip (SEQ. ID. NO. 144) |
| Peptide 145 | Lys-Leu-Lys-Gln-Leu-Leu-Glu-Asn-Leu-Leu-Glu-Arg-Phe-Leu-Asp-Leu-Val-Nip (SEQ. ID. NO. 145) |
| Peptide 146 | Lys-Leu-Lys-Gln-Lys-Leu-Glu-Glu-Leu-Leu-Glu-Arg-Phe-Leu-Asp-Leu-Val-Nip (SEQ. ID. NO. 146) |
| Peptide 147 | Lys-Leu-Lys-Gln-Lys-Leu-Glu-Glu-Leu-Leu-Glu-Lys-Phe-Leu-Glu-Leu-Val-Nip (SEQ. ID. NO. 147) |
| Peptide 148 | Lys-Leu-Lys-Gln-Lys-Leu-Leu-Glu-Leu-Leu-Glu-Arg-Phe-Leu-Asp-Leu-Val-Nip (SEQ. ID. NO. 148) |
| Peptide 149 | Lys-Leu-Lys-Gln-Trp-Leu-Glu-Asn-Leu-Leu-Glu-Arg-Phe-Leu-Asp-Leu-Val-Nip (SEQ. ID. NO. 149) |
| Peptide 150 | Lys-Leu-Lys-Lys-Gln-Leu-Glu-Glu-Leu-Leu-Glu-Arg-Phe-Leu-Asp-Leu-Val-Nip (SEQ. ID. NO. 150) |
| Peptide 151 | Lys-Lys-Leu-Gln-Leu-Leu-Ala-Glu-Leu-Leu-Glu-Arg-Phe-Ala-Asp-Leu-Val-Nip (SEQ. ID. NO. 151) |

TABLE 7-continued

| | |
|---|---|
| Peptide 152 | Lys-Lys-Leu-Gln-Ala-Leu-Ala-Glu-Leu-Leu-Glu-Arg-Phe-Ala-Asp-Leu-Val-Nip (SEQ. ID. NO. 152) |
| Peptide 153 | Lys-Leu-Lys-Gln-Lys-Leu-Glu-Glu-Trp-Gly-Glu-Arg-Phe-Leu-Asp-Leu-Val-Nip (SEQ. ID. NO. 153) |
| Peptide 154 | Lys-Leu-Lys-Lys-Gln-Leu-Asp-Glu-Leu-Leu-Arg-Glu-Phe-Leu-Glu-Leu-Val-Nip (SEQ. ID. NO. 154) |
| Peptide 155 | Lys-Leu-Lys-Gln-Glu-Leu-Lys-Glu-Leu-Leu-Glu-Arg-Phe-Leu-Asp-Leu-Val-Nip (SEQ. ID. NO. 155) |
| Peptide 253 | Lys-Leu-Lys-Gln-Lys-Leu-Ala-Glu-Leu-Leu-Glu-Gln-Leu-Leu-Glu-Lys-Leu-Leu-Glu-Leu-Leu-azPro (SEQ. ID. NO. 253) |
| Peptide 254 | Lys-Leu-Lys-Gln-Lys-Trp-Ala-Glu-Leu-Aib-Glu-Asn-Leu-Leu-Glu-Arg-Phe-Leu-Asp-Leu-Val-azPro (SEQ. ID. NO. 254) |
| Peptide 255 | Lys-Leu-Lys-Lys-Lys-Leu-Ala-Lys-Leu-Leu-Glu-Glu-Leu-Leu-Glu-Arg-Phe-Leu-Asp-Leu-Val-azPro (SEQ. ID. NO. 255) |
| Peptide 256 | Lys-Leu-Lys-Lys-Gln-Leu-Ala-Glu-Leu-Glu-Arg-Leu-Leu-Glu-Asn-Phe-Leu-Asp-Leu-Val-azPro (SEQ. ID. NO. 256) |
| Peptide 257 | Lys-Leu-Lys-Gln-Lys-Leu-Ala-Glu-Leu-Leu-Glu-Arg-Leu-Leu-Glu-Asn-Phe-Leu-Asp-Leu-(D-Val)-azPro (SEQ. ID. NO. 257) |
| Peptide 258 | Lys-Leu-Lys-Gln-Lys-Leu-Ala-Glu-Leu-Leu-Glu-Asn-Leu-Leu-Glu-Arg-Phe-Leu-azPro (SEQ. ID. NO. 258) |
| Peptide 259 | Lys-Lys-Lys-Gln-Lys-Leu-Ala-Glu-Leu-Leu-Glu-Asn-Leu-Leu-Glu-Arg-Phe-Leu-Asp-Leu-Val-azPro (SEQ. ID. NO. 259) |
| Peptide 260 | Gln-Lys-Leu-Ala-Glu-Leu-Leu-Glu-Asn-Leu-Leu-Glu-Arg-Phe-Leu-Asp-Leu-Val-azPro (SEQ. ID. NO. 260) |
| Peptide 261 | Lys-Leu-Lys-Gln-Lys-Leu-Ala-Glu-Leu-Leu-Glu-Asn-Leu-Leu-Glu-Arg-Phe-Leu-Asp-Leu-azPro (SEQ. ID. NO. 261) |
| Peptide 262 | Lys-Leu-Lys-Lys-Gln-Leu-Ala-Asn-Leu-Leu-Glu-Asp-Leu-Leu-Arg-Glu-Phe-Leu-Glu-Leu-Val-azPro (SEQ. ID. NO. 262) |
| Peptide 264 | Lys-Leu-Lys-Gln-Lys-Leu-Ala-Glu-Leu-Leu-Glu-Asn-Leu-Leu-azPro (SEQ. ID. NO. 264) |
| Peptide 269 | Lys-Leu-Lys-Gln-Trp-Leu-Glu-Asn-Leu-Leu-Glu-Arg-Phe-Leu-Asp-Leu-Val-azPro (SEQ. ID. NO. 269) |
| Peptide 271 | Lys-Lys-Leu-Gln-Leu-Leu-Ala-Glu-Leu-Leu-Glu-Arg-Phe-Ala-Asp-Leu-Val-azPro (SEQ. ID. NO. 271) |
| Peptide 272 | Lys-Lys-Leu-Gln-Ala-Leu-Ala-Glu-Leu-Leu-Glu-Arg-Phe-Ala-Asp-Leu-Val-azPro (SEQ. ID. NO. 272) |
| Peptide 273 | Lys-Leu-Lys-Gln-Lys-Leu-Glu-Glu-Trp-Gly-Glu-Arg-Phe-Leu-Asp-Leu-Val-azPro (SEQ. ID. NO. 273) |
| Peptide 274 | Lys-Leu-Lys-Lys-Gln-Leu-Asp-Glu-Leu-Leu-Arg-Glu-Phe-Leu-Glu-Leu-Val-azPro (SEQ. ID. NO. 274) |
| Peptide 275 | Lys-Leu-Lys-Gln-Glu-Leu-Lys-Glu-Leu-Leu-Glu-Arg-Phe-Leu-Asp-Leu-Val-azPro (SEQ. ID. NO. 275) |
| Peptide 345 | Lys-Leu-Lys-Gln-Lys-Leu-Ala-Glu-Leu-Leu-Glu-Gln-Leu-Leu-Glu-Lys-Leu-Leu-Glu-Leu-Leu-Pip (SEQ. ID. NO. 345) |
| Peptide 346 | Lys-Leu-Lys-Gln-Lys-Trp-Ala-Glu-Leu-Aib-Glu-Asn-Leu-Leu-Glu-Arg-Phe-Leu-Asp-Leu-Val-Pip (SEQ. ID. NO. 346) |
| Peptide 347 | Lys-Leu-Lys-Lys-Lys-Leu-Ala-Lys-Leu-Leu-Glu-Glu-Leu-Leu-Glu-Arg-Phe-Leu-Asp-Leu-Val-Pip (SEQ. ID. NO. 347) |
| Peptide 348 | Lys-Leu-Lys-Lys-Gln-Leu-Ala-Glu-Leu-Glu-Arg-Leu-Leu-Glu-Asn-Phe-Leu-Asp-Leu-Val-Pip (SEQ. ID. NO. 348) |
| Peptide 349 | Lys-Leu-Lys-Gln-Lys-Leu-Ala-Glu-Leu-Leu-Glu-Asn-Leu-Leu-Glu-Arg-Phe-Leu-Asp-Leu-(D-Val)-Pip (SEQ. ID. NO. 349) |
| Peptide 350 | Lys-Leu-Lys-Gln-Lys-Leu-Ala-Glu-Leu-Leu-Glu-Asn-Leu-Leu-Glu-Arg-Phe-Leu-Pip (SEQ. ID. NO. 350) |
| Peptide 351 | Lys-Lys-Lys-Gln-Lys-Leu-Ala-Glu-Leu-Leu-Glu-Asn-Leu-Leu-Glu-Arg-Phe-Leu-Asp-Leu-Val-Pip (SEQ. ID. NO. 351) |
| Peptide 352 | Gln-Lys-Leu-Ala-Glu-Leu-Leu-Glu-Asn-Leu-Leu-Glu-Arg-Phe-Leu-Asp-Leu-Val-Pip (SEQ. ID. NO. 352) |
| Peptide 353 | Lys-Leu-Lys-Gln-Lys-Leu-Ala-Glu-Leu-Leu-Glu-Asn-Leu-Leu-Glu-Arg-Phe-Leu-Asp-Leu-Pip (SEQ. ID. NO. 353) |
| Peptide 354 | Lys-Leu-Lys-Lys-Gln-Leu-Ala-Asn-Leu-Leu-Glu-Asp-Leu-Leu-Arg-Glu-Phe-Leu-Glu-Leu-Val-Pip (SEQ. ID. NO. 354) |
| Peptide 356 | Lys-Leu-Lys-Gln-Lys-Leu-Ala-Glu-Leu-Leu-Glu-Asn-Leu-Leu-Pip (SEQ. ID. NO. 356) |
| Peptide 361 | Lys-Leu-Lys-Gln-Trp-Leu-Glu-Asn-Leu-Leu-Glu-Arg-Phe-Leu-Asp-Leu-Val-Pip (SEQ. ID. NO. 361) |
| Peptide 363 | Lys-Lys-Leu-Gln-Leu-Leu-Ala-Glu-Leu-Leu-Glu-Arg-Phe-Ala-Asp-Leu-Val-Pip (SEQ. ID. NO. 363) |
| Peptide 364 | Lys-Lys-Leu-Gln-Ala-Leu-Ala-Glu-Leu-Leu-Glu-Arg-Phe-Ala-Asp-Leu-Val-Pip (SEQ. ID. NO. 364) |
| Peptide 365 | Lys-Leu-Lys-Gln-Lys-Leu-Glu-Glu-Trp-Gly-Glu-Arg-Phe-Leu-Asp-Leu-Val-Pip (SEQ. ID. NO. 365) |

TABLE 7-continued

| | |
|---|---|
| Peptide 366 | Lys-Leu-Lys-Lys-Gln-Leu-Asp-Glu-Leu-Leu-Arg-Glu-Phe-Leu-Glu-Leu-Val-Pip (SEQ. ID. NO. 366) |
| Peptide 367 | Lys-Leu-Lys-Gln-Glu-Leu-Lys-Glu-Leu-Leu-Glu-Arg-Phe-Leu-Asp-Leu-Val-Pip (SEQ. ID. NO. 367) |
| Peptide 437 | Lys-Leu-Lys-Gln-Lys-Leu-Ala-Glu-Leu-Leu-Glu-Gln-Leu-Leu-Glu-Lys-Leu-Leu-Glu-Leu-Leu-azPip (SEQ. ID. NO. 437) |
| Peptide 438 | Lys-Leu-Lys-Gln-Lys-Trp-Ala-Glu-Leu-Aib-Glu-Asn-Leu-Leu-Glu-Arg-Phe-Leu-Asp-Leu-Val-azPip (SEQ. ID. NO. 438) |
| Peptide 439 | Lys-Leu-Lys-Lys-Lys-Leu-Ala-Lys-Leu-Leu-Glu-Glu-Leu-Leu-Glu-Arg-Phe-Leu-Asp-Leu-Val-azPip (SEQ. ID. NO. 439) |
| Peptide 440 | Lys-Leu-Lys-Lys-Gln-Leu-Ala-Glu-Leu-Leu-Glu-Arg-Leu-Leu-Glu-Asn-Phe-Leu-Asp-Leu-Val-azPip (SEQ. ID. NO. 440) |
| Peptide 441 | Lys-Leu-Lys-Gln-Lys-Leu-Ala-Glu-Leu-Leu-Glu-Asn-Leu-Leu-Glu-Arg-Phe-Leu-Asp-Leu-(D-Val)-azPip (SEQ. ID. NO. 441) |
| Peptide 442 | Lys-Leu-Lys-Gln-Lys-Leu-Ala-Glu-Leu-Leu-Glu-Asn-Leu-Leu-Glu-Arg-Phe-Leu-azPip (SEQ. ID. NO. 442) |
| Peptide 443 | Lys-Lys-Lys-Gln-Lys-Leu-Ala-Glu-Leu-Leu-Glu-Asn-Leu-Leu-Glu-Arg-Phe-Leu-Asp-Leu-Val-azPip (SEQ. ID. NO. 443) |
| Peptide 444 | Gln-Lys-Leu-Ala-Glu-Leu-Leu-Glu-Asn-Leu-Leu-Glu-Arg-Phe-Leu-Asp-Leu-Val-azPip (SEQ. ID. NO. 444) |
| Peptide 445 | Lys-Leu-Lys-Gln-Lys-Leu-Ala-Glu-Leu-Leu-Glu-Asn-Leu-Leu-Glu-Arg-Phe-Leu-Asp-Leu-azPip (SEQ. ID. NO. 445) |
| Peptide 446 | Lys-Leu-Lys-Lys-Gln-Leu-Ala-Asn-Leu-Leu-Glu-Asp-Leu-Leu-Arg-Glu-Phe-Leu-Glu-Leu-Val-azPip (SEQ. ID. NO. 446) |
| Peptide 448 | Lys-Leu-Lys-Gln-Lys-Leu-Ala-Glu-Leu-Leu-Glu-Asn-Leu-Leu-azPip (SEQ. ID. NO. 448) |
| Peptide 453 | Lys-Leu-Lys-Gln-Trp-Leu-Glu-Asn-Leu-Leu-Glu-Arg-Phe-Leu-Asp-Leu-Val-azPip (SEQ. ID. NO. 453) |
| Peptide 455 | Lys-Lys-Leu-Gln-Leu-Leu-Ala-Glu-Leu-Leu-Glu-Arg-Phe-Ala-Asp-Leu-Val-azPip (SEQ. ID. NO. 455) |
| Peptide 456 | Lys-Lys-Leu-Gln-Ala-Leu-Ala-Glu-Leu-Leu-Glu-Arg-Phe-Ala-Asp-Leu-Val-azPip (SEQ. ID. NO. 456) |
| Peptide 457 | Lys-Leu-Lys-Gln-Lys-Leu-Glu-Glu-Trp-Gly-Glu-Arg-Phe-Leu-Asp-Leu-Val-azPip (SEQ. ID. NO. 457) |
| Peptide 458 | Lys-Leu-Lys-Lys-Gln-Leu-Asp-Glu-Leu-Leu-Arg-Glu-Phe-Leu-Glu-Leu-Val-azPip (SEQ. ID. NO. 458) |
| Peptide 459 | Lys-Leu-Lys-Gln-Glu-Leu-Lys-Glu-Leu-Leu-Glu-Arg-Phe-Leu-Asp-Leu-Val-azPip (SEQ. ID. NO. 459) | or a pharmaceutically acceptable salt thereof

Some illustrative ApoA-I Mimics having an acetylated N-terminus and an amidated C-terminus are set forth in Tables 8 and 9 below:

TABLE 8

| | |
|---|---|
| Peptide 64 | $H_3C(O)$C-Lys-Leu-Lys-Gln-Lys-Leu-Ala-Glu-Leu-Gly-Glu-Asn-Leu-Leu-Glu-Arg-Phe-Leu-Asp-Leu-Val-Inp-$NH_2$ (SEQ. ID. NO. 64) |
| Peptide 65 | $H_3C(O)$C-Lys-Leu-Lys-Gln-Lys-Leu-Glu-Glu-Leu-Leu-Glu-Arg-Leu-Leu-Asp-Leu-Val-Inp-$NH_2$ (SEQ. ID. NO. 65) |
| Peptide 66 | $H_3C(O)$C-Lys-Leu-Lys-Gln-Lys-Leu-Glu-Glu-Leu-Leu-Glu-Lys-Phe-Leu-Asp-Leu-Val-Inp-$NH_2$ (SEQ. ID. NO. 66) |
| Peptide 67 | $H_3C(O)$C-Lys-Leu-Lys-Gln-Lys-Leu-Glu-Glu-Leu-Leu-Glu-Arg-Phe-Leu-Asp-Leu-Val-Inp-$NH_2$ (SEQ. ID. NO. 67) |
| Peptide 68 | $H_3C(O)$C-Lys-Leu-Lys-Gln-Lys-Leu-Glu-Glu-Leu-Leu-Glu-Arg-Phe-Leu-Glu-Leu-Val-Inp-$NH_2$ (SEQ. ID. NO. 68) |
| Peptide 69 | $H_3C(O)$C-Lys-Leu-Lys-Gln-Lys-Leu-Glu-Glu-Leu-Leu-Glu-Lys-Phe-Leu-Glu-Leu-Val-Inp-$NH_2$ (SEQ. ID. NO. 69) |
| Peptide 70 | $H_3C(O)$C-Lys-Leu-Lys-Asn-Lys-Leu-Glu-Glu-Leu-Leu-Glu-Arg-Phe-Leu-Asp-Leu-Val-Inp-$NH_2$ (SEQ. ID. NO. 70) |
| Peptide 71 | $H_3C(O)$C-Lys-Leu-Lys-Gln-Lys-Leu-Glu-Glu-Leu-Leu-Glu-Arg-Phe-Leu-Asp-Leu-Leu-Inp-$NH_2$ (SEQ. ID. NO. 71) |
| Peptide 72 | $H_3C(O)$C-Lys-Leu-Lys-Gln-Lys-Leu-Glu-Glu-Trp-Leu-Glu-Arg-Phe-Leu-Asp-Leu-Val-Inp-$NH_2$ (SEQ. ID. NO. 72) |
| Peptide 73 | $H_3C(O)$C-Lys-Leu-Lys-Gln-Lys-Leu-Glu-Glu-Leu-Leu-Glu-Lys-Phe-Leu-Asp-Leu-Leu-Inp-$NH_2$ (SEQ. ID. NO. 73) |
| Peptide 74 | $H_3C(O)$C-Arg-Leu-Lys-Gln-Arg-Leu-Glu-Glu-Leu-Leu-Asp-Lys-Phe-Leu-Glu-Leu-Ala-Inp-$NH_2$ (SEQ. ID. NO. 74) |
| Peptide 75 | $H_3C(O)$C-Lys-Leu-Lys-Gln-Lys-Leu-Glu-Glu-Leu-Leu-Glu-Arg-Phe-Phe-Asp-Leu-Val-Inp-$NH_2$ (SEQ. ID. NO. 75) |
| Peptide 76 | $H_3C(O)$C-Lys-Leu-Lys-Gln-Lys-Leu-Glu-Glu-Leu-Leu-Glu-Lys-Leu-Leu-Glu-Leu-Leu-Inp-$NH_2$ (SEQ. ID. NO. 76) |

TABLE 8-continued

| Peptide 77 | H₃C(O)C-Lys-Leu-Lys-Gln-Lys-Leu-Glu-Glu-Leu-Leu-Glu-Lys-Leu-Leu-Glu-Leu-Val-Inp-NH₂ (SEQ. ID. NO. 77) |
|---|---|
| Peptide 78 | H₃C(O)C-Lys-Leu-Arg-Gln-Arg-Leu-Glu-Glu-Leu-Leu-Asp-Lys-Phe-Leu-Glu-Leu-Ala-Inp-NH₂ (SEQ. ID. NO. 78) |
| Peptide 79 | H₃C(O)C-Orn-Leu-Orn-Gln-Orn-Leu-Glu-Glu-Leu-Leu-Glu-Arg-Phe-Leu-Asp-Leu-Val-Inp-NH₂ (SEQ. ID. NO. 79) |
| Peptide 80 | H₃C(O)C-Lys-Leu-Orn-Gln-Orn-Leu-Glu-Glu-Leu-Leu-Glu-Orn-Phe-Leu-Asp-Leu-Val-Inp-NH₂ (SEQ. ID. NO. 80) |
| Peptide 81 | H₃C(O)C-Lys-Leu-Arg-Gln-Arg-Phe-Glu-Glu-Leu-Leu-Asp-Lys-Phe-Leu-Glu-Leu-Ala-Inp-NH₂ (SEQ. ID. NO. 81) |
| Peptide 82 | H₃C(O)C-Lys-Leu-Lys-Gln-Lys-Trp-Glu-Glu-Leu-Leu-Glu-Arg-Phe-Leu-Asp-Leu-Val-Inp-NH₂ (SEQ. ID. NO. 82) |
| Peptide 83 | H₃C(O)C-Lys-Leu-Lys-Gln-Lys-Leu-Glu-Asn-Leu-Leu-Glu-Arg-Phe-Leu-Asp-Leu-Val-Inp-NH₂ (SEQ. ID. NO. 83) |
| Peptide 84 | H₃C(O)C-Lys-Leu-Lys-Gln-Lys-Leu-Glu-Glu-Gly-Leu-Glu-Arg-Phe-Leu-Asp-Leu-Val-Inp-NH₂ (SEQ. ID. NO. 84) |
| Peptide 85 | H₃C(O)C-Lys-Leu-Lys-Gln-Lys-Leu-Glu-Glu-Leu-Gly-Glu-Arg-Phe-Leu-Asp-Leu-Val-Inp-NH₂ (SEQ. ID. NO. 85) |
| Peptide 86 | H₃C(O)C-Lys-Leu-Lys-Gln-Lys-Gly-Glu-Glu-Leu-Leu-Glu-Arg-Phe-Leu-Asp-Leu-Val-Inp-NH₂ (SEQ. ID. NO. 86) |
| Peptide 87 | H₃C(O)C-Lys-Leu-Lys-Gln-Lys-Leu-Glu-Glu-Leu-Leu-Glu-Lys-Phe-Leu-Glu-Leu-Leu-Inp-NH₂ (SEQ. ID. NO. 87) |
| Peptide 88 | H₃C(O)C-Lys-Leu-Lys-Gln-Glu-Leu-Leu-Glu-Arg-Phe-Leu-Asp-Leu-Val-Inp-NH₂ (SEQ. ID. NO. 88) |
| Peptide 89 | H₃C(O)C-Lys-Gln-Lys-Leu-Glu-Glu-Leu-Leu-Glu-Arg-Phe-Leu-Asp-Leu-Val-Inp-NH₂ (SEQ. ID. NO. 89) |
| Peptide 90 | H₃C(O)C-Lys-Gln-Lys-Leu-Lys-Glu-Leu-Leu-Glu-Arg-Phe-Leu-Asp-Leu-Val-Inp-NH₂ (SEQ. ID. NO. 90) |
| Peptide 91 | H₃C(O)C-Lys-Gln-Leu-Lys-Glu-Leu-Leu-Glu-Arg-Phe-Leu-Asp-Leu-Val-Inp-NH₂ (SEQ. ID. NO. 91) |
| Peptide 92 | H₃C(O)C-Lys-Gln-Lys-Leu-Ala-Glu-Leu-Leu-Glu-Arg-Phe-Leu-Asp-Leu-Val-Inp-NH₂ (SEQ. ID. NO. 92) |
| Peptide 93 | H₃C(O)C-Lys-Gln-Lys-Leu-Glu-Asn-Leu-Leu-Glu-Arg-Phe-Leu-Asp-Leu-Val-Inp-NH₂ (SEQ. ID. NO. 93) |
| Peptide 156 | H₃C(O)C-Lys-Leu-Lys-Gln-Lys-Leu-Ala-Glu-Leu-Gly-Glu-Asn-Leu-Leu-Glu-Arg-Phe-Leu-Asp-Leu-Val-Nip-NH₂ (SEQ. ID. NO. 156) |
| Peptide 157 | H₃C(O)C-Lys-Leu-Lys-Gln-Lys-Leu-Glu-Glu-Leu-Leu-Glu-Arg-Leu-Leu-Asp-Leu-Val-Nip-NH₂ (SEQ. ID. NO. 157) |
| Peptide 158 | H₃C(O)C-Lys-Leu-Lys-Gln-Lys-Leu-Glu-Glu-Leu-Leu-Glu-Lys-Phe-Leu-Asp-Leu-Val-Nip-NH₂ (SEQ. ID. NO. 158) |
| Peptide 159 | H₃C(O)C-Lys-Leu-Lys-Gln-Lys-Leu-Glu-Glu-Leu-Leu-Glu-Arg-Phe-Leu-Asp-Leu-Val-Nip-NH₂ (SEQ. ID. NO. 159) |
| Peptide 160 | H₃C(O)C-Lys-Leu-Lys-Gln-Lys-Leu-Glu-Glu-Leu-Leu-Glu-Arg-Phe-Leu-Asp-Leu-Val-Nip-NH₂ (SEQ. ID. NO. 160) |
| Peptide 161 | H₃C(O)C-Lys-Leu-Lys-Gln-Lys-Leu-Glu-Glu-Leu-Leu-Glu-Lys-Phe-Leu-Glu-Leu-Val-Nip-NH₂ (SEQ. ID. NO. 161) |
| Peptide 162 | H₃C(O)C-Lys-Leu-Lys-Asn-Lys-Leu-Glu-Glu-Leu-Leu-Glu-Arg-Phe-Leu-Asp-Leu-Val-Nip-NH₂ (SEQ. ID. NO. 162) |
| Peptide 163 | H₃C(O)C-Lys-Leu-Lys-Gln-Lys-Leu-Glu-Glu-Leu-Leu-Glu-Arg-Phe-Leu-Asp-Leu-Leu-Nip-NH₂ (SEQ. ID. NO. 163) |
| Peptide 164 | H₃C(O)C-Lys-Leu-Lys-Gln-Lys-Leu-Glu-Glu-Trp-Leu-Glu-Arg-Phe-Leu-Asp-Leu-Val-Nip-NH₂ (SEQ. ID. NO. 164) |
| Peptide 165 | H₃C(O)C-Lys-Leu-Lys-Gln-Lys-Leu-Glu-Glu-Leu-Leu-Glu-Lys-Phe-Leu-Asp-Leu-Leu-Nip-NH₂ (SEQ. ID. NO. 165) |
| Peptide 166 | H₃C(O)C-Arg-Leu-Lys-Gln-Arg-Leu-Glu-Glu-Leu-Leu-Asp-Lys-Phe-Leu-Glu-Leu-Ala-Nip-NH₂ (SEQ. ID. NO. 166) |
| Peptide 167 | H₃C(O)C-Lys-Leu-Lys-Gln-Lys-Leu-Glu-Glu-Leu-Leu-Glu-Arg-Phe-Phe-Asp-Leu-Val-Nip-NH₂ (SEQ. ID. NO. 167) |
| Peptide 168 | H₃C(O)C-Lys-Leu-Lys-Gln-Lys-Leu-Glu-Glu-Leu-Lys-Glu-Leu-Leu-Glu-Leu-Leu-Nip-NH₂ (SEQ. ID. NO. 168) |
| Peptide 169 | H₃C(O)C-Lys-Leu-Lys-Gln-Lys-Leu-Glu-Glu-Leu-Leu-Glu-Lys-Leu-Leu-Glu-Leu-Val-Nip-NH₂ (SEQ. ID. NO. 169) |
| Peptide 170 | H₃C(O)C-Lys-Leu-Arg-Gln-Arg-Leu-Glu-Glu-Leu-Leu-Asp-Lys-Phe-Leu-Glu-Leu-Ala-Nip-NH₂ (SEQ. ID. NO. 170) |
| Peptide 171 | H₃C(O)C-Orn-Leu-Orn-Gln-Orn-Leu-Glu-Glu-Leu-Leu-Glu-Arg-Phe-Leu-Asp-Leu-Val-Nip-NH₂ (SEQ. ID. NO. 171) |

TABLE 8-continued

| | |
|---|---|
| Peptide 172 | H₃C(O)C-Lys-Leu-Orn-Gln-Orn-Leu-Glu-Glu-Leu-Leu-Glu-Orn-Phe-Leu-Asp-Leu-Val-Nip-NH₂ (SEQ. ID. NO. 172) |
| Peptide 173 | H₃C(O)C-Lys-Leu-Arg-Gln-Arg-Phe-Glu-Glu-Leu-Leu-Asp-Lys-Phe-Leu-Glu-Leu-Ala-Nip-NH₂ (SEQ. ID. NO. 173) |
| Peptide 174 | H₃C(O)C-Lys-Leu-Lys-Gln-Lys-Trp-Glu-Glu-Leu-Leu-Glu-Arg-Phe-Leu-Asp-Leu-Val-Nip-NH₂ (SEQ. ID. NO. 174) |
| Peptide 175 | H₃C(O)C-Lys-Leu-Lys-Gln-Leu-Leu-Glu-Asn-Leu-Leu-Glu-Arg-Phe-Leu-Asp-Leu-Val-Nip-NH₂ (SEQ. ID. NO. 175) |
| Peptide 176 | H₃C(O)C-Lys-Leu-Lys-Gln-Lys-Leu-Glu-Glu-Gly-Leu-Glu-Arg-Phe-Leu-Asp-Leu-Val-Nip-NH₂ (SEQ. ID. NO. 176) |
| Peptide 177 | H₃C(O)C-Lys-Leu-Lys-Gln-Lys-Leu-Glu-Glu-Leu-Gly-Glu-Arg-Phe-Leu-Asp-Leu-Val-Nip-NH₂ (SEQ. ID. NO. 177) |
| Peptide 178 | H₃C(O)C-Lys-Leu-Lys-Gln-Lys-Gly-Glu-Glu-Leu-Leu-Glu-Arg-Phe-Leu-Asp-Leu-Val-Nip-NH₂ (SEQ. ID. NO. 178) |
| Peptide 179 | H₃C(O)C-Lys-Leu-Lys-Gln-Lys-Leu-Glu-Glu-Leu-Leu-Glu-Lys-Phe-Leu-Glu-Leu-Leu-Nip-NH₂ (SEQ. ID. NO. 179) |
| Peptide 180 | H₃C(O)C-Lys-Leu-Lys-Gln-Glu-Leu-Leu-Glu-Arg-Phe-Leu-Asp-Leu-Val-Nip-NH₂ (SEQ. ID. NO. 180) |
| Peptide 181 | H₃C(O)C-Lys-Gln-Lys-Leu-Glu-Glu-Leu-Leu-Glu-Arg-Phe-Leu-Asp-Leu-Val-Nip-NH₂ (SEQ. ID. NO. 181) |
| Peptide 182 | H₃C(O)C-Lys-Gln-Lys-Leu-Lys-Glu-Leu-Leu-Glu-Arg-Phe-Leu-Asp-Leu-Val-Nip-NH₂ (SEQ. ID. NO. 182) |
| Peptide 183 | H₃C(O)C-Lys-Gln-Leu-Lys-Glu-Leu-Leu-Glu-Arg-Phe-Leu-Asp-Leu-Val-Nip-NH₂ (SEQ. ID. NO. 183) |
| Peptide 184 | H₃C(O)C-Lys-Gln-Lys-Leu-Ala-Glu-Leu-Leu-Glu-Arg-Phe-Leu-Asp-Leu-Val-Nip-NH₂ (SEQ. ID. NO. 184) |
| Peptide 185 | H₃C(O)C-Lys-Gln-Lys-Leu-Glu-Asn-Leu-Leu-Glu-Arg-Phe-Leu-Asp-Leu-Val-Nip-NH₂ (SEQ. ID. NO. 185) |
| Peptide 276 | H₃C(O)C-Lys-Leu-Lys-Gln-Lys-Leu-Ala-Glu-Leu-Gly-Glu-Asn-Leu-Leu-Glu-Arg-Phe-Leu-Asp-Leu-Val-azPro-NH₂ (SEQ. ID. NO. 276) |
| Peptide 277 | H₃C(O)C-Lys-Leu-Lys-Gln-Lys-Leu-Glu-Glu-Leu-Leu-Glu-Arg-Leu-Leu-Asp-Leu-Val-azPro-NH₂ (SEQ. ID. NO. 277) |
| Peptide 278 | H₃C(O)C-Lys-Leu-Lys-Gln-Lys-Leu-Glu-Glu-Leu-Leu-Glu-Lys-Phe-Leu-Asp-Leu-Val-azPro-NH₂ (SEQ. ID. NO. 278) |
| Peptide 279 | H₃C(O)C-Lys-Leu-Lys-Gln-Lys-Leu-Glu-Glu-Leu-Leu-Glu-Arg-Phe-Leu-Asp-Leu-Val-azPro-NH₂ (SEQ. ID. NO. 279) |
| Peptide 280 | H₃C(O)C-Lys-Leu-Lys-Gln-Lys-Leu-Glu-Glu-Leu-Leu-Glu-Arg-Phe-Leu-Glu-Leu-Val-azPro-NH₂ (SEQ. ID. NO. 280) |
| Peptide 281 | H₃C(O)C-Lys-Leu-Lys-Gln-Lys-Leu-Glu-Glu-Leu-Leu-Glu-Lys-Phe-Leu-Glu-Leu-Val-azPro-NH₂ (SEQ. ID. NO. 281) |
| Peptide 282 | H₃C(O)C-Lys-Leu-Lys-Asn-Lys-Leu-Glu-Glu-Leu-Leu-Glu-Arg-Phe-Leu-Asp-Leu-Val-azPro-NH₂ (SEQ. ID. NO. 282) |
| Peptide 283 | H₃C(O)C-Lys-Leu-Lys-Gln-Lys-Leu-Glu-Glu-Leu-Leu-Glu-Arg-Phe-Leu-Asp-Leu-Leu-azPro-NH₂ (SEQ. ID. NO. 283) |
| Peptide 284 | H₃C(O)C-Lys-Leu-Lys-Gln-Lys-Leu-Glu-Glu-Trp-Leu-Glu-Arg-Phe-Leu-Asp-Leu-Val-azPro-NH₂ (SEQ. ID. NO. 284) |
| Peptide 285 | H₃C(O)C-Lys-Leu-Lys-Gln-Lys-Leu-Glu-Glu-Leu-Leu-Glu-Lys-Phe-Leu-Asp-Leu-Leu-azPro-NH₂ (SEQ. ID. NO. 285) |
| Peptide 286 | H₃C(O)C-Arg-Leu-Lys-Gln-Arg-Leu-Glu-Glu-Leu-Leu-Asp-Lys-Phe-Leu-Glu-Leu-Ala-azPro-NH₂ (SEQ. ID. NO. 286) |
| Peptide 287 | H₃C(O)C-Lys-Leu-Lys-Gln-Lys-Leu-Glu-Glu-Leu-Leu-Glu-Arg-Phe-Phe-Asp-Leu-Val-azPro-NH₂ (SEQ. ID. NO. 287) |
| Peptide 288 | H₃C(O)C-Lys-Leu-Lys-Gln-Lys-Leu-Glu-Glu-Leu-Leu-Glu-Lys-Leu-Leu-Glu-Leu-Leu-azPro-NH₂ (SEQ. ID. NO. 288) |
| Peptide 289 | H₃C(O)C-Lys-Leu-Lys-Gln-Lys-Leu-Glu-Glu-Leu-Leu-Glu-Lys-Leu-Leu-Glu-Leu-Val-azPro-NH₂ (SEQ. ID. NO. 289) |
| Peptide 290 | H₃C(O)C-Lys-Leu-Arg-Gln-Arg-Leu-Glu-Glu-Leu-Leu-Asp-Lys-Phe-Leu-Glu-Leu-Ala-azPro-NH₂ (SEQ. ID. NO. 290) |
| Peptide 291 | H₃C(O)C-Orn-Leu-Orn-Gln-Orn-Leu-Glu-Glu-Leu-Leu-Glu-Arg-Phe-Leu-Asp-Leu-Val-azPro-NH₂ (SEQ. ID. NO. 291) |
| Peptide 292 | H₃C(O)C-Lys-Leu-Orn-Gln-Orn-Leu-Glu-Glu-Leu-Leu-Glu-Orn-Phe-Leu-Asp-Leu-Val-azPro-NH₂ (SEQ. ID. NO. 292) |
| Peptide 293 | H₃C(O)C-Lys-Leu-Arg-Gln-Arg-Phe-Glu-Glu-Leu-Leu-Asp-Lys-Phe-Leu-Glu-Leu-Ala-azPro-NH₂ (SEQ. ID. NO. 293) |
| Peptide 294 | H₃C(O)C-Lys-Leu-Lys-Gln-Lys-Trp-Glu-Glu-Leu-Leu-Glu-Arg-Phe-Leu-Asp-Leu-Val-azPro-NH₂ (SEQ. ID. NO. 294) |

TABLE 8-continued

| Peptide 295 | H₃C(O)C-Lys-Leu-Lys-Gln-Leu-Leu-Glu-Asn-Leu-Leu-Glu-Arg-Phe-Leu-Asp-Leu-Val-azPro-NH₂ (SEQ. ID. NO. 295) |
| Peptide 296 | H₃C(O)C-Lys-Leu-Lys-Gln-Lys-Leu-Glu-Glu-Gly-Leu-Glu-Arg-Phe-Leu-Asp-Leu-Val-azPro-NH₂ (SEQ. ID. NO. 296) |
| Peptide 297 | H₃C(O)C-Lys-Leu-Lys-Gln-Lys-Leu-Glu-Glu-Leu-Gly-Glu-Arg-Phe-Leu-Asp-Leu-Val-azPro-NH₂ (SEQ. ID. NO. 297) |
| Peptide 298 | H₃C(O)C-Lys-Leu-Lys-Gln-Lys-Gly-Glu-Glu-Leu-Leu-Glu-Arg-Phe-Leu-Asp-Leu-Val-azPro-NH₂ (SEQ. ID. NO. 298) |
| Peptide 299 | H₃C(O)C-Lys-Leu-Lys-Gln-Lys-Leu-Glu-Glu-Leu-Leu-Glu-Lys-Phe-Leu-Glu-Leu-Leu-azPro-NH₂ (SEQ. ID. NO. 299) |
| Peptide 300 | H₃C(O)C-Lys-Leu-Lys-Gln-Glu-Leu-Leu-Glu-Arg-Phe-Leu-Asp-Leu-Val-azPro-NH₂ (SEQ. ID. NO. 300) |
| Peptide 301 | H₃C(O)C-Lys-Gln-Lys-Leu-Glu-Glu-Leu-Leu-Glu-Arg-Phe-Leu-Asp-Leu-Val-azPro-NH₂ (SEQ. ID. NO. 301) |
| Peptide 302 | H₃C(O)C-Lys-Gln-Lys-Leu-Lys-Glu-Leu-Leu-Glu-Arg-Phe-Leu-Asp-Leu-Val-azPro-NH₂ (SEQ. ID. NO. 302) |
| Peptide 303 | H₃C(O)C-Lys-Gln-Leu-Lys-Glu-Leu-Leu-Glu-Arg-Phe-Leu-Asp-Leu-Val-azPro-NH₂ (SEQ. ID. NO. 303) |
| Peptide 304 | H₃C(O)C-Lys-Gln-Lys-Leu-Ala-Glu-Leu-Leu-Glu-Arg-Phe-Leu-Asp-Leu-Val-azPro-NH₂ (SEQ. ID. NO. 304) |
| Peptide 305 | H₃C(O)C-Lys-Gln-Lys-Leu-Glu-Asn-Leu-Leu-Glu-Arg-Phe-Leu-Asp-Leu-Val-azPro-NH₂ (SEQ. ID. NO. 305) |
| Peptide 368 | H₃C(O)C-Lys-Leu-Lys-Gln-Lys-Leu-Ala-Glu-Leu-Gly-Glu-Asn-Leu-Leu-Glu-Arg-Phe-Leu-Asp-Leu-Val-Pip-NH₂ (SEQ. ID. NO. 368) |
| Peptide 369 | H₃C(O)C-Lys-Leu-Lys-Gln-Lys-Leu-Glu-Glu-Leu-Leu-Glu-Arg-Leu-Leu-Asp-Leu-Val-Pip-NH₂ (SEQ. ID. NO. 369) |
| Peptide 370 | H₃C(O)C-Lys-Leu-Lys-Gln-Lys-Leu-Glu-Glu-Leu-Leu-Glu-Lys-Phe-Leu-Asp-Leu-Val-Pip-NH₂ (SEQ. ID. NO. 370) |
| Peptide 371 | H₃C(O)C-Lys-Leu-Lys-Gln-Lys-Leu-Glu-Glu-Leu-Leu-Glu-Arg-Phe-Leu-Asp-Leu-Val-Pip-NH₂ (SEQ. ID. NO. 371) |
| Peptide 372 | H₃C(O)C-Lys-Leu-Lys-Gln-Lys-Leu-Glu-Glu-Leu-Leu-Glu-Arg-Phe-Leu-Glu-Leu-Val-Pip-NH₂ (SEQ. ID. NO. 372) |
| Peptide 373 | H₃C(O)C-Lys-Leu-Lys-Gln-Lys-Leu-Glu-Glu-Leu-Leu-Glu-Lys-Phe-Leu-Glu-Leu-Val-Pip-NH₂ (SEQ. ID. NO. 373) |
| Peptide 374 | H₃C(O)C-Lys-Leu-Lys-Asn-Lys-Leu-Glu-Glu-Leu-Leu-Glu-Arg-Phe-Leu-Asp-Leu-Val-Pip-NH₂ (SEQ. ID. NO. 374) |
| Peptide 375 | H₃C(O)C-Lys-Leu-Lys-Gln-Lys-Leu-Glu-Glu-Leu-Leu-Glu-Arg-Phe-Leu-Asp-Leu-Leu-Pip-NH₂ (SEQ. ID. NO. 375) |
| Peptide 376 | H₃C(O)C-Lys-Leu-Lys-Gln-Lys-Leu-Glu-Glu-Trp-Leu-Glu-Arg-Phe-Leu-Asp-Leu-Val-Pip-NH₂ (SEQ. ID. NO. 376) |
| Peptide 377 | H₃C(O)C-Lys-Leu-Lys-Gln-Lys-Leu-Glu-Glu-Leu-Leu-Glu-Lys-Phe-Leu-Asp-Leu-Leu-Pip-NH₂ (SEQ. ID. NO. 377) |
| Peptide 378 | H₃C(O)C-Arg-Leu-Lys-Gln-Arg-Leu-Glu-Glu-Leu-Leu-Asp-Lys-Phe-Leu-Glu-Leu-Ala-Pip-NH₂ (SEQ. ID. NO. 378) |
| Peptide 379 | H₃C(O)C-Lys-Leu-Lys-Gln-Lys-Leu-Glu-Glu-Leu-Leu-Glu-Arg-Phe-Phe-Asp-Leu-Val-Pip-NH₂ (SEQ. ID. NO. 379) |
| Peptide 380 | H₃C(O)C-Lys-Leu-Lys-Gln-Lys-Leu-Glu-Glu-Leu-Leu-Glu-Lys-Leu-Leu-Glu-Leu-Leu-Pip-NH₂ (SEQ. ID. NO. 380) |
| Peptide 381 | H₃C(O)C-Lys-Leu-Lys-Gln-Lys-Leu-Glu-Glu-Leu-Leu-Glu-Lys-Leu-Leu-Glu-Leu-Val-Pip-NH₂ (SEQ. ID. NO. 381) |
| Peptide 382 | H₃C(O)C-Lys-Leu-Arg-Gln-Arg-Leu-Glu-Glu-Leu-Leu-Asp-Lys-Phe-Leu-Glu-Leu-Ala-Pip-NH₂ (SEQ. ID. NO. 382) |
| Peptide 383 | H₃C(O)C-Orn-Leu-Orn-Gln-Orn-Leu-Glu-Glu-Leu-Leu-Glu-Arg-Phe-Leu-Asp-Leu-Val-Pip-NH₂ (SEQ. ID. NO. 383) |
| Peptide 384 | H₃C(O)C-Lys-Leu-Orn-Gln-Orn-Leu-Glu-Glu-Leu-Leu-Glu-Orn-Phe-Leu-Asp-Leu-Val-Pip-NH₂ (SEQ. ID. NO. 384) |
| Peptide 385 | H₃C(O)C-Lys-Leu-Arg-Gln-Arg-Phe-Glu-Glu-Leu-Leu-Asp-Lys-Phe-Leu-Glu-Leu-Ala-Pip-NH₂ (SEQ. ID. NO. 385) |
| Peptide 386 | H₃C(O)C-Lys-Leu-Lys-Gln-Lys-Trp-Glu-Glu-Leu-Leu-Glu-Arg-Phe-Leu-Asp-Leu-Val-Pip-NH₂ (SEQ. ID. NO. 386) |
| Peptide 387 | H₃C(O)C-Lys-Leu-Lys-Gln-Leu-Leu-Glu-Asn-Leu-Leu-Glu-Arg-Phe-Leu-Asp-Leu-Val-Pip-NH₂ (SEQ. ID. NO. 387) |
| Peptide 388 | H₃C(O)C-Lys-Leu-Lys-Gln-Lys-Leu-Glu-Glu-Gly-Leu-Glu-Arg-Phe-Leu-Asp-Leu-Val-Pip-NH₂ (SEQ. ID. NO. 388) |
| Peptide 389 | H₃C(O)C-Lys-Leu-Lys-Gln-Lys-Leu-Glu-Glu-Leu-Gly-Glu-Arg-Phe-Leu-Asp-Leu-Val-Pip-NH₂ (SEQ. ID. NO. 389) |

TABLE 8-continued

| Peptide 390 | H₃C(O)C-Lys-Leu-Lys-Gln-Lys-Gly-Glu-Glu-Leu-Leu-Glu-Arg-Phe-Leu-Asp-Leu-Val-Pip-NH₂ (SEQ. ID. NO. 390) |
| Peptide 391 | H₃C(O)C-Lys-Leu-Lys-Gln-Lys-Leu-Glu-Glu-Leu-Leu-Glu-Lys-Phe-Leu-Glu-Leu-Leu-Pip-NH₂ (SEQ. ID. NO. 391) |
| Peptide 392 | H₃C(O)C-Lys-Leu-Lys-Gln-Glu-Leu-Leu-Glu-Arg-Phe-Leu-Asp-Leu-Val-Pip-NH₂ (SEQ. ID. NO. 392) |
| Peptide 393 | H₃C(O)C-Lys-Gln-Lys-Leu-Glu-Glu-Leu-Leu-Glu-Arg-Phe-Leu-Asp-Leu-Val-Pip-NH₂ (SEQ. ID. NO. 393) |
| Peptide 394 | H₃C(O)C-Lys-Gln-Lys-Leu-Lys-Glu-Leu-Leu-Glu-Arg-Phe-Leu-Asp-Leu-Val-Pip-NH₂ (SEQ. ID. NO. 394) |
| Peptide 395 | H₃C(O)C-Lys-Gln-Leu-Lys-Glu-Leu-Leu-Glu-Arg-Phe-Leu-Asp-Leu-Val-Pip-NH₂ (SEQ. ID. NO. 395) |
| Peptide 396 | H₃C(O)C-Lys-Gln-Lys-Leu-Ala-Glu-Leu-Leu-Glu-Arg-Phe-Leu-Asp-Leu-Val-Pip-NH₂ (SEQ. ID. NO. 396) |
| Peptide 397 | H₃C(O)C-Lys-Gln-Lys-Leu-Glu-Asn-Leu-Leu-Glu-Arg-Phe-Leu-Asp-Leu-Val-Pip-NH₂ (SEQ. ID. NO. 397) |
| Peptide 460 | H₃C(O)C-Lys-Leu-Lys-Gln-Lys-Leu-Ala-Glu-Leu-Gly-Glu-Asn-Leu-Leu-Glu-Arg-Phe-Leu-Asp-Leu-Val-azPip-NH₂ (SEQ. ID. NO. 460) |
| Peptide 461 | H₃C(O)C-Lys-Leu-Lys-Gln-Lys-Leu-Glu-Glu-Leu-Leu-Glu-Arg-Leu-Leu-Asp-Leu-Val-azPip-NH₂ (SEQ. ID. NO. 461) |
| Peptide 462 | H₃C(O)C-Lys-Leu-Lys-Gln-Lys-Leu-Glu-Leu-Leu-Glu-Lys-Phe-Leu-Asp-Leu-Val-azPip-NH₂ (SEQ. ID. NO. 462) |
| Peptide 463 | H₃C(O)C-Lys-Leu-Lys-Gln-Lys-Leu-Glu-Glu-Leu-Leu-Glu-Arg-Phe-Leu-Asp-Leu-Val-azPip-NH₂ (SEQ. ID. NO. 463) |
| Peptide 464 | H₃C(O)C-Lys-Leu-Lys-Gln-Lys-Leu-Glu-Glu-Leu-Leu-Glu-Arg-Phe-Leu-Glu-Leu-Val-azPip-NH₂ (SEQ. ID. NO. 464) |
| Peptide 465 | H₃C(O)C-Lys-Leu-Lys-Gln-Lys-Leu-Glu-Glu-Leu-Leu-Glu-Lys-Phe-Leu-Glu-Leu-Val-azPip-NH₂ (SEQ. ID. NO. 465) |
| Peptide 466 | H₃C(O)C-Lys-Leu-Lys-Asn-Lys-Leu-Glu-Glu-Leu-Leu-Glu-Arg-Phe-Leu-Asp-Leu-Val-azPip-NH₂ (SEQ. ID. NO. 466) |
| Peptide 467 | H₃C(O)C-Lys-Leu-Lys-Gln-Lys-Leu-Glu-Glu-Leu-Leu-Glu-Arg-Phe-Leu-Asp-Leu-Leu-azPip-NH₂ (SEQ. ID. NO. 467) |
| Peptide 468 | H₃C(O)C-Lys-Leu-Lys-Gln-Lys-Leu-Glu-Glu-Trp-Leu-Glu-Arg-Phe-Leu-Asp-Leu-Val-azPip-NH₂ (SEQ. ID. NO. 468) |
| Peptide 469 | H₃C(O)C-Lys-Leu-Lys-Gln-Lys-Leu-Glu-Glu-Leu-Leu-Glu-Lys-Phe-Leu-Asp-Leu-Leu-azPip-NH₂ (SEQ. ID. NO. 469) |
| Peptide 470 | H₃C(O)C-Arg-Leu-Lys-Gln-Arg-Leu-Glu-Glu-Leu-Leu-Asp-Lys-Phe-Leu-Glu-Leu-Ala-azPip-NH₂ (SEQ. ID. NO. 470) |
| Peptide 471 | H₃C(O)C-Lys-Leu-Lys-Gln-Lys-Leu-Glu-Glu-Leu-Leu-Glu-Arg-Phe-Asp-Leu-Val-azPip-NH₂ (SEQ. ID. NO. 471) |
| Peptide 472 | H₃C(O)C-Lys-Leu-Lys-Gln-Lys-Leu-Glu-Glu-Leu-Leu-Glu-Lys-Leu-Leu-Glu-Leu-Leu-azPip-NH₂ (SEQ. ID. NO. 472) |
| Peptide 473 | H₃C(O)C-Lys-Leu-Lys-Gln-Lys-Leu-Glu-Glu-Leu-Leu-Glu-Lys-Leu-Leu-Glu-Leu-Val-azPip-NH₂ (SEQ. ID. NO. 473) |
| Peptide 474 | H₃C(O)C-Lys-Leu-Arg-Gln-Arg-Leu-Glu-Glu-Leu-Leu-Asp-Lys-Phe-Leu-Glu-Leu-Ala-azPip-NH₂ (SEQ. ID. NO. 474) |
| Peptide 475 | H₃C(O)C-Orn-Leu-Orn-Gln-Orn-Leu-Glu-Glu-Leu-Leu-Glu-Arg-Phe-Leu-Asp-Leu-Val-azPip-NH₂ (SEQ. ID. NO. 475) |
| Peptide 476 | H₃C(O)C-Lys-Leu-Orn-Gln-Orn-Leu-Glu-Glu-Leu-Leu-Glu-Orn-Phe-Leu-Asp-Leu-Val-azPip-NH₂ (SEQ. ID. NO. 476) |
| Peptide 477 | H₃C(O)C-Lys-Leu-Arg-Gln-Arg-Phe-Glu-Glu-Leu-Leu-Asp-Lys-Phe-Leu-Glu-Leu-Ala-azPip-NH₂ (SEQ. ID. NO. 477) |
| Peptide 478 | H₃C(O)C-Lys-Leu-Lys-Gln-Lys-Trp-Glu-Glu-Leu-Leu-Glu-Arg-Phe-Leu-Asp-Leu-Val-azPip-NH₂ (SEQ. ID. NO. 478) |
| Peptide 479 | H₃C(O)C-Lys-Leu-Lys-Gln-Leu-Leu-Glu-Asn-Leu-Leu-Glu-Arg-Phe-Leu-Asp-Leu-Val-azPip-NH₂ (SEQ. ID. NO. 479) |
| Peptide 480 | H₃C(O)C-Lys-Leu-Lys-Gln-Lys-Leu-Glu-Glu-Gly-Leu-Glu-Arg-Phe-Leu-Asp-Leu-Val-azPip-NH₂ (SEQ. ID. NO. 480) |
| Peptide 481 | H₃C(O)C-Lys-Leu-Lys-Gln-Lys-Leu-Glu-Glu-Leu-Gly-Glu-Arg-Phe-Leu-Asp-Leu-Val-azPip-NH₂ (SEQ. ID. NO. 481) |
| Peptide 482 | H₃C(O)C-Lys-Leu-Lys-Gln-Lys-Gly-Glu-Glu-Leu-Leu-Glu-Arg-Phe-Leu-Asp-Leu-Val-azPip-NH₂ (SEQ. ID. NO. 482) |
| Peptide 483 | H₃C(O)C-Lys-Leu-Lys-Gln-Lys-Leu-Glu-Glu-Leu-Leu-Glu-Lys-Phe-Leu-Glu-Leu-Leu-azPip-NH₂ (SEQ. ID. NO. 483) |
| Peptide 484 | H₃C(O)C-Lys-Leu-Lys-Gln-Glu-Leu-Leu-Glu-Arg-Phe-Leu-Asp-Leu-Val-azPip-NH₂ (SEQ. ID. NO. 484) |

TABLE 8-continued

| | |
|---|---|
| Peptide 485 | H₃C(O)C-Lys-Gln-Lys-Leu-Glu-Glu-Leu-Leu-Glu-Arg-Phe-Leu-Asp-Leu-Val-azPip-NH₂ (SEQ. ID. NO. 485) |
| Peptide 486 | H₃C(O)C-Lys-Gln-Lys-Leu-Lys-Leu-Leu-Glu-Arg-Phe-Leu-Asp-Leu-Val-azPip-NH₂ (SEQ. ID. NO. 496) |
| Peptide 487 | H₃C(O)C-Lys-Gln-Leu-Lys-Glu-Leu-Leu-Glu-Arg-Phe-Leu-Asp-Leu-Val-azPip-NH₂ (SEQ. ID. NO. 487) |
| Peptide 488 | H₃C(O)C-Lys-Gln-Lys-Leu-Ala-Glu-Leu-Leu-Glu-Arg-Phe-Leu-Asp-Leu-Val-azPip-NH₂ (SEQ. ID. NO. 488) |
| Peptide 489 | H₃C(O)C-Lys-Gln-Lys-Leu-Glu-Asn-Leu-Leu-Glu-Arg-Phe-Leu-Asp-Leu-Val-azPip-NH₂ (SEQ. ID. NO. 489) | or a pharmaceutically acceptable salt thereof

TABLE 9

| | |
|---|---|
| Peptide 65 | H₃C(O)C-Lys-Leu-Lys-Gln-Lys-Leu-Glu-Glu-Leu-Leu-Glu-Arg-Leu-Leu-Asp-Leu-Val-Inp-NH₂ (SEQ. ID. NO. 65) |
| Peptide 66 | H₃C(O)C-Lys-Leu-Lys-Gln-Lys-Leu-Glu-Glu-Leu-Leu-Glu-Lys-Phe-Leu-Asp-Leu-Val-Inp-NH₂ (SEQ. ID. NO. 66) |
| Peptide 67 | H₃C(O)C-Lys-Leu-Lys-Gln-Lys-Leu-Glu-Glu-Leu-Leu-Glu-Glu-Arg-Phe-Leu-Asp-Leu-Val-Inp-NH₂ (SEQ. ID. NO. 67) |
| Peptide 68 | H₃C(O)C-Lys-Leu-Lys-Gln-Lys-Leu-Glu-Glu-Leu-Leu-Glu-Arg-Phe-Leu-Glu-Leu-Val-Inp-NH₂ (SEQ. ID. NO. 68) |
| Peptide 69 | H₃C(O)C-Lys-Leu-Lys-Gln-Lys-Leu-Glu-Glu-Leu-Leu-Glu-Lys-Phe-Leu-Glu-Leu-Val-Inp-NH₂ (SEQ. ID. NO. 69) |
| Peptide 70 | H₃C(O)C-Lys-Leu-Lys-Asn-Lys-Leu-Glu-Glu-Leu-Leu-Glu-Arg-Phe-Leu-Asp-Leu-Val-Inp-NH₂ (SEQ. ID. NO. 70) |
| Peptide 71 | H₃C(O)C-Lys-Leu-Lys-Gln-Lys-Leu-Glu-Glu-Leu-Leu-Glu-Arg-Phe-Leu-Asp-Leu-Leu-Inp-NH₂ (SEQ. ID. NO. 71) |
| Peptide 72 | H₃C(O)C-Lys-Leu-Lys-Gln-Lys-Leu-Glu-Glu-Leu-Trp-Glu-Arg-Phe-Leu-Asp-Leu-Val-Inp-NH₂ (SEQ. ID. NO. 72) |
| Peptide 73 | H₃C(O)C-Lys-Leu-Lys-Gln-Lys-Leu-Glu-Glu-Leu-Leu-Glu-Lys-Phe-Leu-Asp-Leu-Leu-Inp-NH₂ (SEQ. ID. NO. 73) |
| Peptide 74 | H₃C(O)C-Arg-Leu-Lys-Gln-Arg-Leu-Glu-Glu-Leu-Leu-Asp-Lys-Phe-Leu-Glu-Leu-Ala-Inp-NH₂ (SEQ. ID. NO. 74) |
| Peptide 75 | H₃C(O)C-Lys-Leu-Lys-Gln-Lys-Leu-Glu-Glu-Leu-Leu-Glu-Arg-Phe-Phe-Asp-Leu-Val-Inp-NH₂ (SEQ. ID. NO. 75) |

TABLE 9-continued

| | |
|---|---|
| Peptide 76 | H₃C(O)C-Lys-Leu-Lys-Gln-Lys-Leu-Glu-Glu-Leu-Trp-Glu-Arg-Phe-Leu-Asp-Leu-Val-Inp-NH₂ (SEQ. ID. NO. 76) |
| Peptide 77 | H₃C(O)C-Lys-Leu-Lys-Gln-Lys-Leu-Glu-Glu-Leu-Leu-Glu-Lys-Leu-Leu-Glu-Leu-Inp-NH₂ (SEQ. ID. NO. 77) |
| Peptide 78 | H₃C(O)C-Lys-Leu-Lys-Gln-Lys-Leu-Glu-Glu-Leu-Leu-Glu-Lys-Leu-Leu-Glu-Leu-Val-Inp-NH₂ (SEQ. ID. NO. 78) |
| Peptide 79 | H₃C(O)C-Lys-Leu-Arg-Gln-Arg-Leu-Glu-Glu-Leu-Leu-Asp-Lys-Phe-Leu-Glu-Leu-Ala-Inp-NH₂ (SEQ. ID. NO. 79) |
| Peptide 80 | H₃C(O)C-Orn-Leu-Orn-Gln-Orn-Leu-Glu-Glu-Leu-Leu-Glu-Arg-Phe-Leu-Asp-Leu-Val-Inp-NH₂ (SEQ. ID. NO. 80) |
| Peptide 81 | H₃C(O)C-Lys-Leu-Orn-Gln-Orn-Leu-Glu-Glu-Leu-Leu-Glu-Orn-Phe-Leu-Asp-Leu-Val-Inp-NH₂ (SEQ. ID. NO. 81) |
| Peptide 82 | H₃C(O)C-Lys-Leu-Arg-Gln-Arg-Phe-Glu-Glu-Leu-Leu-Asp-Lys-Phe-Leu-Glu-Leu-Ala-Inp-NH₂ (SEQ. ID. NO. 82) |
| Peptide 83 | H₃C(O)C-Lys-Leu-Lys-Gln-Lys-Trp-Glu-Glu-Leu-Leu-Glu-Arg-Phe-Leu-Asp-Leu-Val-Inp-NH₂ (SEQ. ID. NO. 83) |
| Peptide 84 | H₃C(O)C-Lys-Leu-Lys-Gln-Leu-Leu-Glu-Asn-Leu-Leu-Glu-Arg-Phe-Leu-Asp-Leu-Val-Inp-NH₂ (SEQ. ID. NO. 84) |
| Peptide 87 | H₃C(O)C-Lys-Leu-Lys-Gln-Lys-Leu-Glu-Glu-Leu-Leu-Glu-Lys-Phe-Leu-Glu-Leu-Leu-Inp-NH₂ (SEQ. ID. NO. 87) |
| Peptide 88 | H₃C(O)C-Lys-Leu-Lys-Gln-Glu-Leu-Leu-Glu-Arg-Phe-Leu-Asp-Leu-Val-Inp-NH₂ (SEQ. ID. NO. 88) |
| Peptide 89 | H₃C(O)C-Lys-Gln-Lys-Leu-Glu-Glu-Leu-Leu-Glu-Arg-Phe-Leu-Asp-Leu-Val-Inp-NH₂ (SEQ. ID. NO. 89) |
| Peptide 90 | H₃C(O)C-Lys-Gln-Lys-Leu-Lys-Glu-Leu-Leu-Glu-Arg-Phe-Leu-Asp-Leu-Val-Inp-NH₂ (SEQ. ID. NO. 90) |
| Peptide 91 | H₃C(O)C-Lys-Gln-Leu-Lys-Glu-Leu-Leu-Glu-Arg-Phe-Leu-Asp-Leu-Val-Inp-NH₂ (SEQ. ID. NO. 91) |
| Peptide 93 | H₃C(O)C-Lys-Gln-Lys-Leu-Glu-Asn-Leu-Leu-Glu-Arg-Phe-Leu-Asp-Leu-Val-Inp-NH₂ (SEQ. ID. NO. 93) |
| Peptide 157 | H₃C(O)C-Lys-Leu-Lys-Gln-Lys-Leu-Glu-Glu-Leu-Leu-Glu-Arg-Leu-Leu-Asp-Leu-Val-Nip-NH₂ (SEQ. ID. NO. 157) |
| Peptide 158 | H₃C(O)C-Lys-Leu-Lys-Gln-Lys-Leu-Glu-Glu-Leu-Leu-Glu-Lys-Phe-Leu-Asp-Leu-Val-Nip-NH₂ (SEQ. ID. NO. 158) |

TABLE 9-continued

| Peptide 159 | H₃C(O)C-Lys-Leu-Lys-Gln-Lys-Leu-Glu-Glu-Leu-Leu-Glu-Arg-Phe-Leu-Asp-Leu-Val-Nip-NH₂ (SEQ. ID. NO. 159) |
| Peptide 160 | H₃C(O)C-Lys-Leu-Lys-Gln-Lys-Leu-Glu-Glu-Leu-Leu-Glu-Arg-Phe-Leu-Glu-Leu-Val-Nip-NH₂ (SEQ. ID. NO. 160) |
| Peptide 161 | H₃C(O)C-Lys-Leu-Lys-Gln-Lys-Leu-Glu-Glu-Leu-Leu-Glu-Lys-Phe-Leu-Glu-Leu-Val-Nip-NH₂ (SEQ. ID. NO. 161) |
| Peptide 162 | H₃C(O)C-Lys-Leu-Lys-Asn-Lys-Leu-Glu-Glu-Leu-Leu-Glu-Arg-Phe-Leu-Asp-Leu-Val-Nip-NH₂ (SEQ. ID. NO. 162) |
| Peptide 163 | H₃C(O)C-Lys-Leu-Lys-Gln-Lys-Leu-Glu-Glu-Leu-Leu-Glu-Arg-Phe-Leu-Asp-Leu-Leu-Nip-NH₂ (SEQ. ID. NO. 163) |
| Peptide 164 | H₃C(O)C-Lys-Leu-Lys-Gln-Lys-Leu-Glu-Glu-Trp-Leu-Glu-Arg-Phe-Leu-Asp-Leu-Val-Nip-NH₂ (SEQ. ID. NO. 164) |
| Peptide 165 | H₃C(O)C-Lys-Leu-Lys-Gln-Lys-Leu-Glu-Glu-Leu-Leu-Glu-Lys-Phe-Leu-Asp-Leu-Leu-Nip-NH₂ (SEQ. ID. NO. 165) |
| Peptide 166 | H₃C(O)C-Arg-Leu-Lys-Gln-Arg-Leu-Glu-Glu-Leu-Leu-Asp-Lys-Phe-Leu-Glu-Leu-Ala-Nip-NH₂ (SEQ. ID. NO. 166) |
| Peptide 167 | H₃C(O)C-Lys-Leu-Lys-Gln-Lys-Leu-Glu-Glu-Leu-Leu-Glu-Arg-Phe-Phe-Asp-Leu-Val-Nip-NH₂ (SEQ. ID. NO. 167) |
| Peptide 168 | H₃C(O)C-Lys-Leu-Lys-Gln-Lys-Leu-Glu-Glu-Leu-Leu-Glu-Lys-Leu-Leu-Glu-Leu-Leu-Nip-NH₂ (SEQ. ID. NO. 168) |
| Peptide 169 | H₃C(O)C-Lys-Leu-Lys-Gln-Lys-Leu-Glu-Glu-Leu-Leu-Glu-Lys-Leu-Leu-Leu-Val-Nip-NH₂ (SEQ. ID. NO. 169) |
| Peptide 170 | H₃C(O)C-Lys-Leu-Arg-Gln-Arg-Leu-Glu-Glu-Leu-Leu-Asp-Lys-Phe-Leu-Glu-Leu-Ala-Nip-NH₂ (SEQ. ID. NO. 170) |
| Peptide 171 | H₃C(O)C-Orn-Leu-Orn-Gln-Orn-Leu-Glu-Glu-Leu-Leu-Glu-Arg-Phe-Leu-Asp-Leu-Val-Nip-NH₂ (SEQ. ID. NO. 171) |
| Peptide 172 | H₃C(O)C-Lys-Leu-Orn-Gln-Orn-Leu-Glu-Glu-Leu-Leu-Glu-Orn-Phe-Leu-Asp-Leu-Val-Nip-NH₂ (SEQ. ID. NO. 172) |
| Peptide 173 | H₃C(O)C-Lys-Leu-Arg-Gln-Arg-Phe-Glu-Glu-Leu-Leu-Asp-Lys-Phe-Leu-Glu-Leu-Ala-Nip-NH₂ (SEQ. ID. NO. 173) |
| Peptide 174 | H₃C(O)C-Lys-Leu-Lys-Gln-Lys-Trp-Glu-Glu-Leu-Leu-Glu-Arg-Phe-Leu-Asp-Leu-Val-Nip-NH₂ (SEQ. ID. NO. 174) |
| Peptide 175 | H₃C(O)C-Lys-Leu-Lys-Gln-Leu-Leu-Glu-Asn-Leu-Leu-Glu-Arg-Phe-Leu-Asp-Leu-Val-Nip-NH₂ (SEQ. ID. NO. 175) |
| Peptide 176 | H₃C(O)C-Lys-Leu-Lys-Gln-Lys-Leu-Glu-Glu-Gly-Leu-Glu-Arg-Phe-Leu-Asp-Leu-Val-Nip-NH₂ (SEQ. ID. NO. 176) |
| Peptide 179 | H₃C(O)C-Lys-Leu-Lys-Gln-Lys-Leu-Glu-Glu-Leu-Leu-Glu-Lys-Phe-Leu-Glu-Leu-Leu-Nip-NH₂ (SEQ. ID. NO. 179) |
| Peptide 180 | H₃C(O)C-Lys-Leu-Lys-Gln-Glu-Leu-Leu-Glu-Arg-Phe-Leu-Asp-Leu-Val-Nip-NH₂ (SEQ. ID. NO. 180) |
| Peptide 181 | H₃C(O)C-Lys-Gln-Lys-Leu-Glu-Glu-Leu-Leu-Glu-Arg-Phe-Leu-Asp-Leu-Val-Nip-NH₂ (SEQ. ID. NO. 181) |
| Peptide 182 | H₃C(O)C-Lys-Gln-Lys-Leu-Lys-Glu-Leu-Leu-Glu-Arg-Phe-Leu-Asp-Leu-Val-Nip-NH₂ (SEQ. ID. NO. 182) |
| Peptide 183 | H₃C(O)C-Lys-Gln-Leu-Lys-Glu-Leu-Leu-Glu-Arg-Phe-Leu-Asp-Leu-Val-Nip-NH₂ (SEQ. ID. NO. 183) |
| Peptide 185 | H₃C(O)C-Lys-Gln-Lys-Leu-Glu-Asn-Leu-Leu-Glu-Arg-Phe-Leu-Asp-Leu-Val-Nip-NH₂ (SEQ. ID. NO. 185) |
| Peptide 277 | H₃C(O)C-Lys-Leu-Lys-Gln-Lys-Leu-Glu-Glu-Leu-Leu-Glu-Arg-Phe-Leu-Asp-Leu-Val-azPro-NH₂ (SEQ. ID. NO. 277) |
| Peptide 278 | H₃C(O)C-Lys-Leu-Lys-Gln-Lys-Leu-Glu-Glu-Leu-Leu-Glu-Lys-Phe-Leu-Asp-Leu-Val-azPro-NH₂ (SEQ. ID. NO. 278) |
| Peptide 279 | H₃C(O)C-Lys-Leu-Lys-Gln-Lys-Leu-Glu-Glu-Leu-Leu-Glu-Arg-Phe-Leu-Asp-Leu-Val-azPro-NH₂ (SEQ. ID. NO. 279) |
| Peptide 280 | H₃C(O)C-Lys-Leu-Lys-Gln-Lys-Leu-Glu-Glu-Leu-Leu-Glu-Arg-Phe-Leu-Glu-Leu-Val-azPro-NH₂ (SEQ. ID. NO. 280) |
| Peptide 281 | H₃C(O)C-Lys-Leu-Lys-Gln-Lys-Leu-Glu-Glu-Leu-Leu-Glu-Lys-Phe-Leu-Glu-Leu-Val-azPro-NH₂ (SEQ. ID. NO. 281) |
| Peptide 282 | H₃C(O)C-Lys-Leu-Lys-Asn-Lys-Leu-Glu-Glu-Leu-Leu-Glu-Arg-Phe-Leu-Asp-Leu-Val-azPro-NH₂ (SEQ. ID. NO. 282) |
| Peptide 283 | H₃C(O)C-Lys-Leu-Lys-Gln-Lys-Leu-Glu-Glu-Leu-Leu-Glu-Arg-Phe-Leu-Asp-Leu-Val-azPro-NH₂ (SEQ. ID. NO. 283) |
| Peptide 284 | H₃C(O)C-Lys-Leu-Lys-Gln-Lys-Leu-Glu-Glu-Trp-Leu-Glu-Arg-Phe-Leu-Asp-Leu-Val-azPro-NH₂ (SEQ. ID. NO. 284) |
| Peptide 285 | H₃C(O)C-Lys-Leu-Lys-Gln-Lys-Leu-Glu-Glu-Leu-Leu-Glu-Lys-Phe-Leu-Asp-Leu-Leu-azPro-NH₂ (SEQ. ID. NO. 285) |

TABLE 9-continued

| Peptide 286 | H₃C(O)C-Arg-Leu-Lys-Gln-Arg-Leu-Glu-Glu-Leu-Leu-Asp-Lys-Phe-Leu-Glu-Leu-Ala-azPro-NH₂ (SEQ. ID. NO. 286) |
| Peptide 287 | H₃C(O)C-Lys-Leu-Lys-Gln-Lys-Leu-Glu-Glu-Leu-Leu-Glu-Arg-Phe-Phe-Asp-Leu-Val-azPro-NH₂ (SEQ. ID. NO. 287) |
| Peptide 288 | H₃C(O)C-Lys-Leu-Lys-Gln-Lys-Leu-Glu-Glu-Leu-Leu-Glu-Lys-Leu-Leu-Glu-Leu-Leu-azPro-NH₂ (SEQ. ID. NO. 288) |
| Peptide 289 | H₃C(O)C-Lys-Leu-Lys-Gln-Lys-Leu-Glu-Glu-Leu-Leu-Glu-Lys-Leu-Leu-Glu-Leu-Val-azPro-NH₂ (SEQ. ID. NO. 289) |
| Peptide 290 | H₃C(O)C-Lys-Leu-Arg-Gln-Arg-Leu-Glu-Glu-Leu-Leu-Asp-Lys-Phe-Leu-Glu-Leu-Ala-azPro-NH₂ (SEQ. ID. NO. 290) |
| Peptide 291 | H₃C(O)C-Orn-Leu-Orn-Gln-Orn-Leu-Glu-Glu-Leu-Leu-Glu-Arg-Phe-Leu-Asp-Leu-Val-azPro-NH₂ (SEQ. ID. NO. 291) |
| Peptide 292 | H₃C(O)C-Lys-Leu-Orn-Gln-Orn-Leu-Glu-Glu-Leu-Leu-Glu-Orn-Phe-Leu-Asp-Leu-Val-azPro-NH₂ (SEQ. ID. NO. 292) |
| Peptide 293 | H₃C(O)C-Lys-Leu-Arg-Gln-Arg-Phe-Glu-Glu-Leu-Leu-Asp-Lys-Phe-Leu-Glu-Leu-Ala-azPro-NH₂ (SEQ. ID. NO. 293) |
| Peptide 294 | H₃C(O)C-Lys-Leu-Lys-Gln-Lys-Trp-Glu-Glu-Leu-Leu-Glu-Arg-Phe-Leu-Asp-Leu-Val-azPro-NH₂ (SEQ. ID. NO. 294) |
| Peptide 295 | H₃C(O)C-Lys-Leu-Lys-Gln-Leu-Leu-Glu-Asn-Leu-Leu-Glu-Arg-Phe-Leu-Asp-Leu-Val-azPro-NH₂ (SEQ. ID. NO. 295) |
| Peptide 296 | H₃C(O)C-Lys-Leu-Lys-Gln-Lys-Leu-Glu-Glu-Gly-Leu-Glu-Arg-Phe-Leu-Asp-Leu-Val-azPro-NH₂ (SEQ. ID. NO. 296) |
| Peptide 299 | H₃C(O)C-Lys-Leu-Lys-Gln-Lys-Leu-Glu-Glu-Leu-Leu-Glu-Lys-Phe-Leu-Glu-Leu-Leu-azPro-NH₂ (SEQ. ID. NO. 299) |
| Peptide 300 | H₃C(O)C-Lys-Leu-Lys-Gln-Glu-Leu-Leu-Glu-Arg-Phe-Leu-Asp-Leu-Val-azPro-NH₂ (SEQ. ID. NO. 300) |
| Peptide 301 | H₃C(O)C-Lys-Gln-Lys-Leu-Glu-Glu-Leu-Leu-Glu-Arg-Phe-Leu-Asp-Leu-Val-azPro-NH₂ (SEQ. ID. NO. 301) |
| Peptide 302 | H₃C(O)C-Lys-Gln-Lys-Leu-Lys-Glu-Leu-Leu-Glu-Arg-Phe-Leu-Asp-Leu-Val-azPro-NH₂ (SEQ. ID. NO. 302) |
| Peptide 303 | H₃C(O)C-Lys-Gln-Leu-Lys-Glu-Leu-Leu-Glu-Arg-Phe-Leu-Asp-Leu-Val-azPro-NH₂ (SEQ. ID. NO. 303) |
| Peptide 305 | H₃C(O)C-Lys-Gln-Lys-Leu-Glu-Asn-Leu-Leu-Glu-Arg-Phe-Leu-Asp-Leu-Val-azPro-NH₂ (SEQ. ID. NO. 305) |

TABLE 9-continued

| Peptide 369 | H₃C(O)C-Lys-Leu-Lys-Gln-Lys-Leu-Glu-Glu-Leu-Leu-Glu-Arg-Leu-Leu-Asp-Leu-Val-Pip-NH₂ (SEQ. ID. NO. 369) |
| Peptide 370 | H₃C(O)C-Lys-Leu-Lys-Gln-Lys-Leu-Glu-Glu-Leu-Leu-Glu-Lys-Phe-Leu-Asp-Leu-Val-Pip-NH₂ (SEQ. ID. NO. 370) |
| Peptide 371 | H₃C(O)C-Lys-Leu-Lys-Gln-Lys-Leu-Glu-Glu-Leu-Leu-Glu-Arg-Phe-Leu-Asp-Leu-Val-Pip-NH₂ (SEQ. ID. NO. 371) |
| Peptide 372 | H₃C(O)C-Lys-Leu-Lys-Gln-Lys-Leu-Glu-Glu-Leu-Leu-Glu-Arg-Phe-Leu-Glu-Leu-Val-Pip-NH₂ (SEQ. ID. NO. 372) |
| Peptide 373 | H₃C(O)C-Lys-Leu-Lys-Gln-Lys-Leu-Glu-Glu-Leu-Leu-Glu-Lys-Phe-Leu-Glu-Leu-Val-Pip-NH₂ (SEQ. ID. NO. 373) |
| Peptide 374 | H₃C(O)C-Lys-Leu-Lys-Asn-Lys-Leu-Glu-Glu-Leu-Leu-Glu-Arg-Phe-Leu-Asp-Leu-Val-Pip-NH₂ (SEQ. ID. NO. 374) |
| Peptide 375 | H₃C(O)C-Lys-Leu-Lys-Gln-Lys-Leu-Glu-Glu-Leu-Leu-Glu-Arg-Leu-Leu-Asp-Leu-Val-Pip-NH₂ (SEQ. ID. NO. 375) |
| Peptide 376 | H₃C(O)C-Lys-Leu-Lys-Gln-Lys-Leu-Glu-Glu-Trp-Leu-Glu-Arg-Phe-Leu-Asp-Leu-Val-Pip-NH₂ (SEQ. ID. NO. 376) |
| Peptide 377 | H₃C(O)C-Lys-Leu-Lys-Gln-Lys-Leu-Glu-Glu-Leu-Leu-Glu-Lys-Phe-Leu-Asp-Leu-Leu-Pip-NH₂ (SEQ. ID. NO. 377) |
| Peptide 378 | H₃C(O)C-Arg-Leu-Lys-Gln-Arg-Leu-Glu-Glu-Leu-Leu-Asp-Lys-Phe-Leu-Glu-Leu-Ala-Pip-NH₂ (SEQ. ID. NO. 378) |
| Peptide 379 | H₃C(O)C-Lys-Leu-Lys-Gln-Lys-Leu-Glu-Glu-Leu-Leu-Glu-Arg-Phe-Asp-Leu-Val-Pip-NH₂ (SEQ. ID. NO. 379) |
| Peptide 380 | H₃C(O)C-Lys-Leu-Lys-Gln-Lys-Leu-Glu-Glu-Leu-Leu-Glu-Lys-Leu-Leu-Glu-Leu-Leu-Pip-NH₂ (SEQ. ID. NO. 380) |
| Peptide 381 | H₃C(O)C-Lys-Leu-Lys-Gln-Lys-Leu-Glu-Glu-Leu-Leu-Glu-Lys-Leu-Leu-Glu-Leu-Val-Pip-NH₂ (SEQ. ID. NO. 381) |
| Peptide 382 | H₃C(O)C-Lys-Leu-Arg-Gln-Arg-Leu-Glu-Glu-Leu-Leu-Asp-Lys-Phe-Leu-Glu-Leu-Ala-Pip-NH₂ (SEQ. ID. NO. 382) |
| Peptide 383 | H₃C(O)C-Orn-Leu-Orn-Gln-Orn-Leu-Glu-Glu-Leu-Leu-Glu-Arg-Phe-Leu-Asp-Leu-Val-Pip-NH₂ (SEQ. ID. NO. 383) |
| Peptide 384 | H₃C(O)C-Lys-Leu-Orn-Gln-Orn-Leu-Glu-Glu-Leu-Leu-Glu-Orn-Phe-Leu-Asp-Leu-Val-Pip-NH₂ (SEQ. ID. NO. 384) |

TABLE 9-continued

| | |
|---|---|
| Peptide 385 | H₃C(O)C-Lys-Leu-Arg-Gln-Arg-Phe-Glu-Glu-Leu-Leu-Asp-Lys-Phe-Leu-Glu-Leu-Ala-Pip-NH₂ (SEQ. ID. NO. 385) |
| Peptide 386 | H₃C(O)C-Lys-Leu-Lys-Gln-Lys-Trp-Glu-Glu-Leu-Leu-Glu-Arg-Phe-Leu-Asp-Leu-Val-Pip-NH₂ (SEQ. ID. NO. 386) |
| Peptide 387 | H₃C(O)C-Lys-Leu-Lys-Gln-Leu-Leu-Glu-Asn-Leu-Leu-Glu-Arg-Phe-Leu-Asp-Leu-Val-Pip-NH₂ (SEQ. ID. NO. 387) |
| Peptide 388 | H₃C(O)C-Lys-Leu-Lys-Gln-Lys-Leu-Glu-Glu-Gly-Leu-Glu-Arg-Phe-Leu-Asp-Leu-Val-Pip-NH₂ (SEQ. ID. NO. 388) |
| Peptide 391 | H₃C(O)C-Lys-Leu-Lys-Gln-Lys-Leu-Glu-Glu-Leu-Leu-Glu-Lys-Phe-Leu-Glu-Leu-Leu-Pip-NH₂ (SEQ. ID. NO. 391) |
| Peptide 392 | H₃C(O)C-Lys-Leu-Lys-Gln-Glu-Leu-Leu-Glu-Arg-Phe-Leu-Asp-Leu-Val-Pip-NH₂ (SEQ. ID. NO. 392) |
| Peptide 393 | H₃C(O)C-Lys-Gln-Lys-Leu-Glu-Glu-Leu-Leu-Glu-Arg-Phe-Leu-Asp-Leu-Val-Pip-NH₂ (SEQ. ID. NO. 393) |
| Peptide 394 | H₃C(O)C-Lys-Gln-Lys-Leu-Lys-Glu-Leu-Leu-Glu-Arg-Phe-Leu-Asp-Leu-Val-Pip-NH₂ (SEQ. ID. NO. 394) |
| Peptide 395 | H₃C(O)C-Lys-Gln-Leu-Lys-Glu-Leu-Leu-Glu-Arg-Phe-Leu-Asp-Leu-Val-Pip-NH₂ (SEQ. ID. NO. 395) |
| Peptide 397 | H₃C(O)C-Lys-Gln-Lys-Leu-Glu-Asn-Leu-Leu-Glu-Arg-Phe-Leu-Asp-Leu-Val-Pip-NH₂ (SEQ. ID. NO. 397) |
| Peptide 461 | H₃C(O)C-Lys-Leu-Lys-Gln-Lys-Leu-Glu-Glu-Leu-Leu-Glu-Arg-Leu-Leu-Asp-Leu-Val-azPip-NH₂ (SEQ. ID. NO. 461) |
| Peptide 462 | H₃C(O)C-Lys-Leu-Lys-Gln-Lys-Leu-Glu-Glu-Leu-Leu-Glu-Lys-Phe-Leu-Asp-Leu-Val-azPip-NH₂ (SEQ. ID. NO. 462) |
| Peptide 463 | H₃C(O)C-Lys-Leu-Lys-Gln-Lys-Leu-Glu-Glu-Leu-Leu-Glu-Arg-Phe-Leu-Asp-Leu-Val-azPip-NH₂ (SEQ. ID. NO. 463) |
| Peptide 464 | H₃C(O)C-Lys-Leu-Lys-Gln-Lys-Leu-Glu-Leu-Leu-Glu-Lys-Phe-Leu-Asp-Leu-Val-azPip-NH₂ (SEQ. ID. NO. 464) |
| Peptide 465 | H₃C(O)C-Lys-Leu-Lys-Gln-Lys-Leu-Glu-Glu-Leu-Leu-Glu-Lys-Phe-Leu-Glu-Leu-Val-azPip-NH₂ (SEQ. ID. NO. 465) |
| Peptide 466 | H₃C(O)C-Lys-Leu-Lys-Asn-Lys-Leu-Glu-Glu-Leu-Leu-Glu-Arg-Phe-Leu-Asp-Leu-Val-azPip-NH₂ (SEQ. ID. NO. 466) |
| Peptide 467 | H₃C(O)C-Lys-Leu-Lys-Gln-Lys-Leu-Glu-Glu-Leu-Leu-Glu-Arg-Phe-Leu-Asp-Leu-Leu-azPip-NH₂ (SEQ. ID. NO. 467) |
| Peptide 468 | H₃C(O)C-Lys-Leu-Lys-Gln-Lys-Leu-Glu-Glu-Trp-Leu-Glu-Arg-Phe-Leu-Asp-Leu-Val-azPip-NH₂ (SEQ. ID. NO. 468) |
| Peptide 469 | H₃C(O)C-Lys-Leu-Lys-Gln-Lys-Leu-Glu-Glu-Leu-Leu-Glu-Lys-Phe-Leu-Asp-Leu-Val-azPip-NH₂ (SEQ. ID. NO. 469) |
| Peptide 470 | H₃C(O)C-Arg-Leu-Lys-Gln-Arg-Leu-Glu-Glu-Leu-Leu-Asp-Lys-Phe-Leu-Glu-Leu-Ala-azPip-NH₂ (SEQ. ID. NO. 470) |
| Peptide 471 | H₃C(O)C-Lys-Leu-Lys-Gln-Lys-Leu-Glu-Glu-Leu-Leu-Glu-Arg-Phe-Asp-Leu-Val-azPip-NH₂ (SEQ. ID. NO. 471) |
| Peptide 472 | H₃C(O)C-Lys-Leu-Lys-Gln-Lys-Leu-Glu-Glu-Leu-Leu-Glu-Lys-Leu-Leu-Glu-Leu-Leu-azPip-NH₂ (SEQ. ID. NO. 472) |
| Peptide 473 | H₃C(O)C-Lys-Leu-Lys-Gln-Lys-Leu-Glu-Glu-Leu-Leu-Glu-Lys-Leu-Leu-Glu-Leu-Val-azPip-NH₂ (SEQ. ID. NO. 473) |
| Peptide 474 | H₃C(O)C-Lys-Leu-Arg-Gln-Arg-Leu-Glu-Glu-Leu-Leu-Asp-Lys-Phe-Leu-Glu-Leu-Ala-azPip-NH₂ (SEQ. ID. NO. 474) |
| Peptide 475 | H₃C(O)C-Orn-Leu-Orn-Gln-Orn-Leu-Glu-Glu-Leu-Leu-Glu-Arg-Phe-Leu-Asp-Leu-Val-azPip-NH₂ (SEQ. ID. NO. 475) |
| Peptide 476 | H₃C(O)C-Lys-Leu-Orn-Gln-Orn-Leu-Glu-Glu-Leu-Leu-Glu-Orn-Phe-Leu-Asp-Leu-Val-azPip-NH₂ (SEQ. ID. NO. 476) |
| Peptide 477 | H₃C(O)C-Lys-Leu-Arg-Gln-Arg-Phe-Glu-Glu-Leu-Leu-Asp-Lys-Phe-Leu-Glu-Leu-Ala-azPip-NH₂ (SEQ. ID. NO. 477) |
| Peptide 478 | H₃C(O)C-Lys-Leu-Lys-Gln-Lys-Trp-Glu-Glu-Leu-Leu-Glu-Arg-Phe-Leu-Asp-Leu-Val-azPip-NH₂ (SEQ. ID. NO. 478) |
| Peptide 479 | H₃C(O)C-Lys-Leu-Lys-Gln-Leu-Leu-Glu-Asn-Leu-Leu-Glu-Arg-Phe-Leu-Asp-Leu-Val-azPip-NH₂ (SEQ. ID. NO. 479) |
| Peptide 480 | H₃C(O)C-Lys-Leu-Lys-Gln-Lys-Leu-Glu-Glu-Gly-Leu-Glu-Arg-Phe-Leu-Asp-Leu-Val-azPip-NH₂ (SEQ. ID. NO. 480) |
| Peptide 483 | H₃C(O)C-Lys-Leu-Lys-Gln-Lys-Leu-Glu-Glu-Leu-Leu-Glu-Lys-Phe-Leu-Glu-Leu-Leu-azPip-NH₂ (SEQ. ID. NO. 483) |
| Peptide 484 | H₃C(O)C-Lys-Leu-Lys-Gln-Glu-Leu-Leu-Glu-Arg-Phe-Leu-Asp-Leu-Val-azPip-NH₂ (SEQ. ID. NO. 484) |
| Peptide 385 | H₃C(O)C-Lys-Gln-Lys-Leu-Glu-Glu-Leu-Leu-Glu-Arg-Phe-Leu-Asp-Leu-Val-azPip-NH₂ (SEQ. ID. NO. 485) |

TABLE 9-continued

| Peptide 486 | H₃C(O)C-Lys-Gln-Lys-Leu-Lys-Glu-Leu-Leu-Glu-Arg-Phe-Leu-Asp-Leu-Val-azPip-NH₂ (SEQ. ID. NO. 496) |
| Peptide 487 | H₃C(O)C-Lys-Gln-Leu-Lys-Glu-Leu-Leu-Glu-Arg-Phe-Leu-Asp-Leu-Val-azPip-NH₂ (SEQ. ID. NO. 487) |
| Peptide 489 | H₃C(O)C-Lys-Gln-Lys-Leu-Glu-Asn-Leu-Leu-Glu-Arg-Phe-Leu-Asp-Leu-Val-azPip-NH₂ (SEQ. ID. NO. 489) | or a pharmaceutically acceptable salt thereof.

III. Synthesis of the ApoA-I Mimics

The ApoA-I Mimics can be prepared using virtually any art-known technique for the preparation of peptides. For example, the ApoA-I Mimics can be prepared using conventional step-wise solution or solid phase peptide syntheses, or recombinant DNA techniques.

A. Chemical Synthesis

The ApoA-I Mimics can be prepared using conventional step-wise solution or solid phase synthesis (see, e.g., Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the ApoA-I Mimics can be prepared by way of segment condensation, as described, for example, in Liu et al., 1996, Tetrahedron Lett. 37(7):933-936; Baca, et al., 1995, J. Am. Chem. Soc. 117:1881-1887; Tam et al., 1995, Int. J. Peptide Protein Res. 45:209-216; Schnolzer and Kent, 1992, Science 256:221-225; Liu and Tam, 1994, J. Am. Chem. Soc. 116(10):4149-4153; Liu and Tam, 1994, Proc. Natl. Acad. Sci. USA 91:6584-6588; Yamashiro and Li, 1988, Int. J. Peptide Protein Res. 31:322-334). This is particularly the case with peptides having a glycine residue. Other methods useful for synthesizing the ApoA-I Mimics are described in Nakagawa et al., 1985, J. Am. Chem. Soc. 107:7087-7092.

ApoA-I Mimics having N- and/or C-terminal capping groups can be prepared using standard techniques of organic chemistry. For example, methods for acylating the N-terminus of a peptide or amidating or esterifying the C-terminus of a peptide are well-known in the art. Modes of carrying other modifications at the N- and/or C-terminus will be apparent to those of skill in the art, as will modes of protecting any side-chain functionalities as can be necessary to attach terminal blocking groups.

Pharmaceutically acceptable salts (counter ions) can be conveniently prepared by ion-exchange chromatography or other methods as are well known in the art.

ApoA-I Mimics that are in the form of tandem multimers can be conveniently synthesized by adding the linker(s) to the peptide chain at the appropriate step in the synthesis. Alternatively, the helical segments can be synthesized and each segment reacted with the linker. Of course, the actual method of synthesis will depend on the composition of the linker. Suitable protecting schemes and chemistries are well known, and will be apparent to those of skill in the art.

ApoA-I Mimics that are in the form of branched networks can be conveniently synthesized using the trimeric and tetrameric resins and chemistries described in Tam, 1988, Proc. Natl. Acad. Sci. USA 85:5409-5413 and Demoor et al., 1996, Eur. J. Biochem. 239:74-84. Modifying the synthetic resins and strategies to synthesize branched networks of higher or lower order, or which contain combinations of different ApoA-I Mimic helical segments, is well within the capabilities of those of skill in the art of peptide chemistry and/or organic chemistry.

Formation of disulfide linkages, if desired, can be conducted in the presence of mild oxidizing agents. Chemical oxidizing agents can be used, or the ApoA-I Mimics can simply be exposed to atmospheric oxygen to effect these linkages. Various methods are known in the art, including those described, for example, by Tam et al., 1979, Synthesis 955-957; Stewart et al., 1984, Solid Phase Peptide Synthesis, 2d Ed., Pierce Chemical Company Rockford, Ill.; Ahmed et al., 1975, J. Biol. Chem. 250:8477-8482; and Pennington et al., 1991 Peptides 1990 164-166, Giralt and Andreu, Eds., ESCOM Leiden, The Netherlands. An additional alternative is described by Kamber et al., 1980, Helv. Chim. Acta 63:899-915. A method conducted on solid supports is described by Albericio, 1985, Int. J. Peptide Protein Res. 26:92-97. Any of these methods can be used to form disulfide linkages in the peptides of the invention.

ApoA-I Mimics having one or more internal glycine residues can be synthesized in relatively high yield by way of segment condensation, thereby providing advantages for large-scale production. Segment condensation, i.e., the joining together of small constituent peptide chains to form a larger peptide chain, has been used to prepare many biologically active peptides, including 44-amino acid residue mimics of ApoA-I (see, e.g., Nakagawa et al., 1985, J. Am Chem. Soc. 107:7087-7083; Nokihara et al., 1989, Peptides 1988: 166-168; Kneib-Cordonnier et al., 1990, Int. J. Pept. Protein Res. 35:527-538).

Advantages of synthesis via segment condensation include the ability to condense pre-formed segments in the solution phase and the ease of purification of the final product. Drawbacks of the method include low coupling efficiency and yield at the condensation step and low solubility of certain peptide sequences. The coupling efficiency of the condensation step can be increased by increasing the coupling time. Typically, increasing the coupling time results in increased racemezation of the product (Sieber et al., 1970, Helv. Chim. Acta 53:2135-2150). However, since glycine lacks a chiral center it does not undergo racemezation (proline residues, due to steric hindrance, also undergo little or no racemezation at long coupling times). Thus, embodiments containing internal glycine residues can be synthesized in bulk in high yield via segment condensation by synthesizing constituent segments which take advantage of the fact that glycine residues do not undergo racemezation. Thus, ApoA-I Mimics having one or more internal glycine residues provide synthetic advantages for large-scale bulk preparation.

B. Recombinant Synthesis

If the ApoA-I Mimic is composed entirely of genetically-encoded amino acid residues, or a portion of it is so composed, the ApoA-I Mimic or the relevant portion can also be synthesized using conventional recombinant genetic engineering techniques.

For recombinant production, a polynucleotide sequence encoding the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Sambrook et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y. each of which is incorporated by reference herein in its entirety.)

To increase efficiency of production, the polynucleotide can be designed to encode multiple units of the peptide separated by enzymatic cleavage sites—either homopolymers (repeating peptide units) or heteropolymers (different peptides strung together) can be engineered in this way. The resulting polypeptide can be cleaved (e.g., by treatment with the appropriate enzyme) in order to recover the peptide units. This can increase the yield of peptides driven by a single promoter. In one embodiment, a polycistronic polynucleotide can be designed so that a single mRNA is transcribed which encodes multiple peptides (i.e., homopolymers or heteropolymers) each coding region operatively linked to a cap-independent translation control sequence; e.g., an internal ribosome entry site (IRES). When used in appropriate viral expression systems, the translation of each peptide encoded by the mRNA is directed internally in the transcript; e.g., by the IRES. Thus, the polycistronic construct directs the transcription of a single, large polycistronic mRNA which, in turn, directs the translation of multiple, individual peptides. This approach eliminates the production and enzymatic processing of polyproteins and can significantly increase yield of peptide driven by a single promoter.

A variety of host-expression vector systems can be utilized to express the ApoA-I Mimics. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems can vary in their strength and specificities. Depending on the host/vector system utilized, any of a number of suitable transcription and translation elements, including constitutive and inducible promoters, can be used in the expression vector. For example, when cloning in bacterial systems, inducible promoters such as pL of bacteriophage λ, plac, ptrp, ptac (ptrplac hybrid promoter) and the like can be used; when cloning in insect cell systems, promoters such as the baculovirus polyhedron promoter can be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) can be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) can be used; when generating cell lines that contain multiple copies of expression product, SV40-, BPV- and EBV-based vectors can be used with an appropriate selectable marker.

In cases where plant expression vectors are used, the expression of sequences encoding the ApoA-I Mimics can be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) can be used; alternatively, plant promoters such as the small subunit of RUBISCO (Coruzzi et al., 1984, EMBO J. 3:1671-1680; Broglie et al., 1984, Science 224:838-843) or heat shock promoters, e.g., soybean hsp17.5-E or hsp17.3-B (Gurley et al., 1986, Mol. Cell. Biol. 6:559-565) can be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, N.Y., Section VIII, pp. 421-463; and Grierson & Corey, 1988, Plant Molecular Biology, 2d Ed., Blackie, London, Ch. 7-9.

In one insect expression system that can be used to produce the ApoA-I Mimics, *Autographa californica*, nuclear polyhidrosis virus (AcNPV) is used as a vector to express the foreign genes. The virus grows in *Spodoptera frugiperda* cells. A coding sequence can be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., see Smith et al., 1983, J. Virol. 46:584; Smith, U.S. Pat. No. 4,215,051). Further examples of this expression system can be found in Current Protocols in Molecular Biology, Vol. 2, Ausubel et al., eds., Greene Publish. Assoc. & Wiley Interscience.

In mammalian host cells, a number of viral-based expression systems can be utilized. In cases where an adenovirus is used as an expression vector, a coding sequence can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, Proc. Natl. Acad. Sci. (USA) 81:3655-3659). Alternatively, the vaccinia 7.5 K promoter can be used, (see, e.g., Mackett et al., 1982, Proc. Natl. Acad. Sci. (USA) 79:7415-7419; Mackett et al., 1984, J. Virol. 49:857-864; Panicali et al., 1982, Proc. Natl. Acad. Sci. 79:4927-4931).

Other expression systems for producing the ApoA-I Mimics will be apparent to those having skill in the art.

C. Purification

The ApoA-I Mimics can be purified by art-known techniques such as reverse phase chromatography, high performance liquid chromatography, ion exchange chromatography, gel electrophoresis, affinity chromatography and the like. The actual conditions used to purify a particular ApoA-I Mimic can depend, in part, on synthesis strategy and on factors such as net charge, hydrophobicity, hydrophilicity, etc., and will be apparent to those having skill in the art. Multimeric branched peptides can be purified, e.g., by ion exchange or size exclusion chromatography.

For affinity chromatography purification, any antibody which specifically binds the ApoA-I Mimic can be used. For the production of antibodies, various host animals, including but not limited to rabbits, mice, rats, etc., can be immunized by injection with a peptide. The peptide can be attached to a suitable carrier, such as BSA, by means of a side chain functional group or linkers attached to a side chain functional group. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to an ApoA-I Mimic can be prepared using any technique which provides for the production of antibody molecules by continuous cell lines in culture. These include but are not limited to the hybridoma technique described by Kohler and Milstein, 1975, Nature 256:495-497, or Kaprowski, U.S. Pat. No. 4,376,110 which is incorporated by reference herein; the human B-cell hybridoma technique) Kosbor et al., 1983, Immunology Today 4:72; Cote et al., 1983, Proc. Natl. Acad. Sci. U.S.A. 80:2026-2030); and the EBV-hybridoma technique (Cole et al., 1985, Monoclonal Antibodies and Cancer Therapy, Alan R. Liss, Inc., pp. 77-96 (1985)). In addition, techniques developed for the production of "chimeric antibodies" Morrison et al., 1984, Proc. Natl. Acad. Sci. U.S.A. 81:6851-6855; Neuberger et al., 1984, Nature 312:604-608; Takeda et al., 1985, Nature 314:452-454, Boss, U.S. Pat. No. 4,816,397; Cabilly, U.S. Pat. No. 4,816,567; which are incorporated by reference herein) by splicing the genes from a mouse antibody molecule of appropriate antigen specificity together with genes from a human antibody molecule of appropriate biological activity can be used. Or "humanized" antibodies can be prepared (see, e.g., Queen, U.S. Pat. No. 5,585,089 which is incorporated by reference herein). Alternatively, techniques described for the production of single chain antibodies (U.S. Pat. No. 4,946,778) can be adapted to produce peptide-specific single chain antibodies.

Antibody fragments which contain deletions of specific binding sites can be generated by known techniques. For example, such fragments include but are not limited to $F(ab')_2$ fragments, which can be produced by pepsin digestion of the antibody molecule and Fab fragments, which can be generated by reducing the disulfide bridges of the $F(ab')_2$ fragments. Alternatively, Fab expression libraries can be constructed (Huse et al., 1989, Science 246:1275-1281) to allow rapid and easy identification of monoclonal Fab fragments with the desired specificity for the peptide of interest.

The antibody or antibody fragment specific for the desired ApoA-I Mimic can be attached, for example, to agarose, and the antibody-agarose complex is used in immunochromatography to purify peptides of the invention. See, Scopes, 1984, Protein Purification: Principles and Practice, Springer-Verlag New York, Inc., N.Y., Livingstone, 1974, Methods In Enzymology: Immunoaffinity Chromatography of Proteins 34:723-731.

IV. Compositions

In one embodiment, the invention provides compositions comprising an effective amount of an ApoA-I Mimic and a pharmaceutically acceptable carrier or vehicle.

The compositions can be formulated for administration to a mammal by injection. Injectable preparations include sterile suspensions, solutions or emulsions of the active ingredient in aqueous or oily vehicles. The compositions can also comprise formulating agents, such as suspending, stabilizing and/or dispersing agent. The formulations for injection can be presented in unit dosage form, e.g., in ampules or in multidose containers, and can contain added preservatives. Alternatively, the injectable formulation can be provided in powder form for reconstitution with a suitable vehicle, including but not limited to sterile pyrogen free water, buffer, dextrose solution, etc., before use. To this end, an ApoA-I Mimic can be lyophilized, or a co-lyophilized peptide-lipid complex can be prepared. The stored preparations can be supplied in unit dosage forms and reconstituted prior to use in vivo.

For prolonged delivery, the composition can be formulated as a depot preparation, for administration by implantation; e.g., subcutaneous, intradermal, or intramuscular injection. Thus, for example, the ApoA-I Mimic can be formulated with suitable polymeric or hydrophobic materials (e.g., as an emulsion in an acceptable oil) or ion exchange resins, or as sparingly soluble derivatives; e.g., as a sparingly soluble salt form of the ApoA-I Mimic.

In other embodiment, the compositions are administered intravenously. Alternatively, transdermal delivery systems manufactured as an adhesive disc or patch which slowly releases the active ingredient for percutaneous absorption can be used. To this end, permeation enhancers can be used to facilitate transdermal penetration of the ApoA-I Mimic. A particular benefit can be achieved by incorporating the ApoA-I Mimic into a nitroglycerin patch for use in a mammal having a Condition such as ischemic heart disease or hypercholesterolemia.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the ApoA-I Mimic.

For buccal administration, the compositions can take the form of tablets or lozenges formulated in conventional manner. For rectal and vaginal routes of administration, the active ingredient can be formulated as solutions (for retention enemas) suppositories or ointments.

For administration by inhalation, the ApoA-I Mimic can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the ApoA-I Mimic and a suitable powder base such as lactose or starch.

The compositions can, if desired, be presented in a pack or dispenser device which can contain one or more unit dosage forms containing the ApoA-I Mimic. The pack can for example comprise metal or plastic foil, such as a blister pack. The pack or dispenser device can be accompanied by instructions for administration.

In some embodiments, one can formulate or administer the ApoA-I Mimic as a complex with a lipid. Accordingly, the invention includes ApoA-I Mimic/lipid complexes, compositions thereof, and methods for their administration. The complexes can have several advantages since they can have an increased half-life in the circulation, particularly when the complex has a similar size and density to HDL, and especially the pre-$\beta$-1 or pre-$\beta$-2 HDL populations. The complexes can be conveniently be prepared using any of a number of methods described below. Stable preparations having a relatively long shelf life can be made by lyophilization, —the co-lyophilization procedure described below being one embodiment. The lyophilized complexes can be used to prepare bulk for pharmaceutical reformulation, or to prepare individual aliquots or dosage units which can be reconstituted by rehydration with sterile water or an appropriate buffered solution prior to administration to a subject.

A variety of methods well known to those skilled in the art can be used to prepare the complexes. For example, a number of available techniques for preparing liposomes or proteoliposomes can be used. For example, the ApoA-I Mimic can be cosonicated (using a bath or probe sonicator) with appropriate lipids to form complexes. Alternatively the ApoA-I Mimic can be combined with preformed lipid vesicles resulting in the spontaneous formation of peptide-lipid complexes. In yet another alternative, the complexes can be formed by a detergent dialysis method; e.g., a mixture of the ApoA-I Mimic, lipid and detergent is dialyzed to remove the detergent and reconstitute or form complexes (see, e.g., Jonas et al., 1986, Methods in Enzymol. 128:553-582).

Alternatively, the complexes can be prepared by the methods disclosed in U.S. Pat. No. 6,004,925 ("'925 patent"), the entire disclosure of which is herein incorporated by reference. In the methods of the '925 patent, the ApoA-I Mimic and lipid are combined in a solvent system which co-solubilizes each ingredient and which can be completely removed by lyophilization. To this end, solvent pairs are selected to ensure co-solubility of both the ApoA-I Mimic and the lipid. In one embodiment, the ApoA-I Mimic of the complex can be dissolved in an aqueous or organic solvent or mixture of solvents (solvent 1). The lipid, such as a phospholipid, component is dissolved in an aqueous or organic solvent or mixture of solvents (solvent 2) which is miscible with solvent 1, and the two solutions are mixed. Alternatively, the ApoA-I Mimic and lipid can be incorporated into a co-solvent system; i.e., a mixture of the miscible solvents. Alternatively, the ApoA-I Mimic and lipid can be suspended in a solvent or mixture of solvents. In one embodiment, the mixture of solvents is a mixture of organic solvent and water. Examples of organic solvents include, but are not limited to, acetic acid, xylene, cyclohexane, and methanol. Examples of solvent mixtures include, but are not limited to, acetic acid and xylene, acetic acid and cyclohexane, and methanol and xylene. A suitable proportion of ApoA-I Mimic to lipids can be first determined empirically so that the resultant complexes possess the appropriate physical and chemical properties; i.e., usually (but not necessarily) similar in size to HDL. The resultant mixture is frozen and lyophilized to dryness. Sometimes an additional solvent is added to the mixture to facilitate lyophilization. This lyophilized product may be stored for long periods and will typically remain stable.

Alternatively, the complexes can be prepared by co-lyophilization of the ApoA-I Mimic with peptide in solutions or suspensions. The homogeneous solution of peptide and phospholipids of choice in an organic solvent or organic solvent mixture can be lyophilized, and peptide/phospholipid complexes can be formed spontaneously by hydration of the lyophilized powder with an aqueous buffer.

The lyophilized product may be reconstituted in order to obtain a solution or suspension of the complex. To this end, the lyophilized powder is rehydrated with an aqueous solution to a suitable volume (often 5-20 mg peptide/mL which is convenient for intravenous injection). In one embodiment, the lyophilized powder is rehydrated with phosphate buffered saline, saline bicarbonate, or a physiological saline solution. The pH of the mixture can be adjusted to 7.5-8.5. The mixture can be agitated or vortexed to facilitate rehydration, and in most cases, the reconstitution step can be conducted at a temperature equal to or greater than the phase transition temperature of the lipid component of the complexes. Within minutes, a clear preparation of reconstituted lipid-protein complexes results.

An aliquot of the resultant reconstituted preparation can be characterized to confirm that the complexes in the preparation have the desired size distribution; e.g., the size distribution of HDL. Characterization of the reconstituted preparation can be performed using any method known in the art, including, but not limited to, size exclusion filtration chromatography, gel filtration chromatography, column filtration chromatography, gel permeation chromatography, and native page electrophoresis. In one embodiment, the reconstituted preparation is characterized by gel filtration chromatography. The size of the resultant complexes may be determinative of their efficacy. In the examples described below, a Pharmacia Superose 6 FPLC gel filtration chromatography system is used. The buffer that is used contains 150 mM NaCl in 50 mM phosphate buffer, pH about 7.0 to about 9, in one embodiment 7.5-8.5, in another embodiment 7.4. A typical sample volume is 20 to 200 microliters of complexes containing 5 mg peptide/mL. The column flow rate is 0.5 mL/min. A series of proteins of known molecular weight and Stokes's diameter as well as human HDL are used as standards to calibrate the column. The proteins and lipoprotein complexes are monitored by absorbance or scattering of light of wavelength 254 or 280 nm.

The reconstituted preparation can also be characterized to determine the concentration, final pH and osmolality of resulting solution, as well as the concentration and integrities of peptide and individual lipids. ApoA-I Mimic and lipid concentration of the complexes can be measured by any method known in the art, including, but not limited to, protein and phospholipid assays, and chromatographic methods such as high performance liquid chromatography ("HPLC"), gel filtration chromatography, gas chromatography ("GC"). The chromatographs can be coupled with various detectors including, but not limited to, mass spectrometers, UV or diode-array, fluorescent, and elastic light scattering detectors. The integrity of the ApoA-I Mimic and lipid in the complexes can be determined by the chromatographic techniques described above, as well as by amino acid analysis, thin layer chromatography, and standard assays to determine lipid oxidation for lipids.

The lipid of the ApoA-I Mimic/lipid complex can be one or more of a variety of lipids, including, but not limited to, saturated, unsaturated, natural and synthetic lipids and phospholipids, and pharmaceutically acceptable salts thereof. Typical salts include, but are not limited to, sodium, calcium, magnesium, and potassium salts.

Suitable lipids of the ApoA-I Mimic/lipid complexes include, but are not limited to, ($C_1$-$C_6$) alkyl chain phospholipids, phosphatidylcholine (PC), egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, 1-palmitoyl-2-oleoylphosphatidylcholine, 1-oleoyl-2-palmitylphosphatidylcholine, dioleoylphosphatidylcholine, dioleoylphosphatidylethanolamine, dilauroylphosphatidylglycerol phosphatidylcholine, phosphatidylserine, phosphatidylethanolamine, phosphatidylinositol, sphingomyelin, sphingolipids, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, sphingomyelin, brain sphingomyelin, dipalmitoylsphingomyelin, distearoylsphingomyelin, phosphatidic acid, galactocerebroside, gangliosides, cerebrosides, dilaurylphosphatidylcholine, (1,3)-D-mannosyl-(1,3) diglyceride, aminophenylglycoside, 3-cholesteryl-6'-(glycosylthio)hexyl ether glycolipids, and cholesterol and its derivatives.

In one embodiment, the lipid of the ApoA-I Mimic/lipid complex is a neutral phospholipid. The neutral phospholipid can be any phospholipid that has a net charge of about zero at physiological pH. In some embodiments, the neutral phospholipid is a zwitterion that has a net charge of about zero at physiological pH.

In another embodiment, the neutral phospholipid is a lecithin (also known as phosphatidylcholine). In some embodiments, the neutral phospholipid is a mixture of neutral phospholipids that comprises about 5 to about 100 wt % lecithin. In other embodiments, the mixture of neutral phospholipids comprises about 100 wt % lecithin. In some embodiments, the neutral phospholipid is a mixture of neutral phospholipids that comprises about 5 to about 100 mole % lecithin. In other embodiments, the mixture of neutral phospholipids comprises about 100 mole % lecithin.

In another embodiment, the neutral phospholipid is a sphingomyelin. In some embodiments, the neutral phospholipid is a mixture of neutral phospholipids that comprises about 5 to about 100 wt % sphingomyelin. In other embodiments, the neutral phospholipid is a mixture of neutral phospholipids that comprises about 100 wt % sphingomyelin. In some embodiments, the neutral phospholipid is a mixture of neutral phospholipids that comprises about 5 to about 100 mole % sphingomyelin. In other embodiments, the neutral phospholipid is a mixture of neutral phospholipids that comprises about 100 mole % sphingomyelin.

In another embodiment, the neutral phospholipid of the ApoA-I Mimic/lipid complex is a mixture of neutral phospholipids that comprises a lecithin and a sphingomyelin. The molar ratio of lecithin to sphingomyelin can vary, but typically ranges from about 20:about 1 to about 1:about 20. In some embodiments, the lecithin:sphingomyelin molar ratio ranges from about 10:about 3 to about 10:about 6. In other embodiments, the lecithin:sphingomyelin molar ratio ranges from about 1:about 20 to about 3:about 10.

In another embodiment, the neutral phospholipid of the ApoA-I Mimic/lipid complex is a mixture of neutral phospholipids that comprises lechitin, sphingomyelin and one or more additional neutral phospholipids. Typically, the additional neutral phospholipid comprises from about 5 to about 100 wt % of the mixture.

In another embodiment, the lipid of the ApoA-I Mimic/lipid complex is a charged phospholipid. Suitable charged phospholipids include, but are not limited to, phosphatidylinositol, phosphatidylserine, phosphatidylglycerol and phosphatidic acid.

In one embodiment, the lipid of the ApoA-I Mimic/lipid complex is a mixture of at least one neutral phospholipid and at least one charged phospholipid. The total amount of charged phospholipids(s) in the lipid mixture can vary, but typically ranges from about 0.2 to about 10 wt % of the lipid mixture. In some embodiments, the total amount of charged phospholipids(s) in the lipid mixture is about 0.2 to about 2 wt %, about 0.2 to about 3 wt %, about 0.2 to about 4 wt %, about 0.2 to about 5 wt %, about 0.2 to about 6 wt %, about 0.2 to about 7 wt %, about 0.2 to about 8 wt % or about 0.2 to about 9 wt % of the lipid mixture. In some embodiments, the total amount of charged phospholipids(s) in the lipid mixture is about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9 or about 3.0, about 4, about 5, about 6, about 7, about 8, about 9, or about 10 wt % of the lipid mixture. The total amount of neutral phospholipid(s) in the lipid mixture can also vary, and can depend upon the amount of charged phospholipid(s) and any other lipids included. In one embodiment, the total amount of neutral phospholipids(s) in the lipid mixture is about about 90 to 99.8 wt % of the lipid mixture. In one embodiment, the lipid of the ApoA-I Mimic/lipid complex is a mixture of sphingomyelin and a charged phospholipid. In another embodiment, the lipid of the ApoA-I Mimic/lipid complex is a mixture of sphingomyelin, dipalmitoylphosphatidylcholine ("DPPC"), and a charged phospholipid.

In one embodiment, the lipid of the ApoA-I Mimic/lipid complex is sphingomyelin. In another embodiment, the spingomyelin is obtained from milk, egg or brain or made synthetically. In another embodiment, the lipid of the ApoA-I Mimic/lipid complex is a sphingomyelin analog or derivative. Suitable sphingomyelin analogs or derivatives include, but are not limited to, palmitoylsphingomyelin, stearoylsphingomyelin, D-erythrose-sphingomyelin, and D-erythrose-dihydrosphingomyelin.

In another embodiment, the sphingomyelin is artificially enriched in one particular saturated or unsaturated acyl chain. For example, milk sphingomyelin (Avanti Phospholipid, Alabaster, Ala.) has long saturated acyl chains. Milk sphingomyelin comprises about 20% of C16:0 (16 carbon, saturated) acyl chain compared with egg sphingomyelin, which comprises 80% of C16:0. Using solvent extraction, milk sphingomyelin can be enriched in one particular acyl chain to obtain a composition having an acyl chain concentration comparable with, e.g., egg sphingomyelin. Acyl chains that may be utilized by the invention include, but are not limited to saturated acyl chains (such as dipalmitoyl, distearoyl, diarachidonyl, and dibenzoyl acyl chains), unsaturated chains (such as diolcoyl chains), mixed chains of saturated and unsaturated acyl chains (such as palmitoyl or oleoyl chains), saturated and/or unsaturated chains of mixed lengths, and ether analogs of saturated and unsaturated acyl chains.

The sphingomyelin may be semi-synthetic such that it has a particular acyl chain. For example, milk sphingomyelin can first be purified from milk, then one particular acyl chain, e.g., the C16:0 acyl chain, can be cleaved and replaced by another acyl chain (such as palmitic acid or oleic acid).

Sphingomyelin can also be entirely synthesized, by e.g., large-scale synthesis. See, e.g., Dong et al, U.S. Pat. No. 5,220,043; Weis, 1999, Chem. Phys. Lipids 102(1-2):3-12. In one embodiment, a predefined saturation level and fatty acid composition is selected for the synthetic sphingomyelin.

In another embodiment, the lipid of the ApoA-I Mimc/lipid complex is a mixture of sphingomyelin and another lipid. In this embodiment, the sphingomyelin typically comprises from about 25 to about 75 wt % of the mixture.

In another embodiment, the lipid of the ApoA-I Mimc/lipid complex is a mixture of sphingomyelin and DPPC. In another embodiment, the lipid of the ApoA-I Mimic/lipid complex is a mixture of sphingomyelin, DPPC, and dipalmitoylphosphatidylglycerol ("DPPG"). In one embodiment, DPPG is present at about 0 to about 10% mole or weight % of the mixture. In another embodiment, DPPG is present at about 2 to about 4 mole or weight % of the mixture. In another embodiment, sphingomyelin and DPPG are present in the mixture in a weight or molar ratio of about 1:about 1. In another embodiment, the sphingomyelin, DPPC, and DPPG are present in a weight or molar ratio of about 1:about 1:about 0.06, respectively. In another embodiment, the sphingomyelin, DPPC, and DPPG are present in a molar ratio of 1.04:1:0.061, respectively. In another embodiment, the sphingomyelin, DPPC, and DPPG are present in a weight ratio of 1:1:0.062, respectively. In another embodiment, the mixture is about 48.5 mole or weight % sphingomyelin, about 48.5 mole or weight % DPPC, and about 3 mole or weight % DPPG.

In another embodiment, the ApoA-I Mimic/lipid complex comprises one or more additional peptides. In one embodiment, the additional peptide is ApoA-I.

In one embodiment, the weight ratio of total peptide to lipid in each ApoA-I Mimic/lipid complex is about 1:about 0.5 to about 1:about 5. In another embodiment, the weight ratio of total peptide to lipid in each ApoA-I Mimic/lipid complex is about 1:about 1 to about 1:about 5. In another embodiment, the weight ratio of total peptide to lipid in each ApoA-I Mimic/lipid complex is about 1:about 2 to about 1:about 5. In another embodiment, the weight ratio of total peptide to lipid in each ApoA-I Mimic/lipid complex is about 1:about 2.5. In another embodiment, the weight ratio of total peptide to lipid in each ApoA-I Mimic/lipid complex is about 1:about 3 to 1:about 5. In another embodiment, the molar ratio of total peptide to lipid in each ApoA-I Mimic/lipid complex is about 1:about 2.5 to about 1:about 20. In another embodiment, the molar ratio of total peptide to lipid in each ApoA-I mimic/lipid complex is about 1:about 9.2.

Where the lipid of the ApoA-I Mimic/lipid complex is a mixture of sphingomyelin, DPPC, and DPPG, the peptide:sphingomyelin:DPPC:DPPG weight ratio is typically about 1:about 1:about 1:about 0.08, respectively. In one embodiment, the peptide:sphingomyelin:DPPC:DPPG weight ratio is 1:1.2125:1.2125:0.075, respectively. The peptide:sphingomyelin:DPPC:DPPG molar ratio is typically about 1:about 4:about 4:about 0.03, respectively. In one embodiment, the peptide:sphingomyelin:DPPCDPPG molar ratio is 1:4.55:4.36:0.27, respectively.

In another embodiment, the ApoA-I Mimic/lipid complex comprises about 40 to about 85 wt % lipid and about 15 to about 60 wt % peptide.

In another embodiment, each ApoA-I Mimic/lipid complex is about 2 to about 12 nm in diameter.

V. Methods for Treating or Preventing a Condition

While not being bound by any particular theory, it is believed that the helix formed by the ApoA-I Mimics of the invention closely mimics the structural and functional properties of the amphipathic helical regions of native ApoA-I that are important for effecting lipid-binding, cholesterol efflux, and/or LCAT activation, thereby resulting in peptides that exhibit high ApoA-I-like activity. In one embodiment, the ApoA-I Mimics function by forming amphipathic helices (in the presence of lipids), binding lipids, forming pre-β-like or HDL-like complexes, activating LCAT, increasing serum HDL concentration and promoting cholesterol efflux.

In one embodiment, the ApoA-I Mimics activate LCAT. In another embodiment, the ApoA-I Mimics do not activate LCAT. In another embodiment, the ApoA-I Mimics activate LCAT, but only to a degree that does not result in an acceleration of cholesterol esterification. In another embodiment, the ApoA-I Mimics activate LCAT, and thereby accelerate cholesterol esterification, but wherein the acceleration of cholesterol esterification due to LCAT activation, without more, is insufficient to treat or prevent a Condition.

In one embodiment, the invention provides methods for treating or preventing a Condition, comprising administering an effective amount of an ApoA-I Mimic to a mammal in need thereof Examples of dyslipidemia include any disorder for which increasing serum HDL concentration, activating LCAT, and promoting cholesterol efflux and RCT is beneficial. Such disorders include, but are not limited to, hyperproteinemia (such as hyperchlyomicronemia), high low-density lipoprotein serum concentration, high very low-density lipoprotein serum concentration, hyperlipidemia (such as hypercholesterolemia or hyperglyceridemia (such as hypertriglyceridemia)), low high density lipoprotein serum concentration, hypocholesterolemia, Abetalipoproteinemia, ApoA-I deficiency and Tangier disease.

Examples of cardiovascular disease include, but are not limited to, metabolic syndrome, ischemic heart disease, atherosclerosis, restenosis (e.g., preventing or treating atherosclerotic plaques which develop as a consequence of medical procedures such as balloon angioplasty), endotoxemia (which often results in septic shock), congestive heart failure (such as chronic or acute heart failure), circulatory shock, cardiomyopathy, cardiac transplant, myocardial infarction, a cardiac arrhythmia (such as atrial fibrillation), supraventricular tachycardia, atrial flutter, paroxysmal atrial tachycardia, aneurysm, angina, cerebrovascular accident (stroke), peripheral vascular disease, cerebrovascular disease, kidney disease, atherogenesis, therosclerosis, acute pancreatitis, and coronary artery disease.

Endothelial dysfunction is any imbalance between the vasodilating and vasoconstricting factors and growth-inhibiting and growth-promoting factors produced by the endothelium. Endothelial dysfunction typically impairs the blood vessels' ability to dilate.

Examples of macrovascular disorders include any disorder of a large blood vessel. Such disorders include, but are not limited to, transient ischaemic attack, stroke, angina, myocardial infarction, cardiac failure, and peripheral vascular disease.

Examples of microvascular disorders include any disorder of a small blood vessel. Such disorders include, but are not limited to, diabetic retinopathy (non-proliferative, proliferative, macular oedema), microalbuminuria, macroalbuminuria, end stage renal disease, erectile dysfunction, autonomic neuropathy, peripheral neuropathy, osteomyelitis and lower limb ischaemia.

The ApoA-I Mimics can be administered alone or in combination with one or more other drugs that are useful for treating a Condition. Such therapies include, but are not limited to, simultaneous or sequential administration of the drugs involved.

In one embodiment, methods for treating or preventing a Condition can further comprise administering one or more drugs from one or more of the following classes: ACE (angiotensin converting enzyme) inhibitors, beta blockers, nitrates, calcium channel blockers, diuretics, thrombolytic agents, and blood cholesterol-lowering agents. In another embodiment, the methods of treating or preventing a Condition further comprise administering one or more of: cholestyramine, colestipol, colesevelam, gemfibrozil, ciprofibrate, clofibrate, fenofibrate, bezafibrate, ezetimibe, ramipril, verapamil, nicardipine, diltiazem, carvedilol, nadolol, isosorbide mononitrate, propranolol, isosorbide dinitrate, digoxin, furosemide, metoprolol tartrate, trandolapril, nitroglycerin, amlodipine besylate, oxycodone, clopidogrel, nifedipine, atenolol, lisinopril, aspirin, and lanoxin.

In yet another embodiment, methods for treating or preventing a Condition can further comprise administering one or more of the cholesterol lowering drugs known to one of skill in the art; e.g., bile-acid resins, niacin, and/or statins, such as atorvastatin, simvastatin, pravastatin, fluvastatin and pitavastatin. Such a regimen may produce particularly beneficial therapeutic effects since each drug acts on a different target in cholesterol synthesis and transport; i.e., bile-acid resins affect cholesterol recycling, the chylomicron and LDL population; niacin primarily affects the VLDL and LDL population; the statins inhibit cholesterol synthesis, decreasing the LDL population (and perhaps increasing LDL receptor expression); whereas the ApoA-I Mimics affect RCT, increase HDL, increase LCAT activity and promote cholesterol efflux.

In another embodiment, methods for treating or preventing a Condition can further comprise administering a fibrate, such as clinofibrate, clofibrate, simfibrate, fenofibrate, and benzafibrate.

In yet another embodiment, methods for treating or preventing a Condition can further comprise administering an anti-microbial agent and/or an anti-inflammatory agent, for example, that is useful for treating septic shock induced by endotoxin.

The ApoA-I Mimics can be administered by any suitable route that ensures bioavailability in the circulation. This may be achieved by parenteral routes of administration, including intravenous (IV), intramuscular (IM), intradermal, subcutaneous (SC) and intraperitoneal (IP) injections. However, other routes of administration can be used. For example, absorption through the gastrointestinal tract may be accomplished by oral routes of administration (including but not limited to ingestion, buccal and sublingual routes) provided appropriate formulations (e.g., enteric coatings) are used to avoid or minimize degradation of the peptides, e.g., in the harsh environments of the oral mucosa, stomach and/or small intestine. Alternatively, administration via mucosal tissue such as vaginal and rectal modes of administration may be utilized to avoid or minimize degradation in the gastrointestinal tract. In yet another alternative, the formulations of the invention may be administered transcutaneously (e.g., transdermally), ocularly, or by inhalation. It will be appreciated that the route of administration chosen may vary with the condition, age and compliance of the recipient.

The actual dose of the ApoA-I Mimic used can vary with the route of administration, and can be adjusted to achieve circulating plasma concentrations of ApoA-I Mimic of 100 mg/L to 2 g/L. In one embodiment, the dose of ApoA-I Mimic is adjusted to achieve a serum level of free or complexed ApoA-I Mimic for at least 24 hours following administration that is in the range of about 10 mg/dL to 300 mg/dL higher than a baseline (initial) level prior to administration.

The ApoA-I Mimics may be administered in a variety of different treatment regimens. In one embodiment, the ApoA-I Mimic is administered by injection at a dose between 0.5 mg/kg to 100 mg/kg once a week. In another embodiment, desirable serum levels may be maintained by continuous infusion or by intermittent infusion providing about 0.5 mg/kg/hr to 100 mg/kg/hr of the ApoA-I Mimic. In one embodiment, the ApoA-I Mimic is administered at a dose of about 20 mg/kg.

In another embodiment, the ApoA-I Mimc is administered by intravenous injection once or more per day. In another embodiment, the ApoA-I Mimic is administered by injection once every 3 to 15 days, once every 5 to 10 days, or once every 10 days. In another embodiment, the ApoA-I Mimic is administered in a series of maintenance injections, where the series of maintenance injections is administered once every 6 months to one year. The series of maintenance injections can be administered, for example, over one day (perfusion to maintain a specified plasma level of complexes), several days (e.g., four injections over a period of eight days) or several weeks (e.g., four injections over a period of four weeks).

In yet another embodiment, an escalating dose of ApoA-I Mimic can be administered, starting with about 1 to 5 doses at amount of about 50 mg to about 200 mg per administration, then followed by repeated doses of about 200 mg to about 1 g per administration. Depending on the needs of the patient, administration can be by slow infusion with a duration of more than one hour, by rapid infusion of one hour or less, or by a single bolus injection.

Toxicity and therapeutic efficacy of the ApoA-I Mimics may be determined using standard pharmaceutical procedures in cell culture or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. In one embodiment, the ApoA-I Mimics exhibit large therapeutic indices.

VI. Assay Methods

The ApoA-I Mimics can be assayed for their ability to form α-helices in the presence of lipids, to bind lipids, to form complexes with lipids, to activate LCAT, to promote cholesterol efflux, etc.

Methods and assays for analyzing the structure and/or function of the ApoA-I Mimics are well-known in the art. Several methods are provided below. For example, the circular dichroism (CD) and nuclear magnetic resonance (NMR) assays described in the examples below can be used to analyze the structure of the ApoA-I Mimics, and particularly the degree of helicity in the presence of lipids. The ability to bind lipids can be determined using the fluorescence spectroscopy assay described in the examples below. The ability of the peptides and/or peptide analogues to activate LCAT can be readily determined using the LCAT activation described in the examples below The in vitro and in vivo assays described in the examples below can be used to evaluate the half-life, distribution, cholesterol efflux and effects on RCT.

Generally, ApoA-I Mimics according to the invention that exhibit the properties listed in Table 10 below are considered to be particularly useful.

TABLE 10

|  | Range 1 | Range 2 |
|---|---|---|
| % Helicity in the presence of lipids ($R_i$ = 30) (unblocked peptides having 22 amino acid residues) | >60% | >80% |
| % Helicity in the presence of lipids ($R_i$ = 30) (unblocked peptides having 18 amino acid residues) | >40% | >60% |
| % Helicity in the presence of lipids ($R_i$ = 30) (blocked peptides having 18 or fewer amino acid residues) | >60% | >80% |
| Lipid binding (in the presence of small unilamellar vesicles ("SUVs")) | 0.5-10 µM peptide ($R_i$ = 1-50) | |
| LCAT activation | >38% | >80% |

$R_i$ is the lipid: peptide molar ratio.

The ability of an ApoA-I Mimic to form an α-helix in the presence of lipids can be demonstrated using the CD assay described below. Those peptides which are at least 40% helical (unblocked peptides containing 18 or fewer amino acid residues) or 60% helical (blocked peptides containing 18 or fewer amino acid residues; unblocked peptides containing 22 or more amino acid residues) and that bind to lipids (at a concentration of about 5 µM and a lipid:peptide molar ratio of about 30), particularly those ApoA-I Mimics which contain a fluorescent Trp (W) or Nal residue, can be identified using the fluorescence assay described below. However, for ApoA-I Mimics that do not contain fluorescent residues, binding to lipids is observed when helicity increases in the presence of lipids.

In one embodiment of the invention, the ApoA-I Mimics, particularly those that exhibit lipid binding in the presence of SUVs (0.5-10 µM peptide; lipid:peptide molar ratio in the range of 1 to 50), are screened for their ability to activate LCAT, as peptides which activate LCAT are particularly useful in the methods described herein. In one embodiment, ApoA-I Mimics exhibit at least about 38% LCAT activation as compared with native human ApoA-I (as determined using the LCAT activation assay described herein). In another embodiment, the ApoA-I Mimics exhibit 50%, 60%, 70%, 80% or even 90% LCAT activation as compared with native human ApoA-I.

VII. Other Uses

The ApoA-I Mimics are useful in assays in vitro to measure serum HDL, e.g., for diagnostic purposes. Because the ApoA-I Mimics typically associate with the HDL component of serum, the mimics may be used as "markers" for the HDL population. Accordingly, the present invention also relates to methods for measuring serum HDL concentration, comprising contacting serum HDL with an amount of ApoA-I Mimic that associates with the serum HDL and quantifying the amount of ApoA-I-associated HDL. Moreover, the ApoA-I Mimics may be used as markers for the subpopulation of HDL that is effective in reverse cholesterol transport ("RCT"). To this end, the ApoA-I Mimic may be added to or mixed with a mammalian serum sample comprising HDL; after an appropriate incubation time, the HDL component may be assayed by detecting the incorporated ApoA-I Mimic. This may be accomplished using labeled ApoA-I Mimic (e.g., radiolabels, fluorescent labels, enzyme labels, dyes, etc.), or by immunoassays using antibodies (or antibody fragments) specific for the ApoA-I Mimic.

Alternatively, labeled ApoA-I Mimics are useful in imaging procedures (e.g., CAT scans, MRI scans) to visualize the circulatory system, or to monitor RCT, or to visualize accumulation of HDL at fatty streaks, atherosclerotic lesions, etc. (where the HDL should be active in cholesterol efflux).

The invention further includes the following non-limiting, illustrative examples.

EXAMPLES

Example 1

Synthesis of ApoA-I Mimics

The ApoA-I Mimics are prepared by solid phase peptide synthesis (SPPS) using Fmoc (9-fluorenylmethyloxycarbonyl) chemistry. The C-terminal residue is covalently bound to a 4-methylbenzhydrylamine (MBHA) resin. The other amino acid residues are then incorporated by repetitive removal of the Fmoc protecting group and coupling of protected amino acid. After solid phase assembling of the peptide, the peptide is cleaved from the resin with trifluoroacetic acid (TFA). The crude peptide is recovered by precipitation and dried. The identity of the crude peptide is confirmed by MS analysis and amino acid analysis.

Example 2

Purification of ApoA-I Mimics

Purification of ApoA-I Mimics prepared according to Example 1 is performed by preparative reverse phase HPLC with a C18 stationary phase (grafted silica, 15 µm particle size, 120 Å pore size) using a water/acetonitrile gradient (with 0.1% TFA counter ion). The eluting fractions are detected by UV absorbance at 220 nm. Each run processes approximately 15 g of crude peptide, with pure fractions being pooled and concentrated on a rotary evaporator. The peptide solution is further purified using the C18 HPLC column used in the first purification step. The peptide solution is then concentrated on a rotary evaporator to remove acetonitrile and freeze-dried.

Next, the lyophilized peptide powder is re-solubilized in 90% water/10% acetonitrile and the counter ion is exchanged for acetate through ion exchange chromatography (Dowex resin, 90% water/10% acetonitrile elution media). The purified peptide with acetate counter ion is filtered through a sterile 0.22 micrometer membrane and freeze dried.

Example 3

Synthesis of Peptide 16 (SEQ ID NO: 16)

Peptide 16 (SEQ ID NO: 16) was synthesized on a solid phase support using Fmoc (9-fluorenylmethyloxycarbonyl) chemistry. The C-terminal isonipecotinyl residue was covalently bound to resin via a Wang type linker. Protecting groups used for the amino acids were: t-Butyl group for Glu and Asp, Boc group for Lys, Pbf group for Arg, Trt group for Asn and Gln.

The solid phase assembling of the peptide was performed manually in a 601 reactor equipped with a fritted disk, a mechanical stifling and nitrogen bubbling. The resin, p-methyl-benzhydrylamine resin (polystyrene-1%-divinylbenzene), was swelled and washed with dichloromethane (DCM)/dimethylformamide (DMF) (95/5). Incorporation of the C-terminal residue was achieved by coupling of the C-terminal isonipecotic acid esterified on a MPPA linker (Wang type linker). The coupling reaction was carried out with 1.35 eq of Fmoc-Inp-MPPA-linker, 1.35 eq. of N-hydroxybenzotriazole (HOBt), benzotriazol-1-yl-oxytripyrrolidinophosphonium hexafluorophosphate (PyBOP) and 4.05 eq. of diisopropylethylamine (DIEA) in DMF/DCM (50/50). After coupling, the resin was washed 3 times with DMF.

The peptide chain was assembled on the resin by repetitive removal of the Fmoc protecting group and coupling of protected amino acid. All amino acids were coupled following the same cycle: First, the Fmoc protecting group was removed in piperidine (35% in DMF) by three repeated cycles. (The Fmoc deprotection reaction took about 16 min.) After the removal of the Fmoc protecting group, the resin was washed with DMF in nine repeated cycles. The Fmoc protected amino acid residues (2 eq) were then coupled with 2 equivalents of N,N'-diisopropylcarbodiimide (DIC)/HOBt in a mixture of DMF and DCM (50/50). (The coupling step took about one hour to overnight.) The ninhydrin test was used to determine whether the coupling reaction was complete. If the ninhydrin test indicated that the coupling reaction was incomplete, the coupling was repeated with a lower excess (0.5-1 eq) of amino acid, PYBOP, HOBt in DMF/DCM and DIEA. After the coupling step, the resin was washed with DMF in three repeated cycles.

The peptide was then cleaved from the resin and deprotected. Cleavage from the resin and deprotection were performed by batches in a mixture of TFA/water/anisole (90/5/5 v/v/v) at a concentration of 5 ml/g of peptide to resin for 2.5 hours at room temperature. During progressive addition of the resin to the reagent mixture, temperature was regulated to stay below 25° C. The peptide was soluble in TFA and was extracted from the resin by filtration through a fitted disc. After concentration on a rotary evaporator, the peptide was precipitated in cold methyl-t-butyl ether (MTBE) (0° C.±5° C.) and filtered. The crude peptide was washed with MTBE and dried under reduced pressure in an oven at 30° C.

After removal of the last Fmoc protecting group, the peptide was treated with TFA/H$_2$O for cleavage and removal of the side chain protecting groups. Crude peptide was then precipitated from cold ether and collected by filtration.

Example 4

Purification of Peptide 16 (SEQ ID NO: 16)

Peptide 16 (SEQ ID NO: 16) prepared according to Example 3 was purified by preparative reverse phase HPLC (high pressure liquid chromatography) with a C18 stationary phase using a water/acetonitrile gradient (with TFA counter ion). A Prochrom LC110 column was packed with a new or dedicated stationary C18 phase (grafted silica, 15 micron particle size, 120 Angström pore size). Packing of the column was controlled by a SST for the number of plates and the tailing factor.

On a Prochrom LC110 column, the amount of peptide injected for each run was around 15 g of crude peptide dissolved in water/acetonitrile (80/20) at a concentration of approximately 75 g/L. The column was run with a gradient of buffer B in buffer A (flow rate approximately 450 mL/min and UV detection at 220 nm): buffer A=0.1% TFA in water; buffer B=acetonitrile/0.1% TFA in water (80/20), under the following conditions:

| Column: | Symmetry C18, 5 μm, 250 × 4.6 mm, 100Å |
|---|---|
| Gradient: | 40% buffer B to 55% buffer B in 30 minutes at 1 mL/min |
| Temperature: | 60° C. |
| Detector: | 210 nm |

Eluting fractions were analyzed by analytical HPLC and pooled in four categories: Waste, Front Impure, Pure, and Back Impure, according to preset specifications. The in-process HPLC purity specifications for classifying the fractions into pools are:

| Waste: | <80% |
|---|---|
| Pure: | ≥95% |
| Front and Back Impure: | ≥80% to <95% |

To assure a better recovery yield of the product, the impure fractions close to the pure ones (front impure and back impure) were subjected to a recyling run on the same column. The "pure pools" were concentrated on a rotary evaporator to remove acetonitrile.

Example 5

Counter-ion exchange and drying of Peptide 16 (SEQ ID NO: 16)

The pure pools from Example 4 were mixed and stirred for homogenisation. Concentration of pure Peptide 16 (SEQ ID NO: 16) was performed using reverse phase HPLC on the preparative column that served for purification. On a Prochrom LC110 column, the volume of pure peptide injected for each run was around 20 L at a concentration of approximately 5 g/L. The column was run with a steep gradient of buffer B in buffer A (flow rate approximately 450 ml/min and UV detection at 220 nm): buffer A=0.1% TFA in water; buffer B=acetonitrile/0.1% TFA in water (80/20).

The solvent volume for the whole peak was collected, concentrated on a rotary evaporator to remove acetonitrile and freeze dried on a bottle freeze dryer. The resultant freeze-dried pools of purified peptide were mixed in water/acetonitrile (90/10) at a concentration of 80 g/L and stirred to dissolve completely before ion exchange chromatography on Dowex acetate, strongly basic, 50-100 mesh resin. (Dowex acetate was obtained by treating Dowex Cl resin with 1N NaOH, then rinsing with purified water, treatment with AcOH/H$_2$O (25/75), and rinsing with purified water.) The sample was eluted with water/acetonitrile (90/10). The solvent volume for thewhole peak was collected, and concentrated on a rotary evaporator if the elution volume was too large. The purified peptide solution was filtered through a sterile filtration capsule (0.22 micrometer), and lyophilized on a shelf freeze dryer.

Example 6

Purity Analysis of Peptide 16 (SEQ ID NO: 16)

The purity of Peptide 16 (SEQ ID NO: 16) was determined using analytical reverse phase HPLC analysis. Purity was established by integration of the areas of all peaks (area normalization). The analysis was performed using a Waters Alliance HPLC system with: a module 2695 composed of a dual piston pump, a degasser, an automatic injection system, a Peltier regulated column oven; a UV detector module 2487;

and Empower Pro Version 5.00 software. The column used was a Symmetry C18 (5µ) or equivalent, 250×4.6 mm column. The column temperature was 60° C. Injections were eluted on a gradient profile at a flow rate of 1 mL/min. Eluent A is 0.1% TFA (e.g. Acros 13972) in milli-Q water, while eluent B is 0.1% TFA in acetonitrile HPLC gradient grade (e.g. SDS 00637G). The gradient profile is shown below:

| Time (min) | Eluent A (%) | Eluent B(%) |
|---|---|---|
| 0.0 | 57 | 43 |
| 30.0 | 50 | 50 |
| 45.0 | 20 | 80 |
| 46.0 | 0 | 100 |
| 51.0 | 0 | 100 |
| 52.0 | 57 | 43 |

Peptide 16 (SEQ ID NO: 16) was detected by UV absorbance at 210 nm. The run time was 45 min, with a delay of 22 min between injections for column wash out. Peptide 16 (SEQ ID NO: 16) was weighed out in an HPLC vial and dissolved in purified water to provide a concentration of approximately 1.2 mg/mL. Peptide solutions were injected at 20 µL.

Example 7

Characterization of ApoA-I Mimics by LC-MS

A standard commercially available triple stage quadrupole mass spectrometer (model TSQ 700; Finnigan MAT, San Jose Calif., USA) is used for mass determination. A pneumatically assisted electrospray (ESI) interface is used for sample introduction to the atmospheric pressure ionization source of the mass spectrometer. The interface sprayer is operated at a positive potential of 4.5 kV. The temperature of the steel capillary is held at 200° C., whereas the manifold is at 70° C. Positive ions generated by this ion evaporation process enter the analyzer of the mass spectrometer. The multiplier is adjusted to 1000 V. The analyzer compartment of the mass spectrometer is at 4E-6. All acquisitions are performed at resolution <1µ.

ApoA-I Mimics are analyzed by direct infusion of the purified ApoA-I Mimics using an ABI (Applied Biosystems) microbore system consisting of a syringe pump (model 140B), an UV detector (model 785A) and an oven/injector (model 112A). The solvent system consists of water (solvent A) and acetonitrile (solvent B), each containing 0.1% TFA. ApoA-I Mimics are infused using either a gradient or isocratic conditions and are eluted from an Aquapore C18 column. The flow rate is typically 300 µL/min. Concentration of each ApoA-I Mimic is about 0.03 mg/mL, 20 µL of which is injected (e.g., 30 pmol).

Full scan MS experiments are obtained by scanning quadrupole 1 from m/z 500-1500 in 4 s. Data are acquired using an Alpha DEC station and are processed using the software package provided by Finnigan MAT (BIOWORKS).

Example 8

Characterization of Peptide 16 (SEQ ID NO: 16) by LC-MS

The mass spectral analysis was carried out using a Thermo-Finnigan LCQ Advantage instrument. The source was Electrospray Ionisation (ESI-MS). Parameters MS: Nitrogen Gas Flow=30 arbitrary Units, Spray Voltage=5.2V, Capillary temperature=270° C., Capillary voltage=38V, Tube Lens Offset=55V. A test solution of 100[tg/mL solution of Peptide 16 (SEQ ID NO: 16) in methanol/water/formic acid 47/47/6 v/v/v was analyzed (direct infusion into the MS at a flow rate of 5 µL/min injection with a 500 µL syringe). The result obtained after deconvolution was in agreement with the theoretical value.

Example 9

Amino Acid Analysis of ApoA-I Mimics

Amino acid analysis is performed using an ABI (Applied Biosystems) 420 Amino Acid Analyzer. This system consists of three modules: a hydrolysis and derivatisation instrument, a reverse-phase HPLC and a data system. Peptide samples are applied (3 times in triplicate) on porous glass slides and subsequently hydrolyzed under gas phase conditions (155° C., 90 min.). After removal of the HCl, the resulting amino acids are converted to PTC-AA (Phenylthiocarbamoyl-amino acids) using PITC (Phenylisothiocyanate). After transfer to the HPC sample loop the resulting mixtures are fractionated on an Aquapore C18 column using the gradient mode (Solvent A: 50 mmol ammonium acetate ($NH_4Ac$), pH 5.4, in water; Solvent B: 32 mmol of sodium acetate (NaOAc) in aqueous acetonitrile) under conditions of temperature control. The HPLC data are processed by the software package provided by Applied Biosystems. Quantification is performed relative to a peptide standard delivered by Applied Biosystems.

Example 10

Amino Acid Analysis of Peptide 16 (SEQ ID NO: 16)

Peptide 16 (SEQ ID NO: 16) (about 700 µg) was hydrolyzed by 100 [t.L 6N HCl (e.g. Pierce 24308) at 110° C. for 20 hours into the constitutive amino acids which, after derivatization, were separated and quantified against a standard mixture of amino acids (amino acid Standard H e.g. Pierce 20088). The amino acids were derivatized using o-phtalaldehyde (OPA-reagent e.g. Fluka 5061-3335) and 9-fluorenylmethylchloroformate (Fmoc-reagent e.g. Fluka 5061-3337), then injected on a C-18 HPLC-column. An Agilent 1100 HPLC with UV detector and Chemstation Software was used for the analysis. The column used was a Hypersil ODS column 200×2.1 mm, 5 µm. The gradient used was 0-60% B in 17 min up to 100% B for 7 min at a flow rate of 0.45 mL/min. Buffer A=2.3 g sodium acetate in 1000 mL $H_2O$+180 µL triethylamine, pH adjusted to 7.2 with 2% acetic acid solution+3.3 ml tetrahydrofuran. Buffer B=2.3 g sodium acetate in 200 ml $H_2O$, pH adjusted to 7.2 with 2% acetic acid solution+400 mL acetonitrile+400 mL methanol. Amino acid measurements were performed in triplicate, with amino acids detected by UV absorbance at 368 and 262 nm. Pierce standard solution was injected both before and after the triplicate injection of the peptide sample.

Example 11

Preparation of Peptide/Lipid Complexes by Co-Lyophilization 50 mg of an ApoA-I Mimic is dissolved in 1 mL of glacial acetic acid in a 1 mL clear glass vial with cap. Dissolution of the peptide is aided by occasional vortexing over a period of 10 minutes at room temperature. 50 mg of dipalmitoyl phosphatidylcholine (DPPC; Avanti Polar Lipids, 99% Purity, product #850355) and 50 mg of egg sphingomyelin (NOF) are dissolved in 1 mL of glacial acetic acid. DPPG is dissolved in 90% glacial acetic acid 10% water mixture (v/v) at a concentration of 10 mg/mL. DPPG dissolution is aided by incubation at 37° C. ApoA-I Mimic, sphingomyelin, DPPC and DPPG solutions are mixed to obtain weight ratio of ApoA-I Mimic:sphingomyelin:DPPC:DPPG of 1:1.35:1.35: 0.30, respectively. The resulting solution is frozen at −20° C. and lyophilized for over 12 h.

The lyophilized powder is hydrated in bicarbonate saline buffer (20 mM sodium bicarbonate, 130 mM NaCl, pH 8.2) to obtain 10 mg/mL final concentration of ApoA-I Mimic. The mixture is agitated to facilitate rehydration. Following hydration the pH is adjusted with 1N NaOH solution to pH 7.4. To aid complex formation hydrated powder is incubated in a water bath at 50° C. for 15 minutes following by keeping it at room temperature for 15 min. The heating and cooling is repeated until clear to translucent solution of ApoA-I Mimic/phospholipid complexes in buffer is obtained.

Example 12

Preparation of a Peptide 16 (SEQ ID NO: 16)/lipid complex by homogenization

A sodium phosphate buffer (12 mM, pH 8.2) was prepared and heated to 50° C.

A DPPG dispersion was prepared by dispersing DPPG in buffer at a concentration of 45 mg/mL. A peptide solution was prepared by dissolving Peptide 16 (SEQ ID NO: 16) in buffer at a concentration of 30 mg/ml. The pH of the peptide solution was adjusted to about 8.2 by addition of NaOH. The peptide solution was then combined with the DPPG dispersion and incubated at 50° C. until a clear solution was observed, forming a peptide/DPPG solution.

A sphingomyelin/DPPC dispersion was prepared by dispersing sphingomyelin and DPPC in buffer at a concentration of 38.3 mg/mL of each of sphingomyelin and DPPC. The sphingomyelin/DPPC dispersion was then mixed using high shear mixing.

The peptide/DPPG solution and the sphingomyelin/DPPC solution were combined and homogenized using a high pressure homogenizer (Avestin C3) until the solution became translucent and complexes formed. Following homogenization, an isotonicity agent was added (130 mM NaCl). The solution was then sterile filtered and filled into glass vials. The final concentration of Peptide 16 (SEQ ID NO: 16) in the solution was 15 mg/mL.

Example 13

Figure 5:
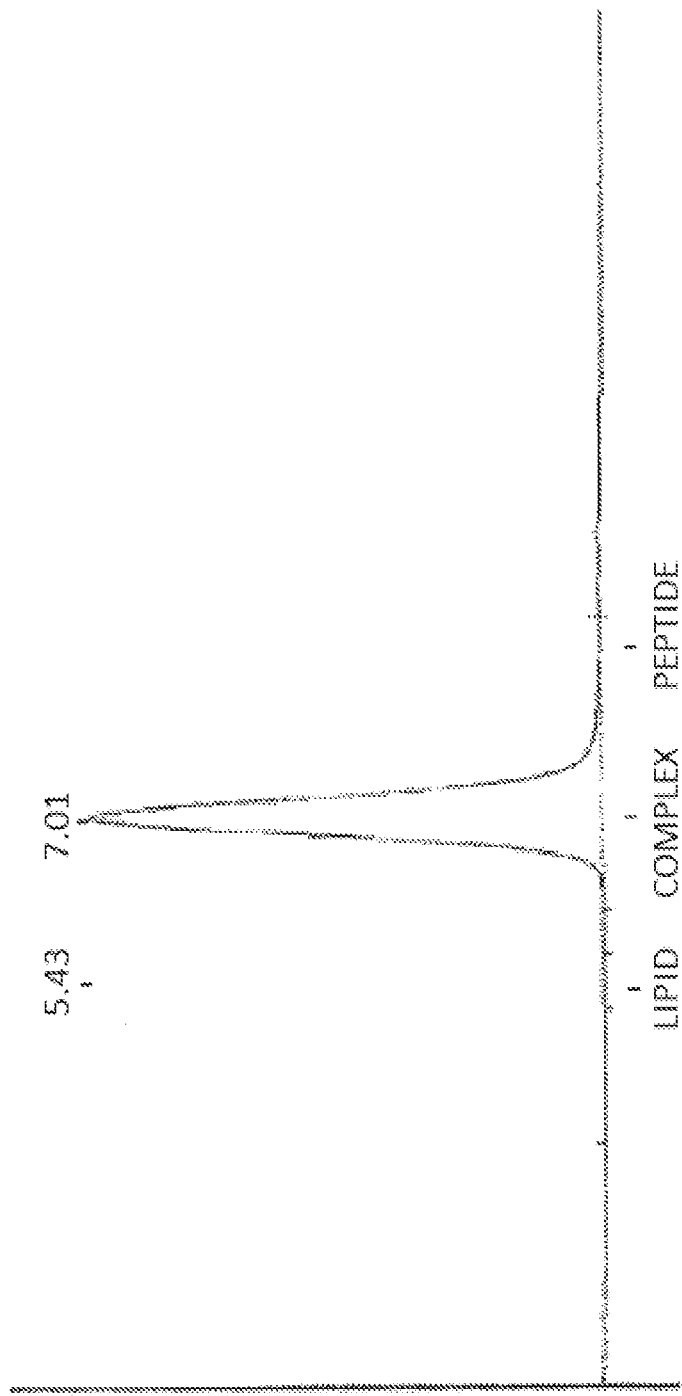
FIG. 5 is a representative gel permeation chromatogram for a Peptide 16 (SEQ ID NO: 16)/lipid complex (the lipids being sphingomyelin, DPPC, and DPPG).

Analysis of a Peptide 16 (SEQ ID NO: 16)/Lipid Complex a. Size Distribution of the Complex The identity of the Peptide 16 (SEQ ID NO: 16)/lipid complex prepared according to Example 12 was verified and the size distribution of the complexes was determined using Gel Permeation Chromatography (GPC). A Tosoh TSK-GEL G3000SW$_{XL}$ (7.8 mm ID, 30 cm length) was used for the separation. Injections were eluted using a 6 mM phosphate buffer containing 150 mM NaCl (pH 7.4) and an isocratic flow rate of 1 ml/min. Samples were prepared by 20× dilution with mobile phase and an injection volume of 100 µL was used. Column performance was checked before each run by injection of four molecular weight standards. The complex was detected by UV at 220 nm wavelength. Identity of the complex was confirmed by comparison of the retention time of the complex to the reference standard. Size distribution of the complex was reported as the percentage of total peak area in the chromatogram. A representative GPC chromatogram for the Peptide 16 (SEQ ID NO: 16)/lipid complex prepared according to Example 12 is shown in FIG. 5.

b. Identity, Purity, and Content of Peptide 16 (SEQ ID NO: 16) of the Complex

The identity, purity and content of Peptide 16 (SEQ ID NO: 16) of the complex was determined using Ultra Performance Liquid Chromatography ("UPLC") with UV detection at 215 nm wavelength. An Acquity BEH C18 100 mm column with I.D. of 2.1 mm and particle size of 1.7 µm was used for this separation. Injections were eluted using a binary gradient mobile phase of 0.1% (v/v) TFA in methanol/acetonitrile/water at 52.5/22.5/22 (v/v/v) ratio and 0.1% (v/v) TFA in methanol/acetonitrile/water at 56/24/20 (v/v/v) ratio. Samples were prepared by 20× dilution and injected using a 7.5 µL injection volume. The combination of mobile-phase organic solvents dissolved the complexes and separated Peptide 16 (SEQ ID NO: 16) from the lipids of the complex. The identity of Peptide 16 (SEQ ID NO: 16) was confirmed by comparison of its retention time to the reference standard. Purity of Peptide 16 (SEQ ID NO: 16) was reported as the percentage of total peak area in the chromatogram. Content of Peptide 16 (SEQ ID NO: 16) was calculated using a calibration curve constructed from diluted solutions of Peptide 16 (SEQ ID NO: 16) reference standard.

c. Determination of Lipid Content in the Complex

The lipid content of the Peptide 16 (SEQ ID NO: 16)/lipid complex prepared according to Example 12 was determined using an enzymatic assay utilizing the DAOS method. The assay kit was manufactured by Wako Pure Chemical Industries, Ltd (Phospholipids C kit). Samples were diluted 75× using phosphate buffer. The enzymes in the assay kit hydrolyzed sphingomyelin and DPPC to release choline, which then reacted with several other enzymes to activate a blue pigment. The blue pigment was detected spectraphotometrically. Samples were quantified from a calibration curve made from dilutions of sodium cholate and the blue pigment. The hydrolyzed sphingomyelin and DPPC both contained choline and are thus quantified by this method.

Example 14

Superose 6 Gel Filtration Chromatography of Human HDL

Human HDL$_2$ is prepared as follows: 300 mL frozen human plasma (Mannheim Blutspendzentrale #1185190) is thawed, adjusted to density 1.25 using solid potassium bromide, and centrifuged for 45 hours at 40,000 PRM using a Ti45 rotor (Beckman) at 20° C. The resultant floating layer is collected, dialyzed against distilled water, adjusted to density 1.07 with solid potassium bromide, and centrifuged as described above for 70 hours. The bottom layer (at a level of 1 cm above the tube bottom) is collected, 0.01% sodium azide is added, and the layer is stored at 4° C. for 4 days. 20 µL of the HDL$_2$ is loaded onto a Pharmacia Superose 6 FPLC gel filtration chromatography system using 0.9% NaCl as column eluate. The column flow rate is 0.5 mL/min. The column eluate is monitored by absorbance or scattering of light of wavelength 254 nm. A series of proteins of known molecular weight and Stokes' diameter are used as standards to calibrate the column for the calculation of Stokes' diameters of the particles (Pharmacia Gel Filtration Calibration Kit Instruction Manual, Pharmacia Laboratory Separation, Piscataway, N.J., revised April 1985).

Example 15

Determination of Peptide 16 (SEQ ID NO: 16) in Rat and Monkey Plasma Using Protein Precipitation with Liquid Chromatography and Tandem Mass Spectrometric Detection (LC-MS/MS)

Concentrations of Peptide 16 (SEQ ID NO: 16) were determined in rat or monkey plasma over the concentration range 1 to 500 μg/mL range using blank matrix. Isotopically labeled Peptide 16 (SEQ ID NO: 16) was used as an internal standard solution and added to thawed plasma samples. The samples were then subjected to protein precipitation using water:acetonitrile: TFA (70:20:10 v/v/v), followed by mixing and centrifugation. The supernatant was transferred to a clean 96 well plate and water:acetonitrile:TFA (70:30:0.1 v/v/v) was added to each well followed by mixing and centrifugation before LC-MS/MS analysis. The LC conditions were: Acquity UPLC and Turbo IonSpray (positive ion) (MS/MS), using a BEH Shield RP 18 column running a gradient of water:acetonitrile:TFA 0.1%.

Concentrations of Peptide 16 (SEQ ID NO: 16) in calibration standards and QC samples were determined using least squares linear regression with the reciprocal of the concentration (1/x) as weighting.

Example 16

Measurement of pharmacokinetics of a Peptide 16 (SEQ ID NO: 16)/Lipid Complex in Rats Pharmacokinetics of a Peptide 16 (SEQ ID NO: 16)/lipid complex (the lipids being sphingomyelin, DPPC, and DPPG in a weight ratio of 1:1.2125:1.2125:0.075, and the peptide: lipid weight ratio being 1:2.5) were evaluated in Windstar rats.

Nine animals per sex per group were included for the evaluation of pharmacokinetics. Animals in the vehicle control group received 130 mM sodium chloride in 12 mM phosphate buffer, pH 8.2, intravenously at 20 mL/Kg. Animals in the Peptide 16 (SEQ ID NO: 16)/lipid complex treatment groups received 15, 30 or 60 mg/kg administered every other day by intravenous infusion. Approximately 0.5 mL of blood was drawn from the retro-orbital sinus under isoflorane anesthesia and collected in tubes containing $Na_3EDTA$ as an anticoagulant from cohorts of 3 animals per group at baseline and 0.0833, 0.5, 1, 2, 6, 12, 24 and 48 hours post-dose on Day 0 and Day 26. Thus, each cohort of animals had blood drawn at three different timepoints. Plasma was separated following centrifugation and stored frozen at −20° C. until analysis. Peptide levels were analyzed by LC-MS/MS as described in Example 8. Pharmacokinetics parameters were determined from individual plasma concentrations by non-compartmental analysis using Kinetica 4.4.1. The plasma levels of Peptide 16 (SEQ ID NO: 16) increased rapidly post-dose, then were quantifiable up to 6 hr following the end of infusion in animals that were administered the Peptide 16 (SEQ ID NO: 16)/lipid complex at 15 and 30 mg/kg doses. Detectable levels of Peptide 16 (SEQ ID NO: 16) were observed up to 12 hrs in animals treated with 60 mg/kg in both sexes. As expected for an intravenously administered drug, the $T_{max}$ was immediate post dose. The estimated half-life of circulating levels of Peptide 16 (SEQ ID NO: 16) was between 0.5 and 5 hours in rats of both sexes, and it appeared to increase in a dose-dependent manner. The clearance and volume of distribution decreased with increasing dose. Based on the volume of distribution it could be inferred that the Peptide 16 (SEQ ID NO: 16)/lipid complex was generally distributed in plasma.

Example 17

Measurement of Pharmacokinetics of a Peptide 16 (SEQ ID NO: 16)/Lipid Complex in Monkeys Pharmacokinetics of a Peptide 16 (SEQ ID NO: 16)/lipid complex (the lipids being sphingomyelin, DPPC, and DPPG in a weight ratio of 1:1.2125:1.2125:0.075, and the peptide: lipid weight ratio being 1:2.5) were evaluated in Cygomolus monkeys.

Animals in the vehicle control group received 130 mM sodium chloride in 12 mM phosphate buffer, pH 8.2, intravenously at 10 mL/Kg. Animals in the Peptide 16 (SEQ ID NO: 16)/lipid complex treatment groups received 15, 30 or 60 mg/kg administered every other day by intravenous infusion. Blood was collected into tubes containing $Na_3EDTA$ as an anticoagulant, at baseline, at the end of infusion, and then at 1, 2, 6, 12, 24 and 48 hours post-dose. At each time point, approximately 1 mL of blood was drawn from the femoral vessel, while the animal was held restrained without any anesthesia. Plasma was separated following centrifugation and stored frozen at −20° C. until analysis. Peptide 16 (SEQ ID NO: 16) levels were analyzed by LC-MS/MS as described in Example 8. Pharmacokinetics parameters were determined from individual plasma concentrations by non-compartmental analysis using Kinetica 4.4.1. Peptide 16 (SEQ ID NO: 16) was detected in plasma for up to 12 hr following the end of infusion in animals administered with the Peptide 16 (SEQ ID NO: 16)/lipid complex at 15 mg/kg in both sexes. Detectable levels of Peptide 16 (SEQ ID NO: 16) were observed up to 24 hrs in animals treated with 30 and 60 mg/kg. The phospholipid levels also increased post dose, then returned to baseline levels over a similar timeframe to that of Peptide 16 (SEQ ID NO: 16). As expected for an intravenously administered drug, the $T_{max}$ was immediate post dose. The estimated half-life of circulating levels of Peptide 16 (SEQ ID NO: 16) was between 2 and 7 hours in monkeys of both sexes, and it appeared to increase in a dose-dependent manner. The clearance and volume of distribution decreased with increasing dose. Based on the volume of distribution it could be inferred that the Peptide 16 (SEQ ID NO: 16)/lipid complex was distributed primarily in the plasma compartment.

Example 18

Cholesterol Mobilization in Rabbits a. Preparation of the Peptide 16 (SEQ ID NO: 16)/Lipid Complex Peptide 16 (SEQ ID NO: 16) was synthesized by F-moc synthesis according to Example 3 and purified by a reverse phase chromatography according to Example 4.

Peptide 16 (SEQ ID NO: 16) was then complexed with a mixture of sphingomyelin, DPPG, and DPPC by co-lyophilization of solutions of Peptide 16 (SEQ ID NO: 16), sphingomyelin, DPPG, and DPPC in a glacial acetic acid: water mixture. The resultant lyophilized powder was reconstituted with buffer (sodium phosphate buffer, 12 mM, pH 8.2) to form a suspension of Peptide 16 (SEQ ID NO: 16)/ lipid complex having a weight ratio of Peptide 16 (SEQ ID NO: 16): sphingomyelin:DPPC:DPPG of 1:1.35:1.35:0.30.

b. Administration of the Peptide 16 (SEQ ID NO: 16)/Lipid Complex to Rabbits

New Zealand male rabbits weighing between 3 to 4 kg were used to demonstrate cholesterol mobilization by the Peptide 16 (SEQ ID NO: 16)/lipid complex.

The animal room conditions were as follows: temperature, 22±2° C.; relative humidity, 55±15%; and a 12 hour light/12 hour dark cycle.

Animals were acclimatized for at least 7 days before the beginning of the study. The animals received ad libitum a controlled pellet diet on a daily basis. Water was available ad libitum throughout the study.

Before administration of the Peptide 16 (SEQ ID NO: 16)/lipid complex, the animals were fasted overnight. The animals were weighed just before administration of the Peptide 16 (SEQ ID NO: 16)/lipid complex. The Peptide 16 (SEQ ID NO: 16)/lipid complex was administered intravenously at a dosage rate of 20 mg/kg. The volume administered was based on weight. Feeding was resumed approximately 6 hours after the administration of the Peptide 16 (SEQ ID NO: 16)/lipid complex.

c. Analysis of Blood Samples

Prior to the collection of blood samples, the animals were fasted overnight. Blood was collected at baseline, then 5 min, 15 min, 30 min, 1 hr, 2 hr, 4 hr, 6 hr, 8 hr, 30 hr and 34 hr after initiating the infusion. Blood samples were withdrawn from the jugular vein or from the marginal vein of the ear. Blood was withdrawn from the jugular vein using a syringe mounted with a needle with EDTA (approximately 1 mL of blood per sampling time). Immediately after collection, blood samples were kept at approximately 4° C. to avoid alteration of the blood sample. Blood specimens were centrifuged (3500 g for 10 minutes at approximately 5° C.). Plasma specimens were separated and aliquoted (3 aliquots of at least 200 µL (aliquots A, B, C)) and stored at approximately −80° C. The remaining blood clot was discarded.

Serum phospholipid (Phospholipid B, Kit #990-54009, Wako Chemicals GmbH, Neuss, Germany), triglycerides (Triglycerides, Kit #1488872, Boehringer Mannheim Corporation, Indianapolis, Ind.), total cholesterol and unesterified cholesterol were determined using commercially available kits for a Hitachi 912 Automatic Analyzer (Roche Diagnostics Corporation, Indianapolis, Ind.).

Lipoprotein profiles were analyzed using gel filtration chromatography on a Superose 6HR 1×30 cm column equipped with on-line detection for total or free cholesterol as described by Kieft et al. (J Lipid Res 1991; 32:859-866, 1991). The area under the peaks corresponding to lipoproteins with the sizes of VLDL, LDL and HDL were integrated. The fraction of the free or total cholesterol of each peak was multiplied by the total plasma cholesterol or free cholesterol determined by an automatic analyzer to determine VLDL, LDL and HDL free and total cholesterol. Esterified cholesterol in serum and in the lipoprotein fractions VLDL, LDL and HDL was calculated by subtracting free cholesterol from total cholesterol values.

Figure 6:
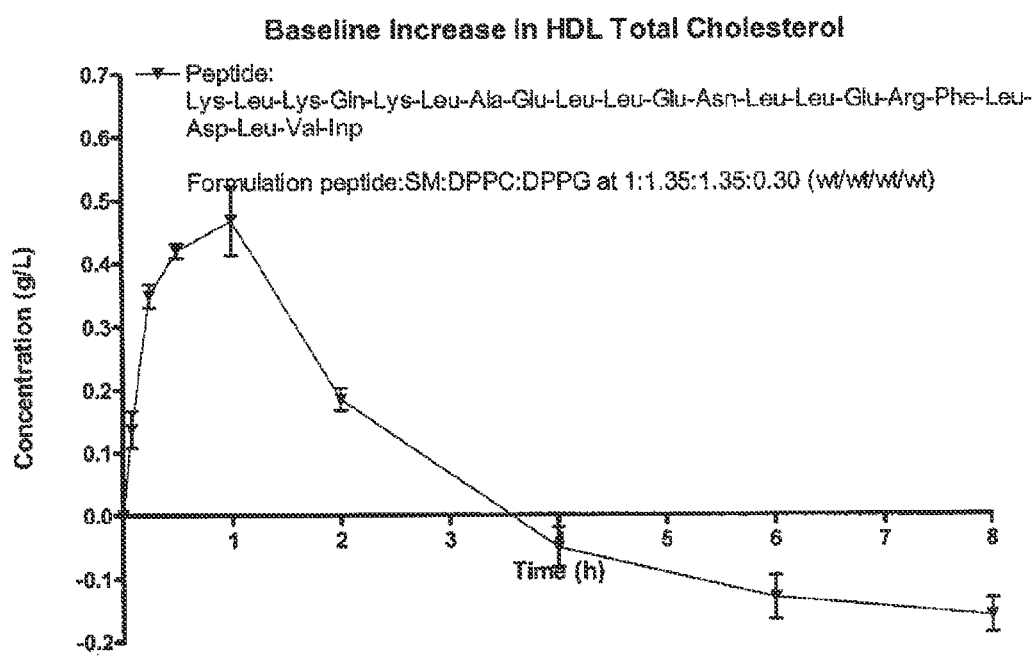
FIG. 6 is a plot of baseline increase in HDL fraction of total cholsterol following administration of a Peptide 16 (SEQ ID NO: 16)/lipid complex (the lipids being sphingomyelin, DPPC, and DPPG, and the components being present in a weight ratio of Peptide 16 (SEQ ID NO: 16): sphingomyelin:DPPC:DPPG of 1:1.35:1.35:0.30) to rabbits.

The increase in HDL fraction of total cholesterol following infusion of complexes was plotted as a function of time and is illustrated in FIG. 6. The rabbits' total HDL cholesterol increased upon administration of the Peptide 16 (SEQ ID NO: 16)/lipid complex, indicating tissue cholesterol mobilization and transfer to HDL.

Example 19

Cholesterol Mobilization in Rabbits a. Preparation of the Peptide 16 (SEQ ID NO: 16)/Lipid Complex The Peptide 16 (SEQ ID NO: 16)/lipid complex was prepared according to Example 12. The Peptide 16 (SEQ ID NO: 16)/lipid complex had a weight ratio of Peptide 16 (SEQ ID NO: 16):sphingomyelin:DPPC:DPPG of 1:1.2125:1.2125:0.075 and a weight ratio of peptide:lipid of 1:2.5.

b. Administration of the Peptide 16 (SEQ ID NO: 16)/Lipid Complex to Rabbits

New Zealand male rabbits weighing between 3 to 4 kg were used to show an increase in HDL levels in rabbits by the Peptide 16 (SEQ ID NO: 16)/lipid complex.

The animal room conditions were as follows: temperature, 22±2° C.; relative humidity, 55±15%; and a 12 hour light/12 hour dark cycle.

Animals were acclimatized for at least 7 days before the beginning of the study. The animals received ad libitum a controlled pellet diet on a daily basis. Water was available ad libitum throughout the study.

Before administration of the Peptide 16 (SEQ ID NO: 16)/lipid complex, the animals were fasted overnight. The animals were weighed just before administration of the Peptide 16 (SEQ ID NO: 16)/lipid complex. To investigate the minimal dose at which cholesterol mobilization could be detected, the animals were dosed with 2.5, 5 and 10 mg/kg of the Peptide 16 (SEQ ID NO: 16)/lipid complex or a phosphate buffered saline control. Four animals were studied per dose group. Feeding was resumed approximately 6 hours after the administration of the Peptide 16 (SEQ ID NO: 16)/lipid complex or phosphate buffered saline control.

c. Analysis of Blood Samples

Prior to the collection of blood samples, the animals were fasted overnight. Blood was collected at baseline, then 5 min, 15 min, 30 min, 1 hr, 2 hr, 4 hr, 6 hr, 8 hr, 30 hr and 34 hr after initiating the infusion. Blood samples were withdrawn from the jugular vein or from the marginal vein of the ear. Blood was withdrawn from the jugular vein using a syringe mounted with a needle with EDTA (approximately 1 mL of blood per sampling time). Immediately after collection, blood samples were kept at approximately 4° C. to avoid alteration of the blood sample. Blood specimens were centrifuged (3500 g for 10 minutes at approximately 5° C.). Plasma specimens were separated and aliquoted (3 aliquots of at least 200 µL (aliquots A, B, C)) and stored at approximately −80° C. The remaining blood clot was discarded.

Serum phospholipid (Phospholipid B, Kit #990-54009, Wako Chemicals GmbH, Neuss, Germany), triglycerides (Triglycerides, Kit #1488872, Boehringer Mannheim Corporation, Indianapolis, Ind.), total cholesterol and unesterified cholesterol were determined with commercially available kits for a Hitachi 912 Automatic Analyzer (Roche Diagnostics Corporation, Indianapolis, Ind.).

Lipoprotein profiles were analyzed using gel filtration chromatography on a Superose 6HR 1×30 cm column equipped with on-line detection for total or free cholesterol as described by Kieft et al. (J Lipid Res 1991; 32:859-866, 1991). The area under the peaks corresponding to lipoproteins with the sizes of VLDL, LDL and HDL were integrated. The fraction of the free or total cholesterol of each peak was multiplied by the total plasma cholesterol or free cholesterol determined by an automatic analyzer to determine VLDL, LDL and HDL free and total cholesterol. Esterified cholesterol in serum and in the lipoprotein fractions VLDL, LDL and HDL was calculated by subtracting free cholesterol from total cholesterol values.

Figure 7:
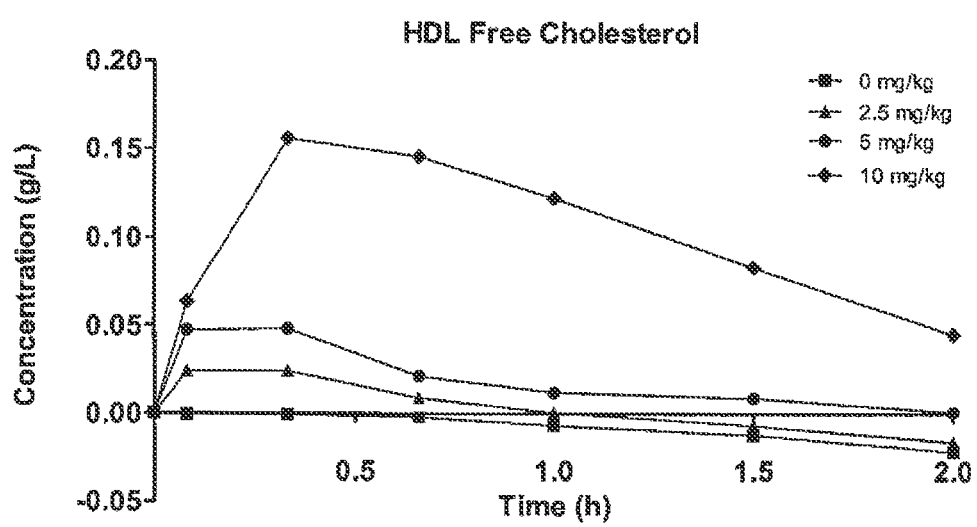
FIG. 7 is a plot of increase in HDL fraction of free cholsterol following administration of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) to rabbits.

The increase in HDL fraction of free cholesterol following infusion of complexes was plotted as a function of time and is illustrated in FIG. 7. A clear increase in HDL free cholesterol over baseline was apparent at a dose of 2.5 mg/kg, indicating high potency of the Peptide 16 (SEQ ID NO: 16)/lipid complex. At five and 20 minutes after starting the infusion, the cholesterol was increased 30% above baseline. These increases were statistically significant ($p<0.05$ by a paired two tailed student T test). In contrast, there was no change from baseline in the placebo treatment group.

Figure 8:
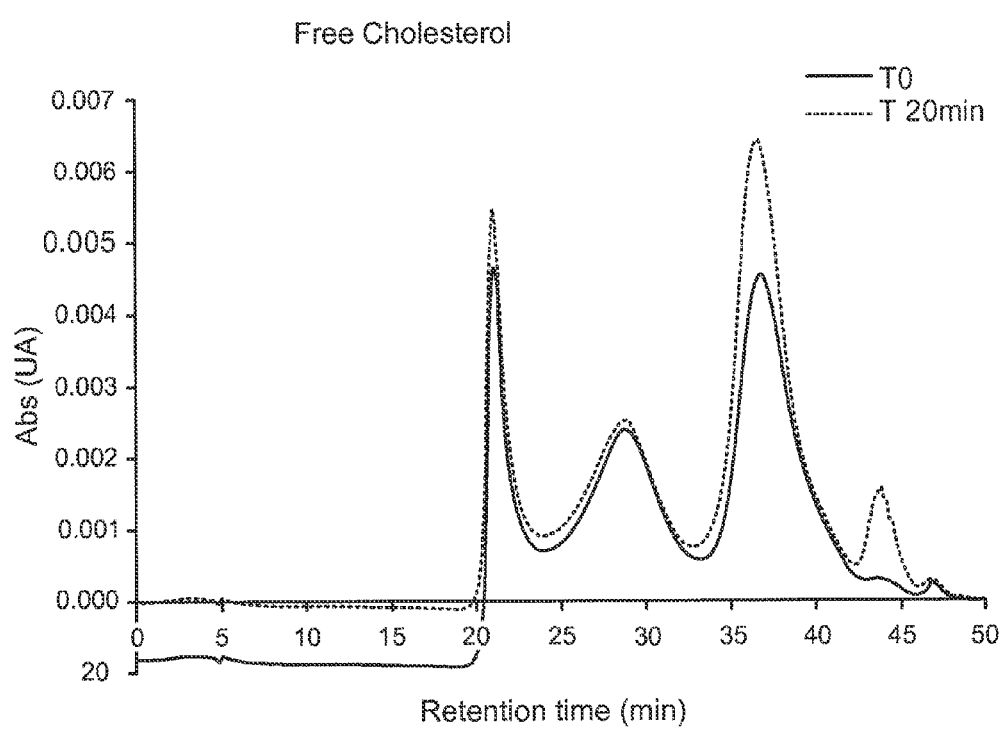
FIG. 8 is a gel permeation chromatography elution profile at baseline (dark line) and 20 min after administration of 2.5 mg/kg of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) to rabbits.

The pharmacological effect of the Peptide 16 (SEQ ID NO: 16)/lipid complex at a 2.5 mg/kg dose was further evident by comparing the original scans of the lipoprotein fractions eluting from the HPLC size exclusion column, which are illustrated in FIG. 8. There is a clear increase relative baseline in the HDL free cholesterol fraction of the HPLC chromatograms following injection.

Example 20

Dose Response of a Peptide 16 (SEQ ID NO: 16)/Lipid Complex

Dose response of a Peptide 16 (SEQ ID NO: 16)/lipid complex (the lipids being sphingomyelin, DPPC, and DPPG in a weight ratio of 1:1.2125:1.2125:0.075, and the peptide: lipid weight ratio being 1:2.5) was evaluated in New Zealand white rabbits.

In a fasted New Zealand White rabbit cholesterol mobilization model, the Peptide 16 (SEQ ID NO: 16)/lipid complex at concentrations of 5, 10, or 15 mg/mL (based upon the peptide concentration) or a phosphate buffered saline vehicle control were administered, intravenously, at a rate of 1 mL/min to fasted animals at an infusion volume of 2 mL/kg. There were three animals per dose group. The final doses were 0, 10, 20 or 30 mg/kg. Blood was collected at baseline, then 5 min, 15 min, 30 min, 1 hr, 2 hr, 4 hr, 6 hr, 8 hr, 30 hr and 34 hr after initiating the infusion. Plasma lipid and lipoprotein levels were then determined. Lipoprotein levels were determined by HPLC size exclusion fractionation with inline free and total cholesterol detection according to a method described by Usui, S., Hara, Y., Hosaki, S., and Okazaki, M., A new on-line dual enzymatic method for simultaneous quantification of cholesterol and triglycerides in lipoproteins by HPLC. *J. Lipid Res.* 43, 805-814 (2002). The area under the main peaks corresponding to lipoproteins with the sizes of VLDL, LDL and HDL were integrated. The fraction of the free or total cholesterol in each peak was multiplied by the total plasma cholesterol or free cholesterol to determine the level of cholesterol in each fraction. Cholesterol ester levels in each fraction were determined by subtracting the free cholesterol from the total cholesterol in each fraction. In this model, increases in plasma or HDL cholesterol levels are indicative of tissue cholesterol mobilization and transfer to HDL.

Figure 9:
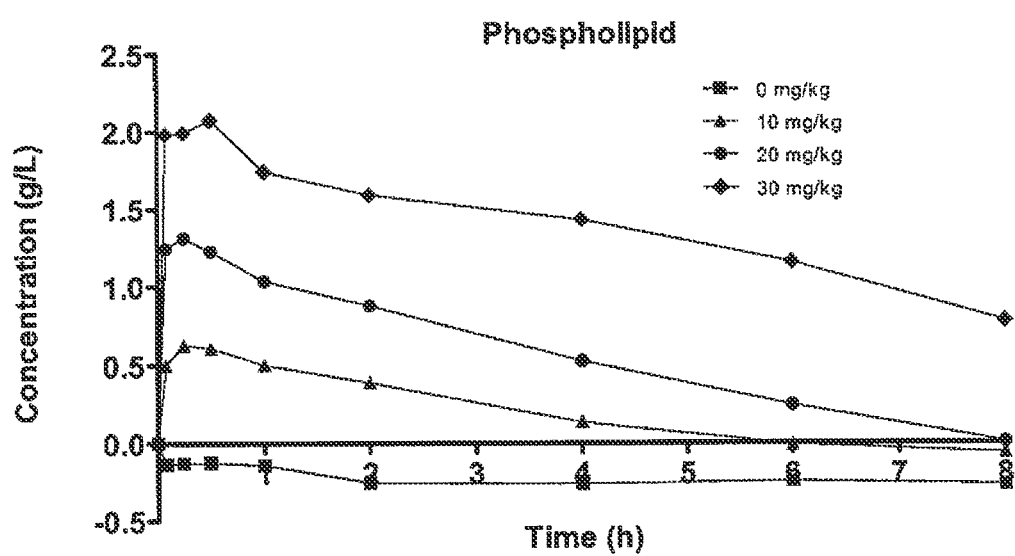
FIG. 9 is a plot of increase in plasma phospholipid following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma phospholipid levels were measured. Baseline values (ranging from 0.96 to 1.18 g/L for the four groups) were subtracted to determine the increase in plasma phospholipid levels. There were 3 animals per group. By 30-34 hours post dose the values had returned to a value at or below baseline.
Figure 10A:
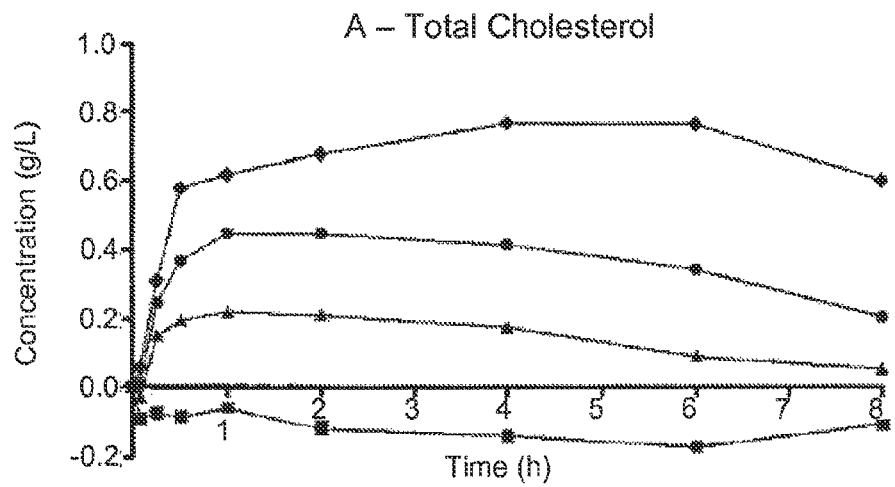
FIG. 10A is a plot of increase in in plasma total cholesterol following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma total cholesterol levels were measured. Baseline values were subtracted to determine the increase in cholesterol levels. The baseline values ranged from 0.59 to 0.77 g/L. There were 3 animals per group. By 30-34 hours post dose the values had returned to a value at or below baseline.
Figure 10B:
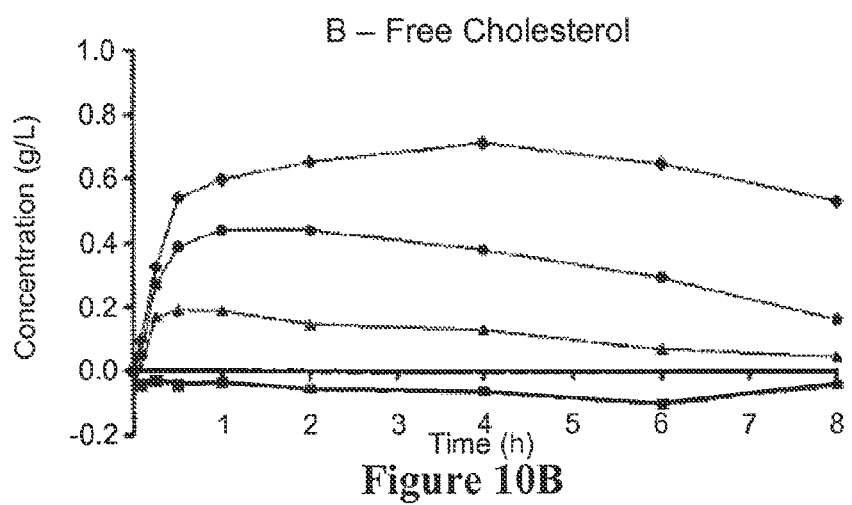
FIG. 10B is a plot of increase in in plasma free cholesterol following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma free cholesterol levels were measured. Baseline values were subtracted to determine the increase in cholesterol levels. The baseline values ranged from 0.21 to 0.27 g/L. There were 3 animals per group. By 30-34 hours post dose the values had returned to a value at or below baseline.
Figure 10C:
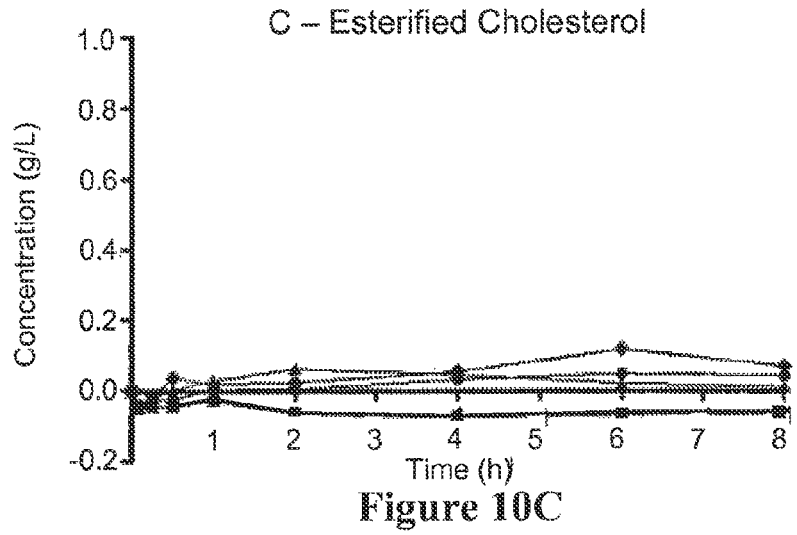
FIG. 10C is a plot of increase in in plasma esterified cholesterol following infusion of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) into fasted rabbits at doses of 0 (square), 10 (triangle), 20 (circle) or 30 (diamond) mg/kg. At various times post dose, plasma esterified cholesterol levels were measured. Baseline values were subtracted to determine the increase in cholesterol levels. The baseline values ranged from 0.39 to 0.52 g/L. There were 3 animals per group. By 30-34 hours post dose the values had returned to a value at or below baseline.

FIG. 9 shows the dose dependent increase plasma phospholipids following infusion of the Peptide 16 (SEQ ID NO: 16)/lipid complex into rabbits. This increase reflects the circulating levels of the Peptide 16 (SEQ ID NO: 16)/lipid complex, since phopholipid is a component of the Peptide 16 (SEQ ID NO: 16)/lipid complex. Peptide 16 (SEQ ID NO: 16) levels peaked within the first 30 minutes then decreased towards baseline levels. A dose dependent increase in cholesterol mobilization was also observed. This was evident by the increase in both the total plasma cholesterol (FIG. 10A) and total HDL cholesterol levels (FIG. 11A). The majority of the cholesterol increase was in the form of free cholesterol (FIGS. 10 and 11).

An increase in total and free cholesterol in the LDL fraction (FIGS. 11C and 11D) was observed at the two highest doses. The increase in free cholesterol was about equal to that of the total cholesterol, indicating little increase in cholesterol ester in this fraction. An increase in free cholesterol in the LDL fraction, in the absence of an increase in cholesterol ester, indicates this increase does not represent an increase in typical cholesterol ester rich LDL. The complexes appearing in this lipoprotein fraction are likely a product of the infused Peptide 16 (SEQ ID NO: 16)/lipid complex that has gained cholesterol through the cholesterol mobilization process. Observed increases in VLDL cholesterol were distributed between the esterified and unesterified cholesterol fractions. Triglyceride levels increased transiently over the first four to six hours at all Peptide 16 (SEQ ID NO: 16)/lipid complex doses (FIG. 12). There was no obvious relationship between the dose and triglyceride increase.

Example 21

Minimal Effective Dose of a Peptide 16 (SEQ ID NO: 16)/Lipid Complex

The minimal effective dose of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) was evaluated in New Zealand white rabbits.

The minimal dose at which cholesterol mobilization could be detected was investigated. Animals were dosed with 0, 2.5, 5 and 10 mg/kg of the Peptide 16 (SEQ ID NO: 16)/lipid complex. Four animals were studied per dose group. A pharmacological effect was most evident by the increase in free cholesterol in the HDL fraction compared to baseline levels (FIG. 13). This was expected because the majority of the initial cholesterol increase after infusion of the Peptide 16 (SEQ ID NO: 16)/lipid complex is free cholesterol in the HDL fraction. In addition, free cholesterol represents about one third of the total HDL cholesterol, making the increase in this fraction easier to detect. A clear increase in HDL free cholesterol over baseline was apparent at a 2.5 mg/kg dose. At five and 20 minutes after starting the infusion, the cholesterol was increased 30% above baseline. These increases were statistically significant ($p<0.05$ by a paired two tailed student T-test). In contrast, there was no change from baseline in the control group.

The pharmacological effect of the Peptide 16 (SEQ ID NO: 16)/lipid complex at a 2.5 mg/kg or 5 mg/kg dose was further evident by comparing the original scans of the lipoprotein fractions eluting from the HPLC size exclusion column. As can be seen in these two examples, in FIG. 14, there is a clear increase in free cholesterol relative baseline in the HDL fraction of the HPLC chromatograms. This is shown by the increase in the area under the HDL peak for the sample collected at 20 minutes after initiating the infusion of the Peptide 16 (SEQ ID NO: 16)/lipid complex (light line in FIG. 14) compared to the area under the HDL peak at baseline (dark line in FIG. 14).

Example 22

Effect of Infusion Rate on Efficacy of a Peptide 16 (SEQ ID NO: 16)/Lipid Complex The effect of infusion rate on efficacy of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) was evaluated in New Zealand white rabbits.

The effect of the rate of infusion of the Peptide 16 (SEQ ID NO: 16)/lipid complex on cholesterol mobilization was investigated. Peptide 16 (SEQ ID NO: 16)/lipid complex at a concentration of 10 mg/mL (based upon peptide concentration) or a phosphate buffered saline vehicle control was infused at a dose volume of 2 mL/kg at a rate of either 1 mL/min or 0.2 mL/min. The final dose of Peptide 16 (SEQ ID NO: 16)/lipid complex was 20 mg/kg. Four animals were studied in the Peptide 16 (SEQ ID NO: 16)/lipid complex groups and two animals in the vehicle control groups. The rabbits ranged in size from 2.2-2.8 kg.

The rate of increase in plasma phospholipid resulting from the infusion of the Peptide 16 (SEQ ID NO: 16)/lipid complex and rate of increase in plasma cholesterol resulting from the subsequent cholesterol mobilization was slower in the animals in which the Peptide 16 (SEQ ID NO: 16)/lipid complex was infused at a slower rate. However, the peak phospholipid and cholesterol mobilization levels were similar. FIG. 15 shows that the increase in HDL free cholesterol following infusion of the Peptide 16 (SEQ ID NO: 16)/lipid complex at rate of 1 mL/min or 0.2 mL/min was similar. Thus in this model, Peptide 16 (SEQ ID NO: 16)/lipid complex infusion rate, over the rates tested, had little or no effect on cholesterol mobilization.

Example 23

Pharmacokinetic Studies on a Peptide 16 (SEQ ID NO: 16)/Lipid Complex in Rats and Monkeys The pharmacokinetics of a Peptide 16 (SEQ ID NO: 16)/lipid complex (the lipids being sphingomyelin, DPPC, and DPPG in a weight ratio of 1:1.2125:1.2125:0.075, and the peptide:lipid weight ratio being 1:2.5) was evaluated in rats and monkeys.

a. Assay Methodology

The concentrations of the Peptide 16 (SEQ ID NO: 16)/lipid complex in rat and monkey plasma were determined using a liquid chromatography with tandem mass spectrometry (LC-MS/MS) technique. Peptide 16 (SEQ ID NO: 16), a component of the Peptide 16 (SEQ ID NO: 16)/lipid complex, was extracted from plasma containing EDTA following precipitation of the protein fraction by acetonitrile. The method measures the extracted Peptide 16 (SEQ ID NO: 16) and an internal standard of an isotopically labeled-Peptide 16 (SEQ ID NO: 16). The extracts were reconstituted and the peptide assayed by ultra performance liquid chromatography combined with tandem mass spectrometers (MS/MS). The calibration range of the method is 1-500 μg/mL with a sample volume of 25 μL. The peptide extraction and LC-MS/MS methods were validated in accordance with general recommendations for bioanalytical method validation and in compliance with GLP (Good Laboratory Practice). The validation data showed that the methods were sensitive, specific, accurate and precise enough for the determination of Peptide 16 (SEQ ID NO: 16)/lipid complex in rat and monkey plasma.

b. Pharmacokinetic Studies in Rats 9 rats per sex per group were included for the evaluation of toxicokinetics of the Peptide 16 (SEQ ID NO: 16)/Lipid complex following dose administration on Day 0 (First dose) and Day 26. Animals in the vehicle control group received 130 mM sodium chloride in 12 mM phosphate buffer, pH 8.2, intravenously at 20 mL/Kg. Animals in Peptide 16 (SEQ ID NO: 16)/lipid complex treatment groups received 15, 30 or 60 mg/kg given every second day by intravenous infusion. Approximately 0.5 mL of blood was drawn from the retro-orbital sinus under isoflurane anesthesia and collected in tubes containing $Na_3EDTA$ as an anticoagulant from cohorts of 3 animals per group at baseline and 0.0833, 0.5, 1, 2, 6, 12, 24 and 48 hours post-dose on Day 0 and Day 26. Thus, each cohort of animals had blood drawn at three different timepoints. Plasma was separated following centrifugation and stored frozen at −20° C. until analyzed at Covance (UK). Peptide levels were analyzed by LC-MS/MS. Toxicokinetic parameters were determined from individual plasma concentrations by non-compartmental analysis using Kinetica 4.4.1.

As shown in the FIGS. 16 and 17, the plasma levels of Peptide 16 (SEQ ID NO: 16) increased rapidly post-dose, then were quantifiable up to 6 hr following the end of infusion in animals given the Peptide 16 (SEQ ID NO: 16)/lipid complex at 15 and 30 mg/kg doses. Detectable levels of peptide were observed up to 12 hrs in animals treated with 60 mg/kg in both sexes. The phospholipid levels increased post dose, then returned to baseline levels over a similar timeframe to that of the peptide. Free cholesterol (unesterified) increased post infusion in a dose dependent manner indicative of cholesterol mobilization. This was followed by a decrease in cholesterol indicating that the Peptide 16 (SEQ ID NO: 16)/lipid complex particles efficiently remove cholesterol from circulation. Similar patterns were observed on Day 0 and Day 26.

The mean toxicokinetic parameters for the Peptide 16 (SEQ ID NO: 16)/lipid complex on Day 0 (first dose) and Day 26 (last dose) are presented in Table 11 below:

TABLE 11

Peptide 16 (SEQ ID NO: 16)/lipid Complex Toxicokinetic Parameters in Rat[†]

| Day | Dose (mg/Kg) | Sex | $C_{max}$ (μg/mL) | $T_{max}$ (h) | $AUC_{0-12}$ (μg · h/mL) | $T_{1/2}$ (h) | CL (mL/Kg/h) | Vd (mL/Kg) |
|---|---|---|---|---|---|---|---|---|
| Day 0 | 15 | Male | 341 | 0.0833 | 851 | 1.36 | 18.0 | 35.4 |
| Day 0 | 30 | Male | 663 | 0.0833 | 2291 | 1.28 | 13.1 | 24.1 |
| Day 0 | 60 | Male | 1390 | 0.0833 | 7497 | 2.16 | 7.90 | 24.7 |
| Day 0 | 15 | Female | 287 | 0.0833 | 671 | 0.835 | 22.5 | 27.1 |
| Day 0 | 30 | Female | 688 | 0.0833 | 2106 | 1.35 | 14.6 | 28.3 |
| Day 0 | 60 | Female | 1427 | 0.0833 | 6689 | 1.72 | 8.93 | 22.1 |
| Day 26 | 15 | Male | 422 | 0.0833 | 1176 | 1.71 | 13.0 | 32.1 |
| Day 26 | 30 | Male | 858 | 0.0833 | 3188 | 1.62 | 9.37 | 21.9 |
| Day 26 | 60 | Male | 1870 | 1.00 | 9889 | 2.56 | 5.86 | 21.6 |
| Day 26 | 15 | Female | 386 | 0.0833 | 841 | 1.01 | 18.1 | 26.3 |
| Day 26 | 30 | Female | 815 | 0.0833 | 2490 | 1.41 | 12.3 | 25.1 |
| Day 26 | 60 | Female | 1537 | 0.0833 | 7804 | 1.79 | 7.64 | 19.7 |

[†]Parameters calculated from Peptide 16 (SEQ ID NO: 16) levels in plasma over time.

The $T_{max}$ was immediate post dose. The estimated half-life of circulating levels of Peptide 16 (SEQ ID NO: 16) was between 0.835 and 2.56 hours in rats of both sexes, and it appeared to increase in a dose dependent manner. The clearance and volume of distribution decreased with increasing dose. Based on the volume of distribution it could be inferred that the Peptide 16 (SEQ ID NO: 16)/lipid complex was generally distributed in plasma compartment (reference plasma volume in rat=30 mL/Kg). See Davies, B and Morris, T. Physiological parameters in laboratory animals and human, Pharmaceutical Research, 10, 1093-1095, 1993.

The increase in $AUC_{(0-12h)}$ and $C_{max}$ with the increase in dose (based on the 15 mg/kg dose) is presented in Table 12. The $C_{max}$ values were dose proportional in both sexes whereas $AUC_{(0-12h)}$ values increased more than a dose proportionally, suggesting longer residence times of the Peptide 16 (SEQ ID NO: 16)/lipid complex in the circulation with increasing dose.

TABLE 12

Increase in AUC and $C_{max}$ with Increase in Dose of Peptide 16 (SEQ ID NO: 16)/Lipid Complex

| | Dose | | | | | |
|---|---|---|---|---|---|---|
| | 15 mg/kg | | 30 mg/kg | | 60 mg/kg | |
| | Males | Females | Males | Females | Males | Females |
| Day 0 | | | | | | |
| Dose Increment | 1 | 1 | 2 | 2 | 4 | 4 |
| Increase in $AUC_{(0-12h)}$ | — | — | 2.69 | 3.14 | 8.81 | 9.96 |
| Increase in $C_{max}$ | — | — | 1.94 | 2.4 | 4.07 | 4.98 |
| Day 26 | | | | | | |
| Dose Increment | 1 | 1 | 2 | 2 | 4 | 4 |
| Increase in $AUC_{(0-12h)}$ | — | — | 2.71 | 2.96 | 8.4 | 9.28 |
| Increase in $C_{max}$ | — | — | 2.03 | 2.11 | 4.43 | 3.98 |

There were no major sex-related differences in pharmacokinetic profiles, AUCs or $C_{max}$ values following single dose and multiple dose administration. Based on $C_{max}$ and AUCs no accumulation of Peptide 16 (SEQ ID NO: 16) or Peptide 16 (SEQ ID NO: 16)/lipid complex was observed during the 4-week administration period.

c. Pharmacokinetic Studies in Monkeys

The toxicokinetics of the Peptide 16 (SEQ ID NO: 16)/lipid complex were evaluated following dose administration in monkeys on Day 0 (First dose) and Day 26. Animals in the vehicle control group received 130 mM sodium chloride in 12 mM phosphate buffer, pH 8.2, intravenously at 10 mL/Kg. Animals in the Peptide 16 (SEQ ID NO: 16)/lipid complex treatment groups received 15, 30 or 60 mg/kg given every second day by intravenous infusion. Blood was collected into tubes containing $Na_3EDTA$ as an anticoagulant, at baseline, at the end of infusion, and then at 1, 2, 6, 12, 24 and 48 hours post-dose on Day 0 and Day 26. At each time point, approximately 1 mL of blood was drawn from the femoral vessel, while the animal was held restrained without any anesthesia. Plasma was separated following centrifugation and stored frozen at −20° C. until analyzed at Covance (UK). Peptide levels were analyzed by LC-MS/MS. Toxicokinetic parameters were determined from individual plasma concentrations by non-compartmental analysis using Kinetica 4.4.1.

As shown in the FIGS. 18 and 19, Peptide 16 (SEQ ID NO: 16) could be detected in plasma for up to 12 hr following the end of infusion in animals given the Peptide 16 (SEQ ID NO: 16)/lipid complex at 15 mg/kg in both sexes. Detectable levels of peptide were observed up to 24 hrs in animals treated with 30 and 60 mg/kg. The phospholipid levels also increased post dose, then returned to baseline levels over a similar timeframe to that of the peptide. Free cholesterol (unesterified) increased post infusion in a dose dependent manner indicative of cholesterol mobilization. This was followed by a decrease in cholesterol indicating that the Peptide 16 (SEQ ID NO: 16)/lipid complex particles efficiently remove cholesterol from circulation. Similar patterns were observed on Day 0 and Day 26.

The mean toxicokinetic parameters for the Peptide 16 (SEQ ID NO: 16)/lipid complex on Day 0 (first dose) and Day 26 (last dose) are presented in Table 13 below:

TABLE 13

Peptide 16 (SEQ ID NO: 16)/Lipid Complex Toxicokinetic Parameters in Monkeys

| Day | Dose (mg/Kg) | Sex | $C_{max}$ (µg/mL) | $T_{max}$ (h) | $AUC_{0-24h}$ (µg · h/mL) | $T_{1/2}$ (h) | CL (mL/Kg/h) | Vd (mL/Kg) |
|---|---|---|---|---|---|---|---|---|
| Day 0 | 15 | Male | 341 | 0.0167 | 1346 | 2.42 | 11.50 | 39.6 |
| Day 0 | 30 | Male | 735 | 0 | 4337 | 2.96 | 6.90 | 29.3 |
| Day 0 | 60 | Male | 1540 | 0 | 13787 | 4.58 | 4.27 | 28.1 |
| Day 0 | 15 | Female | 365 | 0 | 1383 | 2.37 | 11.4 | 38.3 |
| Day 0 | 30 | Female | 736 | 0 | 4337 | 3.04 | 6.81 | 29.4 |
| Day 0 | 60 | Female | 1508 | 0 | 13168 | 3.24 | 4.54 | 21.1 |
| Day 26 | 15 | Male | 443 | 0 | 1539 | 2.66 | 10.00 | 38.8 |
| Day 26 | 30 | Male | 824 | 0 | 3890 | 2.19 | 8.58 | 26.3 |
| Day 26 | 60 | Male | 1674 | 0 | 12182 | 2.82 | 5.07 | 20.8 |
| Day 26 | 15 | Female | 408 | 0 | 1437 | 2.11 | 10.90 | 32.8 |
| Day 26 | 30 | Female | 690 | 0 | 3416 | 2.50 | 8.85 | 32.0 |
| Day 26 | 60 | Female | 1608 | 0 | 13596 | 3.63 | 4.51 | 22.9 |

†Parameters calculated from Peptide 16 (SEQ ID NO: 16) levels in plasma over time.

T = 0 is at the end of infusion.

The $T_{max}$ was immediate post dose. The estimated half-life of circulating levels of Peptide 16 (SEQ ID NO: 16) was between 2.11 and 4.58 hours in monkeys of both sexes, and it appeared to increase in a dose dependent manner. The clearance and volume of distribution decreased with increasing dose. Based on the volume of distribution it could be inferred that Peptide 16 (SEQ ID NO: 16)/lipid complex is distributed primarily in the plasma compartment (plasma volume in primates=45 mL/Kg). See Davies, B and Morris, T. Physiological parameters in laboratory animals and humans. Pharmaceutical Research, 10, 1093-1095, 1993.

The increase in $AUC_{(0-24h)}$ and $C_{max}$ with the increase in dose (based on the 15 mg/kg dose) is presented in Table 14. The $C_{max}$ values were dose proportional in both sexes where as $AUC_{(0-24h)}$ values increased in a more than a dose proportional manner, suggesting a longer residence time of the Peptide 16 (SEQ ID NO: 16)/lipid complex in the circulation with increasing dose.

TABLE 14

Increase in AUC and $C_{max}$ with Increase in Dose of Peptide 16 (SEQ ID NO: 16)/Lipid Complex

| | Dose | | | | | |
|---|---|---|---|---|---|---|
| | 15 mg/kg | | 30 mg/kg | | 60 mg/kg | |
| | Males | Females | Males | Females | Males | Females |
| Day 0 | | | | | | |
| Dose Increment | 1 | 1 | 2 | 2 | 4 | 4 |
| Increase in $AUC_{(0-24h)}$ | — | — | 3.22 | 3.31 | 10.2 | 9.52 |
| Increase in $C_{max}$ | — | — | 2.15 | 2.01 | 4.51 | 4.13 |
| Day 26 | | | | | | |
| Dose Increment | 1 | 1 | 2 | 2 | 4 | 4 |
| Increase in $AUC_{(0-24h)}$ | — | — | 2.53 | 2.38 | 7.91 | 9.46 |
| Increase in $C_{max}$ | — | — | 1.86 | 1.68 | 3.78 | 3.94 |

There were no major sex-related differences in pharmacokinetic profiles, AUCs or $C_{max}$ values following single dose and multiple dose administration.

Based on $C_{max}$ and AUCs no accumulation of the Peptide 16 (SEQ ID NO: 16)/lipid complex or Peptide 16 (SEQ ID NO: 16) was observed during the 4-week administration period.

Example 24

Pharmacokinetic Studies on Peptide 16 (SEQ ID NO: 16) and Peptide 16 (SEQ ID NO: 16)/Lipid Complexes in Mice Total cholesterol, unesterified cholesterol and cholesterol ester (as the difference between total and unesterified cholesterol values) in plasma after injection of one of three peptide formulations were measured.

Peptide formulations: (A) Peptide 16 (SEQ ID NO: 16); (B) Peptide 16 (SEQ ID NO: 16)/DPPC complex (1:2 weight ratio); (C) Peptide 16 (SEQ ID NO: 16)/DPPC complex (1:2.5 weight ratio). Formulations A, B, and C were each provided as solutions at a concentration of 15 mg/ml.

20 C57Bl/6J mice were fasted for at least two weeks with a Rodent Diet with 60% kcal % fat (Reseach diets—D12492). The drinking water was supplemented with 5% glucose. Following 3 h fasting, the peptide formulations were dosed at 30 mg/kg (IV injection—50 μl) and the blood was sampled at 15, 30, 60, 120 and 240 minutes. One pre-dose sample was performed before the injection.

Plasma samples were analyzed for total cholesterol and unesterified cholesterol (kits from Biolabo—CEROOX-SOP002, CEROOX-SOP003). The cholesterol ester was calculated as the difference between total cholesterol and unesterified cholesterol.

The results are shown in FIGS. 20 and 21.

A number of references are disclosed herein, each of which is incorporated by reference herein in its entirety.

The following are some illustrative embodiments of the invention:

1. A 22- to 29-residue peptide having the following Formula I

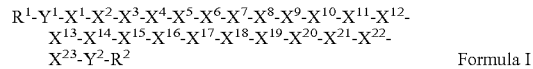

Formula I or a pharmaceutically acceptable salt thereof, wherein:

$X^1$ is absent or a basic achiral amino acid residue, a basic D-amino acid residue, or a basic L-amino acid residue;

$X^2$ is a basic achiral amino acid residue, a basic D-amino acid residue, or a basic L-amino acid residue;

$X^3$ is an aliphatic achiral amino acid residue, an aliphatic D-amino acid residue, or an aliphatic L-amino acid residue;

$X^4$ is a basic achiral amino acid residue, a basic D-amino acid residue, or a basic L-amino acid residue;

$X^5$ is Gln, Asn, D-Gln, D-Asn, or a basic achiral amino acid residue, a basic D-amino acid residue, or a basic L-amino acid residue;

$X^6$ is a basic achiral amino acid residue, a basic D-amino acid residue, or a basic L-amino acid residue;

$X^7$ is a hydrophobic achiral amino acid residue, a hydrophobic D-amino acid residue, or a hydrophobic L-amino acid residue;

$X^8$ is a hydrophobic achiral amino acid residue, a hydrophobic D-amino acid residue, or a hydrophobic L-amino acid residue;

$X^9$ is a hydrophilic achiral amino acid residue, a hydrophilic D-amino acid residue, or a hydrophilic L-amino acid residue;

$X^{10}$ is Leu, Trp, Gly, Nal, D-Leu, D-Trp, or D-Nal;

$X^{11}$ is Gly or an aliphatic achiral amino acid residue, an aliphatic D-amino acid residue, or an aliphatic L-aliphatic amino acid residue;

$X^{12}$ is a hydrophilic achiral amino acid residue, a hydrophilic D-amino acid residue, or a hydrophilic L-amino acid residue;

$X^{13}$ is a hydrophilic achiral amino acid residue, a hydrophilic D-amino acid residue, or a hydrophilic L-amino acid residue;

$X^{14}$ is Leu, Trp, Gly, D-Leu, or D-Trp;

$X^{15}$ is Leu, Gly, or D-Leu;

$X^{16}$ is an acidic achiral amino acid residue, an acidic D-amino acid residue, or an acidic L-amino acid residue;

$X^{17}$ is a hydrophilic achiral amino acid residue, a hydrophilic D-amino acid residue, or a hydrophilic L-amino acid residue;

$X^{18}$ is Leu, Phe, D-Leu, or D-Phe;

$X^{19}$ is Leu, Phe, D-Leu, or D-Phe;

$X^{20}$ is an acidic achiral amino acid residue, an acidic D-amino acid residue, or an acidic L-amino acid residue;

$X^{21}$ is Leu, Phe, D-Leu, or D-Phe;

$X^{22}$ is an aliphatic achiral amino acid residue, an aliphatic D-amino acid residue, or an aliphatic L-amino acid residue; and X²³ is Inp, Nip, azPro, Pip, azPip, D-Nip, or D-Pip;

Y¹ is absent or a sequence of 1 to 7 amino acid residues, wherein each residue of the sequence is independently an achiral, D-, or L-amino acid residue;

Y² is absent or a sequence of 1 to 7 amino acid residues, wherein each residue of the sequence is independently an achiral, D-, or L-amino acid residue;

R¹ is H or an amino protecting group;

R² is OH or a carboxyl protecting group;

wherein: (a) all amino acid residues, other than the terminal amino acid residues and residues immediately adjacent to the terminal amino acid residues, are achiral or L-amino acid residues; or (b) all amino acid residues, other than the terminal amino acid residues and residues immediately adjacent to the terminal amino acid residues, are achiral or D-amino acid residues.

2. The peptide or pharmaceutically acceptable salt of the peptide of embodiment 1, wherein:

X³ is Leu or D-Leu;

X⁷ is Leu, Gly, Nal, D-Leu, or D-Nal;

X⁸ is Ala, Nal, Trp, Gly, Leu, Phe, D-Ala, D-Nal, D-Trp, D-Leu, or D-Phe;

X¹¹ is Leu, Gly, Aib, or D-Leu; and

X²² is Ala, Leu, Val, D-Ala, D-Leu, or D-Val.

3. The peptide or pharmaceutically acceptable salt of the peptide of embodiment 1, wherein:

X¹ is absent, Lys, or D-Lys;

X² is Lys, Orn, D-Lys, or D-Orn;

X⁴ is Lys, Orn, D-Lys, or D-Orn;

X⁵ is Gln, Asn, Lys, Orn, D-Gln, D-Asn, D-Lys, or D-Orn;

X⁶ is Gln, Asn, Lys, Orn, D-Gln, D-Asn, D-Lys, or D-Orn;

X⁹ is Asp, Glu, D-Asp, or D-Glu;

X¹² is Glu, Asp, D-Asp, or D-Glu;

X¹³ is Asn, Gln, D-Asn or D-Gln;

X¹⁶ is Asp, Glu, D-Asp, or D-Glu;

X¹⁷ is Lys, Arg, Orn, D-Lys, D-Arg, or D-Orn; and

X²⁰ is Asp, Glu, D-Asp, or D-Glu.

4. The peptide or pharmaceutically acceptable salt of the peptide of embodiment 3, wherein X¹⁸ is Phe or D-Phe.

5. The peptide or pharmaceutically acceptable salt of the peptide of embodiment 1, wherein the peptide is a 22- or 23-residue peptide.

6. The peptide or pharmaceutically acceptable salt of the peptide of embodiment 5, wherein R¹ is H and R² is OH.

7. The peptide or pharmaceutically acceptable salt of the peptide of embodiment 5, wherein:

X¹ is absent, Lys or D-Lys;

X² is Lys, Orn, D-Lys, or D-Orn;

X³ is Leu or D-Leu;

X⁴ is Lys, Orn, D-Lys, or D-Orn;

X⁵ is Gln, Asn, Lys, Orn, D-Gln, D-Asn, D-Lys, or D-Orn;

X⁶ is Lys, Orn, D-Lys, or D-Orn;

X⁷ is Gly, Leu, Nal, D-Leu, or D-Nal;

X⁸ is Ala, Nal, Trp, Leu, Phe, Gly, D-Ala, D-Nal, D-Trp, D-Leu, or D-Phe;

X⁹ is Asp, Glu, D-Asp, or D-Glu;

X¹¹ is Gly, Leu, Aib, or D-Leu;

X¹² is Glu, Asp, D-Glu, or D-Asp;

X¹³ is Asn, Gln, D-Asn, or D-Gln;

X¹⁶ is Asp, Glu, D-Asp, or D-Glu;

X¹⁷ is Lys, Arg, Orn, D-Lys, D-Arg, or D-Orn;

X²⁰ is Asp, Glu, D-Asp, or D-Glu; and

X²² is Ala, Val, Leu, D-Ala, D-Val, or D-Leu.

8. The peptide or pharmaceutically acceptable salt of the peptide of embodiment 7, wherein: X⁵ is Gln, Asn, D-Gln, or D-Asn and X⁶ is Lys, Orn, D-Lys, or D-Orn; or X⁵ is Lys, Orn, D-Lys, or D-Orn and X⁶ is Gln, Asn, D-Gln, or D-Asn.

9. The peptide or pharmaceutically acceptable salt of the peptide of embodiment 7, wherein X¹ is absent and the peptide is a 22-residue peptide.

10. The peptide or pharmaceutically acceptable salt of the peptide of embodiment 9, wherein each of X⁷, X⁸, X¹⁰, X¹¹, X¹⁴, and X¹⁵ is other than Gly.

11. The peptide or pharmaceutically acceptable salt of the peptide of embodiment 9, wherein only one of X⁷, X⁸, X¹⁰, X¹¹, X¹⁴, and X¹⁵ is Gly.

12. The peptide or pharmaceutically acceptable salt of the peptide of embodiment 9, wherein:

X² and X⁴ are both Lys, Orn, D-Lys, or D-Orn;

X⁵ is Gln, Lys, D-Gln, or D-Lys;

X⁹ is an acidic achiral amino acid residue, an acidic D-amino acid residue, or an acidic L-amino acid residue;

X¹² is Glu, Asn, Gln, Arg, D-Glu, D-Asn, D-Gln, or D-Arg;

X¹³ is Glu, Asn, Gln, Arg, D-Glu, D-Asn, D-Gln, or D-Arg;

X¹⁶ is an acidic achiral amino acid residue, an acidic D-amino acid residue, or an acidic L-amino acid residue;

X¹⁷ is Arg, Lys, Orn, D-Arg, D-Lys, or D-Orn;

X²¹ is Leu or D-Leu; and

X²² is Ala, Val, Leu, D-Ala, D-Val, or D-Leu.

13. The peptide or pharmaceutically acceptable salt of the peptide of embodiment 1, wherein the peptide is:

```
                                        (SEQ. ID. NO. 2)
Lys-Leu-Lys-Gln-Lys-Leu-Trp-Glu-Leu-Leu-Glu-
Asn-Leu-Leu-Glu-Arg-Phe-Leu-Asp-Leu-Val-Inp;

(SEQ. ID. NO. 3)
Lys-Leu-Lys-Gln-Lys-Leu-Ala-Glu-Leu-Gly-Glu-
Asn-Leu-Leu-Glu-Arg-Phe-Leu-Asp-Leu-Val-Inp;

(SEQ. ID. NO. 4)
Lys-Leu-Lys-Gln-Lys-Nal-Ala-Glu-Leu-Gly-Glu-
Asn-Leu-Leu-Glu-Arg-Phe-Leu-Asp-Leu-Val-Inp;

(SEQ. ID. NO. 5)
Lys-Leu-Lys-Gln-Lys-Leu-Trp-Glu-Leu-Gly-Glu-
Asn-Leu-Leu-Glu-Arg-Phe-Leu-Asp-Leu-Val-Inp;

(SEQ. ID. NO. 6)
Lys-Leu-Lys-Gln-Lys-Leu-Ala-Glu-Leu-Gly-Glu-
Asn-Trp-Leu-Glu-Arg-Phe-Leu-Asp-Leu-Val-Inp;

(SEQ. ID. NO. 7)
Orn-Leu-Orn-Gln-Orn-Leu-Ala-Glu-Leu-Gly-Glu-
Asn-Leu-Leu-Glu-Arg-Phe-Leu-Asp-Leu-Val-Inp;

(SEQ. ID. NO. 8)
Lys-Leu-Lys-Gln-Lys-Leu-Ala-Glu-Leu-Gly-Glu-
Asn-Leu-Leu-Glu-Arg-Phe-Phe-Asp-Leu-Val-Inp;

(SEQ. ID. NO. 9)
Lys-Leu-Lys-Gln-Lys-Leu-Ala-Glu-Leu-Gly-Glu-
Asn-Leu-Leu-Glu-Arg-Phe-Leu-Glu-Leu-Val-Inp;

(SEQ. ID. NO. 10)
Lys-Leu-Lys-Gln-Lys-Leu-Ala-Glu-Leu-Leu-Glu-
Asn-Leu-Gly-Glu-Arg-Phe-Leu-Asp-Leu-Val-Inp;

(SEQ. ID. NO. 11)
Lys-Leu-Lys-Gln-Lys-Leu-Ala-Glu-Leu-Leu-Glu-
Asn-Gly-Leu-Glu-Arg-Phe-Leu-Asp-Leu-Val-Inp;

(SEQ. ID. NO. 12)
Lys-Leu-Lys-Gln-Lys-Leu-Ala-Glu-Gly-Leu-Glu-
Asn-Leu-Leu-Glu-Arg-Phe-Leu-Asp-Leu-Val-Inp;

(SEQ. ID. NO. 13)
Lys-Leu-Lys-Gln-Lys-Leu-Gly-Glu-Leu-Leu-Glu-
Asn-Leu-Leu-Glu-Arg-Phe-Leu-Asp-Leu-Val-Inp;
```

-continued (SEQ. ID. NO. 14)
Lys-Leu-Lys-Gln-Lys-Gly-Ala-Glu-Leu-Leu-Glu-
Asn-Leu-Leu-Glu-Arg-Phe-Leu-Asp-Leu-Val-Inp;

(SEQ. ID. NO. 15)
Lys-Leu-Lys-Gln-Lys-Leu-Nal-Glu-Leu-Leu-Glu-
Asn-Leu-Leu-Glu-Arg-Phe-Leu-Asp-Leu-Val-Inp;

(SEQ. ID. NO. 16)
Lys-Leu-Lys-Gln-Lys-Leu-Ala-Glu-Leu-Leu-Glu-
Asn-Leu-Leu-Glu-Arg-Phe-Leu-Asp-Leu-Val-Inp;

(SEQ. ID. NO. 18)
Lys-Leu-Lys-Gln-Lys-Leu-Ala-Glu-Leu-Aib-Glu-
Asn-Leu-Leu-Glu-Arg-Phe-Leu-Asp-Leu-Val-Inp;

(SEQ. ID. NO. 19)
Lys-Leu-Lys-Gln-Lys-Leu-Ala-Glu-Leu-Leu-Glu-
Asn-Leu-Leu-Glu-Lys-Phe-Leu-Asp-Leu-Val-Inp;

(SEQ. ID. NO. 20)
Lys-Leu-Lys-Gln-Lys-Nal-Ala-Glu-Leu-Leu-Glu-
Asn-Leu-Leu-Glu-Arg-Phe-Leu-Asp-Leu-Val-Inp;

(SEQ. ID. NO. 21)
Lys-Leu-Lys-Gln-Lys-Leu-Ala-Glu-Leu-Leu-Glu-
Gln-Leu-Leu-Glu-Lys-Phe-Leu-Asp-Leu-Val-Inp;

(SEQ. ID. NO. 22)
Orn-Leu-Orn-Gln-Orn-Leu-Ala-Glu-Leu-Leu-Glu-
Asn-Leu-Leu-Glu-Arg-Phe-Leu-Asp-Leu-Val-Inp;

(SEQ. ID. NO. 23)
Lys-Leu-Lys-Gln-Lys-Leu-Ala-Glu-Leu-Leu-Glu-
Asn-Trp-Leu-Glu-Arg-Phe-Leu-Asp-Leu-Val-Inp;

(SEQ. ID. NO. 24)
Lys-Leu-Lys-Gln-Lys-Leu-Ala-Glu-Leu-Leu-Glu-
Asn-Leu-Leu-Glu-Arg-Leu-Leu-Asp-Leu-Val-Inp;

(SEQ. ID. NO. 25)
Lys-Leu-Lys-Gln-Lys-Leu-Ala-Glu-Leu-Leu-Glu-
Gln-Leu-Leu-Glu-Lys-Phe-Leu-Glu-Leu-Val-Inp;

(SEQ. ID. NO. 26)
Lys-Leu-Lys-Gln-Lys-Leu-Ala-Glu-Leu-Leu-Glu-
Gln-Leu-Leu-Glu-Lys-Phe-Leu-Glu-Leu-Leu-Inp;

(SEQ. ID. NO. 28)
Lys-Leu-Lys-Gln-Lys-Leu-Ala-Glu-Leu-Aib-Glu-
Asn-Leu-Leu-Glu-Arg-Phe-Phe-Asp-Leu-Val-Inp;

(SEQ. ID. NO. 29)
Lys-Leu-Lys-Gln-Lys-Leu-Leu-Glu-Leu-Leu-Glu-
Asn-Leu-Leu-Glu-Arg-Phe-Leu-Asp-Leu-Val-Inp;

(SEQ. ID. NO. 30)
Lys-Leu-Lys-Gln-Lys-Leu-Ala-Glu-Nal-Leu-Glu-
Asn-Leu-Leu-Glu-Arg-Phe-Leu-Asp-Leu-Val-Inp;

(SEQ. ID. NO. 31)
Lys-Leu-Lys-Gln-Lys-Leu-Ala-Glu-Trp-Leu-Glu-
Asn-Leu-Leu-Glu-Arg-Phe-Leu-Asp-Leu-Val-Inp;

(SEQ. ID. NO. 32)
Orn-Leu-Orn-Gln-Orn-Leu-Ala-Glu-Leu-Leu-Glu-
Asn-Leu-Leu-Glu-Orn-Phe-Leu-Asp-Leu-Val-Inp;

(SEQ. ID. NO. 33)
Lys-Leu-Lys-Gln-Lys-Leu-Phe-Glu-Leu-Leu-Glu-
Asn-Leu-Leu-Glu-Arg-Phe-Leu-Asp-Leu-Val-Inp;

(SEQ. ID. NO. 36)
Lys-Leu-Lys-Arg-Leu-Ala-Asp-Leu-Leu-Glu-
Asn-Leu-Leu-Glu-Lys-Phe-Leu-Glu-Leu-Val-Inp;

(SEQ. ID. NO. 40)
Lys-Leu-Lys-Gln-Lys-Leu-Ala-Glu-Leu-Leu-Glu-
Gln-Leu-Leu-Asp-Lys-Phe-Leu-Glu-Leu-Ala-Inp;

(SEQ. ID. NO. 94)
Lys-Leu-Lys-Gln-Lys-Leu-Trp-Glu-Leu-Leu-Glu-
Asn-Leu-Leu-Glu-Arg-Phe-Leu-Asp-Leu-Val-Nip;

(SEQ. ID. NO. 95)
Lys-Leu-Lys-Gln-Lys-Leu-Ala-Glu-Leu-Gly-Glu-
Asn-Leu-Leu-Glu-Arg-Phe-Leu-Asp-Leu-Val-Nip;

(SEQ. ID. NO. 96)
Lys-Leu-Lys-Gln-Lys-Nal-Ala-Glu-Leu-Gly-Glu-
Asn-Leu-Leu-Glu-Arg-Phe-Leu-Asp-Leu-Val-Nip;

(SEQ. ID. NO. 97)
Lys-Leu-Lys-Gln-Lys-Leu-Trp-Glu-Leu-Gly-Glu-
Asn-Leu-Leu-Glu-Arg-Phe-Leu-Asp-Leu-Val-Nip;

(SEQ. ID. NO. 98)
Lys-Leu-Lys-Gln-Lys-Leu-Ala-Glu-Leu-Gly-Glu-
Asn-Trp-Leu-Glu-Arg-Phe-Leu-Asp-Leu-Val-Nip;

(SEQ. ID. NO. 99)
Orn-Leu-Orn-Gln-Orn-Leu-Ala-Glu-Leu-Gly-Glu-
Asn-Leu-Leu-Glu-Arg-Phe-Leu-Asp-Leu-Val-Nip;

(SEQ. ID. NO. 100)
Lys-Leu-Lys-Gln-Lys-Leu-Ala-Glu-Leu-Gly-Glu-
Asn-Leu-Leu-Glu-Arg-Phe-Phe-Asp-Leu-Val-Nip;

(SEQ. ID. NO. 101)
Lys-Leu-Lys-Gln-Lys-Leu-Ala-Glu-Leu-Gly-Glu-
Asn-Leu-Leu-Glu-Arg-Phe-Leu-Glu-Leu-Val-Nip;

(SEQ. ID. NO. 102)
Lys-Leu-Lys-Gln-Lys-Leu-Ala-Glu-Leu-Leu-Glu-
Asn-Leu-Gly-Glu-Arg-Phe-Leu-Asp-Leu-Val-Nip;

(SEQ. ID. NO. 103)
Lys-Leu-Lys-Gln-Lys-Leu-Ala-Glu-Leu-Leu-Glu-
Asn-Gly-Leu-Glu-Arg-Phe-Leu-Asp-Leu-Val-Nip;

(SEQ. ID. NO. 104)
Lys-Leu-Lys-Gln-Lys-Leu-Ala-Glu-Gly-Leu-Glu-
Asn-Leu-Leu-Glu-Arg-Phe-Leu-Asp-Leu-Val-Nip;

(SEQ. ID. NO. 105)
Lys-Leu-Lys-Gln-Lys-Leu-Gly-Glu-Leu-Leu-Glu-
Asn-Leu-Leu-Glu-Arg-Phe-Leu-Asp-Leu-Val-Nip;

(SEQ. ID. NO. 106)
Lys-Leu-Lys-Gln-Lys-Gly-Ala-Glu-Leu-Leu-Glu-
Asn-Leu-Leu-Glu-Arg-Phe-Leu-Asp-Leu-Val-Nip;

(SEQ. ID. NO. 107)
Lys-Leu-Lys-Gln-Lys-Leu-Nal-Glu-Leu-Leu-Glu-
Asn-Leu-Leu-Glu-Arg-Phe-Leu-Asp-Leu-Val-Nip;

(SEQ. ID. NO. 108)
Lys-Leu-Lys-Gln-Lys-Leu-Ala-Glu-Leu-Leu-Glu-
Asn-Leu-Leu-Glu-Arg-Phe-Leu-Asp-Leu-Val-Nip;

(SEQ. ID. NO. 110)
Lys-Leu-Lys-Gln-Lys-Leu-Ala-Glu-Leu-Aib-Glu-
Asn-Leu-Leu-Glu-Arg-Phe-Leu-Asp-Leu-Val-Nip;

(SEQ. ID. NO. 111)
Lys-Leu-Lys-Gln-Lys-Leu-Ala-Glu-Leu-Leu-Glu-
Asn-Leu-Leu-Glu-Lys-Phe-Leu-Asp-Leu-Val-Nip;

(SEQ. ID. NO. 112)
Lys-Leu-Lys-Gln-Lys-Nal-Ala-Glu-Leu-Leu-Glu-
Asn-Leu-Leu-Glu-Arg-Phe-Leu-Asp-Leu-Val-Nip;

(SEQ. ID. NO. 113)
Lys-Leu-Lys-Gln-Lys-Leu-Ala-Glu-Leu-Leu-Glu-
Gln-Leu-Leu-Glu-Lys-Phe-Leu-Asp-Leu-Val-Nip;

(SEQ. ID. NO. 114)
Orn-Leu-Orn-Gln-Orn-Leu-Ala-Glu-Leu-Leu-Glu-
Asn-Leu-Leu-Glu-Arg-Phe-Leu-Asp-Leu-Val-Nip;

-continued

```
                                          (SEQ. ID. NO. 115)
Lys-Leu-Lys-Gln-Lys-Leu-Ala-Glu-Leu-Leu-Glu-
Asn-Trp-Leu-Glu-Arg-Phe-Leu-Asp-Leu-Val-Nip;

(SEQ. ID. NO. 116)
Lys-Leu-Lys-Gln-Lys-Leu-Ala-Glu-Leu-Leu-Glu-
Asn-Leu-Leu-Glu-Arg-Leu-Leu-Asp-Leu-Val-Nip;

(SEQ. ID. NO. 117)
Lys-Leu-Lys-Gln-Lys-Leu-Ala-Glu-Leu-Leu-Glu-
Gln-Leu-Leu-Glu-Lys-Phe-Leu-Glu-Leu-Val-Nip;

(SEQ. ID. NO. 118)
Lys-Leu-Lys-Gln-Lys-Leu-Ala-Glu-Leu-Leu-Glu-
Gln-Leu-Leu-Glu-Lys-Phe-Leu-Glu-Leu-Leu-Nip;

(SEQ. ID. NO. 120)
Lys-Leu-Lys-Gln-Lys-Leu-Ala-Glu-Leu-Aib-Glu-
Asn-Leu-Leu-Glu-Arg-Phe-Phe-Asp-Leu-Val-Nip;

(SEQ. ID. NO. 121)
Lys-Leu-Lys-Gln-Lys-Leu-Leu-Glu-Leu-Leu-Glu-
Asn-Leu-Leu-Glu-Arg-Phe-Leu-Asp-Leu-Val-Nip;

(SEQ. ID. NO. 122)
Lys-Leu-Lys-Gln-Lys-Leu-Ala-Glu-Nal-Leu-Glu-
Asn-Leu-Leu-Glu-Arg-Phe-Leu-Asp-Leu-Val-Nip;

(SEQ. ID. NO. 123)
Lys-Leu-Lys-Gln-Lys-Leu-Ala-Glu-Trp-Leu-Glu-
Asn-Leu-Leu-Glu-Arg-Phe-Leu-Asp-Leu-Val-Nip;

(SEQ. ID. NO. 124)
Orn-Leu-Orn-Gln-Orn-Leu-Ala-Glu-Leu-Leu-Glu-
Asn-Leu-Leu-Glu-Orn-Phe-Leu-Asp-Leu-Val-Nip;

(SEQ. ID. NO. 125)
Lys-Leu-Lys-Gln-Lys-Leu-Phe-Glu-Leu-Leu-Glu-
Asn-Leu-Leu-Glu-Arg-Phe-Leu-Asp-Leu-Val-Nip;

(SEQ. ID. NO. 128)
Lys-Leu-Lys-Gln-Arg-Leu-Ala-Asp-Leu-Leu-Glu-
Asn-Leu-Leu-Glu-Lys-Phe-Leu-Glu-Leu-Val-Nip;
or (SEQ. ID. NO. 132)
Lys-Leu-Lys-Gln-Lys-Leu-Ala-Glu-Leu-Leu-Glu-
Gln-Leu-Leu-Asp-Lys-Phe-Leu-Glu-Leu-Ala-Nip,
``` or a pharmaceutically acceptable salt of one of the foregoing.

14. The peptide or pharmaceutically acceptable salt of the peptide of embodiment 5, wherein the peptide is a 23-residue peptide.

15. The peptide or pharmaceutically acceptable salt of the peptide of embodiment 14, wherein the peptide is:

```
                                          (SEQ. ID. NO. 17)
Lys-Lys-Leu-Lys-Gln-Lys-Leu-Ala-Glu-Leu-Leu-
Glu-Asn-Leu-Leu-Glu-Arg-Phe-Leu-Asp-Leu-Val-
Inp;
or (SEQ. ID. NO. 109)
Lys-Lys-Leu-Lys-Gln-Lys-Leu-Ala-Glu-Leu-Leu-
Glu-Asn-Leu-Leu-Glu-Arg-Phe-Leu-Asp-Leu-Val-
Nip,
``` or a pharmaceutically acceptable salt of one of the foregoing.

16. The peptide or pharmaceutically acceptable salt of the peptide of embodiment 5, wherein $X^1$ is absent and the peptide is a 22-residue peptide.

17. The peptide or pharmaceutically acceptable salt of the peptide of embodiment 16, wherein the peptide is:

```
                                          (SEQ. ID. NO. 34)
Lys-Leu-Lys-Gln-Leu-Ala-Glu-Leu-Leu-Glu-
Arg-Leu-Leu-Asp-Asn-Phe-Leu-Glu-Leu-Val-Inp;

(SEQ. ID. NO. 35)
Lys-Leu-Lys-Gln-Lys-Leu-Ala-Glu-Leu-Leu-Glu-
Arg-Leu-Leu-Asp-Asn-Phe-Leu-Glu-Leu-Val-Inp;

(SEQ. ID. NO. 126)
Lys-Leu-Lys-Gln-Lys-Leu-Ala-Glu-Leu-Leu-Glu-
Arg-Leu-Leu-Asp-Asn-Phe-Leu-Glu-Leu-Val-Nip;
or (SEQ. ID. NO. 127)
Lys-Leu-Lys-Gln-Lys-Leu-Ala-Glu-Leu-Leu-Glu-
Arg-Leu-Leu-Asp-Asn-Phe-Leu-Glu-Leu-Val-Nip,
``` or a pharmaceutically acceptable salt of one of the foregoing.

18. The peptide or pharmaceutically acceptable salt of the peptide of embodiment 16, wherein:

$X^9$ is Gln, Lys, D-Gln, D-Lys, an acidic achiral amino acid residue, an acidic D-amino acid residue, or an acidic L-amino acid residue;

$X^{12}$ is Asn, D-Asn, an acidic achiral amino acid residue, an acidic D-amino acid residue, or an acidic L-amino acid residue; and $X^{17}$ is Asn, Glu, D-Asn, D-Glu, a basic achiral amino acid residue, a basic D-amino acid residue, or a basic L-amino acid residue.

19. The peptide or pharmaceutically acceptable salt of the peptide of embodiment 16, wherein:

$X^9$ is Gln, Lys, D-Gln, D-Lys, an acidic achiral amino acid residue, an acidic D-amino acid residue, or an acidic L-amino acid residue;

$X^{12}$ is Asn, D-Asn, an acidic achiral amino acid residue, an acidic D-amino acid residue, or an acidic L-amino acid residue; and $X^{17}$ is Asn, Glu, D-Asn, D-Glu, a basic achiral amino acid residue, a basic D-amino acid residue, or a basic L-amino acid residue.

20. The peptide or pharmaceutically acceptable salt of the peptide of embodiment 16, wherein:

$X^2$ is Lys, Orn, D-Lys, or D-Orn;
$X^3$ is Leu or D-Leu;
$X^4$ is Lys, Orn, D-Lys, or D-Orn;
$X^5$ is Lys, Orn, Gln, Asn, D-Lys, D-Orn, D-Gln, or D-Asn;
$X^6$ is Lys, Orn, D-Lys, or D-Orn;
$X^7$ is Leu, Gly, Nal, D-Leu, or D-Nal;
$X^8$ is Ala, Trp, Gly, Leu, Phe, Nal, D-Ala, D-Trp, D-Leu, D-Phe, or D-Nal;
$X^9$ is Asp, Glu, Gln, Lys, D-Asp, D-Glu, D-Gln, or D-Lys;
$X^{11}$ is Leu, Gly, Aib, or D-Leu;
$X^{12}$ is Asp, Glu, Asn, D-Asp, D-Glu, or D-Asn;
$X^{13}$ is Asn, Gln, Glu, Arg, D-Asn, D-Gln, D-Glu, or D-Arg;
$X^{16}$ is Asp, Glu, D-Asp, or D-Glu;
$X^{17}$ is Lys, Arg, Orn, Asn, Glu, D-Lys, D-Arg, D-Orn, D-Asn, or D-Glu;
$X^{20}$ is Asp, Glu, D-Asp, or D-Glu; and
$X^{22}$ is Ala, Val, Leu, D-Ala, D-Val, or D-Leu.

21. The peptide or pharmaceutically acceptable salt of the peptide of embodiment 16, wherein:

$X^9$ is Glu or D-Glu;
$X^{12}$ is Glu or D-Glu;
$X^{13}$ is Asn, Glu, D-Asn, or D-Glu;
$X^{14}$ is Leu or D-Leu;
$X^{15}$ is Leu or D-Leu;
$X^{16}$ is Glu or D-Glu;
$X^{17}$ is Arg, Lys, D-Arg, or D-Lys;

$X^{18}$ is Phe or D-Phe;
$X^{19}$ is Leu or D-Leu;
$X^{21}$ is Leu or D-Leu; and
$X^{22}$ is Val or D-Val.

22. The peptide or pharmaceutically acceptable salt of the peptide of embodiment 16, wherein $X^{11}$ is Gly and each of $X^7$, $X^8$, $X^{10}$, $X^{14}$, and $X^{15}$ is other than Gly.

23. The peptide or pharmaceutically acceptable salt of the peptide of embodiment 16, wherein:
   $X^2$ is Lys, Orn, D-Lys, or D-Orn;
   $X^3$ is Leu or D-Leu;
   $X^4$ is Lys, Orn, D-Lys, or D-Orn;
   $X^5$ is Gln or D-Gln;
   $X^6$ is Lys, Orn, D-Lys, or D-Orn;
   $X^7$ is Leu, Nal, D-Leu, or D-Nal;
   $X^8$ is Ala, Trp, D-Ala, or D-Trp;
   $X^9$ is Glu or D-Glu;
   $X^{10}$ is Leu or D-Leu;
   $X^{11}$ is Gly;
   $X^{12}$ is Glu or D-Glu;
   $X^{13}$ is Asn or D-Asn;
   $X^{14}$ is Leu, Trp, D-Leu, or D-Trp;
   $X^{15}$ is Leu or D-Leu;
   $X^{16}$ is Glu or D-Glu;
   $X^{17}$ is Arg or D-Arg;
   $X^{18}$ is Phe or D-Phe;
   $X^{19}$ is Leu, Phe, D-Leu, or D-Phe;
   $X^{20}$ is Asp, Glu, D-Asp, or D-Glu;
   $X^{21}$ is Leu or D-Leu; and
   $X^{22}$ is Val or D-Val.

24. The peptide or pharmaceutically acceptable salt of the peptide of embodiment 20, wherein the peptide is:

```
                                        (SEQ. ID. NO. 2)
Lys-Leu-Lys-Gln-Lys-Leu-Trp-Glu-Leu-Leu-Glu-
Asn-Leu-Leu-Glu-Arg-Phe-Leu-Asp-Leu-Val-Inp;

(SEQ. ID. NO. 3)
Lys-Leu-Lys-Gln-Lys-Leu-Ala-Glu-Leu-Gly-Glu-
Asn-Leu-Leu-Glu-Arg-Phe-Leu-Asp-Leu-Val-Inp;

(SEQ. ID. NO. 4)
Lys-Leu-Lys-Gln-Lys-Nal-Ala-Glu-Leu-Gly-Glu-
Asn-Leu-Leu-Glu-Arg-Phe-Leu-Asp-Leu-Val-Inp;

(SEQ. ID. NO. 5)
Lys-Leu-Lys-Gln-Lys-Leu-Trp-Glu-Leu-Gly-Glu-
Asn-Leu-Leu-Glu-Arg-Phe-Leu-Asp-Leu-Val-Inp;

(SEQ. ID. NO. 6)
Lys-Leu-Lys-Gln-Lys-Leu-Ala-Glu-Leu-Gly-Glu-
Asn-Trp-Leu-Glu-Arg-Phe-Leu-Asp-Leu-Val-Inp;

(SEQ. ID. NO. 7)
Orn-Leu-Orn-Gln-Orn-Leu-Ala-Glu-Leu-Gly-Glu-
Asn-Leu-Leu-Glu-Arg-Phe-Leu-Asp-Leu-Val-Inp;

(SEQ. ID. NO. 8)
Lys-Leu-Lys-Gln-Lys-Leu-Ala-Glu-Leu-Gly-Glu-
Asn-Leu-Leu-Glu-Arg-Phe-Phe-Asp-Leu-Val-Inp;

(SEQ. ID. NO. 9)
Lys-Leu-Lys-Gln-Lys-Leu-Ala-Glu-Leu-Gly-Glu-
Asn-Leu-Leu-Glu-Arg-Phe-Leu-Glu-Leu-Val-Inp;

(SEQ. ID. NO. 94)
Lys-Leu-Lys-Gln-Lys-Leu-Trp-Glu-Leu-Leu-Glu-
Asn-Leu-Leu-Glu-Arg-Phe-Leu-Asp-Leu-Val-Nip;

(SEQ. ID. NO. 95)
Lys-Leu-Lys-Gln-Lys-Leu-Ala-Glu-Leu-Gly-Glu-
Asn-Leu-Leu-Glu-Arg-Phe-Leu-Asp-Leu-Val-Nip;

(SEQ. ID. NO. 96)
Lys-Leu-Lys-Gln-Lys-Nal-Ala-Glu-Leu-Gly-Glu-
Asn-Leu-Leu-Glu-Arg-Phe-Leu-Asp-Leu-Val-Nip;

(SEQ. ID. NO. 97)
Lys-Leu-Lys-Gln-Lys-Leu-Trp-Glu-Leu-Gly-Glu-
Asn-Leu-Leu-Glu-Arg-Phe-Leu-Asp-Leu-Val-Nip;

(SEQ. ID. NO. 98)
Lys-Leu-Lys-Gln-Lys-Leu-Ala-Glu-Leu-Gly-Glu-
Asn-Trp-Leu-Glu-Arg-Phe-Leu-Asp-Leu-Val-Nip;

(SEQ. ID. NO. 99)
Orn-Leu-Orn-Gln-Orn-Leu-Ala-Glu-Leu-Gly-Glu-
Asn-Leu-Leu-Glu-Arg-Phe-Leu-Asp-Leu-Val-Nip;

(SEQ. ID. NO. 100)
Lys-Leu-Lys-Gln-Lys-Leu-Ala-Glu-Leu-Gly-Glu-
Asn-Leu-Leu-Glu-Arg-Phe-Phe-Asp-Leu-Val-Nip;
or (SEQ. ID. NO. 101)
Lys-Leu-Lys-Gln-Lys-Leu-Ala-Glu-Leu-Gly-Glu-
Asn-Leu-Leu-Glu-Arg-Phe-Leu-Glu-Leu-Val-Nip,
``` or a pharmaceutically acceptable salt of one of the foregoing.

25. The peptide or pharmaceutically acceptable salt of the peptide of embodiment 16, wherein $X^{15}$ is Gly and each of $X^7$, $X^8$, $X^{10}$, $X^{11}$ and $X^{14}$ is other than Gly.

26. The peptide or pharmaceutically acceptable salt of the peptide of embodiment 25, wherein the peptide is:

```
                                       (SEQ. ID. NO. 10)
Lys-Leu-Lys-Gln-Lys-Leu-Ala-Glu-Leu-Leu-Glu-
Asn-Leu-Gly-Glu-Arg-Phe-Leu-Asp-Leu-Val-Inp;
or (SEQ. ID. NO. 102)
Lys-Leu-Lys-Gln-Lys-Leu-Ala-Glu-Leu-Leu-Glu-
Asn-Leu-Gly-Glu-Arg-Phe-Leu-Asp-Leu-Val-Nip,
``` or a pharmaceutically acceptable salt of one of the foregoing.

27. The peptide or pharmaceutically acceptable salt of the peptide of embodiment 16, wherein $X^{14}$ is Gly and each of $X^7$, $X^8$, $X^{10}$, $X^{11}$, and $X^{15}$ is other than Gly.

28. The peptide or pharmaceutically acceptable salt of the peptide of embodiment 27, wherein the peptide is:

```
                                       (SEQ. ID. NO. 11)
Lys-Leu-Lys-Gln-Lys-Leu-Ala-Glu-Leu-Leu-Glu-
Asn-Gly-Leu-Glu-Arg-Phe-Leu-Asp-Leu-Val-Inp;
or (SEQ. ID. NO. 103)
Lys-Leu-Lys-Gln-Lys-Leu-Ala-Glu-Leu-Leu-Glu-
Asn-Gly-Leu-Glu-Arg-Phe-Leu-Asp-Leu-Val-Nip,
``` or a pharmaceutically acceptable salt of one of the foregoing.

29. The peptide or pharmaceutically acceptable salt of the peptide of embodiment 16, wherein $X^{10}$ is Gly and each of $X^7$, $X^8$, $X^{11}$, $X^{14}$, and $X^{15}$ is other than Gly.

30. The peptide or pharmaceutically acceptable salt of the peptide of embodiment 29, wherein the peptide is:

```
                                       (SEQ. ID. NO. 12)
Lys-Leu-Lys-Gln-Lys-Leu-Ala-Glu-Gly-Leu-Glu-
Asn-Leu-Leu-Glu-Arg-Phe-Leu-Asp-Leu-Val-Inp;
or
```

```
                                            (SEQ. ID. NO. 104)
Lys-Leu-Lys-Gln-Lys-Leu-Ala-Glu-Gly-Leu-Glu-
Asn-Leu-Leu-Glu-Arg-Phe-Leu-Asp-Leu-Val-Nip,
``` or
a pharmaceutically acceptable salt of one of the foregoing.

31. The peptide or pharmaceutically acceptable salt of the peptide of embodiment 16, wherein $X^8$ is Gly and each of $X^7$, $X^{10}$, $X^{11}$, $X^{14}$ and $X^{15}$ is other than Gly.

32. The peptide or pharmaceutically acceptable salt of the peptide of embodiment 31, wherein the peptide is:

```
                                             (SEQ. ID. NO. 13)
Lys-Leu-Lys-Gln-Lys-Leu-Gly-Glu-Leu-Leu-Glu-
Asn-Leu-Leu-Glu-Arg-Phe-Leu-Asp-Leu-Val-Inp;
or
                                            (SEQ. ID. NO. 105)
Lys-Leu-Lys-Gln-Lys-Leu-Gly-Glu-Leu-Leu-Glu-
Asn-Leu-Leu-Glu-Arg-Phe-Leu-Asp-Leu-Val-Nip,
``` or
a pharmaceutically acceptable salt of one of the foregoing.

33. The peptide or pharmaceutically acceptable salt of the peptide of embodiment 16, wherein $X^7$ is Gly and each of $X^8$, $X^{10}$, $X^{11}$, $X^{14}$, and $X^{15}$ is other than Gly.

34. The peptide or pharmaceutically acceptable salt of the peptide of embodiment 33, wherein the peptide is:

```
                                             (SEQ. ID. NO. 14)
Lys-Leu-Lys-Gln-Lys-Gly-Ala-Glu-Leu-Leu-Glu-
Asn-Leu-Leu-Glu-Arg-Phe-Leu-Asp-Leu-Val-Inp;
or
                                            (SEQ. ID. NO. 106)
Lys-Leu-Lys-Gln-Lys-Gly-Ala-Glu-Leu-Leu-Glu-
Asn-Leu-Leu-Glu-Arg-Phe-Leu-Asp-Leu-Val-Nip,
``` or
a pharmaceutically acceptable salt of one of the foregoing.

35. The peptide or pharmaceutically acceptable salt of the peptide of embodiment 1, wherein the peptide is:

```
                                             (SEQ. ID. NO. 16)
Lys-Leu-Lys-Gln-Lys-Leu-Ala-Glu-Leu-Leu-Glu-
Asn-Leu-Leu-Glu-Arg-Phe-Leu-Asp-Leu-Val-Inp;
or
                                            (SEQ. ID. NO. 108)
Lys-Leu-Lys-Gln-Lys-Leu-Ala-Glu-Leu-Leu-Glu-
Asn-Leu-Leu-Glu-Arg-Phe-Leu-Asp-Leu-Val-Nip,
``` or
a pharmaceutically acceptable salt of one of the foregoing.

36. A 15- to 22-residue peptide having the following Formula II $$R^1-Y^1-X^1-X^2-X^3-X^4-X^5-X^6-X^7-X^8-X^9-X^{10}-X^{11}-X^{12}-X^{13}-X^{14}-X^{15}-X^{16}-X^{17}-X^{18}-Y^2R^2, \quad \text{Formula II}$$

and pharmaceutically acceptable salts thereof, wherein:
$X^1$ is an achiral, D-, or L-basic amino acid residue;
$X^2$ is Leu or D-Leu;
$X^3$ is an achiral, D-, or L-basic amino acid residue;
$X^4$ is Gln, Asn, D-Gln, or D-Asn;
$X^5$ is Leu, D-Leu, or an achiral, D-, or L-basic amino acid amino acid residue;
$X^6$ is Leu, Trp, Phe, D-Leu, D-Trp, or D-Phe;
$X^7$ is an achiral, D-, or L-acidic amino acid residue;
$X^8$ is Asn, D-Asn, or an achiral, D-, or L-acidic amino acid residue;
$X^9$ is Leu, Trp, D-Leu, or D-Trp;
$X^{10}$ is Leu, Trp, D-Leu, or D-Trp;
$X^{11}$ is an achiral, D-, or L-acidic amino acid residue;
$X^{12}$ is an achiral, D-, or L-basic amino acid residue;
$X^{13}$ is Leu, Phe, D-Leu, or D-Phe;
$X^{14}$ is Leu, Phe, D-Leu, or D-Phe;
$X^{15}$ is an achiral, D-, or L-acidic amino acid residue;
$X^{16}$ is Leu or D-Leu;
$X^{17}$ is an achiral, D-, or L-aliphatic amino acid residue;
$X^{18}$ is Inp, Nip, azPro, Pip, azPip, D-Nip, or D-Pip;
$Y^1$ is absent or an amino acid sequence having from 1 to 4 residues;
$Y^2$ is absent;
$R^1$ is H or an amino protecting group;
$R^2$ is OH or a carboxyl protecting group;
wherein zero to three of residues $X^1$ to $X^{17}$ are absent; and wherein:
a) each chiral amino acid residue is an L-amino acid residue;
b) each chiral amino acid residue is a D-amino acid residue;
c) each chiral amino acid residue is an L-amino acid residue, except that one or more of each chiral terminal amino acid residue and each chiral amino acid residue immediately adjacent thereto is a D-amino acid residue; or
d) each chiral amino acid residue is an D-amino acid residue, except that one or more of each chiral terminal amino acid residue and each chiral amino acid residue immediately adjacent thereto is an L-amino acid residue.

37. The peptide or pharmaceutically acceptable salt of the peptide of embodiment 36, wherein $X^{17}$ is Ala, Leu, Val, D-Ala, D-Leu, or D-Val.

38. The peptide or pharmaceutically acceptable salt of the peptide of embodiment 36, wherein:
$X^1$ is His, Lys, Arg, D-His, D-Lys, or D-Arg;
$X^3$ is Lys, Arg, Orn, D-Lys, D-Arg, or D-Orn;
$X^5$ is Lys, Arg, Orn, D-Lys, D-Arg, or D-Orn;
$X^7$ is Glu or D-Glu;
$X^8$ is Asn, Glu, D-Asn, or D-Glu;
$X^{11}$ is Asp, Glu, D-Asp, or D-Glu;
$X^{12}$ is Arg, Lys, Orn, D-Arg, D-Lys, or D-Orn; and
$X^{15}$ is Asp, Glu, D-Asp, or D-Glu.

39. The peptide or pharmaceutically acceptable salt of the peptide of embodiment 38, wherein $X^{13}$ is Phe or D-Phe.

40. The peptide or pharmaceutically acceptable salt of the peptide of embodiment 36, wherein the peptide is an 18-residue peptide.

41. The peptide or pharmaceutically acceptable salt of the peptide of embodiment 40, wherein $R^1$ is H and $R^2$ is OH.

42. The peptide or pharmaceutically acceptable salt of the peptide of embodiment 41, wherein:
$X^1$ is Arg, Lys, Orn, D-Arg, D-Lys, or D-Orn;
$X^3$ is Arg, Lys, Orn, D-Arg, D-Lys, or D-Orn;
$X^5$ is Arg, Lys, Orn, D-Arg, D-Lys, or D-Orn;
$X^7$ is Glu or D-Glu;
$X^8$ is Glu, Asn, D-Glu, or D-Asn;
$X^{11}$ is Glu, Asp, D-Glu, or D-Asp;
$X^{12}$ is Arg, Lys, Orn, D-Arg, D-Lys, or D-Orn;
$X^{15}$ is Asp, Glu, D-Asp, or D-Glu; and
$X^{17}$ is Ala, Val, Leu, D-Ala, D-Val, or D-Leu.

43. The peptide or pharmaceutically acceptable salt of the peptide of embodiment 36, wherein the peptide is:

```
                                             (SEQ. ID. NO. 53)
Lys-Leu-Lys-Gln-Leu-Leu-Glu-Asn-Leu-Leu-Glu-
Arg-Phe-Leu-Asp-Leu-Val-Inp;
```

-continued (SEQ. ID. NO. 54)
Lys-Leu-Lys-Gln-Lys-Leu-Glu-Glu-Leu-Leu-Glu-Arg-Phe-Leu-Asp-Leu-Val-Inp;

(SEQ. ID. NO. 145)
Lys-Leu-Lys-Gln-Leu-Leu-Glu-Asn-Leu-Leu-Glu-Arg-Phe-Leu-Asp-Leu-Val-Nip;
or (SEQ. ID. NO. 146)
Lys-Leu-Lys-Gln-Lys-Leu-Glu-Glu-Leu-Leu-Glu-Arg-Phe-Leu-Asp-Leu-Val-Nip, or a pharmaceutically acceptable salt of one of the foregoing.

44. The peptide or pharmaceutically acceptable salt of the peptide of embodiment 36, wherein the peptide is:

(SEQ. ID. NO. 65)
$H_3C(O)$C-Lys-Leu-Lys-Gln-Lys-Leu-Glu-Glu-Leu-Leu-Glu-Arg-Leu-Leu-Asp-Leu-Val-Inp-$NH_2$;

(SEQ. ID. NO. 66)
$H_3C(O)$C-Lys-Leu-Lys-Gln-Lys-Leu-Glu-Glu-Leu-Leu-Glu-Lys-Phe-Leu-Asp-Leu-Val-Inp-$NH_2$;

(SEQ. ID. NO. 67)
$H_3C(O)$C-Lys-Leu-Lys-Gln-Lys-Leu-Glu-Glu-Leu-Leu-Glu-Arg-Phe-Leu-Asp-Leu-Val-Inp-$NH_2$;

(SEQ. ID. NO. 68)
$H_3C(O)$C-Lys-Leu-Lys-Gln-Lys-Leu-Glu-Glu-Leu-Leu-Glu-Arg-Phe-Leu-Glu-Leu-Val-Inp-$NH_2$;

(SEQ. ID. NO. 69)
$H_3C(O)$C-Lys-Leu-Lys-Gln-Lys-Leu-Glu-Glu-Leu-Leu-Glu-Lys-Phe-Leu-Glu-Leu-Val-Inp-$NH_2$;

(SEQ. ID. NO. 70)
$H_3C(O)$C-Lys-Leu-Lys-Asn-Lys-Leu-Glu-Glu-Leu-Leu-Glu-Arg-Phe-Leu-Asp-Leu-Val-Inp-$NH_2$;

(SEQ. ID. NO. 71)
$H_3C(O)$C-Lys-Leu-Lys-Gln-Lys-Leu-Glu-Glu-Leu-Leu-Glu-Arg-Phe-Leu-Asp-Leu-Leu-Inp-$NH_2$;

(SEQ. ID. NO. 72)
$H_3C(O)$C-Lys-Leu-Lys-Gln-Lys-Leu-Glu-Glu-Trp-Leu-Glu-Arg-Phe-Leu-Asp-Leu-Val-Inp-$NH_2$;

(SEQ. ID. NO. 73)
$H_3C(O)$C-Lys-Leu-Lys-Gln-Lys-Leu-Glu-Glu-Leu-Leu-Glu-Lys-Phe-Leu-Asp-Leu-Leu-Inp-$NH_2$;

(SEQ. ID. NO. 74)
$H_3C(O)$C-Arg-Leu-Lys-Gln-Arg-Leu-Glu-Glu-Leu-Leu-Asp-Lys-Phe-Leu-Glu-Leu-Ala-Inp-$NH_2$;

(SEQ. ID. NO. 75)
$H_3C(O)$C-Lys-Leu-Lys-Gln-Lys-Leu-Glu-Glu-Leu-Leu-Glu-Arg-Phe-Phe-Asp-Leu-Val-Inp-$NH_2$;

(SEQ. ID. NO. 76)
$H_3C(O)$C-Lys-Leu-Lys-Gln-Lys-Leu-Glu-Glu-Leu-Trp-Glu-Arg-Phe-Leu-Asp-Leu-Val-Inp-$NH_2$;

(SEQ. ID. NO. 77)
$H_3C(O)$C-Lys-Leu-Lys-Gln-Lys-Leu-Glu-Glu-Leu-Leu-Glu-Lys-Leu-Leu-Glu-Leu-Leu-Inp-$NH_2$;

(SEQ. ID. NO. 78)
$H_3C(O)$C-Lys-Leu-Lys-Gln-Lys-Leu-Glu-Glu-Leu-Leu-Glu-Lys-Leu-Leu-Glu-Leu-Val-Inp-$NH_2$;

(SEQ. ID. NO. 79)
$H_3C(O)$C-Lys-Leu-Arg-Gln-Arg-Leu-Glu-Glu-Leu-Leu-Asp-Lys-Phe-Leu-Glu-Leu-Ala-Inp-$NH_2$;

(SEQ. ID. NO. 80)
$H_3C(O)$C-Orn-Leu-Orn-Gln-Orn-Leu-Glu-Glu-Leu-Leu-Glu-Arg-Phe-Leu-Asp-Leu-Val-Inp-$NH_2$;

(SEQ. ID. NO. 81)
$H_3C(O)$C-Lys-Leu-Orn-Gln-Orn-Leu-Glu-Glu-Leu-Leu-Glu-Orn-Phe-Leu-Asp-Leu-Val-Inp-$NH_2$;

(SEQ. ID. NO. 82)
$H_3C(O)$C-Lys-Leu-Arg-Gln-Arg-Phe-Glu-Glu-Leu-Leu-Asp-Lys-Phe-Leu-Glu-Leu-Ala-Inp-$NH_2$;

(SEQ. ID. NO. 83)
$H_3C(O)$C-Lys-Leu-Lys-Gln-Lys-Trp-Glu-Glu-Leu-Leu-Glu-Arg-Phe-Leu-Asp-Leu-Val-Inp-$NH_2$;

(SEQ. ID. NO. 84)
$H_3C(O)$C-Lys-Leu-Lys-Gln-Leu-Leu-Glu-Asn-Leu-Leu-Glu-Arg-Phe-Leu-Asp-Leu-Val-Inp-$NH_2$;

(SEQ. ID. NO. 87)
$H_3C(O)$C-Lys-Leu-Lys-Gln-Lys-Leu-Glu-Glu-Leu-Leu-Glu-Lys-Phe-Leu-Glu-Leu-Leu-Inp-$NH_2$;

(SEQ. ID. NO. 88)
$H_3C(O)$C-Lys-Leu-Lys-Gln-Glu-Leu-Leu-Glu-Arg-Phe-Leu-Asp-Leu-Val-Inp-$NH_2$;

(SEQ. ID. NO. 89)
$H_3C(O)$C-Lys-Gln-Lys-Leu-Glu-Glu-Leu-Leu-Glu-Arg-Phe-Leu-Asp-Leu-Val-Inp-$NH_2$;

(SEQ. ID. NO. 157)
$H_3C(O)$C-Lys-Leu-Lys-Gln-Lys-Leu-Glu-Glu-Leu-Leu-Glu-Arg-Leu-Leu-Asp-Leu-Val-Nip-$NH_2$;

(SEQ. ID. NO. 158)
$H_3C(O)$C-Lys-Leu-Lys-Gln-Lys-Leu-Glu-Glu-Leu-Leu-Glu-Lys-Phe-Leu-Asp-Leu-Val-Nip-$NH_2$;

(SEQ. ID. NO. 159)
$H_3C(O)$C-Lys-Leu-Lys-Gln-Lys-Leu-Glu-Glu-Leu-Leu-Glu-Arg-Phe-Leu-Asp-Leu-Val-Nip-$NH_2$;

(SEQ. ID. NO. 160)
$H_3C(O)$C-Lys-Leu-Lys-Gln-Lys-Leu-Glu-Glu-Leu-Leu-Glu-Arg-Phe-Leu-Glu-Leu-Val-Nip-$NH_2$;

(SEQ. ID. NO. 161)
$H_3C(O)$C-Lys-Leu-Lys-Gln-Lys-Leu-Glu-Glu-Leu-Leu-Glu-Lys-Phe-Leu-Glu-Leu-Val-Nip-$NH_2$;

(SEQ. ID. NO. 162)
$H_3C(O)$C-Lys-Leu-Lys-Asn-Lys-Leu-Glu-Glu-Leu-Leu-Glu-Arg-Phe-Leu-Asp-Leu-Val-Nip-$NH_2$;

(SEQ. ID. NO. 163)
$H_3C(O)$C-Lys-Leu-Lys-Gln-Lys-Leu-Glu-Glu-Leu-Leu-Glu-Arg-Phe-Leu-Asp-Leu-Leu-Nip-$NH_2$;

(SEQ. ID. NO. 164)
$H_3C(O)$C-Lys-Leu-Lys-Gln-Lys-Leu-Glu-Glu-Trp-Leu-Glu-Arg-Phe-Leu-Asp-Leu-Val-Nip-$NH_2$;

(SEQ. ID. NO. 165)
$H_3C(O)$C-Lys-Leu-Lys-Gln-Lys-Leu-Glu-Glu-Leu-Leu-Glu-Lys-Phe-Leu-Asp-Leu-Leu-Nip-$NH_2$;

(SEQ. ID. NO. 166)
$H_3C(O)$C-Arg-Leu-Lys-Gln-Arg-Leu-Glu-Glu-Leu-Leu-Asp-Lys-Phe-Leu-Glu-Leu-Ala-Nip-$NH_2$;

(SEQ. ID. NO. 167)
$H_3C(O)$C-Lys-Leu-Lys-Gln-Lys-Leu-Glu-Glu-Leu-Leu-Glu-Arg-Phe-Phe-Asp-Leu-Val-Nip-$NH_2$;

(SEQ. ID. NO. 168)
$H_3C(O)$C-Lys-Leu-Lys-Gln-Lys-Leu-Glu-Glu-Leu-Leu-Glu-Lys-Leu-Leu-Glu-Leu-Leu-Nip-$NH_2$;

```
                                        (SEQ. ID. NO. 169)
H₃C(O)C-Lys-Leu-Lys-Gln-Lys-Leu-Glu-Glu-Leu-
Leu-Glu-Lys-Leu-Leu-Glu-Leu-Val-Nip-NH₂;

(SEQ. ID. NO. 170)
H₃C(O)C-Lys-Leu-Arg-Gln-Arg-Leu-Glu-Glu-Leu-
Leu-Asp-Lys-Phe-Leu-Glu-Leu-Ala-Nip-NH₂;

(SEQ. ID. NO. 171)
H₃C(O)C-Orn-Leu-Orn-Gln-Orn-Leu-Glu-Glu-Leu-
Leu-Glu-Arg-Phe-Leu-Asp-Leu-Val-Nip-NH₂;

(SEQ. ID. NO. 172)
H₃C(O)C-Lys-Leu-Orn-Gln-Orn-Leu-Glu-Glu-Leu-
Leu-Glu-Orn-Phe-Leu-Asp-Leu-Val-Nip-NH₂;

(SEQ. ID. NO. 173)
H₃C(O)C-Lys-Leu-Arg-Gln-Arg-Phe-Glu-Glu-Leu-
Leu-Asp-Lys-Phe-Leu-Glu-Leu-Ala-Nip-NH₂;

(SEQ. ID. NO. 174)
H₃C(O)C-Lys-Leu-Lys-Gln-Lys-Trp-Glu-Glu-Leu-
Leu-Glu-Arg-Phe-Leu-Asp-Leu-Val-Nip-NH₂;

(SEQ. ID. NO. 175)
H₃C(O)C-Lys-Leu-Lys-Gln-Leu-Leu-Glu-Asn-Leu-
Leu-Glu-Arg-Phe-Leu-Asp-Leu-Val-Nip-NH₂;

(SEQ. ID. NO. 176)
H₃C(O)C-Lys-Leu-Lys-Gln-Lys-Leu-Glu-Glu-Gly-
Leu-Glu-Arg-Phe-Leu-Asp-Leu-Val-Nip-NH₂;

(SEQ. ID. NO. 179)
H₃C(O)C-Lys-Leu-Lys-Gln-Lys-Leu-Glu-Glu-Leu-
Leu-Glu-Lys-Phe-Leu-Glu-Leu-Leu-Nip-NH₂;

(SEQ. ID. NO. 180)
H₃C(O)C-Lys-Leu-Lys-Gln-Glu-Leu-Leu-Glu-Arg-
Phe-Leu-Asp-Leu-Val-Nip-NH₂;
or (SEQ. ID. NO. 181)
H₃C(O) H₃C(O) H₃C(O) H₃C(O)C-Lys-Gln-Lys-Leu-
Glu-Glu-Leu-Leu-Glu-Arg-Phe-Leu-Asp-Leu-Val-
Nip-NH₂,
``` or a pharmaceutically acceptable salt of one of the foregoing.

45. A 22- to 29-residue peptide having the following Formula III

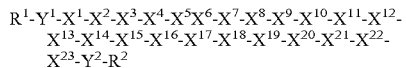

Formula III or a pharmaceutically acceptable salt thereof, wherein:
$X^1$ is absent or an achiral, D-, or L-basic amino acid residue;
$X^2$ is an achiral, D-, or L-basic amino acid residue;
$X^3$ is Leu or D-Leu;
$X^4$ is an achiral, D-, or L-basic amino acid residue;
$X^5$ is an achiral, D-, or L-basic amino acid residue;
$X^6$ is Gln, Asn, D-Gln, or D-Asn;
$X^7$ is Leu or D-Leu;
$X^8$ is Ala or D-Ala;
$X^9$ is Asp or D-Asp;
$X^{10}$ is Leu, Phe, Gly, D-Leu, or D-Phe;
$X^{11}$ is Gly, Leu, or D-Leu;
$X^{12}$ is Arg or D-Arg;
$X^{13}$ is an achiral, D-, or L-acidic amino acid residue;
$X^{14}$ is Leu, Trp, Gly, D-Leu, or D-Trp;
$X^{15}$ is Leu or D-Leu;
$X^{16}$ is Gln or D-Gln;
$X^{17}$ is Glu, Leu, D-Glu, or D-Leu;
$X^{18}$ is Leu, Phe, D-Leu, or D-Phe;
$X^{19}$ is an achiral, D-, or L-aliphatic amino acid residue;
$X^{20}$ is Glu or D-Glu;
$X^{21}$ is Leu, Phe, D-Leu, or D-Phe;
$X^{22}$ is an achiral, D-, or L-aliphatic amino acid residue;
$X^{23}$ is Inp, Nip, azPro, Pip, azPip, D-Nip, or D-Pip;
$Y^1$ is absent or an amino acid sequence having from 1 to 7 residues;
$Y^2$ is absent or an amino acid sequence having from 1 to 7 residues;
$R^1$ is H or an amino protecting group;
$R^2$ is OH or a carboxyl protecting group;
wherein:
a) each chiral amino acid residue is an L-amino acid residue;
b) each chiral amino acid residue is a D-amino acid residue;
c) each chiral amino acid residue is an L-amino acid residue, except that one or more of each chiral terminal amino acid residue and each chiral amino acid residue immediately adjacent thereto is a D-amino acid residue; or
d) each chiral amino acid residue is a D-amino acid residue, except that one or more of each chiral terminal amino acid residue and each chiral amino acid residue immediately adjacent thereto is an L-amino acid residue.

46. The peptide or pharmaceutically acceptable salt of the peptide of embodiment 45, wherein the peptide is a 22- or 23-residue peptide.

47. The peptide or pharmaceutically acceptable salt of the peptide of embodiment 46, wherein the peptide is a 22-residue peptide.

48. The peptide or pharmaceutically acceptable salt of the peptide of embodiment 47, wherein $X^{22}$ is Val, Leu, D-Val, or D-Leu.

49. The peptide or pharmaceutically acceptable salt of the peptide of embodiment 47, wherein:
$X^2$ is Lys or D-Lys;
$X^4$ is Lys or D-Lys;
$X^5$ is Lys or D-Lys;
$X^{13}$ is Glu or D-Glu;
$X^{18}$ is Phe or D-Phe;
$X^{19}$ is Leu or D-Leu; and
$X^{22}$ is Ala, Leu, Val, D-Ala, D-Leu, or D-Val.

50. The peptide or pharmaceutically acceptable salt of the peptide of embodiment 47, wherein:
$X^2$ is Lys or D-Lys;
$X^4$ is Lys or D-Lys;
X5 is Lys or D-Lys;
$X^{13}$ is Glu or D-Glu;
$X^{18}$ is Phe or D-Phe;
$X^{19}$ is Leu or D-Leu; and
$X^{22}$ is Ala, Leu, Val, D-Ala, D-Leu, or D-Val.

51. The peptide or pharmaceutically acceptable salt of the peptide of embodiment 47, wherein $X^{13}$ and $X^{17}$ are Glu or D-Glu.

52. The peptide or pharmaceutically acceptable salt of the peptide of embodiment 46, wherein:
$X^1$ is absent;
$X^2$ is Lys or D-Lys;
$X^4$ is Lys or D-Lys;
$X^5$ is Lys or D-Lys;
$X^{18}$ is Phe or D-Phe;
$X^{19}$ is Leu or D-Leu; and
$X^{22}$ is Val or D-Val.

53. The peptide or pharmaceutically acceptable salt of the peptide of embodiment 47, wherein $X^{13}$ or $X^{17}$ is Glu or D-Glu.

54. The peptide or pharmaceutically acceptable salt of the peptide of embodiment 47, wherein $X^{22}$ is Val or D-Val and $X^6$ is Gln or D-Gln.

55. The peptide or pharmaceutically acceptable salt of the peptide of embodiment 47, wherein $X^{22}$ is Val or D-Val or $X^6$ is Gln or D-Gln.

56. The peptide or pharmaceutically acceptable salt of the peptide of embodiment 47, wherein only one of $X^{10}$, $X^{11}$ and $X^{14}$ is Gly.

57. The peptide or pharmaceutically acceptable salt of the peptide of embodiment 45, wherein the peptide is:

```
                                       (SEQ. ID. NO. 197)
Lys-Leu-Lys-Lys-Gln-Leu-Ala-Asp-Leu-Leu-Arg-
Glu-Leu-Leu-Gln-Glu-Phe-Leu-Glu-Leu-Val-Inp;
or (SEQ. ID. NO. 211)
Lys-Leu-Lys-Lys-Gln-Leu-Ala-Asp-Leu-Leu-Arg-
Glu-Leu-Leu-Gln-Glu-Phe-Leu-Glu-Leu-Val-Nip,
``` or a pharmaceutically acceptable salt of one of the foregoing.

58. The peptide or pharmaceutically acceptable salt of the peptide of embodiment 47, wherein $X^{10}$ is Gly and $X^{17}$ is Glu or D-Glu.

59. The peptide or pharmaceutically acceptable salt of the peptide of embodiment 47, wherein each of $X^{10}$, $X^{11}$ and $X^{14}$ is other than Gly.

60. The peptide or pharmaceutically acceptable salt of the peptide of embodiment 47, wherein $X^{17}$ is Leu or D-Leu.

61. The peptide or pharmaceutically acceptable salt of the peptide of embodiment 60, wherein $X^{14}$ is Trp or D-Trp and $X^{10}$ is Leu, Phe, D-Leu, or D-Phe.

62. The peptide or pharmaceutically acceptable salt of the peptide of embodiment 60, wherein $X^{14}$ is Trp or D-Trp or $X^{10}$ is Leu, Phe, D-Leu, or D-Phe.

63. The peptide or pharmaceutically acceptable salt of the peptide of embodiment 45, wherein $R^1$ is H and $R^2$ is OH.

64. The peptide of any one of embodiments 1 to 63, wherein the peptide is in the form of a pharmaceutically acceptable salt.

65. The peptide of embodiment 64, wherein the salt is a metal salt or organic amine salt.

66. The peptide of embodiment 65, wherein the metal is an alkali metal or alkaline earth metal.

67. The peptide of embodiment 65, wherein the metal is lithium, sodium, potassium, magnesium, calcium, aluminum or zinc.

68. The peptide of embodiment 65, wherein the organic amine is triethylamine, ethanolamine, diethanolamine, triethanolamine, morpholine, N-methylpiperidine, N-ethylpiperidine, or dibenzylamine.

69. The peptide of embodiment 64, wherein the salt is an acid addition salt.

70. The peptide of embodiment 69, wherein the acid addition salt is a hydrochloride, hydrobromide, hydroiodide, nitrate, sulfate, sulfite, bisulfate, phosphate, acid phosphate, isonicotinate, lactate, salicylate, tartrate, bitartrate, ascorbate, gentisinate, gluconate, glucaronate, saccarate, formate, benzoate, glutamate, pantothenate, acetate, fumarate, succinate, methanesulfonate, ethanesulfonate, benzenesulfonate, p-toluylsulfonate, citrate, or maleate salt.

71. The peptide or pharmaceutically acceptable salt of the peptide of any one of embodiments 1 to 63, wherein $R^1$ is an amino protecting group.

72. The peptide or pharmaceutically acceptable salt of the peptide of claim 71, wherein the amino protecting group is dansyl; methoxycarbonyl; ethoxycarbonyl; 9-fluorenylmethoxycarbonyl; 2-chloroethoxycarbonyl; 2,2,2-trichloroethoxycarbonyl; 2-phenylethoxycarbonyl; t-butoxycarbonyl; benzyloxycarbonyl; p-methoxybenzyloxycarbonyl; p-nitrobenzyloxycarbonyl; o-nitrobenzyloxycarbonyl; p-bromobenzyloxycarbonyl; p-chlorobenzyloxycarbonyl; p-iodobenzyloxycarbonyl; 2,4-dichlorobenzyloxycarbonyl; diphenylmethoxycarbonyl; 3,5-dimethoxybenzyloxycarbonyl; phenoxycarbonyl; 2,4,6-tri-t-butylpenoxycarbonyl; 2,4,6-trimethylbenzyloxycarbonyl; formyl; acetyl; chloroacetyl; trichloroacetyl; trifluoroacetyl; phenylacetyl; picolinoyl; benzoyl; p-phenylbenzoyl; phthaloyl; methyl; t-butyl; allyl; [2-(trimethylsilyl)ethoxy]methyl; 2,4-dimethoxybenzyl; 2,4-dinitrophenyl; benzyl; 4-methoxybenzyl; diphenylmethyl; triphenylmethyl; benzenesulfenyl; o-nitrobenzenesulfenyl; 2,4-dinitrobenzenesulfenyl; p-toluenesulfonyl; benzenesulfonyl; 2,3,6-trimethyl-4-methoxybenzenesulfonyl; 2,4,6-trimethoxybenzenesulfonyl; 2,6-dimethyl-4-methoxybenzenesulfonyl; pentamethylbenzenesulfonyl; 4-methoxybenzenesulfonyl; 2,4,6-trimethylbenzenesulfonyl; or benzylsulfonyl.

73. The peptide or pharmaceutically acceptable salt of the peptide of any one of embodiments 1 to 63, wherein $R^2$ is a carboxyl protecting group.

74. The peptide or pharmaceutically acceptable salt of the peptide of claim 73, wherein the carboxyl protecting group is methoxy; ethoxy; 9-fluorenylmethoxy; methoxymethoxy; methylthiomethoxy; tetrahydropyranoxy; tetrahydrofuranoxy; methoxyethoxymethoxy; benzyloxymethoxy; phenacyloxy; p-bromophenacyloxy; cc-methylphenacyloxy; p-methoxyphenacyloxy; desyloxy; 2-chloroethoxy; 2,2,2-thrichloroethoxy, 2-methylthioethoxy; 2-(ptoluenesulfonyl) methoxy; t-butoxy; cyclopentoxy; cyclohexoxy; allyloxy; methallyloxy; cinnamoxy; cc-methylcinnamoxy; phenoxy; 2,6-dimethylphenoxy; 2,6-diisopropylphenoxy; benzyloxy; triphenylmethoxy; diphenylmethoxy; 2,4,6-trimethylbenzyloxy; p-bromobenzyloxy; o-nitrobenzyloxy; N,N-dimethylamido; pyrrolidinyl; or piperidinyl.

75. The peptide or pharmaceutically acceptable salt of the peptide of any one of embodiments 1 to 63, wherein one or more of the peptide's —NH$_2$ or —COOH groups are protected with a protecting group.

76. A composition comprising an effective amount of the peptide or pharmaceutically acceptable salt of the peptide of any one of embodiments 1 to 75, and a pharmaceutically acceptable carrier or vehicle.

77. A method for treating or preventing dyslipidemia, comprising administering an effective amount of the peptide or a pharmaceutically acceptable salt of the peptide of any one of embodiments 1 to 75 to a mammal in need thereof 78. The method of embodiment 77, wherein the dyslipidemia is hyperproteinemia, high low-density lipoprotein serum concentration, high very low-density lipoprotein serum concentration, hyperlipidemia, low high-density lipoprotein serum concentration, hypocholesterolemia, Abetalipoproteinemia, ApoA-I deficiency, or Tangier disease.

79. The method of embodiment 77, wherein the dyslipidemia is hyperlipidemia, hypercholesterolemia, ApoA-I deficiency, or hypertriglyceridemia.

80. The method of embodiment 77, wherein the treating comprises increasing serum high density lipoprotein concentration.

81. A method for treating or preventing a cardiovascular disease, comprising administering an effective amount of the peptide or pharmaceutically acceptable salt of the peptide of any one of embodiments 1 to 75 to a mammal in need thereof 82. The method of claim 81, wherein the cardiovascular disease is metabolic syndrome, ischemic heart disease, atherosclerosis, restenosis, endotoxemia, congestive heart failure, circulatory shock, cardiomyopathy, cardiac transplant, myocardial infarction, a cardiac arrhythmia, supraventricular tachycardia, atrial flutter, paroxysmal atrial tachycardia, aneurysm, angina, cerebrovascular accident, peripheral vascular disease, cerebrovascular disease, kidney disease, atherogenesis, atherosclerosis, acute pancreatitis, or coronary artery disease.

83. The method of claim 81, wherein the cardiovascular disease is atherosclerosis, restenosis, or a metabolic syndrome.

84. A method for treating or preventing endothelial dysfunction, comprising administering an effective amount of the peptide or a pharmaceutically acceptable salt of the peptide of any one of embodiments 1 to 75 to a mammal in need thereof 85. A method for treating or preventing a macrovascular disorder, comprising administering an effective amount of the peptide or a pharmaceutically acceptable salt of the peptide of any one of embodiments 1 to 75 to a mammal in need thereof 86. The method of claim 85, wherein the macrovascular disorder is transient ischaemic attack, stroke, angina, myocardial infarction, cardiac failure, or peripheral vascular disease.

87. A method for treating or preventing a microvascular disorder, comprising administering an effective amount of the peptide or a pharmaceutically acceptable salt of the peptide of any one of embodiments 1 to 75 to a mammal in need thereof 88. The method of claim 87, wherein the microvascular disorder is diabetic retinopathy, microalbuminuria, macroalbuminuria, end stage renal disease, erectile dysfunction, autonomic neuropathy, peripheral neuropathy, osteomyelitis, or lower limb ischaemia.

89. The method of any one of embodiments 77 to 88, wherein the mammal is a human.

90. The method of any one of embodiments 77 to 89, wherein the administering is done orally, intravenously, intramuscularly, intrathecally, subcutaneously, sublingually, nasally, cutaneously, transdermally, ocularly, or by inhalation.

The invention claimed is:

1. A method for treating dyslipidemia, comprising: administering to a mammal in need thereof a peptide/lipid complex in an amount effective to treat the dyslipidemia, wherein the peptide has the sequence of SEQ ID NO: 16, or a pharmaceutically acceptable salt thereof.

2. The method of claim 1, wherein the lipid comprises a phospholipid.

3. The method of claim 2, wherein the phospholipid is sphingomyelin, ($C_1$-$C_{10}$) alkyl chain phospholipids, phosphatidylcholine (PC), egg phosphatidylcholine, soybean phosphatidylcholine, dipalmitoylphosphatidylcholine (DPPC), dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, 1-palmitoy 1-2-oleoylphosphatidylcholine, 1-oleoyl-2-palmitylphosphatidylcholine, dioleoylphosphatidylcholine, dioleoylphosphatidylethanolamine, dilauroylphosphatidylglycerol phosphatidylcholine, phosphatidylserine, phosphatidylethanolamine, phosphatidylinositol, a sphingolipid, phosphatidylglycerol, diphosphatidylglycerol, dimyristoylphosphatidylglycerol, dipalmitoylphosphatidylglycerol (DPPG), distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, sphingomyelin, brain sphingomyelin, dipalmitoylsphingomyelin, distearoylsphingomyelin, phosphatidic acid, galactocerebroside, a ganglioside, a cerebroside, dilaurylphosphatidylcholine, (1,3)-D-mannosyl-(1, 3)diglyceride, aminophenylglycoside, a 3-cholesteryl-6'-(glycosylthio)hexyl ether glycolipid, cholesterol, or a combination thereof.

4. The method of claim 2, wherein the phospholipid is one or more of sphingomyelin, dipalmitoylphosphatidylcholine (DPPC) and dipalmitoylphosphatidylglycerol (DPPG).

5. The method of claim 2, wherein the phospholipid is a mixture of sphingomyelin and dipalmitoylphosphatidylcholine (DPPC) or dipalmitoylphosphatidylglycerol (DPPG).

6. The method of claim 2, wherein the phospholipid is a mixture of sphingomyelin, dipalmitoylphosphatidylcholine (DPPC) and dipalmitoylphosphatidylglycerol (DPPG).

7. The method of claim 5, wherein the ratio of total peptide to lipid is about 1:about 0.5 to about 1:about 5.

8. The method of claim 6, wherein the ratio of total peptide to lipid is about 1:about 0.5 to about 1:about 5.

9. The method of claim 6, wherein the peptide:sphingomyelin:DPPC:DPPG weight ratio is 1:1.2125:1.2125:0.075.

* * * * *